US005958966A

United States Patent [19]
Mann et al.

[11] Patent Number: 5,958,966
[45] Date of Patent: *Sep. 28, 1999

[54] TREATMENT OF ABERRANT CELLULAR STATES WITH BIOMODULATORS

[75] Inventors: Paul L. Mann, Albuquerque, N.Mex.; Eugene Mash, Tucson, Ariz.; Terence J. Scallen, Albuquerque, N.Mex.

[73] Assignee: University of New Mexico, Albuquerque, N.Mex.

[*] Notice: This patent is subject to a terminal disclaimer.

[21] Appl. No.: 08/465,405

[22] Filed: Jun. 5, 1995

Related U.S. Application Data

[63] Continuation of application No. 07/876,313, Apr. 30, 1992, and a continuation-in-part of application No. 07/694,321, May 1, 1991, abandoned.

[51] Int. Cl.⁶ .................................................. A61K 31/40
[52] U.S. Cl. ......................... 514/422; 514/423; 514/883
[58] Field of Search .................................. 514/422, 423, 514/883

[56] References Cited

U.S. PATENT DOCUMENTS

| | | | |
|---|---|---|---|
| 3,983,140 | 9/1976 | Endo et al. | 260/343.5 |
| 4,137,322 | 1/1979 | Endo et al. | 424/273 R |
| 4,198,425 | 4/1980 | Mistui et al. | 424/279 |
| 4,248,889 | 2/1981 | Oka et al. | 424/308 |
| 4,255,444 | 3/1981 | Oka et al. | 424/279 |
| 4,613,610 | 9/1986 | Wareing | 514/406 |
| 4,681,893 | 7/1987 | Roth | 514/422 |
| 4,710,513 | 12/1987 | Willard et al. | 514/460 |
| 4,739,073 | 4/1988 | Kathawala | 548/406 |
| 4,751,235 | 6/1988 | Anderson | 514/299 |
| 4,755,606 | 7/1988 | Wareing | 548/110 |
| 4,761,419 | 8/1988 | Picard et al. | 514/311 |
| 4,808,607 | 2/1989 | Wareing | 514/400 |
| 5,588,715 | 12/1996 | Damon, II | 514/63 |

FOREIGN PATENT DOCUMENTS

| | | |
|---|---|---|
| WO 86/03488 | 6/1986 | WIPO . |
| WO 87/02662 | 5/1987 | WIPO . |
| WO 88/01997 | 3/1988 | WIPO . |
| WO 92/19240 | 11/1992 | WIPO . |
| WO/92/19239 | 11/1992 | WIPO . |

OTHER PUBLICATIONS

Rice, F.A.H., "Isolation from *Penicillium gilmanii* of a Substance the Causes Leucocytosis in Rabbits", pp. 189–192 (1980.

Rice et al, "Chemical Determination of Leucogenenol and Its Production by *Penicillium gilmanii*", Applied Microbiology 15:790–793 (1967).

Rice, F.A.H., "The Structure of Leucogenenol", J. Chem. Soc. (C), pp. 2599–2605 (1971).

Hayflick, Leonard, Ann. Rev. Gerontol Gerrat 1:26–67 (1980).

Schneider et al, "Skin fibroblast cultures derived from members of the Baltimore Longitudinal Study: a new resource for studies of cellular aging", Cytogenet. Cell Genet. 31:40–46 (1981).

Martin et al, "Replicative Life–Span of Cultivated Human C", Laboratory Investigation 93(1),86–(1970).

Goldstein, Samuel, "Replicative Senescence: The Human Fibroblast Comes of Age", Science 249:119 (1990).

Cristofalo et al, "Molecular Biology of Aging", Surgical Clinics of North America 74(1):1–21 (1994).

Rice, Frederick A.H., "Isolation from *Penicillium gilmanii* of a substance that causes leucocytosis in rabbits", Proc. Soc. Exp. Biol. Med. 123(1):189–192 (1966) No. 38743.

Stoessl et al, "Colletruncoic Acid Methyl Ester, a Unique Meroterpenoid from *Colletotrichum truncatum*", Z. Naturforsch. 41c:677–680 (1986).

Dennis et al, "Growth Inhibition of Human Melanoma Tumor Xenografts in Athymic Nude Mice by Swainsonine", Cancer REsearch 50:1867–1872 (1990).

Mohla et al., "Inhibition of Growth of Subcutaneous Xenografts and Metastasis of Human Breast Carcinoma by Swainsonine: Modulation of Tumor Cell HLA Class I Antigens and Host Immune Effector Mechanisms", Anticancer Research 10:1515–1522 (1990).

Dennis, Effects of Swainsonine and Polyinosinic: Polycytidylic Acid on Murine Tumor Cell Growth and Metastasis:, Cancer Research 46:5131–5136 (1986).

Bowlin et al, "Potentiation of Human Lymphokine–activated Killer Cell Activity by Swainsonine, an Inhibitor of Glycoprotein Processing", Cancer Research 49:4109–4113 (1989).

Myc et al, "Effect of Swainsonine on Stimulation and Cell Cycle Progression of Human Lymphocytes", Cancer Research 49:2879–2883 (1989).

Waxdal, "Isolation, Characterization, and Biological Activities of Five Mitogens from Pokeweed", Biochemistry 13(18):–3671–3677 (1974).

Mann et al, "Cell Surface Oligosaccharide Modulation During Differentiation: V. Partial Characterization of the Regulated Surface During Substrate Adhesion and Spreading", Mechanisms of Ageing and Development 62:47–77 (1992).

(List continued on next page.)

*Primary Examiner*—Kevin E. Weddington
*Attorney, Agent, or Firm*—Jones & Volentine, L.L.P.

[57] ABSTRACT

Biomodulators, which regulate cellular differentiation and proliferation, as well as methods of use thereof, e.g., for treating various conditions, e.g., cancer, senescence, immunological disorders and vascular disease; for stimulating normal tissue architecture after injury; for vaccination; for stimulating the production of biologically important molecules by cells or organs in culture; for maintaining organs or tissues outside of a body after removal from the body and prior to transplantation; and for producing of vascular grafts for transplantation; are provided.

8 Claims, 94 Drawing Sheets

OTHER PUBLICATIONS

Kino et al, "Studies of an Immunomodularor, Swainsonine: II. Effect of Swainsonine on Mouse Immunodeficient System and Experimental Murine Tumor", The Journal of Antibiotics 38:936–940 (1985).

Humphries et al., "Augmentation of Murine Natural Killer Cell Activity by Swainsonine, a New Antimetastatic: Immunomodulator", Cancer Research 48: 1410–1415 (1988).

Mann et al., "Biomodulation: An integrated approach to access and manipulate biological information", In: Gabius HJ, Gabius S., eds. Lectins and Cancer, Berlin Heidelberg: Springer–Verlag; 179–206 (1991).

Bitner et al, "Enhanced Tumor Imaging with Pokeweed Mitogen", Nucl. Med, Biol. 20(2):203–210 (1993).

Mann, "Biomodulation: an alternate approach to disease management", Curr. Opin. Invest, Drugs 2(9):1007–1014 (1993).

Mann et al, "Cell Surface Oligosaccharide Modulation During Differentiation: VI. The Effect of Biomodulation on the Senescent and Neoplastic Cell Phenotype", Mechanisms of Ageing and Development 62:79–110 (1992).

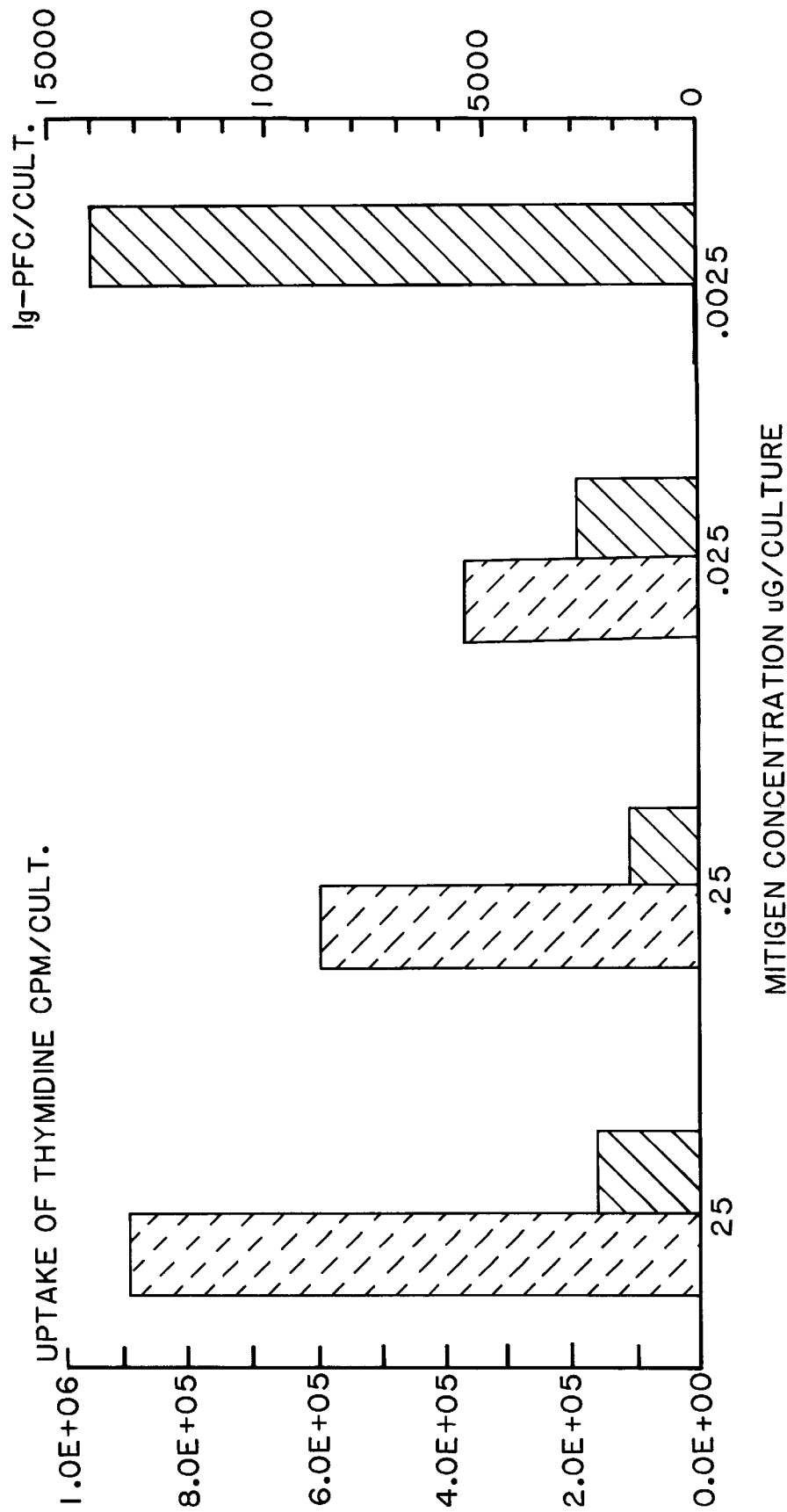

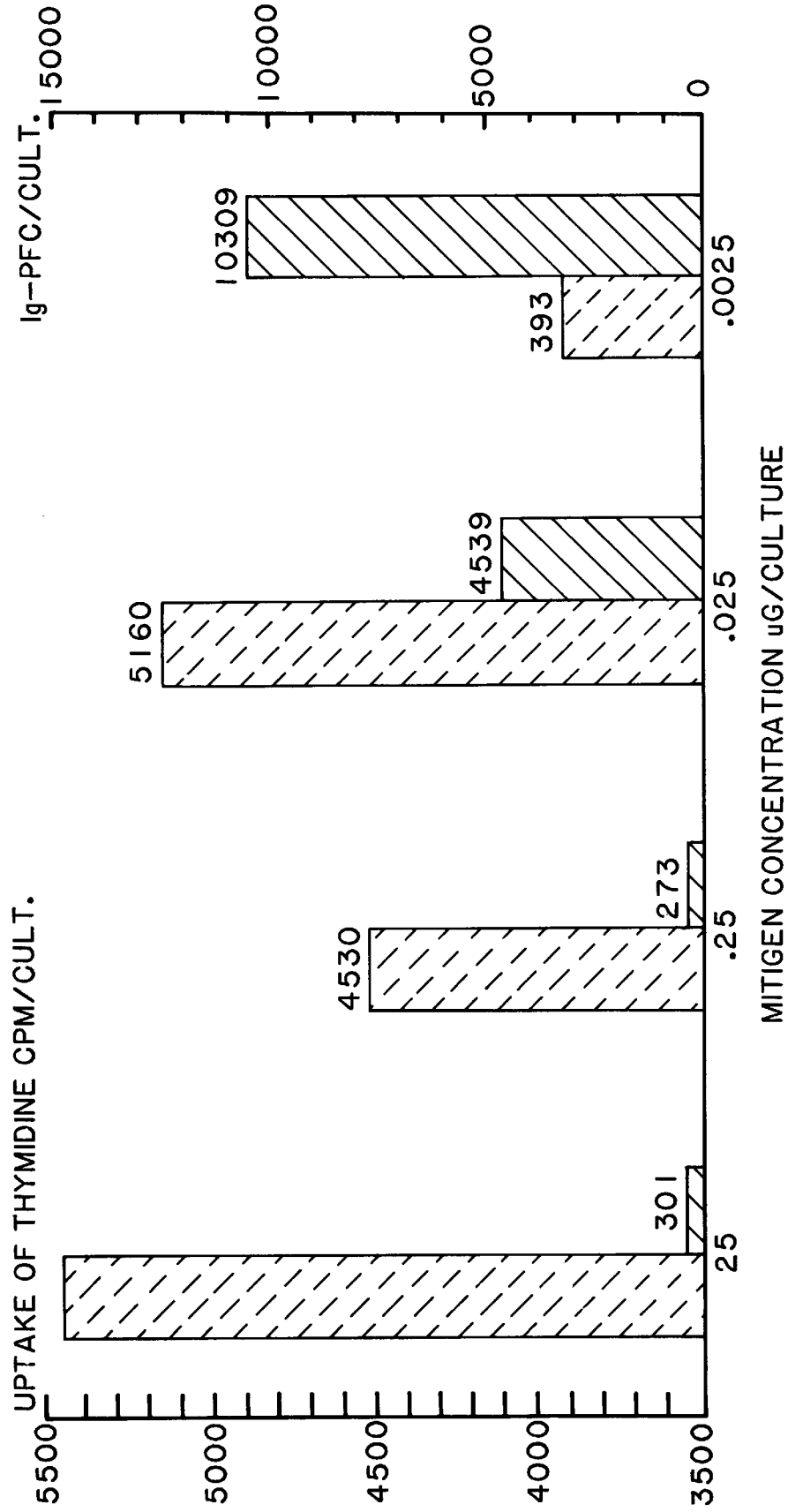
FIG. IB

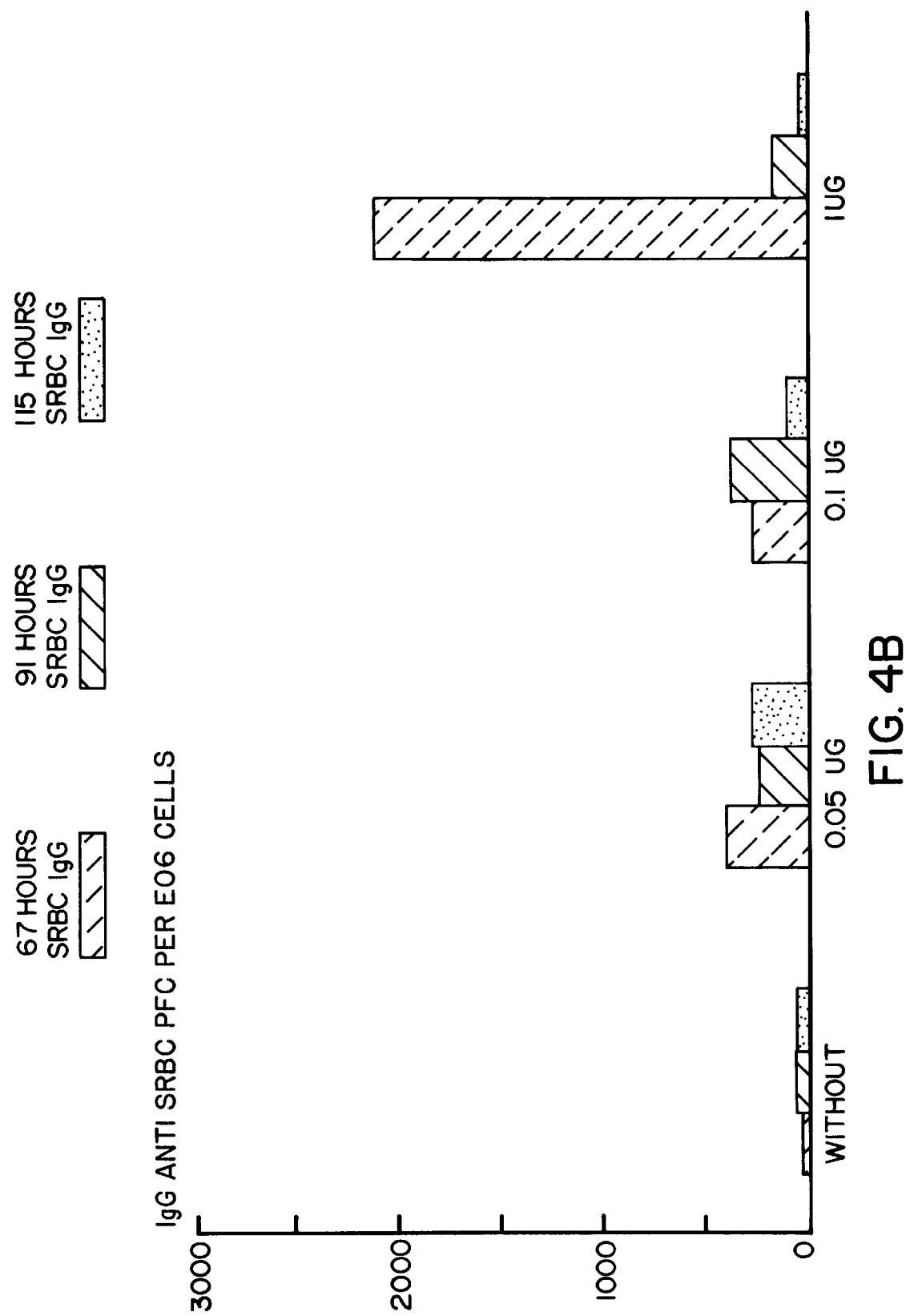

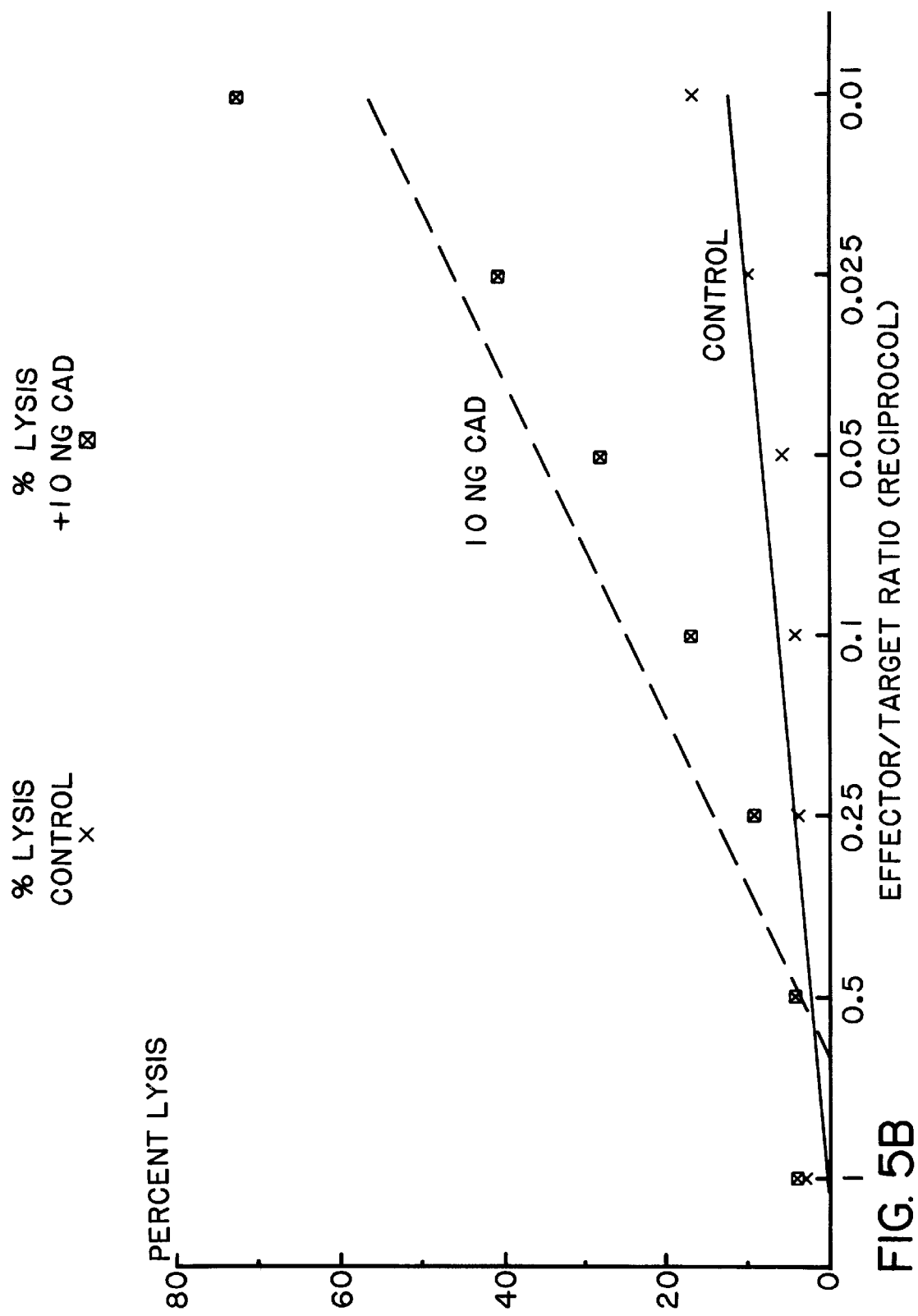

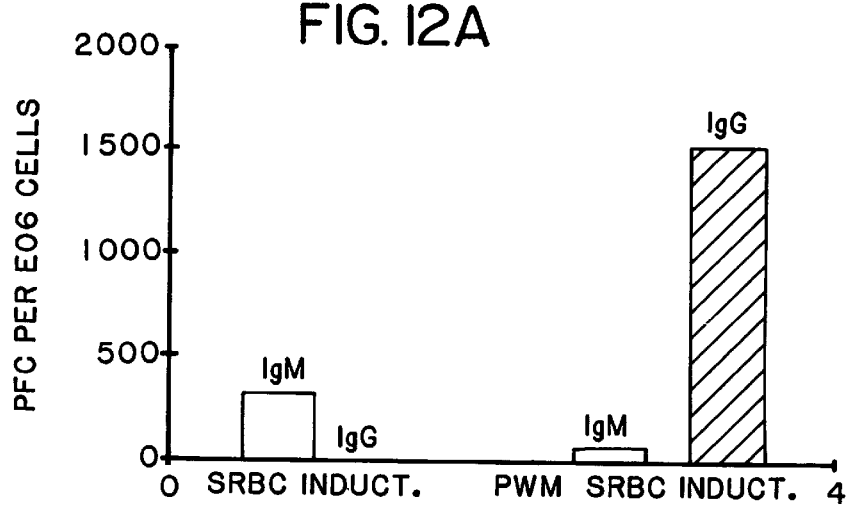
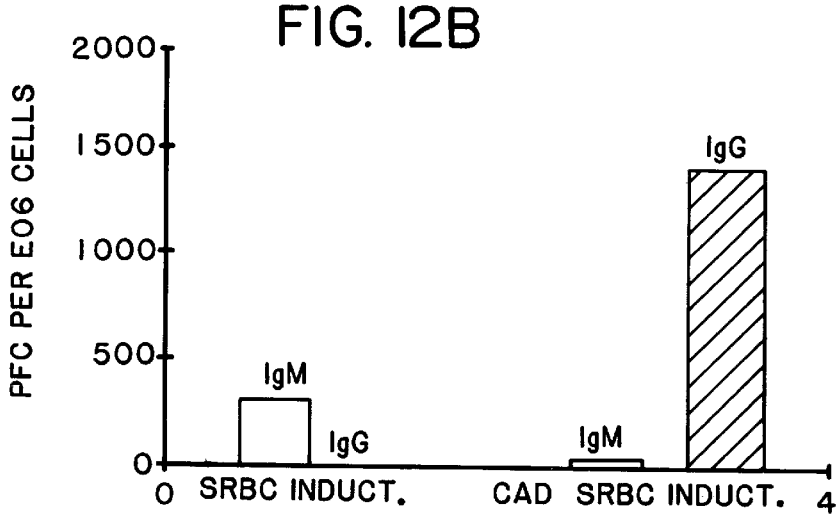
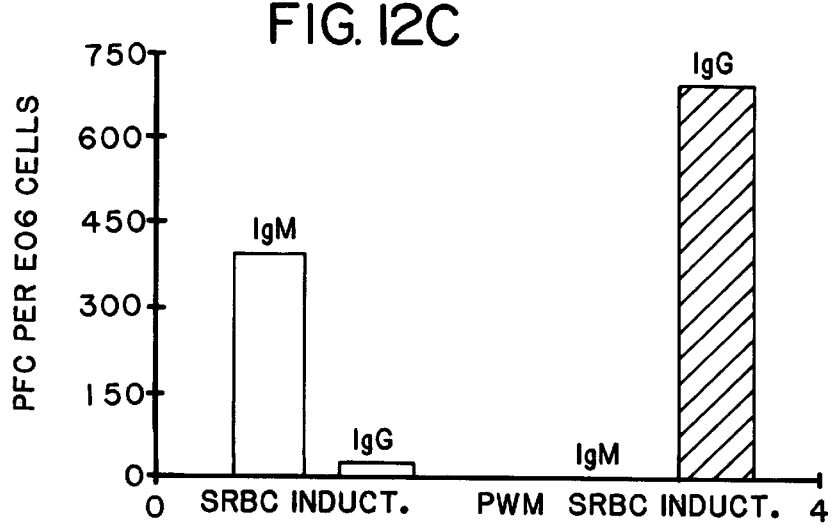

FIG. 16

Bar chart: GENERATION TIME IN H. (Tg) vs. TIME OF TREATMENT WITHDRAWAL IN HOURS

Legend:
- CAD. GLIO. + CAD
- CAN. GLIO. + PWM

Data:
- 72 H. W/O: 22.7, 25
- 144 H. W/O: 19.5, 22.7
- 216 H. W/O: 17.5, 19.5
- 288 H. W/O: 15.8, 18.3

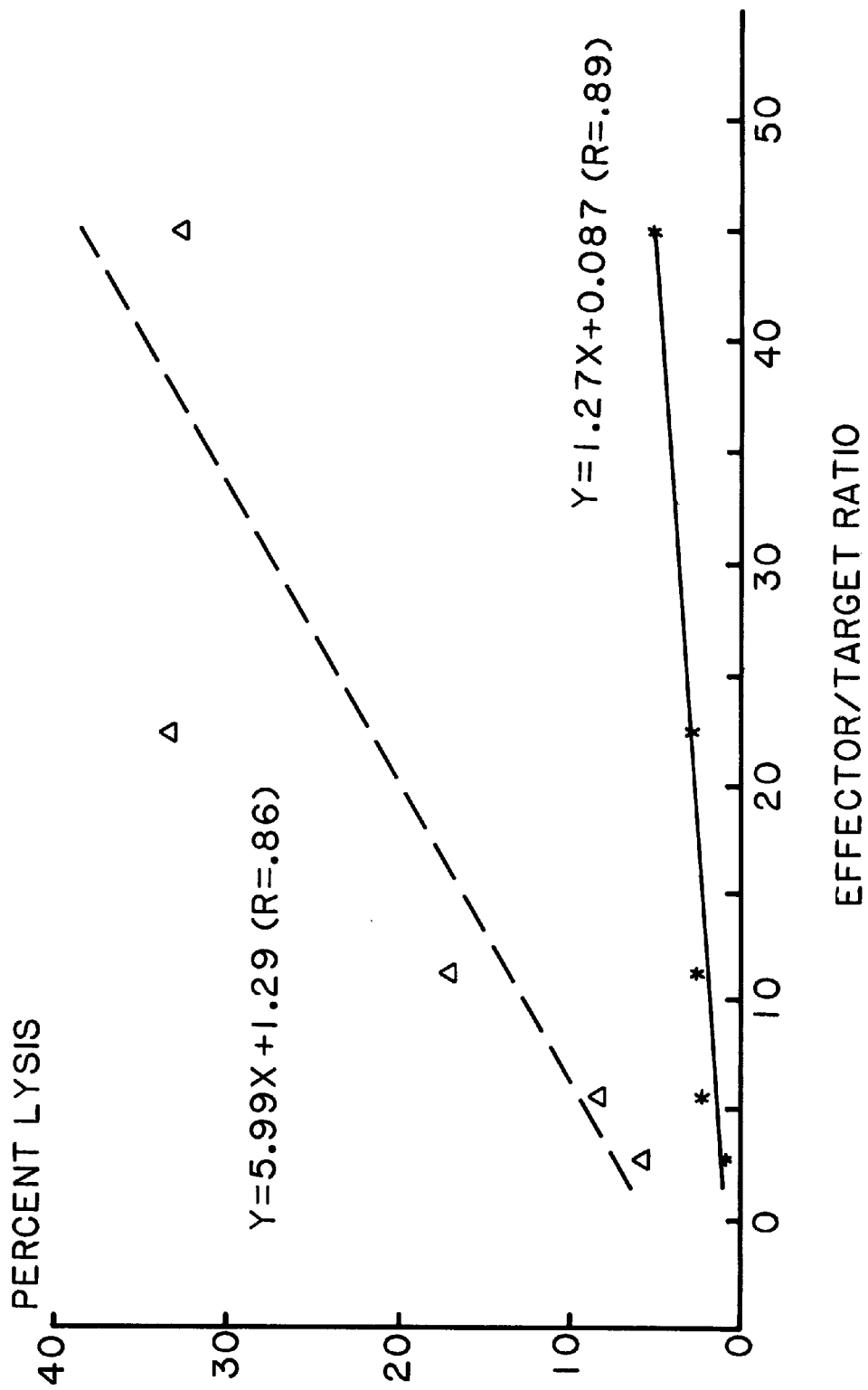

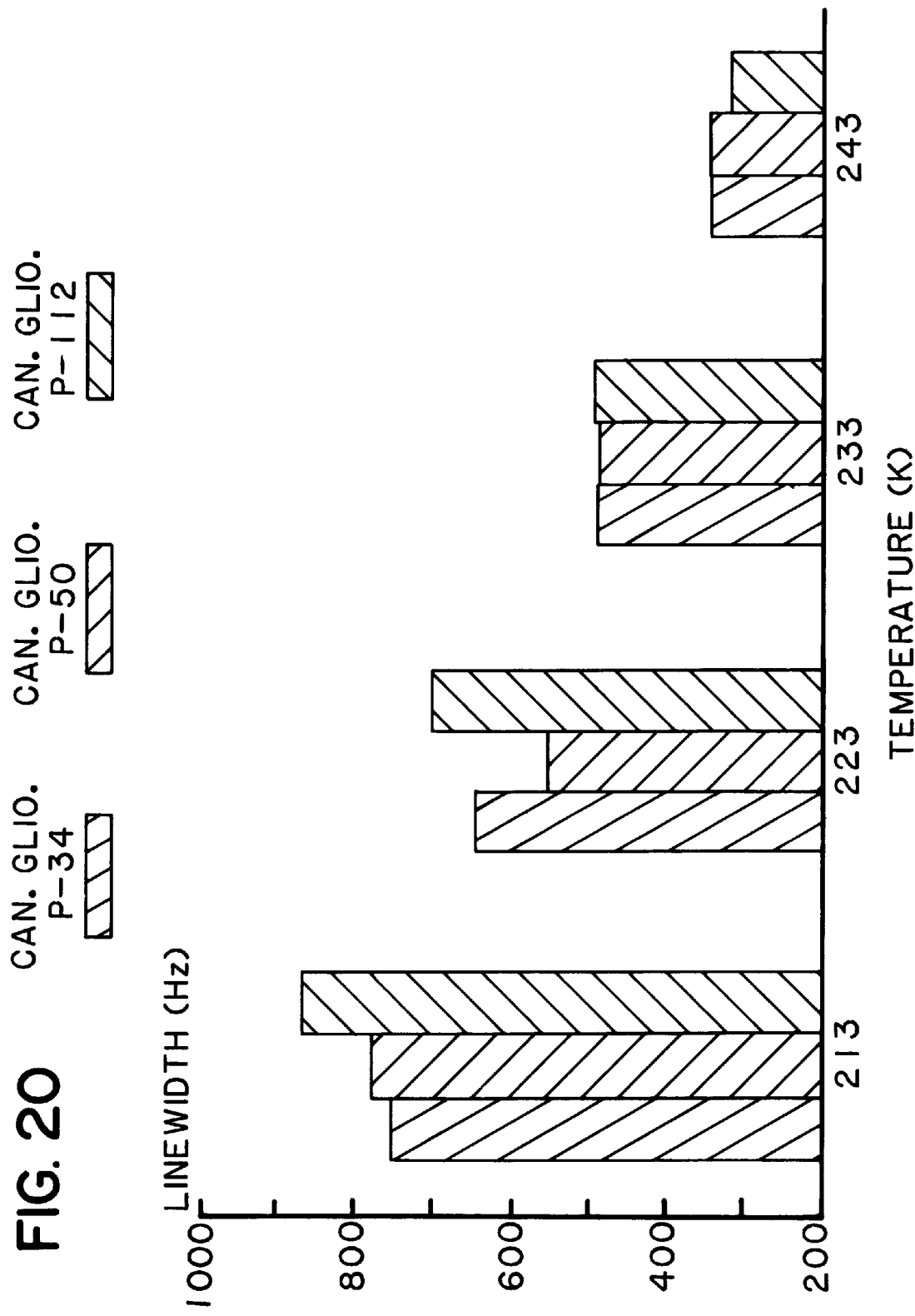

SUMMARY OF CANINE GLIOMA IMPLANTATION MODEL

| ANIMAL NUMBER | TREATMENT | CG IMPLANTATION | MRI OUTCOME | PATHOLOGY |
|---|---|---|---|---|
| I TECHNICAL FAILURES: | | | | |
| 7982 | NONE | 5 E 06 | TECHNICAL FAILURE | |
| 7038 | NONE | 2 E 06 | TECHNICAL FAILURE | |
| 7155 | NONE | 2 E 06 | TECHNICAL FAILURE | |
| II REAGENT CONTROL: | | | | |
| 7112 | NONE | NONE | NORMAL | N.D. |
| III GROWTH CONTROLS: | | | | |
| 7011 | NONE | 2 E 06 | EDEMA, MASS, GROWTH | TUMOUR |
| 7100 | NONE | 2 E 06 | EDEMA, MASS, GROWTH | TUMOUR |
| IV PRE-TREATMENT: | | | | |
| 7026 | HHD-2 10 uG/KG X 52 | 2 E 06 | EDEMA, MASS, GROWTH REGRESSION | NO TUMOUR |
| V SIMULTANEOUS TREATMENT AND IMPLANTATION: | | | | |
| 7906 | HHD-1 10 uG/KG X 12 | 2 E 06 | EDEMA, MASS, GROWTH REGRESSION | NO TUMOUR |
| 7115 | HHD-4 1 uG/KG X 10 | 2 E 06 | EDEMA, MASS, GROWTH REGRESSION | NO TUMOUR |
| VI | | | | |
| 7146 | HHD-4 1 uG/KG X 12 | 2 E 06 | EDEMA, MASS, GROWTH REGRESSION | NO TUMOUR |
| 7156 | PWM 10 uG X 6 | 2 E 06 | EDEMA, MASS, GROWTH REGRESSION | NO TUMOUR |

FIG. 31

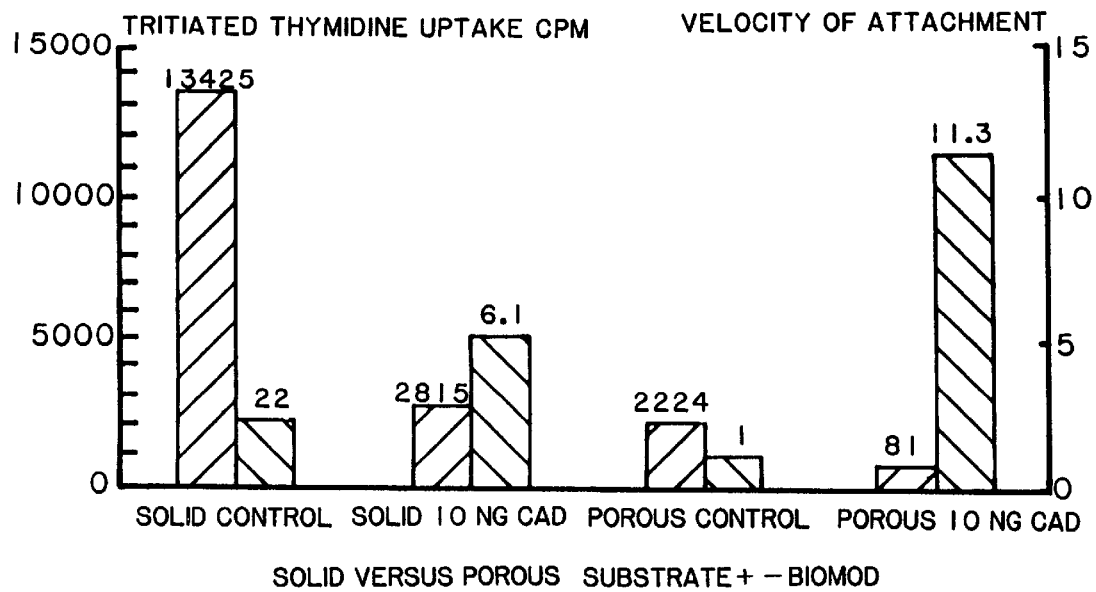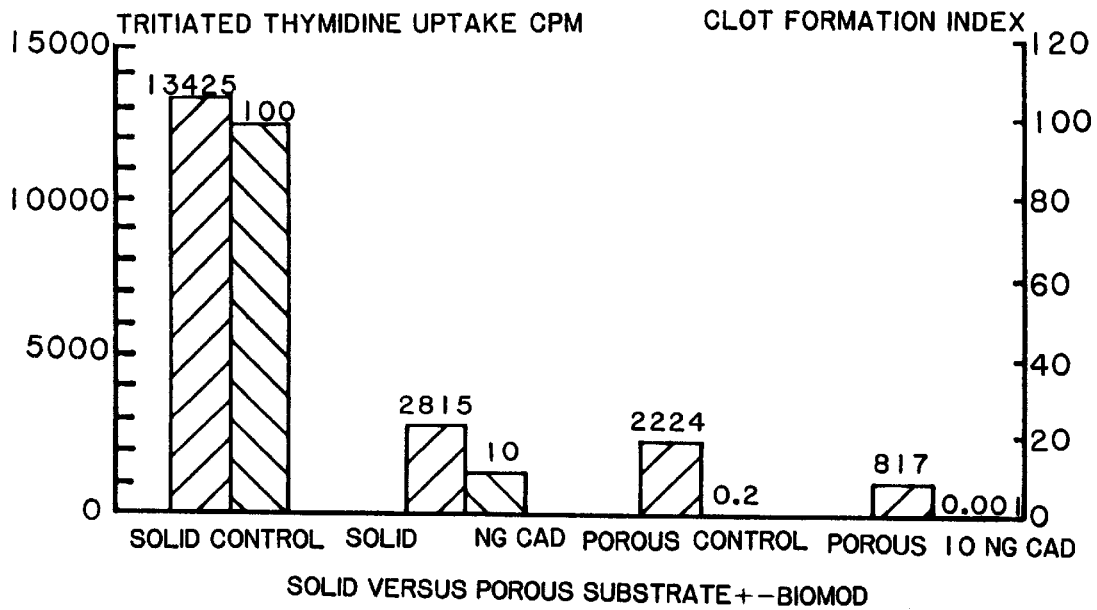

MURINE HYBRIDOMA: STANDARD TECHNOLOGY

| ANTIGEN* | IMMUNIZATION TYPE | IMMUNIZATION** SCHEDULE | PRE-SACRIFICE INDUCTION | | PFC/$10^6$*** AT SACRIFICE | |
|---|---|---|---|---|---|---|
| | | | TYPE | DURATION | IgM | IgG |
| SRBC | Primary | D-5 | NONE | NONE | 326 ±41 | 0 |
| SRBC | Secondary | D-30 D-5 | NONE | NONE | 100 | 100 |
| SRBC | Secondary | D-12 D-5 | NONE | NONE | 400 ±13 | 30 ±4 |

* SRBC antigen was given i.p. at 2x $10^7$ cells in PBS pH 7.0.
  ** Number of days prior to sacrifice.
 *** Plaque Forming Cell Assay (PFC) performed on day of sacrifice.
   + Standard Hybridization Protocol Using PEG. (mw 1540 Baker).
  ++ The number of positive wells and positive colonies; the number in brackets represents the frequency per specific antibody producing cell (PFC) in the hybridizing mixture.

FIG. 48A

| HYBRIDIZATION[+] CONDITIONS | NO. OF POSITIVE WELLS | | NO. OF COLONIES PER WELL | NUMBER[++] SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $5 \times 10^6$ Sp +$2 \times 10^6$ NS-1 | 1/24 | 0 | 1 | $1/5 \times 10^6$ (1:1630) | $1/5 \times 10^6$ (1:1630) | 0 | 0 |
| $10^8$ Sp + | 1/72 | 1/72 | 1 | $1/5 \times 10^7$ ($1:10^4$) | $1/5 \times 10^7$ ($1:10^4$) | $1/10^8$ ($1:2 \times 10^4$) | $1/10^8$ ($1:2 \times 10^4$) |
| $10^7$ Sp + $5 \times 10^6$ NS-1 | 4/24 | 2/24 | 1 | $1/2 \times 10^6$ (1:720) | $1/2 \times 10^6$ (1:720) | $1/5 \times 10^6$ (1:150) | $1/5 \times 10^6$ (1:150) |

FIG. 48B

MURINE HYBRIDOMA: Pre Immunization Induction Primary Response

| ANTIGEN* | IMMUNIZATION TYPE | IMMUNIZATION** SCHEDULE | PRE-SACRIFICE INDUCTION | | PFC/$10^6$*** AT SACRIFICE | |
|---|---|---|---|---|---|---|
| | | | TYPE | DURATION | IgM | IgG |
| SRBC | Primary | D-5 | 1ug PWM #4,Saline | D-26,-12 -9,-5 | 75±6 | 1510±41 |
| SRBC | Primary | D-5 | 1ug CAD RPMI 6.1 i.p. | D-26,-12 -9, -5 | 50 ±4 | 1425 ±65 |
| SRBC | Primary | D-5 | 1ug CAD RPMI 6.1 i.p. | D-30,-16 -12,-8 | 0 | 800 ±29 |

* SRBC antigen was given i.p. at 2x $10^7$ cells in PBS pH 7.0.
 ** Number of days prior to sacrifice.
 *** Plaque Forming Cell Assay (PFC) performed on day of sacrifice.
  + Standard Hybridization Protocol Using PEG. (mw 1540 Baker).
 ++ The number of positive wells and positive colonies; the number in brackets represents the frequency per specific antibody producing cell (PFC) in the hybridizing mixture.

FIG. 49A

| HYBRIDIZATION[+] CONDITIONS | NO. OF POSITIVE WELLS | | NO. OF COLONIES PER WELL | NUMBER[++] SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $5 \times 10^6$ Sp+ $2 \times 10^6$ NS-1 | 2/24 | 14/24 | 4-6 | $1/3 \times 10^5$ (1:550) | $1/6 \times 10^4$ (1:19) | $1/3 \times 10^5$ (1:290) | $1/7 \times 10^4$ (1:58) |
| $5 \times 10^6$ Sp+ $2 \times 10^6$ NS-1 | 0 | 10/24 | 8-10 | $1/5 \times 10^5$ (1:738) | $1/5 \times 10^4$ (1:82) | $1/5 \times 10^5$ (1:712) | $1/5 \times 10^4$ (1:79) |
| $10^7$ Sp + $5 \times 10^1$ NS-1 | 2/24 | 16/24 | 15 | $1/5 \times 10^5$ (1:444) | $1/4 \times 10^4$ (1:30) | $1/6 \times 10^5$ (1:500) | $1/4 \times 10^4$ (1:33) |

FIG. 49B

MURINE HYBRIDOMA: Pre Immunization Induction Secondary Response

| ANTIGEN* | IMMUNIZATION TYPE | IMMUNIZATION** SCHEDULE | PRE-SACRIFICE INDUCTION | | PFC/$10^6$*** AT SACRIFICE | |
|---|---|---|---|---|---|---|
| | | | TYPE | DURATION | IgM | IgG |
| SRBC | Secondary | D-12<br>D-5 | 1ug PWM<br>#4,Saline | D-30,-16<br>-12,-8 | 0 | 695<br>±23 |
| SRBC | Secondary | D-12<br>D-5 | 1ug PWM<br>#4,Saline<br>i.p. | D-30,-16<br>-12,-8<br>-6,-4 | 0 | 700<br>±13 |

* SRBC antigen was given i.p. at 2x $10^7$ cells in PBS pH 7.0.
** Number of days prior to sacrifice.
*** Plaque Forming Cell Assay (PFC) performed on day of sacrifice.
+ Standard Hybridization Protocol Using PEG. (mw 1540 Baker).
++ The number of positive wells and positive colonies; the number in brackets represents the frequency per specific antibody producing cell (PFC) in the hybridizing mixture.

FIG. 50A

| HYBRIDIZATION+ CONDITIONS | NO. OF POSITIVE WELLS | | NO. OF COLONIES PER WELL | NUMBER++ SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $10^7$ Sp + $5 \times 10^6$ NS-1 | 0 | 14/24 | 8 | $1/7 \times 10^5$ (1:500) | $1/9 \times 10^4$ (1:62) | $1/7 \times 10^5$ (1:500) | $1/9 \times 10^4$ (1:62) |
| $10^7$ Sp + $5 \times 10^6$ NS-1 | 0 | 22/24 | 12 | $1/4 \times 10^5$ (1:318) | $1/4 \times 10^4$ (1:27) | $1/4 \times 10^5$ (1:318) | $1/4 \times 10^4$ (1:27) |

FIG. 50B

MURINE HYBRIDOMA: Dose Response of Induction Primary Response

| ANTIGEN* | IMMUNIZATION TYPE | IMMUNIZATION** SCHEDULE | PRE-SACRIFICE INDUCTION | | PFC/$10^6$*** AT SACRIFICE | |
|---|---|---|---|---|---|---|
| | | | TYPE | DURATION | IgM | IgG |
| SRBC | Primary | D-5 | 10ug PWM #4, Saline i.p. | D-14,-12 -9,-7 | 60±11 | 1280±23 |
| SRBC | Primary | D-5 | 1ug PWM #4, Saline i.p. | D-14,-12 -9,-7 -5 | 42±9 | 761±19 |
| SRBC | Primary | D-5 | 0.1ug PWM #4, Saline i.p. | D-14,-12 -9, -7 -5 | 311±31 | 2150±60 |
| SRBC | Primary | D-5 | 1ug LPS-Alk i.p. | D-14,-12 -9, 7 -5 | 9±2 | 71±11 |
| SRBC | Primary | D-5 | 0.25ug LPS-Alk i.p. | D-14,-12 -9, 7 -5 | 80±14 | 3342±41 |
| SRBC | Primary | D-5 | 0.25ug LPS-Alk i.p. | D-14,-12 -9, 7 -5 | 78±9 | 928±41 |

\* SRBC antigen was given i.p. at 2x $10^7$ cells in PBS pH 7.0.
\*\* Number of days prior to sacrifice.
\*\*\* Plaque Forming Cell Assay (PFC) performed on day of sacrifice.
+ Standard Hybridization Protocol Using PEG. (mw 1540 Baker).
++ The number of positive wells and positive colonies; the number in brackets represents the frequency per specific antibody producing cell (PFC) in the hybridizing mixture.

FIG. 51A

| HYBRIDIZATION[+] CONDITIONS | NO. OF POSITIVE WELLS | | NO. OF COLONIES PER WELL | NUMBER[++] SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $10^7$ Sp+ $5 \times 10^1$ NS-1 | 13/48 | 30/48 | 5 | $1/2 \times 10^5$ (1:311) | $1/5 \times 10^4$ (1:62) | $1/3 \times 10^5$ (1:446) | $1/7 \times 10^4$ (1:85) |
| $10^7$ Sp+ $5 \times 10^1$ NS-1 | 32/48 | 32/48 | 9 | $1/2 \times 10^5$ (1:125) | $1/2 \times 10^4$ (1:14) | $1/3 \times 10^5$ (1:250) | $1/3 \times 10^4$ (1:28) |
| $10^7$ Sp+ $5 \times 10^1$ NS-1 | 0/48 | 0/48 | 2 | 0 | 0 | 0 | 0 |
| $10^7$ Sp+ $5 \times 10^1$ NS-1 | 2/48 | 31/48 | 7 | $1/3 \times 10^5$ (1:124) | $1/4 \times 10^4$ (1:3) | $1/3 \times 10^5$ (1:26) | $1/3 \times 10^4$ (1:3) |
| $10^7$ Sp+ $5 \times 10^1$ NS-1 | 14/48 | 21/48 | 10 | $1/2 \times 10^5$ (1:667) | $1/2 \times 10^4$ (1:83) | $1/4 \times 10^5$ (1:1250) | $1/4 \times 10^4$ (1:125) |
| $10^7$ Sp+ $5 \times 10^1$ NS-1 | 7/48 | 18/48 | 10 | $1/4 \times 10^5$ (1:400) | $1/4 \times 10^4$ (1:40) | $1/6 \times 10^5$ (1:556) | $1/6 \times 10^4$ (1:55) |

FIG. 51B

MURINE HYBRIDOMA: Dose Response of Induction Secondary Response

| ANTIGEN* | IMMUNIZATION TYPE | IMMUNIZATION** SCHEDULE | PRE-SACRIFICE INDUCTION | | PFC/$10^6$*** AT SACRIFICE | |
|---|---|---|---|---|---|---|
| | | | TYPE | DURATION | IgM | IgG |
| SRBC | Secondary | D-14<br>D-5 | 10ug PWM<br>#4,Saline<br>i.p. | D-14,-12<br>-9, 7 | 38±4 | 89±10 |
| SRBC | Secondary | D-14<br>D-5 | 1ug PWM<br>#4,Saline<br>i.p. | D-14,-12<br>-9,-7 | 28±3 | 652±9 |
| SRBC | Secondary | D-14<br>D-5 | 0.1ug PWM<br>#4,Saline<br>i.p. | D-14,-12<br>-9, -7<br>-5 | 76±6 | 1250±8 |
| SRBC | Secondary | D-14<br>D-5 | 1ug LPS<br>Alk i.p. | D-14,-12<br>-9, 7<br>-5 | 3±1 | 32±6 |
| SRBC | Secondary | D-14<br>D-5 | 0.25ug LPS<br>Alk i.p. | D-14,-12<br>-9, 7<br>-5 | 13±5 | 162±19 |
| SRBC | Secondary | D-14<br>D-5 | 0.25 LPS<br>Alk i.p. | D-14,-12<br>-9, 7<br>-5 | 25±6 | 1600±39 |

* SRBC antigen was given i.p. at 2x $10^7$ cells in PBS pH 7.0.
** Number of days prior to sacrifice.
*** Plaque Forming Cell Assay (PFC) performed on day of sacrifice.
+ Standard Hybridization Protocol Using PEG. (mw 1540 Baker).
++ The number of positive wells and positive colonies; the number in brackets represents the frequency per specific antibody producing cell (PFC) in the hybridizing mixture.

FIG. 52A

| HYBRIDIZATION+ CONDITIONS | NO. OF POSITIVE WELLS | | NO. OF COLONIES PER WELL | NUMBER++ SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $10^7$ Sp+ $5 \times 10^6$ NS-1 | 34/48 | 48/48 | 9 | $1/10^5$ (1:15) | $1/10^4$ (1:2) | $1/2 \times 10^5$ (1:45) | $1/2 \times 10^4$ (1:3) |
| $10^7$ Sp+ $5 \times 10^6$ NS-1 | 37/48 | 40/48 | 7 | $1/10^5$ (1:90) | $1/10^4$ (1:8) | $1/3 \times 10^5$ (1:170) | $1/2 \times 10^4$ (1:15) |
| $10^7$ Sp+ $5 \times 10^6$ NS-1 | 12/48 | 48/48 | 11 | $1/2 \times 10^5$ (1:212) | $1/2 \times 10^4$ (1:21) | $1/2 \times 10^5$ (1:266) | $1/2 \times 10^4$ (1:27) |
| $10^7$ Sp+ $5 \times 10^6$ NS-1 | 16/48 | 32/48 | 10 | $1/2 \times 10^5$ (1:7) | $1/2 \times 10^4$ (1:1) | $1/3 \times 10^5$ (1:10) | $1/3 \times 10^4$ (1:1) |
| $10^7$ Sp+ $5 \times 10^6$ NS-1 | 4/48 | 10/48 | 10 | $1/7 \times 10^5$ (1:125) | $1/7 \times 10^4$ (1:13) | $1/10^6$ (1:175) | $1/10^5$ (1:18) |
| $10^7$ Sp+ $5 \times 10^6$ NS-1 | 33/48 | 44/48 | 10 | $1/1 \times 10^5$ (1:124) | $1/1 \times 10^4$ (1:3) | $1/2 \times 10^5$ (1:26) | $1/2 \times 10^4$ (1:3) |

FIG. 52B

MURINE HYBRIDOMA: Dose Response of Induction
Timing of Antigen Administration

| ANTIGEN* | IMMUNIZATION TYPE | IMMUNIZATION** SCHEDULE | PRE-SACRIFICE INDUCTION | | | PFC/$10^6$*** AT SACRIFICE | |
|---|---|---|---|---|---|---|---|
| | | | | TYPE | DURATION | IgM | IgG |
| SRBC | Primary | D-14 | 10ug PWM #4,Saline i.p. | D-14,-12 -9, 7 -5 | | 12±4 | 21±9 |
| SRBC | Primary | D-14 | 1ug PWM #4,Saline i.p. | D-14,-12 -9,-7 -5 | | 11±3 | 160±8 |
| SRBC | Primary | D-14 | 0.1ug PWM #4,Saline i.p. | D-14,-12 -9, -7 -5 | | 23±6 | 38±8 |
| SRBC | Primary | D-14 | 1ug LPS Alk i.p. | D-14,-12 -9, 7 -5 | | 5±2 | 12±3 |
| SRBC | Primary | D-14 | 0.25ug LPS Alk i.p. | D-14,-12 -9,-7 -5 | | 120±13 | 6298±320 |
| SRBC | Primary | D-14 | 0.25ug LPS Alk i.p. | D-14,-12 -9,-7 -5 | | 78±9 | 852±130 |

* SRBC antigen was given i.p. at 2x $10^7$ cells in PBS pH 7.0.
** Number of days prior to sacrifice.
*** Plaque Forming Cell Assay (PFC) performed on day of sacrifice.
+ Standard Hybridization Protocol Using PEG. (mw 1540 Baker).
++ The number of positive wells and positive colonies; the number in brackets represents the frequency per specific antibody producing cell (PFC) in the hybridizing mixture.

FIG. 53A

| HYBRIDIZATION+ CONDITIONS | NO. OF POSITIVE WELLS | | NO. OF COLONIES PER WELL | NUMBER++ SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $10^7$ Sp+ $5 \times 10^1$ NS-1 | 10/48 | 6/48 | 6 | $1/6 \times 10^5$ (1:20) | $1/1 \times 10^5$ (1:3) | $1/2 \times 10^6$ (1:55) | $1/3 \times 10^5$ (1:9) |
| $10^7$ Sp+ $5 \times 10^1$ NS-1 | 33/48 | 25/48 | 11 | $1/2 \times 10^5$ (1:29) | $1/2 \times 10^4$ (1:3) | $1/4 \times 10^5$ (1:68) | $1/4 \times 10^4$ (1:6) |
| $10^7$ Sp+ $5 \times 10^1$ NS-1 | 25/48 | 14/48 | 8 | $1/3 \times 10^5$ (1:15) | $1/3 \times 10^4$ (1:2) | $1/7 \times 10^5$ (1:43) | $1/9 \times 10^4$ (1:5) |
| $10^7$ Sp+ $5 \times 10^1$ NS-1 | 14/48 | 12/48 | 5 | $1/4 \times 10^5$ (1:6) | $1/7 \times 10^4$ (1:1) | $1/8 \times 10^5$ (1:14) | $1/2 \times 10^4$ (1:3) |
| $10^7$ Sp+ $5 \times 10^1$ NS-1 | 15/48 | 13/48 | 5 | $1/4 \times 10^5$ (1:2286) | $1/7 \times 10^4$ (1:417) | $1/8 \times 10^5$ (1:4923) | $1/2 \times 10^4$ (1:1428) |
| $10^7$ Sp+ $5 \times 10^1$ NS-1 | 12/48 | 11/48 | 5 | $1/4 \times 10^5$ (1:404) | $1/6 \times 10^4$ (1:58) | $1/9 \times 10^5$ (1:845) | $1/2 \times 10^4$ (1:189) |

FIG. 53B

MURINE HYBRIDOMA: Soluble Antigen

| ANTIGEN* | IMMUNIZATION TYPE | IMMUNIZATION** SCHEDULE | PRE-SACRIFICE INDUCTION | | PFC/$10^6$*** AT SACRIFICE | |
|---|---|---|---|---|---|---|
| | | | TYPE | DURATION | IgM | IgG |
| 100ug Hu Ferritin | Primary | D-14 | 10ug PWM #4,Saline i.p. | D-14,-12 -9,-6 -4 | | ND |
| 100ug Hu Ferritin | Primary | D-14 | 1ug PWM #4,Saline i.p. | D-14,-12 -9, 6 -4 | | ND |
| 100ug Hu Ferritin | Primary | D-14 | 0.1ug PWM #4,Saline i.p. | D-14,-12 -9, 6 -4 | | ND |
| 100ug Hu Ferritin | Secondary | D-14 | 10ug PWM Saline i.p. | D-14,-12 -9, 6 -4 | | ND |
| 100ug Hu Ferritin | Secondary | D-14 | 1ug LPS Saline i.p. | D-14,-12 -9, 6 -4 | | ND |
| 100ug Hu Ferritin | Secondary | D-14 | 0.1ug PWM Saline i.p. | D-14,-12 -9, 6 -4 | | ND |

* SRBC antigen was given i.p. at 2x $10^7$ cells in PBS pH 7.0.
** Number of days prior to sacrifice.
*** Plaque Forming Cell Assay (PFC) performed on day of sacrifice.
+ Standard Hybridization Protocol Using PEG. (mw 1540 Baker).
++ The number of positive wells and positive colonies; the number in brackets represents the frequency per specific antibody producing cell (PFC) in the hybridizing mixture.

FIG. 54A

| HYBRIDIZATION[+] CONDITIONS | NO. OF POSITIVE WELLS | | NO. OF COLONIES PER WELL | NUMBER[++] SPECIFIC Ab PRODUCERS | | NUMBER SPECIFIC IgG, Ab PRODUCERS | |
|---|---|---|---|---|---|---|---|
| | IgM | IgG | | WELL | COLONY | WELL | COLONY |
| $10^7$ Sp+ 5x$10^1$ NS-1 | 32/48 | 28/48 | 10 | 1/2x$10^5$ | 1/2x$10^4$ | 1/4x$10^5$ | 1/4x$10^4$ |
| $10^7$ Sp+ 5x$10^1$ NS-1 | 39/48 | 30/48 | 10 | 1/1x$10^5$ | 1/1x$10^4$ | 1/3x$10^5$ | 1/3x$10^4$ |
| $10^7$ Sp+ 5x$10^1$ NS-1 | 24/48 | 34/48 | 10 | 1/2x$10^5$ | 1/2x$10^4$ | 1/3x$10^5$ | 1/3x$10^4$ |
| $10^7$ Sp+ 5x$10^1$ NS-1 | 26/48 | 38/48 | 10 | 1/2x$10^5$ | 1/2x$10^4$ | 1/3x$10^5$ | 1/3x$10^4$ |
| $10^7$ Sp+ 5x$10^1$ NS-1 | 46/48 | 46/48 | 10 | 1/1x$10^5$ | 1/1x$10^4$ | 1/2x$10^5$ | 1/2x$10^4$ |
| $10^7$ Sp+ 5x$10^1$ NS-1 | 43/48 | 46/48 | 10 | 1/1x$10^5$ | 1/1x$10^4$ | 1/2x$10^5$ | 1/2x$10^4$ |

FIG. 54B

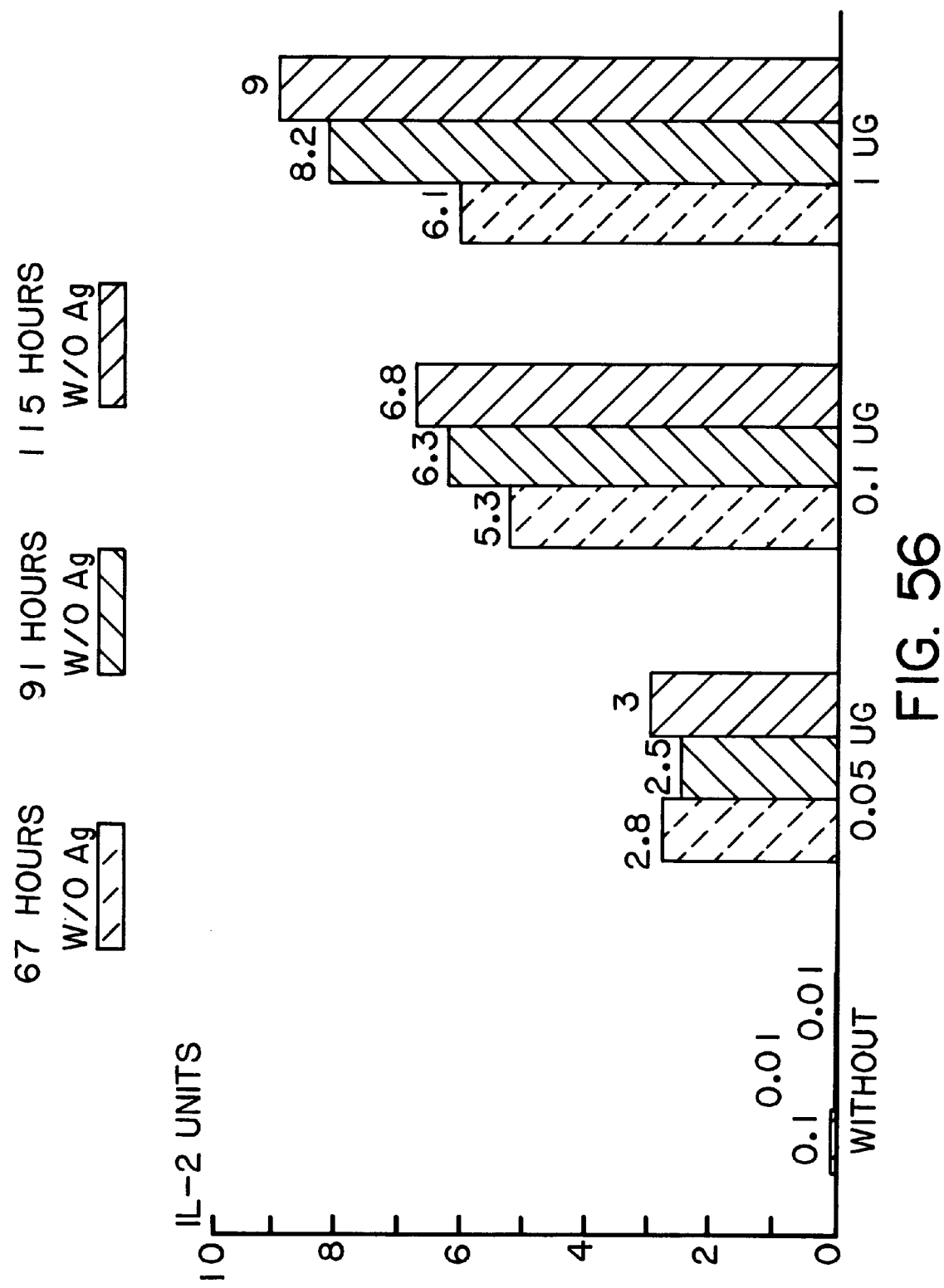

|   | A | B | C | D | E | F | G |
|---|---|---|---|---|---|---|---|
| 1 |   | A value | B value | C value | D value | f ratio | p value |
| 2 | group a = 3 weeks | | | | | | |
| 3 | control | | | | | | |
| 4 | animal 2 | 6.712859 | -0.62841 | 2.566011 | 0.310039 | | |
| 5 | | | | | | | |
| 6 | 0.1 ugm | | | | | | |
| 7 | animal 5 | 1.152948 | -1.86102 | -0.97615 | 0.200828 | 1.250 | 0.794 |
| 8 | animal 6 | 4.376045 | -1.60931 | 0.103761 | 0.213097 | 1.010 | 0.990 |
| 9 | | | | | | | |
| 10 | 1 ugm | | | | | | |
| 11 | animal 8 | 0.896967 | -2.49253 | 0.036663 | 0.272705 | 0.600 | 0.550 |
| 12 | animal 9 | 3.331038 | -0.72666 | 2.335783 | 0.264825 | 2.210 | 0.358 |
| 13 | | | | | | | |
| 14 | 10 ugm | | | | | | |
| 15 | animal 10 | 2.468189 | -1.45441 | 0.012405 | 0.238428 | 1.890 | 0.458 |
| 16 | animal 11 | 2.93218 | -0.8806 | 1.253824 | 0.25423 | 0.910 | 0.912 |
| 17 | animal 12 | 2.93218 | -0.8806 | 0.125382 | 0.25423 | 0.910 | 0.912 |
| 18 | | | | | | | |
| 19 | normal | 1.694586 | -1.3195 | 0.14101 | 0.236532 | 0.810 | 0.804 |
| 20 | | | | | | | |
| 21 | group b = 9 weeks | | | | | | |
| 22 | control | | | | | | |
| 23 | animal 13 | 16.74998 | 0.43588 | 6.556428 | 0.370534 | | |
| 24 | | | | | | | |
| 25 | 0.1 ugm | | | | | | |
| 26 | animal 16 | 1.109375 | -0.78106 | 0.086175 | 0.249111 | 0.070 | 0.006 |
| 27 | animal 18 | 1.821869 | -1.35153 | 0.002368 | 0.284751 | 0.150 | 0.036 |
| 28 | | | | | | | |
| 29 | 1 ugm | | | | | | |
| 30 | animal 19 | 0.746997 | -1.24987 | 0.031721 | 0.258262 | 0.070 | 0.006 |
| 31 | animal 20 | 5.950433 | -1.03875 | 0.188873 | 0.229695 | 0.070 | 0.006 |
| 32 | animal 21 | 7.845311 | -1.295 | 0.269734 | 0.252996 | 0.030 | 0.000 |
| 33 | | | | | | | |
| 34 | 10 ugm | | | | | | |
| 35 | animal 22 | 2.693018 | 2.693018 | -1.06257 | 0.25421 | 0.050 | 0.002 |
| 36 | animal 23 | 1.327648 | -1.71548 | 0.042776 | 0.261804 | 0.030 | 0.000 |
| 37 | animal 24 | 3.67428 | -1.36993 | 0.061723 | 0.244202 | 0.030 | 0.000 |
| 38 | | | | | | | |
| 39 | normal | 1.670819 | -1.32217 | 0.13855 | 0.236543 | 0.060 | 0.004 |
| 40 | | | | | | | |
| 41 | group c = 14 weeks | | | | | | |
| 42 | control | | | | | | |
| 43 | animal 27 | 2.331984 | -1.42843 | 0.007467 | 0.276233 | | |
| 44 | | | | | | | |
| 45 | 0.1 ugm | | | | | | |
| 46 | animal 28 | 3.602136 | -1.0524 | 0.219801 | 0.254431 | 0.580 | 0.524 |
| 47 | animal 29 | 6.146292 | -0.27859 | 631.1716 | 0.152238 | 16.980 | 0.002 |
| 48 | animal 30 | 9.353144 | -0.64616 | 2.348363 | 0.282435 | 3.220 | 0.180 |
| 49 | | | | | | | |
| 50 | 1 ugm | | | | | | |
| 51 | animal 31 | 14.80825 | -1.01953 | 0.486493 | 0.230969 | 17.900 | 0.002 |
| 52 | animal 32 | 6.411553 | -0.59161 | 0.254772 | 0.241422 | 8.200 | 0.022 |
| 53 | animal 33 | 2.250855 | -1.64137 | 0.004943 | 0.286911 | 1.330 | 0.738 |
| 54 | | | | | | | |
| 55 | 10 ugm | | | | | | |
| 56 | animal 34 | 14.4523 | -0.9562 | 0.954034 | 0.277945 | 2.950 | 0.214 |
| 57 | animal 35 | 1.841938 | -2.07728 | 0.07516 | 0.282673 | 1.770 | 0.506 |
| 58 | | | | | | | |
| 59 | normal | 2.252604 | -1.27862 | 0.198029 | 0.236417 | 1.620 | 0.572 |

FIG. 60

| µg SW | No Tumor | | Day 7 Tumor | | Day 14 Tumor | |
|---|---|---|---|---|---|---|
| 0.00 | 0.0526 | +/-0.01 | 0.0762 | +/-0.01 | 0.0397 | +/-0.02 |
| 0.10 | 0.1073 | +/-0.01 | 0.1726 | +/-0.01 | 0.0478 | +/-0.04 |
| 0.01 | 0.0560 | +/-0.02 | 0.0754 | +/-0.07 | 0.0633 | +/-0.03 |

| μg SW | No Tumor | | Day 7 Tumor | | Day 14 Tumor | |
|---|---|---|---|---|---|---|
| 0.0 | 140 | +/-38 | 150 | +/-56 | 164 | +/-62 |
| 0.1 | 209 | +/-61 | 122 | +/-62 | 301 | +/-123 |
| 0.01 | 264 | +/-59 | 136 | +/-40 | 342 | +/-93 |

TREATMENT OF ABERRANT CELLULAR STATES WITH BIOMODULATORS

This application is a continuation of 07/876,313 filed Apr. 30, 1992, and is a continuation-in-part of U.S. Ser. No. 07/694,321, filed May 1, 1991, now abandoned. The entire disclosures of these applications are hereby incorporated by reference.

This application is related to U.S. Ser. Nos. 07/694,325, 07/694,157 and 07/694,151, all of which were filed May 1, 1991, and all entirely incorporated by reference herein.

BACKGROUND OF THE INVENTION

Cellular functions can be broadly divided into two general categories: proliferation (reproduction) and differentiation (specialization of function). According to present theory, the proliferative function is continuously present in the normal cell, and is dominated in the mature cell by the differentiative function, which thus acts as an integrative force to regulate both differentiative and proliferative functions in the mature cell. A failure in the biochemical mechanisms upon which the cell is dependent for control of cell differentiative and proliferative functions thus has important implications, as disruption of normal differentiative and proliferative controls may result in both abnormal cellular function and abnormal cellular growth regulation. Thus, improperly enhanced cellular proliferation, particularly when coupled to impaired cellular differentiation may be the basis for neoplasia. Similarly, the well-known phenomenon of cellular senescence involves a failure of proliferation of terminally differentiated cells after a defined number of cellular generations.

This theory presents the possibility of regulating cell behavior by the use of agents which independently influence cell growth (proliferation) or differentiation. The identification of such agents is of particular interest, for example, because such agents have the potential to induce expression of cellular genes which code for cellular functions and structures characteristic of the normal mature cell type, thereby, e.g., normalizing the cell type, or leading to increased production of cellular products of commercial interest. Similarly, the identification of agents which appropriately enhance cellular proliferation may increase the normally limited lifespan of such cells (and the animals which contain them).

Such phenomena are explored in Mann, P. L., "In vitro Differentiation of Human Peripheral Blood Leukocytes: Considerations for Monoclonal Antibodies" in Radioimmunology and Radiotherapy, 121–141, Burchiel et al., eds., Elsevier (1983), with particular reference to the induction of functionally differentiating cells with limited proliferative capacity. In vitro induction of differentiation in leukocytes with fractionated pokeweed mitogen, anti-immunoglobulin and lipopolysaccharide, followed by exposure to antigen, produced particularly good antibody responses over an extended culture life. Particularly noted was the dual role of pokeweed mitogen as a function of concentration. At certain concentrations of the mitogen, termed "proliferative" concentrations, leukocyte antibody production was stimulated in vitro by inducing proliferation of the cells; however, under this stimulation, the cells rapidly age and prematurely die. In contrast, at other, "differentiative" concentrations of the same mitogen, long-term cultures of differentiated cells producing antigen-specific immunoglobulins at stabilized levels were obtained.

The recognition of proliferative/differentiative cellular phenomena has led to the postulation of a variety of mechanisms by which cellular function is controlled in vivo and by which cellular function may be manipulated.

It has been hypothesized (e.g., Mann, P. L., in Intl. Rev. Cyto. 112, 67–96 (1988)) that there are biomolecules which control and integrate cellular differentiation. The hypothesis suggests that there are various levels of differentiation control related to evolutionary development. Primitive differentiation mechanisms were required at the early stages of cellular evolution to define the cellular boundary, inside versus outside (the modern concept of self/non-self is based on this primitive beginning). These mechanisms were focused at the boundary of the cell, that is the cell surface. Primitive cellular differentiation mechanisms thus are those which relate to the basal differentiation control of cell phenotype and interaction.

The assumption contends that complexity of control developed from, and was integrated into, these primitive mechanisms as a result of increased functional complexity. In addition to the simple primitive regulatory/recognition, a myriad of highly specific and sophisticated mechanisms have been developed as evolution has continued to fine-tune cellular communication and adapt to multi-cell, and organismic existence, and therefore, those primitive mechanisms are common to all cells, and are non-cell-lineage specific. Two models have been used to study these events and control: cellular senescence, a normal growth controlled cellular population which loses the ability to replenish itself; and a neoplastic cell population which does not express any growth control, the antithesis of cellular senescence.

Cellular senescence according to Bell et al. (Science 202, 1158–1163 (1978)) is a terminal differentiation condition, presumably one in which the population is expressing its final, natural differentiation state. According to the present hypothesis, this cell population is simply no longer able to integrate growth control information in an appropriate way at the cell surface. The growth transformed cell model, on the other hand shows aberrant growth regulation and no apparent terminal phenotype.

The cell surface oligosaccharides of both normal and growth transformed cells showed phenotypically related alterations. Inter alia, there are specific decreases in the binding of specific lectins (and carbohydrate specific monoclonal antibodies) to senescent IMR-90 cells when compared to Phase II cells (Mann, et al., Mech. Aging Devel. 38, 207–218 (1987)) which are related to the affinity of binding and not to the simple epitope density (Mann, et al., Mech. Ageing Devel. 44, 1–16, (1988); Mann, Intl. Rev. Cytol. 112, 67–96 (1988)). Thus the concept of a three-dimensional oligosaccharide-dependent surface has developed. This surface is functionally related to the traditional glycocalyx by in-plane mobility measurements of the ligand/lectin complex (Mann, et al., Mech. Aging Devel. 38, 219–230 (1987)).

These cell surface display alterations preceded the morphological evidence of senescence. The hypothesis holds that this surface acts as an information filter, accepting and integrating information from the environment, inducing and regulating the subsequent phenotypic change. Thus, the cell surface display is squarely at the forefront of mechanistic studies. Senescent cells down-regulate their surface displays in specific ways with a specific carbohydrate-dependent temporal sequence. In general, the calculated value of Gibb's Free Energy (GFE), which is the sum of all the oligosaccharide-dependent binding energy, provided a gross view of the status of the cell surface. The morphologically senescent IMR-90 cell had a GFE of 10 KCal less than the Phase II cells and therefore was considered down-regulated.

It was also observed that the regulatory phenomenon of the cell surface was not absolutely specific to the onset of senescence. Normal Phase II IMR-90 cells undergo similar down-regulation of their surfaces in response to low density and contact-induced growth inhibition (Mann, et al., Mech. Aging Devel. 44, 17–33 (1988)). The cell surface oligosaccharide status appears to be a generic regulatory mechanism which permits the cell to respond to non-optimal growth conditions. There are specific differences observed between the pre-senescence and the growth-regulatory down-regulation of the surfaces which have yet to be fully explored, but in general, the normal growth control and cellular senescence appear to be linked as sub-components of cellular differentiation phenomena. The overall hypothesis, which integrates both models holds that (i) the morphological manifestations of cellular senescence, seen at PDL (population doubling level) 45 with the IMR-90 model are the result of inappropriate information integration caused at the cell surface by inappropriate down-regulation of the oligosaccharide display; (ii) that similar regulatory events occur during normal growth in response to low-density and contact-induced growth inhibition; and (iii) neoplastic, growth transformed cells have aberrant cell surface oligosaccharide display, which prevent the cell from expressing growth regulation under any conditions.

Sachs L., Sci. Am. 254, 40–47 (1986) proposed that each cell produces its own differentiation factors in response to endogenous "growth factors" which function as growth inducers for the cell. As the cells multiply (proliferate) under the influence of the growth factors, concentrations of cell differentiative factor(s) produced by the multiplying cells increase(s) sufficiently to induce cellular differentiation. Sachs concludes that these cell-produced differentiation factors are specialized proteins, probably as numerous as the cell types whose maturation they induce. The publication also reports that compounds other than cell-produced differentiation factors, as well as other influences, may directly or indirectly induce differentiation in normal and genetically defective cells in vivo, such as steroid hormones, X-rays, vitamins, bacterial lipopolysaccharides, cytosine arabinoside, adriamycin, methotrexate, lectins and some phorbol esters. No one compound effectively induced differentiation over the broad range of cell types tested.

Research on agents potentially useful for regulating or modulating cellular activity in vitro or in vivo extending over half a century has identified compounds erratically effective in affecting the differentiation and/or proliferation of a very narrow range of cell types under carefully controlled conditions. However, such research has been of limited focus in view of the complexity of the poorly-understood pathways by which cellular proliferation and differentiation are regulated, the unpredictable point at which these prior art compounds intervene in these pathways, and the consequently substantially random nature of the effects of these compounds on the basic underlying mechanisms controlling differentiation and proliferation.

Therefore, there is a need to identify substances which directly affect, e.g., normalize, the primitive control mechanism(s) regulating differentiation and proliferation in cells, to which cells can be exposed in vivo and in vitro to obtain a normalizing alteration in cellular differentiative and proliferativa activity over a broad range of cell types. In particular, it is desirable to provide substances which can induce self-adjustment of aberrant cellular behavior to return aberrant cells to normal function, wherein reproductive (proliferative) and differentiative cellular activities are integrated and responsive to the requirements of the host organism.

SUMMARY OF THE INVENTION

The present invention relates to the provision of such substances, termed "biomodulators," and their uses, e.g., methods of treating various conditions or achieving various results, etc., comprising administering or introducing, etc., a biomodulator.

Suitable biomodulators include:
(a) a compound of formula (I):

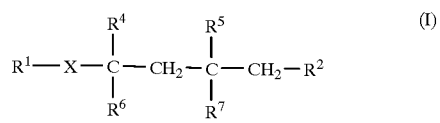

wherein
$R^1$ is an optionally substituted aromatic, cycloaliphatic or heterocyclic ring system,
$R^2$ is $-CH_2OH$, $-CHO$, $-COOR^3$ $-COSR^3$, $-CONR^8R^9$ or the corresponding lactone

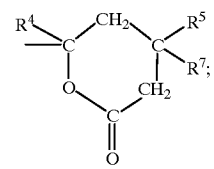

wherein
$R^3$ is H or $C_{1-10}$-alkyl,
$R^4$ and $R^5$ are each independently H or $C_{1-6}$-alkyl,
$R^6$ and $R^7$ are each independently OR, NHR or SR wherein R is H or $C_{1-14}$-alkanoyl,
$R^8$ and $R^9$ are each independently H or $C_{1-10}$-alkyl, and
X is $C_{2-3}$-alkylene, $C_{2-3}$-alkenylene, $C_{2-3}$-alkynylene, a cyclopropylene group, $-OCH_2-$ or $-SCH_2-$.
(b) a compound of formula (II) (swainsonine)

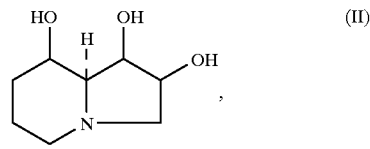

or an indolizidine alkaloid having an electronically similar 1,3-diol structure;
(c) cellular activator and differentiator (CAD); and
(d) pokeweed mitogen,
which have the activity of a biomodulator as defined herein.

In particular, this invention provides a method of regulating differentiative cellular function, comprising administering an effective amount of a biomodulator.

Thus, one aspect of this invention provides a method of treating tumors, comprising administering an effective amount of a biomodulator, particularly CAD or colletruncoic acid.

Other aspects of this invention provide a method of preventing or treating senescence, comprising administering an effective amount of a biomodulator; a method of treating an immune disease or disorder, comprising administering an effective amount of a biomodulator; a method of treating vascular disease, comprising administering an effective amount of a biomodulator; a method of stimulating the expression of normal tissue architecture after damage thereto, comprising administering an effective amount of a biomodulator; a method of vaccination for the prevention of disease, comprising administering an effective amount of a biomodulator and a vaccine, wherein the biomodulator and vaccine are simultaneously bioeffective; a method of stimulating the production of biomolecules by cells or organs in culture, comprising culturing the cells or organs in the presence of an effective amount of a biomodulator; a method of storing an organ or tissue outside of a body after removal from the body an prior to transplantation, comprising contacting said organ or tissue with an effective amount of a biomodulator; and a method of stimulating the growth of endothelial cells, treating a culture of said cells with an effective amount of a biomodulator.

"Biomodulator" as used herein means a natural product or a synthetic compound, e.g., a synthetic analog of a natural product, which regulates cellular differentiative activity, and, generally indirectly, proliferative activity as well, of eucaryotic, particularly mammalian, particularly human, cells. The biomodulatory activity of this invention is non-cell-lineage specific, affecting differentiation and proliferation in substantially all species and substantially all cell types. The activity of these substances is theorized (without wishing to be bound by this theory or any other theory discussed herein) to be at a primitive level of cellular control, common to substantially all cells, and the compounds are therefore non-specific in their effect. Thus, biomodulators as defined herein are distinct from so-called "biological response modifiers", such as, e.g., interleukins, interferons and other "kines", which have more specific activities, and which are specific natural products of specific stimuli produced by specific highly specialized cell types.

Again without wishing to be bound by theory, it is believed that the activity of biomodulators is based upon a generic, cell-surface oligosaccharide-dependent mechanism for "primitive" phenotypic expressions of differentiation. This theory is discussed in P. L. Mann, Intl. Rev. Cytol. 12, 67–95 (1988), which is entirely incorporated herein by reference. The biomodulators of this invention are theorized to induce differentiation by modulating expression of such a cellular differentiative phenotype; inter alia, the biomodulators induce expression of unexpressed genes to significantly diversify cellular function, or to induce significant increase or decrease in existing cellular function. The biomodulators acting solely as differentiation regulators can thus induce control over proliferation by inducing cellular differentiation and thus act as regulators (indirectly) of proliferation. For example, they can normalize the phenotype of an aberrantly growing cell, e.g., by turning on or off a gene or metabolic pathway, thereby to regulate the defect causing the aberrant activity. The biomodulators can also counteract aberrant proliferative or differentiative cellular function by stimulating other intracellular biochemical controls to normalize cellular behavior.

The biomodulators effect their results in very low concentrations and are generally characterized by a relatively low molecular weight, e.g., less than 1,000 daltons. The compounds are non-toxic in the amounts employed in the methods of the present invention.

The applicability of the invention to a broad range of circumstances and hosts such as mammals, including humans, is theorized (without wishing to be bound thereby) to be attributable at least in part to the involved mechanisms controlling cellular differentiative behavior and/or integration of cell proliferation and differentiation activity on a primitive level.

The biomodulators of this invention are useful, for example, as cytostatic agents for inhibiting growth and proliferation of tumor cells and/or inhibiting tumor metastasis. The compounds are broadly capable of inhibiting increases in tumor burden in a host, and/or are also capable of reducing pre-existing tumor burden.

The biomodulators of this invention are further particularly useful in treatment of immune diseases or disorders, such as acquired immune deficiency syndrome (AIDS), through effects on either or both the humoral and cellular immune systems, as well as providing enhanced vaccination methods for the prevention of disease, e.g., by administration with a vaccine.

The biomodulators of this invention are also useful as a treatment or prevention for senescence of cells or hosts comprising such cells (e.g., to delay the onset of senescence or to ameliorate or lessen the rate thereof), e.g., to lengthen mammalian lifespan.

Another aspect of this invention is the use of the biomodulators of this invention for control of vascular disease, in particular through modification of the coagulation and growth patterns of endothelial cells. Yet another aspect is the use of the biomodulators of this invention to stimulate the expression of normal tissue architecture after damage, e.g., after injury such as stroke, surgery, etc., or in general to stimulate the growth of endothelial cells.

Furthermore, the biomodulators of this invention have in vitro uses in a wide variety of application, e.g., stimulating the production of biologically important molecules by cells or organs in culture, maintaining organs and tissues prior to transplantation, production of vascular grafts for transplantation, stimulating the growth of endothelial cells, etc.

Biomodulators

A first category of compounds useful in the methods of the present invention comprises compounds of formula (I):

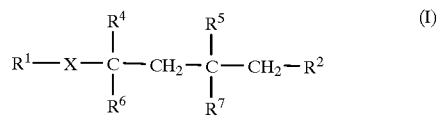

wherein $R^1$ is an optionally substituted aromatic, cycloaliphatic or heterocyclic ring system., $R^2$ is —$CH_2OH$, —CHO, —$COOR^3$ —$COSR^3$, —$CONR^8R^9$ or the corresponding lactone

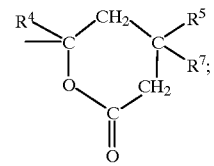

wherein $R^3$ is H or $C_{1-10}$-alkyl, $R^4$ and $R^5$ are each independently H or $C_{1-6}$-alkyl, $R^6$ and $R^7$ are each independently OR, NHR or SR wherein R is H or $C_{1-4}$-alkanoyl, $R^8$ and $R^9$ are each independently H or $C_{1-10}$-alkyl, and X is $C_{2-3}$-alkylene, $C_{2-3}$-alkenylene, $C_{2-3}$-alkynylene, a cyclopropylene group, —$OCH_2$— or —$SCH_2$—.

Particularly preferred compounds within the scope of formula (I) are those which have a steric configuration at the 3,5-carbon atoms of the heptanoic or octanoic acid based diol chain which is substantially electronically similar to that of the 3S,5R, 3S,5S, or 3R,5R configurations of colletruncoic acid. By "substantially electronically similar" is meant that in the energy minimized form, the interhydroxyl distance between the relevant hydroxyl groups is between 4.2–4.4 Å, preferably about 4.3 Å. The electronic similarity of the compounds can be determined, e.g., by performing routine energy minimization calculations, e.g., utilizing conventional calculations, such as those performed by the Chemdraft Computational Package, program MM-2, (C-Graph Software, Inc., Austin, Tex. 78763). In general, compounds which have a configuration 3R,5S (when X is an alkylene group, i.e., is saturated) or equivalently 3S,5R (when X is an alkenylene or alkynylene group, i.e., is unsaturated) will correspond to this most preferred structure. 3R,5R -and 3S,5S- configurations are also preferred.

The radical $R^1$ has a variable effect. In general, the $R^1$ radical is substantially hydrophobic with well defined pockets of electronegativity. Suitable $R^1$ ring groups have 1–4 or more fused and/or covalently bonded rings, optionally substituted by substituents which render this portion of the molecule electronegative (e.g., OH, halo, $NO_2$, $NH_2$, COOH, etc.). The compounds of formula I can possess $R^1$ ring groups having a hydrophobicity and/or electronegativity on the order of those of one or more of the following suitable $R^1$ rings, including $C_{6-25}$ mono-, bi-, tri- or polynuclear-aryl, -aryloxy, -cycloalkyl, -cycloalkenyl, -cycloalkadienyl, etc., as well as heterocyclic rings containing or sharing one or more, e.g., 2 or 3, O, S or N atoms. Where fused systems containing 1–4 or more individual rings are involved, each ring generally contains 4–7 atoms, 1–3, preferably, 1–2, of which are O, N or S atoms, the remainder being C atoms, these generally having 1–4 hetero atoms in total. Thus, heteroaryl and hydroheteroaryl groups are suitable. Examples of suitable $R^1$ groups include benzyl, benzyloxy, phenyl, phenyloxy, naphthyl, naphthyloxy, tetrahydronaphthyl, hexahydronaphthyl, octahydronaphthyl, imidazolyl, pyrimidyl, pyrazolyl, indenyl, quinolinyl, pyrrolyl, indolyl, indolizinyl, etc.

In addition, particularly preferred compounds of formula (I) are those in which n is 1, $R^2$ is $COOR^3$ or the corresponding lactone, $R^4$ and $R^5$ are each H, $R^6$ and $R^7$ are each OH, and X contains a cis or trans double bond.

One subtype of these compounds useful in the methods of the present invention are relatively small (for example, molecular weight less than 1,000 daltons) naturally occurring compounds (in isolated form) having the structure of formula I and the required electronic structure at the 3,5-carbon atoms. For example, the appropriate enantiomer of colletruncoic acid as defined above,

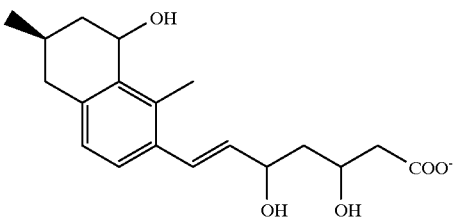

a natural compound isolated as the methyl ester from *Colletotrichum truncatum,* has a structure encompassed by the structural formula described above and has been shown to have biomodulator activity. Colletruncoic acid can be isolated according to the method outlined in Stoessl, A., and Stothers, J. B., Z. Naturforsh. 41c, 677–680 (1986), except as modified in that Stoessl et al. described the natural product as being a racemic methylester, which is incorrect; the correct compound is a free acid of one enantiomer with the noted stereochemistry.

Another subtype of these compounds are synthetic compounds of formula I having the required electronic structure at the 3,5-carbon atoms, as described above. All compounds of formula I can be made, in general, from readily available and/or preparable starting materials according to routine chemical syntheses, for example, according to methods outlined in U.S. Pat. Nos. 4,755,606, 4,613,610, 4,255,444, 4,248,889, 4,761,419, 4,751,235, 4,198,425, 4,137,322, 3,983,140, 4,588,715, 4,710,513, 4,739,073, 4,681,893; WO 84/92903; WO 87/02662; WO 88/01997; and WO 86/03488. For joining $R^1$—X—C (wherein C is the rest of the molecule) when X is —$CH_2CH_2$—, see *Tetrahedron* 1986, 42, 4909–4951. For joining $R^1$—X—C when X is —CH=CH—, a selenoxide or sulfoxide coupling and elimination strategy can be employed (see *J. Org. Chem.,* 1986, 51, 648–657) or, alternatively, Wittig methodology (see *J. Org. Chem.,* 1984, 49, 3994–4003.). When X is —C≡C—, the acetylide $R^1$—C≡C$^-$ can be added to an appropriate aldehyde or ketone. When X is —$OCH_2$— or —$SCH_2$— then $R^1O^-$ or $R^1S^-$ will be condensed with an appropriate electrophile; see *Tetrahedron Lett.,* 1988, 29, 2563–2566. Similarly, the $R^1$ moieties bearing substituted groups can be synthesized either before or after linkage to the remainder of the molecule.

A second general category of compounds having a related structure and having biomodulator activity is constituted by other small, naturally occurring compounds such as, e.g., swainsonine,

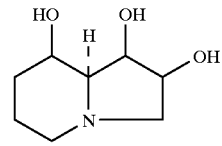

which is a low molecular weight indolizidine alkaloid extracted from *Swainsona Sp.* as well as from a number of other natural sources, and has hydroxy groups on its ring which have an almost identical electronic structure to the hydroxy groups on the heptanoate chain as described above. (Swainsonine is known to have anticancer effects possibly mediated through its inhibition of α-mannosidase II; thus, this effect is not suggestive of its biomodulator role or its range of activities in the other utilities described above.) Swainsonine is commercially available, e.g., from Boerringer-Mannheim or can be isolated according to the method of Hino, M., et al., J. Antibiotics 38, 926–935 (1985). Other members of this category are, e.g., other indolizidine alkaloid compounds retaining the electronic structure of the important "1,3-diol array" of swainsonine, such as swainsonine substituted in the ortho and meta positions on the 6-membered ring by hydroxy groups (castanospermine) and other natural products having an electronically similar 1,3 diol array. Still other suitable alkaloids are related compounds having two 6-membered rings or two 5-membered rings.

In addition to the known natural low molecular weight compounds swainsonine and colletruncoic acid, a third major type of biomodulator is a new compound provided by the present invention having properties similar to the compounds of Formula I. This compound, cellular activator and differentiator or CAD, is isolated from *Penicillium restrictum,* has a molecular weight of about 500, and is believed, without wishing to be bound by theory, to have a similar structure to colletruncoic acid. It can be isolated according to the method outlined in Example 1.

A fourth category of compounds useful in the methods of the present invention are high molecular weight compounds having biomodulator activity, such as pokeweed mitogen (PWM), which is a well known mixture of five isomitogenic glyycopeptides extracted from *Phytolacca americana,* and which is known for its ability to stimulate cellular proliferation. Although its structural relationship to the above described compounds is uncertain, PWM is thought to interact with cells in a similar way and has the same spectrum of effects for the various utilities disclosed herein. Pokeweed mitogen can be isolated according to well-known methods, e.g., according to the method outlined in Riesfeld, R. A., et al., Proc. Natl. Acad. Sci. (U.S.) 58, 2020–2027 (1967). It is noted that the differentiative and proliferative activities of PWM can be separated, i.e., by separating the isotypes, e.g., according to the method outlined in Waxdal, M. J., Biochem. 13, 3671 (1974). For example, subfractions Pa-1 and Pa-5 have differentiative activity and subfractions Pa-2 and Pa-4 have proliferative activity. The differentiative substance is preferred.

Preferred compounds include 3S,5R-colletruncoic acid and the compound obtained by switching the heptanoate chain of 3S,5R-colletruncoic acid with the adjacent methyl group on the ring.

Biomodulator Assays

Five models have been used to demonstrate various aspects of biomodulator effects:

A. The IMR-90 normal fetal lung fibroblast cell line is used to demonstrate the effects of biomodulators on normal cell growth and differentiation control, and several "normal" phenotypic alterations of this control, according to the methods outlined in Mann, P. L., et al., Mech. Ageing Devel. 38, 207–217 (1987). This model is used to correlate the effects of biomodulators on normal cellular mechanisms such as density-dependent growth inhibition, as well as the physical manifestations of phenotypic cellular changes, for example, the cell surface oligosaccharide display (Mann, P. L., et al., Mech. Ageing Devel. 38, 219–230 (1987).

B. The IMR-90 cell line is also used to demonstrate the effects of biomodulators on terminal cellular differentiation in the later phase of the normal growth and differentiation of this cell line, according to the method outlined in Mann, P. L., et al., Mech. Ageing Devel. 44, 17–33 (1988). This model is used to correlate the effects of biomodulators on the senescent phenotype in cultured cells.

C. Human peripheral blood leukocytes (HPBLs) are used to demonstrate the effects of biomodulators on lymphoid differentiation and/or proliferative response, according to the methods outlined in Mann, P. L., in Radioimmunoimaging and Radioimmunotherapy, Burchiel, S. W. and Rhodes, B. A., eds., Elsevier Sci. Publ. N.Y., pp. 121–141 (1983). This model is used to correlate the effects of biomodulators on the expression of immune response in vitro. The plaque assay disclosed in this reference is used for the determination of the effect of biomodulators on the specificity, class and subclass of individual clones. In addition, HPBLs are used to demonstrate the presence or absence of proliferative response to biomodulator stimulation, by measuring the incorporation of $^3$H-thymidine in this cell line, also as disclosed in this reference.

D. A canine glioma cell line (CGs) is used to demonstrate the effects of biomodulators on transformed cells, according to the method outlined in Mann, P. L., et al., Mech. Ageing Devel. 44, 17–33 (1988). This model is used to correlate the effects of biomodulators on the cell surface display characteristics of this aberrant cell line, as in the IMR-90 cells, above, as well as other phenotypic responses, such as generation time, morphology, and the cells' ability to participate in immune reactions. For example, these cells are used in a standard natural killer cell chromium release assay (Brunner et al., Immunol. 14, 181 (1968)), in which it was shown that the natural killer (NK) activity of HPBLs against chromium labeled control and biomodulator-treated CGs shows that the biomodulator-treated CGs are markedly better targets for natural killer activity. The cytotoxic T-*lympholysis* test gives similar results.

E. Various cell lines, including CGs and B-16 melanoma cells, when implanted into experimental animals where they form tumors, as well as spontaneously-occurring tumors in animals, are used to demonstrate the effects of biomodulators in vivo, according to methods outlined herein (Example 5). This model is used to correlate the effects of biomodulators on tumor regression.

All biomodulators will have at least the following effects, which can be measured as indicated above:

a. Biomodulators cause, at a concentration in the general range of 100 pM-1 μm, the differentiation of lymphocytes. This differentiation can be detected by, for example, the increased production of specific and non-specific antibodies in response to the presence of biomodulator in the culture medium, e.g., according to the HPBL method discussed above in C, or the alteration in the class of antibodies being produced by a cell line, e.g., from IgM to IgG, e.g., according to the method disclosed in the same reference.

b. Biomodulators cause, at a concentration in the general range of 100 pM-1 μm, the alteration of the cell surface oligosaccharide display of IMR-90 cells in culture as discussed in A. above.

Activity in both of these assays is a necessary and sufficient measure of whether or not a given substance is a biomodulator, as defined herein.

For compounds as defined herein which additionally have a direct proliferative activity, this activity can be determined by measuring the $^3$H-thymidine incorporation of HPBL cells in culture, e.g., according to the method discussed in C. above.

Activity for Treatment of Tumors

The biomodulators of this invention having differentiation-inducing activity have cytostatic activity against tumor-transformed cells and are effective in therapeutic dosages according to the invention to reduce tumor burden in vivo by inhibiting primary or secondary tumor cell growth, or tumor metastasis, or both. A broad spectrum of tumors is contemplated as susceptible to treatment according to the invention, including both soft tumors such as leukemias and lymphomas, and solid tumors such as melanomas, ovarian tumors, cervical tumors, breast tumors, lung tumors (small cell and non-small cell), colon and stomach tumors, hepatocellular tumors, pancreatic, midgut; bladder and prostate tumors, brain tumors, myelomas, and larynx tumors.

Preferred substances for cytostatic activity within the scope of those disclosed in the various categories are conveniently selected by assaying for high immunological activity in vitro, as this property appears to be a marker for cytostatic activity. (However, in some instances, biomodulators having little or no immunological activity in some assays may be cytostatically active). Numerous in vitro assays for immunological activity are available to those skilled in the art; an exemplary preferred in vitro assay for immunological activity is the HPBL assay described in Mann et al. (1983), supra. Preferred substances according to the invention as cytostatic agents are those exhibiting capacity for boosting either cellular or humoral immune response to established tumors, or both.

Of special interest for this effect are biomodulators which enhance the cellular immune system, in particular the immune response of natural killer (NK) cells, which are generally recognized as a primary line of defense against endogenous tumor-transformed cells, particularly solid tumor cells.

A convenient reliable in vivo test for establishing positive cellular immunological activity is set forth in Example 3, wherein it is demonstrated that biomodulators which have a potentially good stimulatory effect on the cellular immune system, also have a particularly effective cytostatic effect according to the invention against tumor-transformed cells, as shown by the regression of tumor in vivo in animals bearing implanted tumors.

In general, for any specific tumor type, any of the conventional protocols reasonably correlated with: antitumor effects against that tumor type can be used to demonstrate the nature of the activity of a biomodulator with respect to that tumor type.

Similarly, biomodulators can be used for prophylactic treatment, e.g., to increase surveillance of the body's cells to prevent the development of tumors; to treat not only existing disease but also to prevent metastasis; and as adjuvant therapy to alleviate the non-specific effects of other toxic therapies.

Activity for Immunological Effects

Especially preferred immunologically active biomodulators within the scope of the invention include biomodulators exhibiting good immunological enhancement of the humoral and cellular immune systems. As noted above, preferred biomodulators for antitumor applications comprise immunologically active substances capable of increasing in vivo production of immunoobulin fractions, especially IgG, containing antibodies specific to antigenic determinants borne by host tumor cells. Convenient in vitro and in vivo assays for establishing humoral and cellular immunoactivity are described above for antitumor effects, in the Examples and elsewhere herein. Preferred substances according to the invention are those which have activity as immunoenhancers irrespective of their cytostatic activities and exhibiting capacity for boosting either cellular or humoral immune response, or both, e.g., increasing production of in vivo of immunologically important molecules, e.g., IgGs specific to an antigen. The immunological activities of the biomodulators established by the same methods are also correlated with the treatment of immunological diseases and disorders mentioned herein.

Activity for Treatment of Senescence

Biomodulators are useful for testing conditions of cellular senescence at least in view of their indirect proliferative effects engendered by their ability to normalize abnormal differentiative properties. Biomodulators of the various categories especially useful for this method comprise those which have especially good cellular differentiative activity, or which have such activity in a particular dosage range. Particularly preferred biomodulators having such activity include those having the ability to delay terminal differentiation in IMR-90 cells, as described in B. above, and which are effective in therapeutic dosages according to the invention to increase lifespan in vivo. A broad range of conditions and disorders of senescence are susceptible to treatment according to this invention, e.g., decreased immunological competence, cellular death and damage, etc.; most particularly what is achieved is the extension of healthy lifespan.

Preferred biomodulators within the scope of those disclosed in the various categories having antisenescence activity within the scope of the present invention are conveniently selected by assaying antisenescence activity in vitro. In vitro assays for antisenescence activity are known to those skilled in the art; an exemplary suitable in vitro assay is described in Example 6.

Of special interest are compounds which increase the generation number of various cells, both in vitro and in vivo, such that the cells replicate more than the expected number of times as compared with untreated cells.

Activity for Modification of Coagulation and/or Growth Patterns of Endothelial Cells Especially preferred biomodulators of the various categories for this method are those which have anticoagulative and/or antiproliferative activity and/or which increase attachment (differentiation) of endothelial cells in vitro which are effective in therapeutic dosages according to the invention, to increase or decrease coagulation in vivo, or which have such activity in a particular dosage range. A broad range of conditions and disorders of vascular tissue are susceptible to treatment according to this invention, e.g., vascular disease, as well as production of viable transplantable vascular grafts, and maintenance of organs and tissues prior to transplantation. For production of viable transplantable vascular grafts, these cells may be induced to grow on a vascular graft matrix, e.g., microporous polyurethane foam, which supports the shape of the graft.

Activity for Increasing Expression of Biologically Significant Biomolecules

Compounds of the various categories useful for this method comprise those compounds which have differentiative activity, or which have differentiative activity in a particular dosage range. Particular compounds having such activity include compounds which stimulate production of biologically significant biomolecules in cells which can produce such biomolecules, e.g., HPBL cell production of specific IgGs in response to an antigen; HPBL cell production of IL-2. Compounds within the scope of those disclosed in the various categories having biomolecule expression stimulation activity within the scope of the present invention are conveniently selected by assaying for such activity in vitro. In vitro assays for biomolecule expression stimulation activity are known to those skilled in the art; an exemplary in vitro assay suitable for selecting compounds useful for this method is described in Example 12. Assays for in vivo stimulation of production of biologically significant biomolecules are also routine, and are analogous to those described for in vivo enhancement of expression of IgGs noted above.

Activity for Stimulating the Expression of Normal Tissue Architecture after Damage Compounds of the various categories useful for this method comprise those compounds which have differentiative activity, or which have such activity in a particular dosage range. Particular compounds having such activity include compounds having a stimulatory effect on cells which repair tissue damage, and which are effective in therapeutic dosages according to the invention to increase the repair of tissue damage in vivo. Suitable biomodulators having this activity can be determined by assaying for tissue repair in vivo, e.g., according to the methods outlined in Example 10. Thus suitable biomodulators will induce tissue repair such that normal tissue architecture, as determined, e.g., by NMR imaging and/or histology in experimental animals, is restored. A broad range of tissue damage is susceptible to treatment according to this invention, e.g., wounds (e.g., burns, cuts, etc.), surgical procedures, stroke, degenerative conditions, etc., and especially reconstruction of normal tissue architecture and function where tumor tissue is ablated by treatment, e.g., with biomodulators.

Of special interest are compounds which stimulate the repair of both terminally differentiated and non-terminally differentiated tissue.

Activity for Treatment of Autoimmune Disease

Biomodulators apparently affect the development of autoimmune disease in vivo. Autoimmune disease is the inability of the host to differentiate self from non-self. Therefore it is like the other models a regulation problem. The etiology of this diverse series of symptoms include; development of anti-self antibody (usually expressed as anti-DNA antibodies); thymic atrophy; IgG and IgM hyperproduction; and lymphoid hyperplasia.

Use

According to the present invention, cells which exhibit incompetent or abnormal differentiative or proliferative function or whose differentiative or proliferative function is sought to be modified are exposed either in vitro or in vivo to one or more biomodulators per this invention. For example, the biomodulator may improve cellular differentiative function, especially to rectify abnormal differentiative function or to diversify cellular differentiative function, or may improve cellular proliferative function, especially to rectify abnormal proliferative function. Within the scope of the present invention, "differentiative function" refers to substantially all differentiative functions of the normal mature cell, including bioproduction of cellular proteins, carbohydrates and fats such as cholesterol, hormones, sugars, immunomolecules such as globulins and antibodies; growth regulation functions which maintain or impose normal growth patterns and cell structure regulation functions which provide cellular structures characteristic of normal cellular differentiative function, such as cellular membrane composition, e.g., oligosaccharide structure or cytoplasmic composition. Thus, the present invention provides methods of normalizing or restoring regulation of cellular functions comprising virtually all functions characteristic of the individuated cell, i.e., those functions not peculiar to early progenitor cells having a purely proliferative capability, and further provides a method for increasing biologically adequate cellular differentiative functions by inducing expression of unexpressed cellular differentiative function, for example, to diversify expression of differentiative function, or to induce differentiative function in immature, substantially non-individuated cells, or in abnormally differentiated cells, e.g., transformed or aberrant cells.

Furthermore, the present invention provides methods of normalizing or restoring regulation of cellular functions comprising those aspects which maintain the proliferative capability of the cells which are characteristic of the progenitor cell lines, including the ability to proliferate beyond a relatively fixed number of cellular generations, to repair damage to terminally differentiated tissue types, to exist in culture indefinitely in a non-transformed state, etc.

While it would appear that the two functions of the biomodulators are inconsistent with each other, in fact effects of the biomodulators of this invention are balanced in their effects by a mechanism which is not yet understood. Thus, the enhancement of the proliferative function effected by the biomodulators, while preventing or delaying cellular senescence characterized by failure of the reproductive function of the cell, does not result in uncontrolled cellular reproduction characteristic of malignancy. Similarly, the enhancement of the differentiative function effected by the biomodulators does not cause premature cellular senescence, nor induce unwanted differentiation, e.g., terminal differentiation, of all progenitor cells in vivo, which would leave the body unable to produce new cell types from such progenitor cells, e.g., for repair of injury and replacement of damaged cells.

A unique aspect of the biomodulators is in restoring cellular biochemical balance to cells exhibiting abnormal differentiative or proliferative function owing to known or unknown factors, such as toxic substances introduced into the organism from the environment; biochemical imbalance of the organism caused by metabolic disturbances, diseases or disorders; or injury to the cell, organ or organism. The biomodulators are also useful in the rectification of cellular function heretofore regarded as "normal", such as arresting senescence of cells both in vivo and in vitro, and diversification of cellular function with respect to existing cellular function within acceptable ranges of normal cellular function.

The differentiative activity of the biomodulators of the present invention according functions to stimulate phenotypic cellular expression, including rectification of abnormal cell production, reassertion of normal cellular function, correction of cellular incompetence, restoration of normal growth patterns, modulation of aberrant cellular structures, and, further, diversification and/or expansion of existing cellular function within the genetic capabilities of the cell.

The proliferative aspect of this differentiative activity of the biomodulators of the present invention according functions to integrate appropriate proliferative response in the overall growth control/differentiation of the non-aberrant phenotype. Thus, this aspect of biomodulator activity is involved in preventing premature expression of senescence or terminal differentiation, tissue repair, regeneration, normal growth control, e.g., in endothelial cells.

The term "abnormal" as used herein to modify differentiative and proliferative function refers to cellular differentiative and proliferative functions as described above which are outside of accepted or acceptable ranges; thus, "abnormal differentiative function" refers to cellular differentiative function manifested in cellular morphology and/or activity above or below accepted standards, and which in vivo tend to result in malfunction of the organism resulting in distress, debilitation, and or death of the organism.

Exposure of cells to the biomodulators according to the present invention invokes cellular mechanisms which promote normal differentiative and/or proliferative function or which expand or diversify such function. In applications wherein the biomodulators are employed to improve abnormal differentiative or proliferative function, at least a 10% improvement in such function is contemplated, i.e., at least a 10%, preferably at least a 20%, improvement in the parameter of interest with reference to the conventional measurement of such parameter, is contemplated.

Of course, this invention also includes all larger desirable improvements, e.g., at least 30, 50, 75, 100, 150%, etc., and higher, as well as all lower improvements which correlate with effects considered to be significant for a given application.

For example, if bioproduction of a cell is abnormally low or high, at least a 10% increase or decrease by mass, respectively, of the product of interest over a comparable time period is contemplated. Thus, if a given leukocyte biomass typically produces 10 $\mu$g of IgG over a one-hour period under normal in vitro conditions, the same biomass will produce at least 11 $\mu$g IgG over the same time period under the same cultural conditions on exposure to the biomodulators of the invention. Similarly, the growth rate of a biomass of malignant cells exhibiting an abnormal growth rate is typically decreased by at least about 10% on exposure to the biomodulators of the invention. Analogously, in vivo, rectification of abnormal cellular differentiative function of at least about 10% is established by comparing cell or organ function before and after exposure to the biomodulators of the invention according to standard measuring techniques, such as, e.g., blood determinations for the product of interest, NMR or CAT scans for evaluation of cellular activity, weight assessments for determination of cell growth, and a variety of other biotechnical diagnostic procedures.

For use of biomodulators according to the invention to diversify or expand cellular differentiative function, a similar, approximately at least 10%, preferably about at least 20%, increase in cellular differentiative function, based on conventional measurements of the parameter of interest is contemplated. For example, exposure of murine splenocytes according to the invention to the biomodulators under conditions enhancing differentiative function stimulates the production of antibodies, with at least a 10% increase in antibody diversity with respect to affinity, avidity, and/or specificity of the antibody pool produced. With respect to modification of cell structure, at least about a 10% change in cell structure, particularly cell component biochemical characteristics, chemical characteristics or stereochemical arrangement of cell components is contemplated. For example, a change in the oligosaccharide content of cell-surface membranes, as measured, for example, by lectin binding, of at least about 10%, preferably at least about 20%, is contemplated. As hereinbefore described, oligosaccharide cell-surface membrane characteristics have been correlated with cellular growth patterns, and a modulation of abnormal cell membrane oligosaccharide content with the biomodulators of the invention to provide at least about 10% reduction in abnormally high reproduction rates, as observed in malignant cells, for example, or at least about a 10% increase in abnormally low cell reproduction rates, as observed in senescent cells, for example, is within the scope of the invention. In this instance, for example, improvements in cell differentiative function are measurable in vitro by either a change in the rate of lectin binding, reflecting a change in oligosaccharide cell-surface membrane characteristics, or by a direct measurement of cell reproduction activity, typically determined by change in generation time ($T_g$) as described, e.g., in the Examples.

Application of Biomodulators

Suitable dosages of the biomodulators described herein according to the present invention can be routinely determined for a given use using conventional protocols indicated herein or otherwise known. Dosages in excess of the therapeutic dosage range are typically ineffective to increase the desired response and may, for example, cause adverse effects, e.g., stimulate tumor growth, while dosages below the range are substantially ineffective, for example, in inhibiting tumor burden. The biomodulators of the invention are generally effective for all uses of this invention in dosage units in mammals of from about 1 ng/kg to about 100 µg/kg. Dosages vary with the type of biomodulator used, and for a given application vary more with the amount of aberrant tissue than with the size of the animal. Suitable times of administration for the biomodulation can be routinely determined, and can be, e.g., 1–3 times/day to once a week. The course of treatment will vary with the condition to be treated, and will generally continue until the desired effect is achieved. These data are merely exemplary and not intended to be limiting in any fashion. Precise dosages for a given patient and circumstances will be determined routinely as for any other medical application.

The biomodulators have no observed toxic side effects at therapeutic dosage levels. Any conventional route of administration can be employed, such as parenteral or enteral routes, e.g., i.v., i.p., subcutaneous or oral administration, employing conventional pharmaceutically acceptable carriers such as physiological saline, and optional adjuvants. For example, for treatment of tumors in humans, i.v. injection of the biomodulators at the therapeutic dosage levels as anti-tumor agents on a regimen of at least alternate days until tumor response is noted, preferably by non-invasive diagnostic techniques such as nuclear magnetic resonance imaging, is recommended. Initial tumor response (such as tumor deformity or the presence of tumor-associated edema) may be observable as early as about two weeks from the start of the therapeutic regimen. After substantial tumor response has been achieved, dosage frequency may be decreased to, for example, a weekly basis.

Optimization of the treatment protocols for each of the mentioned indications, for each of the biomodulators and for each patient is routinely determined by one of ordinary skill in the art, and depends upon a variety of factors, including age, sex, the disease or disorder being treated and the severity thereof, as well as the activity of the specific biomodulator at a given concentration and for a given indication.

In an exemplary procedure, administration of a therapeutic dosage of a cytostatic compound is begun on a human tumor host on Monday of week 1. 100 ng/kg is administered i.v. or i.p. Monday, Wednesday and Friday of week 1; this procedure is repeated on continuous weeks 2, 3, 4 and following weeks with NMR monitoring on a weekly basis until the desired reduction in tumor burden is achieved. While the regimen may be continued thereafter, experimental evidence indicates that tumor rebound after treatment is not significantly incident to the therapeutic process of the invention.

For in vitro application, the amounts of biomodulator which are effective are also routinely determinable by one of ordinary skill in the art, depending upon the type of cells being used, the degree of differentiation required, the type of biomodulator employed, etc. For example, suitable dosages can routinely be determined within the aforedescribed range of 100 pM, 1 µM.

It is further noted that a unique feature of the biomodulator effect is that, in general, the optimal dosage as determined by any of the in vitro models are generally predictive for applicable in vivo dosages. Thus, for example, a dosage of 10 µg of a biomodulator which is optimal in tissue culture is also optimal in in vivo applications.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above and below, if any, are hereby incorporated by reference.

EXAMPLES

Example 1

Isolation and Purification of CAD

CAD was purified according to a slight modification of the method of Rice (Proc. Soc. Exp. Biol. Med. 123, 189

(1966). *Penicillium restrictum* (PITT PR 1471-3/73) was grown as a surface culture on a Czapek-Dox medium (pH 4.5 to 5.2) for 4 to 6 weeks. Two liters of the culture medium were harvested by filtration through fluted filter papers and the filtrate extracted with diethyl ether for 6 to 8 hours. The extracted culture medium was then poured through 50 g of Amberlite 120 (H) contained in a fluted filter. The filtrate (pH 2.5 to 3.1) was immediately filtered through a column of Amberlite 45A (OH) (600 g in a column 5×54 cm). When the culture medium reached the top of the column, distilled water was added and the column was washed free of adsorbed ucose with additional distilled water (at least 14 L). The biologically active material was then eluted from the column by adding at the top of the column 30 ml of concentrated ammonia diluted to 250 ml with distilled water. Additional distilled water was added as the level approached the top of the resin column. After approximately 500 ml was passed through the column, the eluate was slightly alkaline to test paper and 1200 ml was collected. The 1200 ml was evaporated to 40–50 ml on a rotary evaporator under reduced pressure at 50–50° C. (bath temp.), then freeze dried.

CAD was further purified via HPLC techniques. 100 μg of CAD, partially purified as described above, was applied to a $C_{18}$—HPLC column in a water-methanol gradient, which was 100% water at T0 and 100% methanol at T100. The major peak observed at 210 nm eluted from the column at 93.7 minutes. This result was unexpected and originally thought to represent the elution of phthalates or other potential contaminates from the column. The failure to observe peaks via simultaneous observation at 254 nm suggests that the peaks are not due to phthalates. Pooled samples of the peak collected at 93.7 minutes were evaluated in our biomodulator assay following total removal of solvent under vacuum. The pooled peak gave high biomodulator activity. A sample of CAD was dissolved in water and treated with $NaBH_4$ to reduce carbonyl containing CAD components. No change in the retention time of the 93.7 minute peak was observed suggesting that the compound does not contain either an aldehyde or ketone group.

Example 2

In vitro Immunological Activity of Biomodulator

A. Purification of PWM and separation of the differentiative and proliferative functions Pokeweed Mitogen (PWM) and three of its iso-mitogens, Pa-1 and Pa-5, which are primarily differentiative in nature, and Pa-2 which is primarily proliferative, were prepared according to the method of Waxdal, supra, except that the iso-mitogens were finally purified by isoelectric focusing. The differentiative activity of these natural products was measured by their ability to elicit immunoobulin synthesis and secretion in vitro in the HPBL plaque forming test (biomodulator assay C., above). Their proliferative activity was measured by the incorporation of $^3$H-thymidine into newly synthesized DNA. It is clear that Pa-2 has a minimal effect on differentiation and a large proliferative component, while Pa-1 and Pa-5 have maximal differentiative potential. These data are summarized in FIG. 1 and which shows the incorporation of $^3$H-thymidine and immunoobulin plaque forming colonies per culture in response to various concentration of (1a) crude PWM, (1b) the purified Pa-1 subfraction, (1c) the purified Pa-2 subfraction, and (1d) the purified Pa-5 subfraction.

B. Stimulation of specific antibody production by addition of antigen

FIG. 7 shows data from a series of experiments designed to gain a further understanding of the differentiation response itself. The crude PWM at 2.5 μg produced a very strong differentiation response in these HPBL's with only a moderate proliferative response. This response could be converted from non-specific (Ig-PFC) antibody production to specific (IgG/IgM PFC) simply by adding antigen to the stimulated culture. Thus, this assay system measures not only differentiation but also the control of specificity. A dose of 2.5 μg of Pa-2, the strong proliferator, while not at a concentration sufficient to induce the proliferation response, is still capable of inhibiting the differentiative response of the crude PWM. This shows the sensitivity of the differentiation response.

C. Differentiative and proliferative activities of CAD

CAD from *P. restrictum* was tested for proliferative and differentiative activity, as shown in FIG. 3. CAD had only minute proliferative capacity at any concentration tested. On the other hand it had moderate differentiative capacity and probably more importantly, below 0.01 μg a large portion of the response was convertible into an antigen-specific differentiative response. Thus it is clear that it is possible to separate the two functionalities completely.

The differentiation and proliferation capacity of the CAD was screened at different stages of the purification procedure. The crude material had both activities present, differentiation as assayed for by the PFC assay and the incorporation of $^3$H-thymidine into newly synthesized DNA for the proliferative response. By the end of the ion exchange step the activity is primarily differentiative. These data indicated a peak activity at 500 picogram/ml. This is similar to the concentrations which show optimal activity in the tumor regression studies.

Experiments designed to investigate the inter-relationship between the present primitive biomodulators, and an example of the more specific biological response modifiers, in this case Interleukin 2 (IL-2), a known cellular differentiator and proliferator, were performed. In this series of experiments with HPBL's the cultures were established and treated with various concentrations of PWM (this particular preparation, although crude, is relatively free of proliferative capacity), and then after 24 hours of culture SRBC specific antigen was added. FIGS. 4a–b shows the results from the IgG anti-SRBC specific response (the PFC assay). In this experiment there was a maximum PFC response after 67 hours of culture. There is a clear time and PWM dose-dependency as has been noted above. When supernatants from these cultures were tested for IL-2 production with the Collaborative Research EIA assay kit the following results were noteworthy: the dose kinetics were similar to those seen with the plaque assay in that 1 μg PWM produced optimal IL-2 expression (approximately 6–9 U). However, the time kinetics indicated that maximum IL-2 expression was at 115 hours of culture, when the functional cell phenotype had already returned to baseline levels. This may suggest 1) temporal displacement and dissociation of the two phenomena; 2) the differentiation response is inhibited by the high IL-2 production; or 3) there are complex series of effector functions involved in the secretion (IL-2) and membrane regulation of the product (IL-2R) and the simple assay of IL-2 levels is insufficient to establish the full functional picture.

Some general comments can be made at this stage. There is a temporal relationship between the biomodulator-induced antibody effector function and the IL-2 secretion. Addition of specific antigen to the biomodulator-induced non-specific response actually reduces the IL-2 secretion by approximately 30% (data not shown) and shifts the optimal reactivity to longer incubation times at lower biomodulator concentrations. Bowlin et al. Can. Res. 49, 4109 (1989) first showed that Sw treatment augmented lymphoid IL-2R expression and IL-2 induced proliferation following mitogenic stimulation and further work showed that Sw treatment also augmented the LAK induction at normally suboptimal stimulation doses (Sw is a potentiator).

FIGS. 5a–b shows the effect of the biomodulator treatment of the target cells (5a) and treatment of effector cells (5b) in a chromium release CMI assay. In this case CG targets were treated with 10 ng of CAD for 10 days prior to their use as targets in the cytotoxicity assay. The treatment had minimal effects on the generation time at this stage of the treatment regimen but had a documented effect on the cell surface display, causing an "up" regulation. The effector cells in this case were HPBL's. There is a four fold increase in the cytotoxic capacity of these HPBL's for the biomodulator treated targets versus their untreated controls. FIG. 5b shows that treatment of the effector cells has a similar effect on the overall effectiveness of the cytotoxic event. In this case the effector cells were treated for 72 hours in vitro with 10 ng of CAD prior to testing. Both fresh and control cultured HPBL's were tested at the time of the assay. As in the other examples shown above the biomodulator effect was concentration-dependent. The CAD at both high (10 μg) and low (1 pg) was not as effective as the 10 ng optimal dose in inducing this response. In other experiments (data not shown) the biomodulator effect was also tested against so-called Natural Killer activity, using the K-562 system. In these cases the biomodulator treatment induced lymphoid cell surface changes which correlated with more effective specific and non-specific target lysis and in some cases a marked improvement in effector/target conjugation. These experiments plus the recent IL-2 data present an interesting potential for the investigation of IL-2 secretion, receptor regulation and the inter-relationship of these with the biomodulator effect. IL-2R regulation and its functional regulation appear to have significant ramifications for our studies. The sub-hypothesis relevant to these data holds that IL2 is a highly specific biological response modifier and requires very close monitoring in vivo for its appropriate function. It is this purported regulation of production and use that is lacking when simple injections of the material are made in vivo. The biomodulators regulate the production of the IL-2 and the expression and regulation of the IL-2R thereby providing the necessary connectivity between primitive differentiation control and specific production effector functions.

FIG. 6 shows data from still another cellular immunity model system, the P-815 C57BL/6J Cytotoxic T Lympholysis (CTL) assay. In this case the P-815 is injected into the H-2 incompatible host and in the Brunner and Cerotini model an antigen specific lympholysis event occurs with an optimum on day 11 at an effector/target ratio of 100:1 with 30% lysis. If the spleens of the injected animals are removed on day three there is no observable cytotoxicity; however, if the spleen cells are treated with biomodulator (in this case PWM at 100 ng) there is an enormous increase in the cytotoxicity event. FIG. 6 shows a lysis of approximately 80% at effector/target ratios of 40:1. Our model involves at least seven point cytotoxicity curves and for comparison purposes we calculate the slope, intercept and correlation coefficients, and then use that data for further analyses. The slope represents a measure of the efficiency of kill and in the biomodulator treated cells is approximately 1.6 versus 0.24 for the control antigen driven response on day 11. This represents a seven fold increase in simple cytotoxicity efficiency. Again this is concentration dependent and the kinetics of the response are such that if the cells are left in culture for times which approximate the in vivo 11 day optimum then the lysis values approach the untreated controls. The earlier high lysis reactions are not as tightly controlled in terms of specificity (data not shown) in that increases in lysis are noted in the YAC and EL-4 target controls. These data also suggest an IL-2 induced LAK response as discussed above. This measure of target specificity returns to control values as the length of time in culture approximates the 11 day control.

These data demonstrate the ability of the biomodulator to increase both humoral and cellular immune response in several well known models. The question of target specificity in particular and the general question of regulated modulation of the immune responsiveness are still open. However, some of the data on the CTL/NK models suggests that the biomodulator has the ability to "lift" the restrains placed on the response by in vivo antigen administration (perhaps through graded secretion of IL-2 or modulation of IL-2R), and that these restraints are involved with specificity control.

Example 3

In vivo Immunological Activity of Biomodulators

A. CAD restores T-cell activity in nude and neonatally thymectomized mice 10 ng CAD was injected into nude and neonatally thymectomized mice three times per week for 7 weeks before sacrifice. Neonatally thymectomized and congenitally athymic animals were compared in terms of their T-cell response to a panel of mitogens and to T-helper pressure. The neonatally thymectomized and nude animals did not response to T-cell mitogens or T-helper pressure, but appeared to have normal B-cell responses. The CAD injections restored the T-cell mitogenic and helper functions with the neonatally thymectomized animals and partially restored (approx. 40% of control) the activity with the pleiotropic nude defect. This data suggests that the biomodulators are active in vivo in dosages predicted by the in vitro screening assays.

B. CAD causes induction of specific antigen response in vivo

FIG. 7 shows the effect of in vivo administration of biomodulators (in this case CAD) on the mouse's capacity to response to a standard poly-antigenic-system such as Sheep Red Blood Cells (SRBC) as measured by the plaque assay (PFC's per million effector cells). The Balbc/J mouse was given injections of 10 ng CAD three times per week for 3 weeks, on the Friday of the last week one injection of SRBC antigen was administered and the animal was sacrificed on the next Tuesday, five days after antigen. The data show a large increase in IgG specific PFC production in the biomodulator treated animal. Again these responses are biomodulator concentration dependent and the optimal doses were well approximated by the in vitro studies shown above. If a secondary antigen injection is given and the biomodulator treatment continued the total number of specific PFC's is decreased but the apparent affinity of the antibody product is increased. Similar data were observed with both particulate and soluble antigen systems, and with the TNP-hapten model.

C. PWM induces specific antibody production in response to T-independent antigen in vivo FIG. 8 shows data from a series of experiments designed to test the ability of the biomodulator to modify the in vivo response to a T-independent antigen (TNP-Ficoll), using the plaque assay. In this case both IgM and IgG hapten specific responses were recorded as well as non-antigen specific plaque responses (Ig-PFC) using a Protein A coated red blood cell target. PWM induced a highly significant increase in all classes of PFC over simple antigen driven controls. The proportion of Ig to specific IgG was approximately 2.5:1 which suggests an amazing level of specificity control for this reaction. Dextran, a purported poly B-cell activator had some stimulatory effect but was clearly different from the biomodulator effect.

D. Biomodulators and Cell Mediated Lympholysis: Cellular Immunity

Brunner and Cerotini (Immunol. 14, 181 (1968)) developed the concept of cell mediated lympholysis (CML) in which H-2 incompatible mastocytoma cells elicit a T-cell response specific to the original tumor cell approximately 11 days after injection. Numerically, this response results in a 30–50% kill of tumor cells when effector cells (spleen) are mixed with chromium labelled tumor at ratios of 50:1 to 100:1. Control mechanisms for this response are very important as they would provide insights into the biological sense of self and also provide opportunities for manipulation. Fitch et al. (J. Immunol. 116:761 (1976)) and Nordin and Hirano (J. Immunol. 116:1115 (1976)) showed that MLR-dependent suppression of the responses arose on day 2. This suppression is presumably related to the biological need to maintain absolute control over specificity. The suppression was proliferation dependent. Natural Killer (NK) activity is a distinct type of cellular immunity which does not require prior antigen exposure and is apparently targeted at aberrant cell behavior.

P 815 mastocytoma cells are grown in culture or as an ascites (DBA H-2/d) and injected into C57BL/6J mice (H-2/b). A typical cytotoxicity curve results (FIG. 1). The specificity of the response is assessed by testing the cytotoxicity against EL-4 cells (Balbc/J H-2/k) which are NK insensitive and histoincompatible with the original target. The NK system is studied in the same way but using YAC cells as the targets as they are NK sensitive.

FIG. 9 shows data from a typical experiment. Seven effector/target ratios are tested and the percent lysis calculated. The open trianes represent D 11 data, closed circles D 9 and open circles D 3 through 7 data. For ease of discussion, these data will be converted into regression data. By performing a simple linear regression on the data shown in FIG. 1, we can determine the efficiency of kill by comparing the slope of the regressions. The linear regression of the data for day 9 in FIG. 1 is: y=0.26x+1.59 with a correlation coefficient of 0.99. The regression for day 11 is y=0.24x+10.5 with a coefficient of 0.95.

FIG. 10 shows data from experiments where the mice were sacrificed on day 3, 5 and 9 (first number on figure) and their spleen cells placed into culture with 1 µg of PWM. The culture was continued for another 2 days (the second number on the figure). FIG. 2 shows that the addition of a biomodulator increases the efficiency of kill by 8–10 fold and decreases the time required to express the CML from 11 days to 5 days (compare D 3+2 at slope of 1.6 with D 11 with a slope of 0.24).

FIG. 11a shows that, when the time in culture is extended, the optimal response is obtained after 48 hours in culture when the animal is sacrificed 3 days after induction. The subsequent curves can be shown to nest around these values and gradually decrease to the day 11 in vivo values. A number of biomodulators have been shown to induce this "early" intense response. Either semi-allogeneic (B6D2F1) (FIG. 11b) or allogeneic (Balbc/J) cells (FIG. 11c) mixed with the C57BL spleen cells induces the same degree of increased CML, indicating that biomodulator and truly biological signals are effective. Hydrocortisone treatment of the mouse (2 mg given day -2) reduced the biomodulator effect. Hydrocortisone has been shown to inactivate the suppressor T-cell subpopulation, thus it appears that the biomodulator is affecting the same T-cell population. Hydroxyurea is a non-specific inhibitor of DNA synthesis, and when used at 10-5 M it does not inhibit the biomodulator effect on CML, thus suggesting that the biomodulator effect is non-proliferative.

E. Biomodulators and Humoral Immunity

The humoral immunity involves the assessment of specific and non-specific antibody production at the sine cell level using the plaque assay system. T-dependent and T-independent antigens are tested to provide additional information. Sheep red blood cells (SRBC) are used as the T-dependent antigen and Tri-nitrophenyl (TNP) hapten conjugated to SRBC is the T-independent antigen.

FIG. 12a shows data from a series of experiments designed to determine the level of specific antibody production, and its class as a function of antigen administration. The left hand of this histogram represents the typical "antigen-driven" access route to humoral immunity, and represents the traditional definition of immune competence. When a poly-antigenic antigen such as the T-dependent SRBC system is used, a clear distinction between primary and secondary responses can be seen. In this case, the primary response to antigen leads to 326 IgM producing cells per million cells in the spleen and no IgG producers. After a secondary exposure to the antigen, a percentage of the response can be seen to be IgG in class specificity. In this case, the antigen is expected to be differentiator and antigen. The right-hand panel of this histogram shows that when the biomodulator-PWM is injected i.p. into the animal in the absence of antigen, it supplies the differentiator signal and that, if a sine injection of antigen is then given, the result is a much more intense response as well as a high level of IgG production.

FIG. 12b shows similar data for CAD. In this case, an optimal dose is in the 1–10 ng range. This correlates very well with the in vitro data. Our hypothesis predicts that the in vitro models can be used to predict and optimize the dosage schedules for in vivo application.

FIG. 12c shows that the biomodulator effect is less apparent after a secondary injection of the antigen presumably because of the competition between the signals. In this case, the left hand of the panel shows the effect of the antigen driven secondary response where a small but significant IgG response is observed. The biomodulator apparently produces a lower response when compared to the primary in FIG. 2. However, the affinity of the product was significantly increased over simple antigen-driven models, and the secondary response with the biomodulator produced a very large increase in affinity, suggesting that the biomodulator is still regulatory in the secondary response.

The data in FIG. 12 also show that the in vivo use of the biomodulator is dose-dependent. FIG. 13a shows the dose dependent effect of PWM on the humoral response. (This graph is somewhat misleading in that it indicates that 0.1 µg is optimal. However, if the affinity of the product is the assay parameter, then the 1.0 µg is a: better dose.) FIG. 13b shows the dose response of CAD. In this case, 1 ng appears to produce the highest amount and affinity product.

FIG. 14 shows some experimental results in which a highly specific antigenic system was used instead of the poly-antigenic SRBC antigen. The TNP-Ficoll antigen is also considered to be T-independent, in that it does not require T-cell help to mount a humoral response. The TNP-Ficoll antigen is administered as the SRBC antigen was above, by i.p. injection and the response assessed by conjugating the TNP hapten directly to the SRBC target, thus obviating any potential "carrier" effect. The biomodulator amplifies this response as was seen with the T-dependent response to SRBC antigen. The left-hand panel of this Figure shows the response to the T-cell independent antigen TNP-Ficoll by itself. In this case, a third experimental parameter has been added to the study, the production of non-specific immunoobulin (Ig-PFC). This parameter provides information on the general status of the humoral response regardless of antigen specificity. The TNP-Ficoll antigen does elicit a modest Ig-PFC response but little if any IgG specific response. The middle panel shows the data for the biomodulator induced response. In this case there is a very large specific and non-specific augmentation. The right-hand panel shows the effect of Dextran, a Poly-B-Cell Activator (PBA). In this case, there was a marked cellular proliferation but little differentiative response.

Example 4

Biomodulator Effects on Aberrantly Growth-Related Cell Population

A. The effect of biomodulation on the Tg of growth transformed cells

Canine glioma (CG) cells are used as a comparison counterpart for the studies on control mechanisms for normal cell growth patterns. They are approximately the same size as IMR-90s, have similar substrate adhesion characteristics and require similar treatments (in terms of trypsin concentrations, and exposure times) during sub-culturing. Under untreated control culture conditions these cells have a Tg of approximately 15 hours, as compared to approximately 30 hours for the IMR-90 cell line. FIG. 15 shows the effect of CAD and PWM on the Tg of this cell line. After 72 hours of treatment the CAD has apparently increased the Tg to approximately 27 hours and the PWM treatment shows an increase to 19 hours. There is no evidence of overt toxicity. The PWM shows no toxicity until concentrations of >100 $\mu$g are used. The CAD has never shown signs of cellular cytotoxicity even at doses of 100,000 times the optimal dose (1 to 10 ng). After three cycles of biomodulator treatment (approximately 200 hours of continuous exposure) both CAD and PWM show significant increases (P>0.01) in Tg as compared to the untreated controls.

B. The effect of treatment withdrawal on the Tg of the CG cells in culture

Data (not shown) indicated that after 10 cycles of treatment with either CAD or PWM the Tg of the CGs stabilizes at approximately 25 to 30 hours and remains at that level for at least 20 passages cultured without further addition of the biomodulators. FIG. 5 shows the effect of treatment withdrawal after only 3 to 5 cycles of treatment, when the effect is still transitory. As can be observed by the data in FIG. 16 after treatment withdrawal the Tg of the cells increases with culture time. The slope of this response curve is shallower than the increase in Tg seen after treatment (FIG. 15) indicating either residual biomodulator present after withdrawal or an influence on the plasticity of the cells. This plasticity may be self-regulatory after initiation with the biomodulators. The fact that a resistance to Tg reversion develops with the length of treatment suggests that the biomodulator may have a pleiotropic effect on the cell phenotype. Subjectively, the biomodulator effect appears to be non-cell-lineage specific, affecting both fibroblasts and glioma cells in a similar dose-dependent manner. In the case of the normal fibroblast the treatment must be given before the phenotypic alteration occurs (PDL 35–38) and in the case of the existing aberrant phenotype of the CGs the addition of the biomodulator reverses or partially reverses the aberrant phenotype. This suggests that the phenotypic change in the neoplastic cell population is an unstable condition whereas the senescent transformation, once initiated is stable and therefore difficult to reverse.

TABLE 1

THE EFFECT OF TREATMENT TIME ON GENERATION TIME CANINE GLIOMA CELLS

| Biomodulator | # Treatment Cycles | Tg* |
|---|---|---|
| Control | — | 15.3 |
| CAD | 4 | 15.9 |
|  | 10 | 24.6 |
| PWM | 4 | 15.8 |
|  | 10 | 23.7 |

*The generation time [Tg] of canine glioma cells after various numbers of treatment cycles with biomodulators: final Tg taken after 10 cycles after last treatment cycle.

Table 1 summarizes these data. CAD treatment for four cycles results in a small increase in Tg. After 10 cycles the Tg alterations become stable and are significantly different from the control values. These Tgs remain stable for as many as 20 passages after withdrawal of the biomodulator. Similar results were found with PWM. Table 1 shows that regardless of the treatment regimen or the biomodulator the Tg increases tend to stabilize at 24 to 25 hours which represents a 40% increase the generation time of these cells. This is in the absence of any overt toxicity and therefore it is assumed to be the result of an inherent control mechanism(s) which has been re-established or reactivated by the biomodulator treatment.

C. Biomodulator effect on the cell surface oligosaccharide display of the CGs

The top panel of FIG. 17 shows the Scatchard analysis of competition data of alpha-methyl-mannopyranoside for the CON-A/MANNOSE specificity. There is a sine binding affinity class of approximately 1700 L/M and a binding capacity of $1\times10^{-3}$ M. This can be contrasted with the CON-A/MANNOSE specificity on the IMR-90 surface which has a high and low affinity configuration. Taken together these affinity differences account for almost 10 kcal of additional binding energy retrievable from interactions in the case of the IMR-90s which is unavailable to the CGs. It should be noted that the binding capacity in both cases is almost identical suggesting that the differences are arrangement-dependent in nature. The bottom panel of FIG. 17 shows a visual representation of the Scatchard analysis of the CGs after treatment with PWM for 7 cycles or approximately 500 hours of continuous treatment. This treatment regimen results in an increase in the Tg of the cells as well as changes in the proton linewidth of unfrozen water (shown below). Under these conditions the CON-A/MANNOSE specificity bifurcates into two affinity classes, this in turn results in an increase in the GFE retrievable by this specificity. This display more closely resembles that of the growth regulated IMR-90s. It should be noted that the actual lines on these figures are visual estimates however, the data in the boxes are calculated values. It is these values that are used to estimate the GFE for comparison purposes.

D. Galactose specificity on CGs

FIG. 18 shows similar data for galactose specificity on CGs. The untreated control cells show a Scatchard analysis indicative of a sine binding class of affinity 7582 and a binding capacity of $3 \times 10^{-4}$ M. After PWM treatment the affinity increases by 300% whereas the binding capacity again remains constant. The final major cell surface specificity for CGs is N-acetyl-glucosamine. The treatment regimens used have no effect on the affinity or binding capacity of this specificity.

TABLE 2

THE EFFECT OF BIOMODULATOR ON THE CELL SURFACE DISPLAY OF CANINE GLIOMA CELLS

| Treatment | # of Cycles | Gibb's Free Energy |
| --- | --- | --- |
| Control | — | 14.9 kcal |
| Swainsonine | 2 | 15.2 kcal |
|  | 4 | 20.5 kcal |
|  | 7 | 21.9 kcal |
| Pokeweed Mitogen | 2 | 15.8 kcal |
|  | 4 | 14.4 kcal |
|  | 7 | 23.7 kcal |

The GFE values were calculated for the con-a/mannose, RCA/galactose, and WGA/N-acetyl-glucosamine specificities.

Table 2 summarizes the biomodulator treatment data for the CGs. As has been observed above, the PWM requires longer periods of exposure to stabilize the effect. The Swainsonine (Sw) treated cells show an increase in their GFE by 4 cycles of treatment (approximately 300 hours of exposure) whereas the PWM requires 500 hours. In the case of the growth transformed cells the biomodulator reverses an unregulated state whereas in the case of the senescence of normally growth regulated cells the treatment prevents the down-regulation of the same oligosaccharide display.

E. Phenotypic result of the treatment of growth transformed cells with biomodulator: chromium release cytotoxicity assay FIG. 19 shows the results from a series of experiments designed to test treated and untreated CGs as non-specific targets in a chromium release cytotoxicity assay. In these experiments labelled target cells (CGs) are mixed with various numbers of effector cells (HPBLs) and the amount of chromium released into the supernatant is related to the number of targets lysed by the effectors. In turn, this function has been shown to be the summation of a complex series of reactions, including; recognition, conjugation of effector and target, and the lysis process itself. The percentage lysis for treated and untreated targets was assessed at eight different effector/target ratios. The slope of the linear regression of this data provides an assessment of the efficiency of recognition/conjugation/lysis. The slope of the treated cell response is approximately five fold higher than that of the untreated control. The linear correlation coefficient for the treated data is well below the 0.95 expected value. This is probably due to the "plateau" of lysis between 40:1 and 20:1 ratios. In other experiments it was found that data expressed from effector/target ratios of 100:1 to 1:1 cluster broadly into two groups which are best analyzed separately. At an effector/target ratio of approximately 20:1 the treated cells produce a 35% target cell lysis whereas the control cells produce a lysis of 4%. Thus, the treatment of the CGs results in increases in Tg, "up-regulation" of the cell surface oligosaccharide display, and an enhanced ability of these cells to participate in cell mediated lympholysis.

F. Other physical changes on the cell surface: NMR linewidth measurements

FIG. 20 shows the effect of CG passage level on the proton NMR linewidth measurements of the "bound" fraction of water at the cellular surface. These measurements correlate with the status of the cell surface oligosaccharide display. When the GFE decreases, as in cellular senescence, the linewidth measurements decrease, indicating an increased frequency of motion of unfrozen water on the surface. In turn this increased frequency of motion is interpreted as suggesting a less well organized surface. Additional data which supports this phenomenological connection between linewidth changes and the functional surface organization include; t-butanol extraction results in uniform decreases in the linewidth; biomodulator treatment of PDL-35 IMR-90s prevents the linewidth changes observed with the senescent populations; and the correlation between the cell surface organization changes and the linewidth data. FIG. 9 shows data from CGs assessed at passage 34, 50, and 112. There is no significant passage-dependent relationship of the linewidth measurement; however, by passage 112 the linewidths are increasing, the oligosaccharide displays are becoming unstable and the growth pattern of the cells as well as the ability of the CGs to act as targets in cytotoxicity are also becoming less stable. The cells used for all these experiments are between passage 30 and passage 75.

FIG. 21 shows data from a series of experiments designed to test the effect of biomodulator on the linewidth parameter of CGs. In these cases treatment with Sw, CAD and PWM all resulted in significant (P>0.01) decreases in linewidth as compared with the control values. These results were obtained after one treatment, and suggest that the physical changes precede both the oligosaccharide changes and the subsequent phenotypic changes. These results are in contrast to the IMR-90 data where the down-regulated senescent population showed decreases in the water proton linewidth. This is another example of the potential functional/physical/phenotypic changes between growth regulated/down-regulated and unregulated cells. In the growth transformed population we use the term unregulated to distinguish the models. In this case the linewidth for the CG controls are much higher than the IMR-90 values and the re-regulation results in a lowering of these values, approaching the data for the IMR-90s.

TABLE 3

THE EFFECT OF BIOMODULATOR ON T-2* LINEWIDTH

| Temperature [k] | One Week of Treatment | | Four Week of Treatment | |
| --- | --- | --- | --- | --- |
|  | PWM | SW | PWM | BW |
| 213 | 600 | 580 | 410 ± 10 | 480 ± 35 |
| 223 | 400 | 325 | 350 ± 22 | 330 ± 40 |
| 233 | 350 | 285 | 300 ± 10 | 300 ± 8 |
| 243 | 275 | 265 | 225 ± 15 | 230 ± 10 |

T-2*performed after 1 week of treatment of canine glioma cells with biomodulator and after 4 weeks of treatment: the 4 week values are mean ± SD of triplicate determinations.

Table 3 summarizes the biomodulator effect on the linewidth measurements. In this case data is presented for two different time points, one week and four weeks after initiation of treatment. Both PWM and Sw affect the decrease in linewidth after one week of treatment with the Sw data showing a higher level of linewidth reduction than the PWM treatment. After four weeks of treatment the values have decreased to stable, similar levels. Even after one week of treatment the linewidths are significantly (P>0.01) different from those of the untreated controls. The standard deviations of triplicate determinations at four weeks of treatment are as narrow as the untreated controls which is evidence of the stability of these determinations.

TABLE 4

THE EFFECT OF TREATMENT WITHDRAWAL ON T-2* LINEWIDTHS

| Temperature [k] | PWM | SW |
|---|---|---|
| 213 | 725 ± 18 | 520 ± 26 |
| 223 | 560 ± 23 | 510 ± 18 |
| 233 | 450 ± 30 | 430 ± 15 |
| 243 | 380 ± 20 | 360 ± 10 |

*Canine glioma cells treated with biomodulator for 4 weeks followed by 1 week of culture without any treatment: mean ± SD of 3 determinations.

Table 4 shows data from a series of experiments designed to test the stability of the linewidth parameter as a function of the withdrawal of the biomodulator. After four weeks of treatment followed by one week of treatment withdrawal the PWM treated cultures revert to values which are similar to the untreated control. The Sw treatment appears to be more stable to withdrawal, and these values are still significantly different from control values. This is similar to the data found with Tg and oligosaccharide display values.

TABLE 5

THE EFFECT OF t-BUTANOL EXTRACTION ON CONTROL AND TREATED CANINE GLIOMA CELLS T-2* LINEWIDTHS

| Temperature [k] | Untreated Control | Control | SW | CAD | PWM |
|---|---|---|---|---|---|
| 213 | 687 ± 48 | 367 ± 15 | 316 ± 33 | 381 ± 23 | 371 ± 88 |
| 223 | 470 ± 43 | 337 ± 29 | 271 ± 13 | 319 ± 29 | 326 ± 23 |
| 233 | 414 ± 39 | 299 ± 30 | 243 ± 29 | 299 ± 48 | 270 ± 80 |
| 243 | 316 ± 18 | 229 ± 9 | 194 ± 7 | 225 ± 20 | 224 ± 65 |

Table 5 is a summary of a series of experiments designed to determine whether the growth transformed cells have the same dynamic range of linewidth values as normal cells. The present hypothesis maintains that this physical parameter is capable of predicting the differentiation status and therefore to contrast normal and growth transformed phenotypes. To be a functional, predictive parameter the linewidth measurement must have a wide dynamic range and similar base-line values. t-butanol has been shown to extract cell surface material from the cytoplasmic membrane in a non-cytolytic manner, and to disorganize the cell surface oligosaccharide display so that a baseline noise pattern is seen. The hypothesis maintains that the "organization" of the oligosaccharide display acts like an informational filter. Thus down-regulation of the display, as is seen in the senescent model, suggests that the cell is not receiving the appropriate information, whereas the general lack of organization or disorganization of the display, as seen with the growth transformed cells, suggests that these cells are not regulating with incoming signals. t-Butanol treatment is known to reduce the cell surface display of IMR-90s to a noise pattern; Table 5 shows data which indicates that t-butanol has similar effects on growth transformed cells. The untreated controls and all the biomodulator treated CGs show the same linewidth values after the butanol extraction. These linewidths are similar to those found after the extraction of IMR-90 cells. Thus, both growth controlled and transformed cells have similar base-line linewidth values. Phase II IMR-90s have linewidth values of 350 Hz at 223° K. and 300 Hz values for the Phase III cells. The CGs have values of 575 Hz before treatment and 326±23 Hz after biomodulator.

In summary, then the biomodulators delay the appearance of the normal growth control phenomenon, cellular senescence, at the same time as they maintain the Tg, cell surface oligosaccharide display, and water proton linewidth values on the treated cells. In the case of the unregulated CGs the biomodulators reduce the cells' Tg, induce a re-regulation of the cellular oligosaccharide display, increase the recognition potential of the cells in a cell mediated lympholysis assay, and change the linewidth data when compared to controls.

Example 5

In vivo Antiproliferative Activity of CAD, Pokeweed Mitogen and Colletruncoic Acid A. Inhibition of Metastasis by CAD C57 BL/6 mice were injected I.M. with B-16 melanoma cells, maintained in culture in the right flank or shoulder. Tumor growth was monitored on a daily basis by physical measurement and by MRI/MRS on a weekly basis. Treatment routes were via intraperitoneal injection using various CAD between 1 µg and 0.001 µg per animal on a M, W, F injection schedule. The animals were terminated by $CO_2$ when the tumors had become 1.0 cm in diameter. Lung metastases were counted.

FIG. 22 shows the optimal dosage of 0.001 µg of (A1) completely inhibited metastasis of melanoma tumors.

B. Effect of various biomodulators on tumor growth in nude rats

Various biomodulators were tested in vivo for their effects on canine glioma tumors established and monitored as above for mice, but in nude rats. FIG. 22 shows the progression of the untreated tumors in the control rats. FIGS. 29–30 show the progression of the tumors over time with treatment with, respectively, PWM, Sw, CAD, HHD-2, HHD-3, HHD-4, and HHD-7. HHD-7 showed the best regression, while HHD-3 showed no regression effect, just delay of the control growth pattern.

C. Effect of PWM on growth of induced CG tumors in dogs

Canine glioma cells (about $1 \times 10^6$ cells) were surgically implanted in the brain cortex of a 20 kg female dog. MRI was used to follow the progression of the tumors. Localizer images were obtained using a T-1-weighted sequence with an echo time of 20 msec and a repetition time of 500 msec. The field of view was 16 cm, and the resolution was 256×126 complex points. The slice thickness was 3 mm, and the interslice space was 1.5 mm. Intermediate and T-2-weighted images were acquired in the axial plane to delineate margins of edema. The organization and vascularization of the tumor were observed as a ring of hyperintense signal in T-1-weighted MR images acquired fifteen minutes following intravenous injection of 1.5 cc of a 0.5 M solution of gadolinium diethylenetriaminepentaacetic acid (Gd-DTPA). The Cd-DTPA is partitioned into the vascular space, and permits visualization of the tumor mass from the surrounding edema. The tumor dimensions reached about 12×12×20 mm ten days after injection.

The dog was then treated with 10 μg PWM/kg three times per week. At day 17, the size of the tumor was reduced to about 8×8×8 mm, and at day 24 the tumor was reduced to about 3×3×3 mm in size, with minimal vascularization. The animal suffered no deleterious side effects from the treatment regimen.

Similar experiments using different biomodulators and different times of administration are detailed in FIG. 31. In particular, the MRI images of a control dog (FIG. 32) and dog number 7146 (FIG. 33), which was treated with HHD-4, are shown. The tumor can clearly be seen in the images of the control dog, which had to be euthanized; the treated animal, which was imaged ten days after commencement of treatment for the tumor, the presence of which was confirmed by MRI, is still alive. See also the MRI scans in FIGS. 43 and 44.

Several of these dogs were further tested for the effect of the treatment on their humoral immunity (Table 2).

Overall, 15 dogs were implanted with tumors and treated with PWM, and 100% tumor regression was found.

D. Spontaneous Tumors

Similarly, even domestic dogs of various breeds suffering from various tumors mast cell, carcinoma, melanoma and osteosarcoma) were donated for research purposes and treated with PWM as for the induced tumors. Again, 100% regression was found.

Example 6

The Effect of Biomodulators on Normally Growth Regulated Cell Populations

The cells used in these studies are IMR-90 human fetal lung fibroblasts originally obtained from ATCC. The culture conditions for these normal growth regulated cells has been described previously. The growth conditions are crucial in order to obtain reproducible PDL values for the onset of cellular senescence. These cells were growth in as close to optimal conditions as possible. Generally the cells were sub-cultured at 30% surface substrate confluency and grown to approximately 80 to 90% surface substrate confluency before passaging. Cells were maintained in continuous culture, the biomodulators, diluted in PBS, were added to the cells at the time of sub-culturing. PBS carrier was added to the control cultures. Cell size was measured with a calibrated eye-piece on the microscope at the time of counting. Viability was determined by Trypan Blue exclusion. Triplicate cultures were prepared for each data point. Generation times (Tg) were calculated by standard methods.

The other cell line used for these studies was Canine Glioma (CG) cell line developed by Salzman. This is a transplantable tumor line. It has similar size and substrate adhesive properties to the IMR-90. The CGs have a stable Tg of approximately 16 hours versus 30 hours for the IMR-90s. They have similar cell surface oligosaccharide displays, in terms of specificity and binding capacity.

The cell surface oligosaccharide display was assessed by methods developed previously. In brief, cells from a sub-culturing were aliquotted into 96 well trays at $5 \times 10^5$ cells per ml, 100 μL aliquots. After 16 hours of culture the cells were washed, fixed, and blocked with 0.1% BSA/PBS. Optimal lectin concentrations (5 μg/ml)were used to give 80 to 90% saturation of the available sites. Three carbohydrate ligands at 10 μg concentrations in triplicate or quadruplicate were then used to prepare competition curves for the lectin binding. The Bound over Free (B/F) ratio was calculated and the Ligand microprocessor program was used to determine the optimal fit of the data to a polynomial generated model. The Gibb's Free Energy (GFE) was calculated from the Scatchard data on the competition assay by the following equation: $GFE = -RT \ln K_{equit}$. The proton NMR linewidth measurements were conducted as described previously.

FIG. 34 shows the effect of CAD on the PDL and Tg of IMR-90 human fibroblasts in vitro. In these experiments the control and test cultures are maintained under as close to optimal growth conditions as possible. Some of these conditions include; sub-culturing cells at no lower than 30% surface confluency to minimize lag phase; sub-culturing the cells at 80–90% surface confluency to minimize contact-induced growth inhibition; and efficient handling of the cells during all manipulations to minimize mechanical damage. Under these conditions the non-treated IMR-90 cells show morphological signs of senescence at approximately PDL 45. At the same time the cell population Tg begins to increase dramatically. We consider that the population has undergone a senescence transformation when their Tg increases by more than 200% in one passage. This increase in Tg is evidenced by a very large increase in the standard deviation in the 40 to 50 PDL data point of the top panel. The addition of CAD at a dose of 0.01 μg/culture at PDL 35 stabilizes the Tg of these cells at approximately 40 H through PDL 70. From PDL 70 to approximately 90 the Tg shows a moderate increase to 40 to 45 H. In both cases the standard deviation of the data suggests a highly reproducible phenomenon. As the cells progress from PDL 90 to 100 the Tg increases significantly and the cells finally senesce by PDL 106. During the biomodulator-dependent extension of PDL the morphology of the cells remains similar to that observed with Phase II untreated cells. In general the treated cells at PDL 106 are smaller than the untreated senescent IMR-90s at PDL 45.

FIG. 35 shows data from a similar series of experiments designed to test the effect of PWM on the Tg and the highest attainable PDL for IMR-90s in culture. In this case a similar pattern of extended growth in Phase II is observed to that shown in FIG. 34, with the ultimate senescence phenotype being delayed to approximately PDL 75. These cells are morphologically similar to those seen in Phase II. Again the notable exception in this process is that average size of the senescent cells is smaller than that seen with the untreated controls.

TABLE 6

THE DOSE-DEPENDENT EFFECT OF BIOMODULATION ON THE SENESCENCE PHENOTYPE

| Biomodulator | | PDL at Senescence |
|---|---|---|
| Control | | 45 to 48 |
| | 10 μg | 40 to 45 |
| PWM | 1.0 | 85 to 88 |
| | 0.1 | 50 to 55 |
| | 10 μg | 75 to 80 |
| CAD | 0.01 | >100 |
| | 0.0001 | 45 to 50 |

*Senescence phenotype was defined as the PDL at which there was a greater than 100% increase in the generation time from the two previous passage level.

Table 6 summarizes the biomodulator effect on the appearance of the senescence phenotype. PWM does not extend the senescence PDL of IMR-90 culture treated with 10 μg doses, and may slightly reduce it. The 0.1 μg doses of PWM extends the PDL at senescence slightly (by 5 PDLs). The 1.0 μg doses almost double the PDL expectancy of these cells in culture while maintaining a Phase II morphology. This dose-response curve mirrors the data presented above on the proliferative/differentiative effects of PWM and CAD on HPBLs in vitro. In that case the 10–25 μg doses were found to be proliferative in nature whereas the lower doses were differentiative. Similar results are seen with the dose-response data for CAD. CAD was shown to have little overt proliferative activity on the HPBL model and this is also supported with the PDL-extension data. The 10 μg doses extend the PDL significantly whereas the optimal effect is found at doses which are three logs lower. The effect is diminished as the CAD is diluted another two logs. This extensive response curve is typical of the biomodulators which are comparatively free of proliferative activity. On the other hand biomodulators which have significant proliferative potential show narrow dose-response curves with a much higher level of variability of optimal response. This instability of optimal dose, which we infer is related to the admixture of proliferative capacity in these biomodulators, is a potential explanation for the inability of the PWM to extend the PDL to the same levels as the CAD.

FIG. 36 shows data from the cell surface oligosaccharide analyses of the biomodulator treated IMR-90 cells at PDL 79. The IMR-90 cells at this PDL are almost twice the untreated senescence level and are morphologically similar to Phase II untreated cells. The top panel of FIG. 36 shows the visual representation of the Scatchard analyses of Mannose specific carbohydrate display. This is a micro-processor based analysis which attempts to "fit" the data to a number of models and determines the optimal pattern. In this case the analysis suggests a two site fit for the binding of CON-A to IMR-90 cells. Alpha-methyl-mannopyranoside, paranitro-phenyl-mannopyranoside and mannose were used as soluble ligand competitors. The affinity of binding for the sites is slightly lower (N.S.) than that found for untreated Phase II cells but is significantly higher (P>0.01) than that found for untreated senescent cells. These data still suggest an up-regulated status for the biomodulator treated cells at this advanced PDL. The bottom panel of FIG. 36 shows results from similar experiments on the galactose specificity on IMR-90 cells. In this case there is also a maintenance of an up-regulated configuration of this specificity. The N-acetyl-glucosamine specificity is the final major binding specificity on the IMR-90s and shows no change with biomodulator treatment.

TABLE 7

THE EFFECT OF BIOMODULATION
ON THE GFE OF IMR-90S

| Biomodulator | PDL | Gibb's Free Energy |
|---|---|---|
| Control | 35 | 35.6 |
| Control | 45 | 26.4 |
| 0.01 μg CAD | 75 | 33.0 |
| 0.01 μg CAD | 79 | 34.3 |
| 0.01 μg CAD | 98 | 27.4 |

The GFE values were calculated for the CON-A/mannose, RCA/galactose, and WGA/N-acetyl-glucosamine specificities.

Table 7 shows a summary of the effect of the biomodulator treatment on the cell surface oligosaccharide display. The Gibb's Free Energy (GFE) parameter is used here to gain an overview of the cell surface oligosaccharide display. It is the sum of all the individual specificities such as shown in FIG. 3 plus those of the N-acetyl-glucosamine specificity. The untreated control PDL 35 cells show a GFE of approximately 35 Kcal whereas the senescent IMR-90s at PDL 45 show a 30% reduction in GFE to approximately 26 Kcal. The biomodulator treated cells show a typical Phase II GFE of approximately 35 Kcal until PDL 98 where the GFE begins to fall to the untreated senescent levels. These data correlate with the morphological phenotypes shown in FIG. 1 where the Tg of the treated cells was similar to Phase II untreated cells until PDL 100. They also support the hypothesis that the cell surface oligosaccharide display is predictive of the cellular senescence status of that population.

Example 7

Antisenescence Effects of Biomodulators In Vivo

TABLE 8

THE EFFECT OF PDL AND CHRONOLOGICAL AGE
ON CELL SURFACE OLIGOSACCHARIDE STRUCTURES

| Cell Line | Chrono. Age | Total PDLs | % Total PDL* |
|---|---|---|---|
| AG 147A | 3 days | 54 | 82 |
| AG 2261 | 61 years | 22 | 80 |

Chronological age is the age at which the donations were made total PDLs in culture to reach morphological senescence.
*PDL at which down-regulation of the CON-A binding site was first noted as a % of total-.

Table 8 shows that the oligosaccharide display characteristics of the in vitro cell lines are mirrored in the in vivo biological environment. Cells taken from individuals 3 days old and 61 years old were tested for the number of PDLs it took to reach morphological senescence. It was found that, as a percentage of the total PDLs, the down-regulation of the oligosaccharide display occurred at almost an identical time prior to the onset of senescence.

FIG. 37 shows data from neonatally thymectomized and congenitally athymic Nu/Nu mice which were treated with CAD. In both cases there was a significant increase in T-cell differentiation. The standard three times a week treatment with 10 ng CAD gave complete reversal of the negative T-cell response in the thymectomized animals and 41% reversal in the congenitally athymic mice, as measured by response to T-cell mitogen. T-cells are decreased in the in vivo aging process. Therefore, it can be extrapolated that T-cell competence will be enhanced in the senescent animal.

FIG. 38 shows preliminary results from a series of in vivo responses in 13 month old C57BL/6 mice. The LPS (lipopolysaccharide) response, which is B-cell specific, is the control, and biomodulator treatment (PWM, 3x/week, i.p., 21 days before sacrifice) doubles the CON-A response. Similarly, the humoral immunity is shown to be enhanced by biomodulator treatment.

FIG. 39 shows the effect of biomodulator (PWM) on nude rat T-cell differentiation in vivo. The control nude rat lacks functional T-cells and therefore response at baseline to CON-A. 1 or 10 μg PWM 3x/week i.p. for 21 days induces a marked T-cell response on day 11 at the same time that there is a physical reduction in tumor size. The T-cell response is directly correlated-to biomodulator dose and biomodulator ability to induce tumor regression.

Example 8

In vitro Effect of Biomodulators on Endothelial
Cell Growth and Differentiation for the Production
of Transplantable Blood Vessel Grafts FIG. 40a shows the effect of biomodulators (PWM at 1 μg/culture, or 10 ng CAD on endothelial cells in vitro)

(FBHE, fetal bovine heart endothelial cells, and HUVE, human umbilical vein endothelial cells). Again, the solid substrate represents normal growth substrate and the cells proliferate and are poorly differentiated. (adherence index). The addition of CAD decreases proliferation and increases the differentiative expression. Alterations in substrate (i.e., a microporous substrate, for example, a microporous polyurethane foam suitable for human implantation) controls the proliferation but doesn't improve the differentiation. Finally, the addition of the biomodulator to the microporous model gives optimal results. Similar results are shown in FIG. 40*b*. This time the deposition of radiolabelled fibrin (clot) was used to assess the differentiative function of the endothelial cell surface. The endothelial cell's differentiative function in the body is to "control" coagulation functions at its surface, pro-coagulant to stop bleeding to death and most of the time anti-coagulant to prevent occlusion. The typical graft is very pro-coagulant and the typical graft covered with endothelial cells is also very quickly occluded because of the proliferative/pro-coagulant activity shown above. We have apparently controlled this with both substrate and biomodulator.

Example 9

Regeneration of Damaged Tissue

In the process of performing the in vivo tumor assays discussed in Example 5, there was a surprising finding in the animals treated with biomodulator in which tumor regression was achieved, upon histological and MRI examination of the previous tumor-bearing regions of the animals' brains. Contrary to the usual findings where tumor regression is reported, when tumors are treated with biomodulator, not only does the tumor regress, but the normal tissue architecture is re-established.

FIG. 41 is a series of prints of MRI scans of control dog #7657 (BOZO) implanted on Mar. 5, 1987 with CG tumor. The progression shows a massively growing tumor mass. On Mar. 26, 1987 the dog showed neurological deficit and was sacrificed. The histology (FIG. 42) shows a gross brain slice with the tumor in place. This widely proliferating mass causes normal tissue displacement and destruction. Even in human cases where spontaneous tumor regression has been observed the progressive tissue destruction is permanent.

FIG. 42 shows MRI from another control dog #7011 (OREO), with similar effects.

FIG. 43 shows a collage of MRIs from dog #7146 (ONE EYED JACK). The first panel was a pre-implantation normal scan. The tumor was implanted on Mar. 14, 1988, and the BM (HHD-4, at 1 $\mu$g/kg) was initiated on Mar. 19, 1988 M, W, F standard regimen. The second panel Mar. 14, 1988 shows the tumor. The third panel Mar. 18, 1988 shows a much larger tumor with its own vascular supply. This is the criterion for treatment. It is estimated from the control studies and our measurements on tumor size that this dog would have to be destroyed within 5 days of Mar. 18, 1988. The final panel was taken on Mar. 29, 1988 and shows complete tumor regression with a small amount of residual edema (another MRI on Apr. 29, 1988 showed a completely normal brain).

FIG. 44 shows a similar experiment on dog #7115 (CITO). FIG. 45 shows a 40× objective microscopic field of a treated dog's brain. The end of the needle track used for tumor injection is seen and is used for orientation. The pathologist report finds no residual tumor cells at the site or elsewhere in the brain. The pathologist found no indication of scar tissue or aberrant cell or tissue morphology.

Pathology reports taken from dogs immediately following the last MRI evidence of active tumor indicate the presence of host immune cells at the tumor site (presumably involved in tumor regression). By 3–6 weeks after the last signs of tumor the brain architecture returns to completely normal limits (no scar, no tumor, no leukocytes).

FIG. 46 shows a collage of histology specimens through the CG/muscle interface in the CG/RNU model. The histology stain toluidine blue is in the lower right hand position for orientation. The top left panel shows a 7 day tumor implant treated with PWM 1 $\mu$g M, W, F standard protocol. The bright cells are those stained with FITC anti-Thy 1.1 antibody. The presence of these cells suggests the infiltration of primitive T-cells into the area. The next panel shows an adjacent section stained with anti-T-help antibody. At this stage (day 7) there is only the beginnings of T-help cells (by day 11 this increases markedly). The lower left panel is the control of just the fluorescent secondary antibody for comparison purposes.

FIG. 47*a* shows another histology slice with the infiltrating Thy 1.1 cells brightly stained with the antibody. The round structures are cross-sections from the microvasculature in the CG/host muscle area.

FIG. 47*b* shows the same section as FIG. 8 stained with toluidine blue. The dark cells (heavy staining) suggest the presence and degranulation of mast cells. Mast cells secrete histamine, serotonin, and heparin, all products used in tissue maintenance and repair.

Example 10

Vaccination Augmentation with Biomodulators

Methods:

Antigen: usually SRBC at 2×10$^7$ per injection i.p.; also protein, haptenic antigens, and particulate antigens have also been used.

Standard protocol: antigen is injected into 4–6 week old female BALB/C mice at various time points before sacrifice (5 days for primary and two time points for secondary), spleens taken, cell suspensions prepared, cells counted and PFC assay performed. Data expressed as PFC (IgM, IgG). These same cells were then hybridized by standard protocol and prepared for monoclonal work-up. Data expressed as antibody producers per well, per colony, and frequency per original PFC. See Table 12.

A. Preparation of Cell-Suspensions

Mouse Spleen Cells

Mice are killed by neck dislocation, their spleens are removed aseptically and transferred into a bacteriological-type plastic petri dish containing 10 ml GKN. The cells are teased from the capsule with a spatula. Clumps of cells are further dispersed by pipetting up and down with a 10 ml plastic pipette. The suspension is transferred to a 15 ml polypropylene tube where clumps are allowed to settle for 2 to 3 minutes. The cell suspension is decanted into another tube and centrifuged for 15 minutes at 170 g at R.T. The cells are washed again in GKN and finally resuspended in 1–2 ml GKN. An aliquot of the cells is counted (20 $\mu$l+1 ml trypan blue solution). The viability is consistently above 95%.

B. Cell Fusion

1. Choice of Animal

The choice of animal depends mainly on the availability of appropriate tissue culture lines for fusion. So far, only rat and mouse myeloma lines are available. Rabbit and human lines which might be advantageous in some respects have not yet been described. Cross-species fusions work for mouse myeloma×rat lymphocytes, but not very efficiently for mouse myeloma×rabbit or human lymphocytes. At the moment, the mouse seems to be the best choice because myeloma lines exist which have lost their own Ig production (the rat line still expresses light chains) and all IgG classes of the mouse (but not the rat) bind to Protein A of *Staphylococcus aureus*, which facilitates purification of Ab (see section VI).

All the mouse myeloma lines are derived from the BALB/c strain of mice. Hybridomas obtained with BALB/c lymphocytes will grow as tumors in this strain when injected intraperitoneally, thus generating high titred ascitic fluid. Since the immune response against a given antigen may not be optimal in the BALB/c strain, another strain of mice (e.g., C57BL/6) can be used as well. Female mice (easier to handle), 8 to 12 weeks old (e.g., Bomholtgaard, Ry, Denmark) were used.

2. Immunization

Alum-precipitation: 2.5 ml protein solution (at least 1 mg/ml) +1.5 ml 1 M NaHCO$_3$ +dropwise, 2.5 ml 10% AlK(SO$_4$)$_2$ Spin, wash with PBS, resuspend in appropriate volume. *Bordetella pertussis:* Schweizer Serum and Impfinstitut, Bern.

Procedure

For soluble antigens, inject 100 μg antigen (protein) precipitated in alum, mixed with $2 \times 10^9$ killed *Bordetella pertussis* organisms intraperitoneally. Boost 4–6 weeks later with 100–200 μg antigen in saline. Take spleens 3 days later. For cellular antigens inject $2 \times 10^7$ cells i.p., repeat 2–3 weeks later, boost after 3 weeks with the same dose, take spleens 3 days later. In general, animals should have a 4-week rest before last boost. This boost should be given i.p. or i.v. so that antigen reaches the spleen. Spleens are removed 3 days later. Since the time interval is critical for the derivation of specific hybridoma lines, avoid depending on only one spleen. Either pool 3 spleens or make 3 separate fusions. Lymph node cells can also be used. In vitro antigen stimulation of primed spleen cells or transfer to irradiated host mice of primed spleen cells together with antigen may help in getting an extra enrichment of the B cells of interest.

3. Cell Lines Used for Fusion

In the early days, myeloma cells secreting Ig were used: X63-Ag8 (IgG$_1$, κ). Variants of these lines were selected to contain only light chains and finally no chains at all.

|  | No. Chrom. | Ig | Derived From | Ref. |
|---|---|---|---|---|
| X63-Ag8.6.5.3 | 58 | none | X63-Ag8 | A |
| Sp1/O-Ag14 | 72 | none | (X63-Ag8 × BALB/c) | B |

References:
A. J. Immunol. 123:1548.
B. Nautre 276:269.

Cells were grown in DMEM (Dulbecco's modified Eagles Medium) or in RPMI medium, supplemented with 10% FCS. Optimal growth is obtained at cell numbers between $10^4$ and $5 \times 10^5$ cells/ml. For fusion in logarithmic growth were used.

4. Cell Fusion with Polyethylene Glycol (PEG)

$10^8$ washed spleen cells (derived from one immunized mouse) and $5 \times 10^7$ 8-azaguanin resistant myeloma cells (X63Ag8.6.5.3; FO; Sp2/0-Ag14) are combined in a 50 ml conical tube (Falcon 2070). The tube is filled up with GKN and spun for 10 min. at 170 to 200 g at room temperature. All the supernatant is carefully withdrawn. A total of 0.5 ml 50% PEG-solution is added dropwise to the pellet under agitation (to break up the pellet) over a period of one minute at room temperature. After 90 seconds, 5–10 ml of GKN are added slowly (initially dropwise) over a period of 5 minutes to dilute out the PEG. Leave for 10 minutes and disrupt big clumps of cells by pipetting gently about 5 times with a 10 ml pipette. Dilute into 500 ml DMEM-10% FCS containing HAT (complete HAT). 1 ml aliquots are distributed into 480 wells of Costar-Trays (Costar Tissue Culture Cluster 24, Cat. No. 3524, Costar, 205 Broadway, Cambridge, Mass., U.S.A.) already containing 1 ml HAT-medium and $10^5$ peritoneal cells or $10^6$ spleen cells. These feeder layers are prepared the day before fusion. The trays are kept in a fully humidified incubator at 37° C. in an atmosphere of 5% CO$_2$ in air.

After 3 days and twice a week thereafter, 1 ml medium is removed (using a Pasteur pipette fitted to a suction pump) and replaced with HAT-medium.

After 7 to 10 days, the wells are inspected for hybrids and the HAT-medium can be replaced by HT-medium. Supernatants of growing hybrids which are at least 10% confluent are removed and tested for specific antibody. Cell populations which are of interest are expanded by transfer into cell culture bottles for freezing, cloning and product-analysis. At this stage it is advisable to add $10^6$ peritoneal cells per culture bottle.

References

Köhler, G., and Milstein, C., 1975. Continuous cultures of fused cells secreting antibody of predefined specificity. Nature 256:495.

Galfré, G., Howe, S. C., Milstein, C., Butcher, G. W., and Howard, J. C., 1977. Antibodies to major histocompatibility antigens produced by hybrid cell lines. Nature 266:550.

Trucco, M. M., Stocker, J. W., and Ceppellini, R., 1978. Monoclonal antibodies to human lymphocyte antigens. In: Current Topics in Immunology and Microbiology, Vol. 81, Eds. Potter and Melchers, Karger, Basel.

C. Cloning

Soft Agar Cloning and Detection of Hybrid Clones with Anti-SRBC

Heterogeneous mixtures of hybrid or lymphoid tumor lines are separated by localized growth of single cells in soft agar. After growth of colonies to a size easily visible by the naked eye, they can be picked from the agar with a Pasteur pipette (usually after 8–10 days). Clones secreting sheep red blood cell specific antibodies can be revealed by an overlay hemolysis technique.

Material:
1) Petri dishes, 0 9 cm (Falcon, Becton-Dickinson-France, 38100 Grenoble, France).
2) 2.5% Agar (Difco Laboratories, Detroit, Mich., U.S.A.) in tridistilled H$_2$O, autoclaved.
3) Dulbecco's modified minimal essential medium (DMEM) (GIBCO-Biocult, Paisley, Scotland, PA3 YEP) supplemented with penicillin/streptomycin (100 units/1 ml), glutamine (4 mM), sodium pyruvate (1 mM), and heat-inactivated horse serum (GIBCO) (DMEM) or 20% FCS.
4) Costar trays (Costar, Data Packaging Corp., Cambridge, Mass. 02138, U.S.A.)
5) PBS; 10 mM phosphate buffer pH 7.2, 0.9% sodium chloride
6) Indubiose A37 (L'Industrie Biologique Française, Gennevilliers, France) 0.6% in PBS, sterile. Dissolved by boiling twice briefly. Kept in a 45° C. water bath.
7) Sheep red blood cells (SRC) washed 3× with saline and made up 25% in saline (1:4 dilution).

8) Guinea pig complement (GPC'). Fresh guinea pig serum is absorbed at 4° C. with 10% packed SRC, filter-sterilized and kept in 2 ml aliquots frozen at −20° C.

9) Rabbit anti-mouse immunoobulin. Made by injecting rabbits intraperitoneally with 0.5 mg purified MOPC21 immunoobulin (IgG$_1$, κ), emulsified in Freund's complete adjuvants.

When a good plaque-developing titer is observed (usually after the third injection given in 3-week intervals) the rabbit is exsanguinated. The serum is absorbed with 10% packed SRC, heat-inactivated for 30 minutes at 56° C., filter-sterilized and kept frozen in 2 ml aliquots at −20° C.

For 10 plates:
Procedure:

Dissolve 30 ml 2.5% Agar in boiling water.

Put into 45° C. water bath.

Warm up 117 ml DMEM+3 ml 10× DMEM in 45° C. water bath.

Mix Agar and DMEM (=DMEM-Agar, 0.5%) and add 75×10$^6$ spleen cells.

Put 10 ml into each of 10 petri dishes (=bottom layer) and put DMEM-Agar back at 45° C.

Let solidify for 15 minutes at room temperature.

Mix cells in DMEM and DMEM-Agar at a ratio of 1:1.

Drop 2 ml of cell-Agar-Mix on bottom-layer so that the whole area is covered.

Grow for about 10 days in humid $CO_2$-incubator, 37° C.

Prepare 0.6% Agarose in PBS by boiling and keep at 45° C.

Add to 3 ml Agarose 0.1 ml 25% SRC, 0.2 ml GBC' (and 0.03−0.1 ml anti-mouse Ig developing serum for detection of indirect lysis). Work quickly, keep warm.

Overlay colonies with 3 ml Agarose-SRC mix.

Incubate in humid $CO_2$ incubator at 37° C. for 1 to 2 hours.

Areas of lysed SRBC are seen on top of those colonies secreting anti-SRG Ig.

Pick colonies with Pasteur pipette where only few colonies grew. Put into 1–2 ml of DMEM in costar trays.

D. Testing for Specific Antibody and Antibody Subclass
1. The Jerne Sine Cell Plaque Assay This is by far the most sensitive test for specific antibody. Less than 1 specific antibody secreting cell in 10$^6$ cells can be detected and the secreting cell can be inspected microscopically. Moreover, from the number of plated cells and the scored plaque number the fraction of secreting cells can be determined. It is used to detect antibody directed against heterologous red blood cells or any hapten or antigen which can be coupled to them (see below).

Testing for Anti-Sheep Red Blood Cell Activity of Hybridoma Cell Lines

Material:
1) Petri dishes ∅ 9 cm.
2) PBS: 10 mM phosphate buffer pH 7.2, 0.9% sodium chloride.
3) Indubiose A37, 0.6% in PBS. Dissolved by boiling twice shortly. Kept in 45° C. water bath.
4) Sheep red blood cells (SRBC) washed 2× with saline and made up 25% (1:4) in saline.
5) Guinea pig complement (GPC'). Fresh guinea pig serum is absorbed at 4° C. with 10% packed SRC, filter-sterilized and kept in 2 ml aliquots frozen at −20° C.
6) Rabbit anti-mouse immunoobulin (provided).
7) Cells of provided test panel, washed 2× in PBS (keep first supernatant) and resuspended in PBS at 10$^4$ cells/ml.

Procedure:
1) Prepare 25 tubes containing 2 ml of 0.6% Indubiose in PBS in 45° C. water bath.
2) Add to these: 0.1 ml 1:4 dil. SRC or TNP-SRC
   0.1 ml GPC'
   0.1 ml of cells.

Mix and pour into petri dish. Shake quickly and vigorously to obtain a thin layer on the plate, let solidify for 10 minutes at room temperature, then incubate for 2 hours at 37° C.

3) Do the same as in step 2, but also add 5 μl rabbit anti-mouse Ig per tube.
   a. TNP-Coupling of Horse Red Blood Cells Material and Solutions:
      24,6-trinitrobenzene-sulfonic acid (TNBS) Sheep and horse red blood cells (SRBC and HRBC)
      0.01 M Na-phosphate pH 7.1 in 0.9% NaCl (PBS)
      Glycol-ycine (y-y) 11 mg/ml Coupling:
1 ml washed packed red blood cells are resuspended in 7 ml PBS containing 10 mg TNBS at room temperature. After 20 minutes, the reaction is stopped by adding 1 ml y-y in PBS (11 mg/ml). After 3 washes with PBS the TNP-coupled red cells can be kept for up to one week at 4° C.

References:
Rittenberg, M. B., and Pratt, K. L. (1969), Proc. Exp. Soc. Biol. Med. 132, 575.

Jerne, N. K., Henry, C., Nordin, A. A., Fuji, H., Koros, A. M. C., and Lefkovits, I. (1974), Transplant. Rev. 18, 130.

b. Protein A-Coupled SRBC for Detection of:
   1) Cells secreting different Ig classes (plaque assay).
   2) Supernatants containing immuno-globulin of different classes (spot test).

The methods are based on the property of Protein A from *Staphylococcus aureus* to bind the Fc portion of IgG of some mammalian species. The Protein A plaque assay has been described by E. Gronowicz et al. (Eur. J. Immunol. 6, 558, 1976).

Reagents:
saline (0.15 M NaCl)
chromium chloride 0.05 M
Protein A from *Staphylococcus aureus* (Pharmacia, Uppsala) 0.5 mg/ml in saline (SPA)
sheep erythrocytes kept in Alsever's solution for one week to one month (SRBC)
BSS (Earle's Balanced Salt Solution)

Method: Combine in a 50 ml plastic tube the reagents and mix thoroughly after each individual addition
10 ml saline;
50 μl chromium chloride 0.05 M;
1 ml SPA 0.5 mg/ml;
1 ml packed SRBC (washed 4 times with 10 to 20 volumes of saline, spun 10 minutes at 600 g).

The addition of reagents has to be done quickly and in this order. Incubate in water bath at 30° C. for 60–90 minutes, with occasional mixing. After incubation, fill the tube with saline and spin at 600 g. Wash 2× with BSS and resuspend at 25% in BSS. The coupled cells must be used within a week and must be rewashed before use.

Protein A-Plaque Assay

Reagents

Aqar:

0.5% Bacto Agar Difco in BSS. BSS with glucose is needed for the plaque assay, not for the spot test. Dissolve the agar by boiling until completely clear, then transfer in a 46° C. water bath. Once equilibrated, add DEAE-Dextran (Pharmacia, Uppsala) at 50 mg/ml in BSS, to a final concentration of 0.75 gg/ml (1.5 ml of the stock solution/100 ml agar). (The agar solution becomes milky after addition of DEAE-Dextran.)

Complement:

Guinea pig serum (GIBCO, Behringwerke). The reconstituted complement is kept at −20° C. and diluted before use. The appropriate dilution has to be checked for each batch and usually ranges between ⅓ and ⅕.

Developing antisera:

Class-specific antisera are available from Bionetics (Kensington, Md., U.S.A.) and must be titrated using reference sera or cells. Reference sera, as well as myeloma proteins or tumors are also available from Bionetics. Sera must be made in rabbits or other species whose IgG do bind to SPA.

Note:

All reagents should be kept as close as possible to sterility, to avoid growth of bacterial colonies during the incubation.

Plague Assay: Combine in a hemolysis tube (4–5 cm long):

20–100 μg cell suspension containing 100–500 secreting cells

20 μl SPA-SRBC 25%

25 μl complement at the appropriate dilution

20 μl developing antiserum at the appropriate dilution

Mix on vortex and add 300 μl agar solution. Mix by hand (not on vortex). Pour the mixture in a 9 cm diameter Petri dish and spread the agar over a spot of ~7 cm diameter using the edge of the tube. Use both top and bottom of the dish. After 2–3 minutes, the plates are closed and transferred within 5–10 minutes into a humidified incubator at 37° C. The plates are distributed in a single layer to provide a fast equilibration, and after 15–30 minutes are turned upside-down and piled up. The plates are incubated at 37° C. for a minimum of 3 hours to a maximum of 6 hours.

The counting can be performed immediately, but the plates can also be kept up to 2 days at 4° C.

2. Spot Test

Agar plates are prepared as indicated in points 2 and 3 (page 16). Four plates (one of each kind) contain:

C'+SRC

C'+TNP-HRC

C'+SRC+RαMIg

C'+TNP-HRC+RαMIg.

Label on back of the petri dish the positions of your 8 hybridoma supernatants and add 5 μl of culture supernatant. Leave dishes open until the drop is soaked in. Then incubate at 37° C. for 30 minutes.

3. Agglutination

Prepare 24 ml each of 0.25% SRC and 0.25% TNP-SRC in PBS. Divide the SRC solution into two 12-ml aliquots and add to one half 0.12 ml RαMIg. You now have 3 solutions. Distribute each solution into one microtiter tray (Cooke M220-25AR) with U-shaped cone (0.1 ml into each well).

Add to each row (A–H) into the first well 0.1 ml of test supernatant and make a 2-fold serial dilution up to well 11. Leave on the bench for 2–3 hours.

4. Ouchterlony Test for Ig Class and Subclass

The easiest way to determine the class and subclass specificity is an Ouchterlony analysis. For this one should concentrate the supernatants about 10-fold.

To 1 ml of supernatant add slowly 1 ml of saturated ammonium sulfate solution. After 3 hours in the cold centrifuge at 10,000 g for 10 minutes. Take up pellet in 0.1 ml of $H_2O$.

Use class+subclass specific rabbit anti-mouse $\mu$, $\alpha$, $\tau_{1,2a,2b,3}$ and $\kappa$, antisera (Litton Bionetics, Kensington, Md., 20795, U.S.A.).

Ouchterlony trays (Meloy, Springfield, Va., 22150, U.S.A., No. H401).

Place about 20 μl of concentrated supernatant in the middle part of Ouchterlony plate and arrange 20 μl of specific antisera around it. Use 10 μnormal mouse serum as control for activity of antisera.

It is advisable to countercheck serological determinations by, for example, SDS-PAGE of radiolabeled supernatants. This separates $\mu$, $\epsilon$, $\alpha$, $\tau$ and may reveal $\tau_{2b}$ as a double band running slightly slower than the other $\tau$ subclasses. Or use functional properties (lytic activity of IgM, $IgG_{2a}$ and $IgG_{2b}$; Prot A or Con A binding (IgG versus IgM)).

5. $^{51}Cr$ Release Assay

This assay is widely used to test for complement-dependent cytotoxic antibody directed against blastoid cells. As targets either lymphoblastoid cell lines (LCL) or stimulated peripheral blood lymphocytes (PBL) are used.

Dead cells are removed from LCL by centrifugation through Urovision Ficoll (density 1,090). The viable cells are collected from the interface and washed twice in RPMI 1640 medium supplemented with 10% fetal calf serum (FCS) (400×g, 10 minutes, 4° C.). For PHA- or pokeweed-mitogen-stimulated blasts from the PBL the dead cell removal is not required.

$2 \times 10^6$ blastoid cells are spun (400×g, 10 minutes, 4° C.) in a conical tube and 500 μCi of $^{51}Cr$-sodium chromate ($Na_2$ $^{51}CrO_4$-DJS4, Radiochemical Centre, Amersham, Bucks, U.K.) are added directly to the resuspended pellet. Samples are incubated for 2 hours in a 37° C. water bath, with occasional shaking and then washed 3 times with cold RPMI 1640, 10% FCS medium. It is important to keep the cell suspension at 4° C. To reduce the spontaneous $^{51}Cr$-release the cell suspension is left on ice for 20 minutes between the second and third washing. The supernatants from at least the first wash must be collected in a bottle as radioactive waste. It is advisable to do the manipulation behind a lead shield.

The labeled cells are then resuspended at a concentration of $2 \times 10$ cells/ml. Fifty μl of this suspension (10,000 cells) are counted in a gamma counter to determine the input. If necessary, the cell concentration is adjusted to have at least 15,000 cpm in 50 μl. Fifty Al aliquots of this cell suspension are placed into Lacham plastic tubes (0.5×3.5 cm) or in the wells of a U-bottomed microtiter tray (Cooke, MIC Plates, Et. No. M26AR). Fifty μl of culture supernatant and 50 μl of an absorbed rabbit complement are added. All these operations must be done on ice. Assays are performed in triplicates.

After 1½ hours of incubation at 37° C., the cells are resuspended and centrifuged (400×g, 10 minutes, 4° C.). 75 μl of the supernatant are removed for counting.

The spontaneous release (SR) is determined in the negative control containing cells and normal medium. The results are not reliable if the release of the control done with complement and cells only (C'R) is more than 30% of the total input (TI). The total input can be calculated as the sum of radioactivity in the supernatant and the pellet. The percentage of C'R can be determined using the following formula:

$$\%C'R = \frac{\overline{x}\,\text{cpm}\,C'R - \overline{x}\,\text{cpm}\,SR}{\overline{x}\,\text{cpm}\,TI/2 - \overline{x}\,\text{cpm}\,SR} \times 100$$

The percentage of specific killing (SK) is calculated in the following way:

$$\%SK = \frac{\overline{x}\,\text{cpm sample} - \overline{x}\,\text{cpm}\,C'R}{\overline{x}\,\text{cpm}\,TI/2 - \overline{x}\,\text{cpm}\,C'R} \times 100$$

The Murine System

The principal drawbacks of the current murine hybridoma technology spring from a numbers problem. In turn, this numbers problem limits the scope of the reagents possible. That is, if you only have an efficiency of one in $10^6$ in the actual fusion process and the natural frequency of specific antigen-sensitive -cells in the spleen population is one in $10^4$, there is no latitude for choosing an appropriate epitope-specific antibody, let alone putting a design dimension into the experiment. The other major problems concern the class, subclass and affinity of the antibody produced. Although very little thought has been given to exactly what characteristics of the antibody would be desirable for particular application, an IgG antibody of high affinity is generally considered desirable. Typically an IgM of very low affinity is produced under standard hybridoma conditions. These problems can be viewed as related to the induction of the response, and that is where we began.

FIG. 48 shows typical control data for the standard hybridoma technology. Under a primary response protocol, the hybridizing mixture has approximately 300 IgM PFC/$10^6$ cells which results in only 1 positive well in 24 and gives an overall efficiency of 1 in $5 \times 10^6$. In more realistic terms, there were 1630 specific antibody producing cells in the original fusion mixture, of which only one managed to be hybridized and survive. After a secondary immunization schedule, things have improved somewhat and the overall efficiency is 1 in $2.5 \times 10^6$ for IgM or 1 in 1000 for specific antibody cells. The IgG clonal production was 1 in $5 \times 10^6$ but the efficiency for specific IgG-producing cells is 1 in 150. There appear to be 2 events occurring in concert: firstly, the overall probability of the fusion event occurring is outrageously small; and secondly, the cells which are secreting antibody have a relatively high fusion preference.

FIG. 49 shows effect of biomodulators on monoclonal antibodies production. The biomodulator was given day -16, -12, -9, -5 (antigen given day -5) assay as above. These studies were used to develop the "standard biomodulator-enhanced monoclonal antibodies protocol which is: M, W. F injection i.p. of biomodulator (1 µg, PWM, 10 ng, CAD, etc.) for 3 weeks with antigen on F of the last week followed by sacrifice on T.

By specific manipulation of the animal with inducers, the level of IgG producers at the time of hybridization was raised from 0 to approximately $10^3/10^6$ spleen cells. The hybridoma data shows a dramatic increase in both overall and specific cell efficiency, 1 in $5 \times 10^4$ and 1 in 30–80, respectively.

FIG. 50 shows the effect of secondary immunization on biomodulator-induced monoclonal antibodies. This figure demonstrates a complete shift to IgG producers and further improvement in the apparent overall efficiency. Of course, the specific cell efficiency is more relevant here and it shows that approximately 4% of the specific antibody-producing cells at the time of hybridization go on to produce successful antibody-producing clones.

FIG. 51 shows the effect of primary dose, i.e., the effect of the dosage level of the inducer on the response. Both 10 µg and 1 µg doses of PWM are effective, whereas the 0.1 µg dose shows no increased hybridoma capability. This is in spite of the fact that this dosage caused the highest specific PFC production. Thus, it appears that, at least with this inducer, the 2 relevant phenomena (induction and increased fusion efficiency) are separated. This is particularly interesting in view of our desire to be able to "design" specific products. The alkaline lipopolysaccharide (LPS-ALK) induction shows a relatively simple dose response variation with the 0.25 µg dose giving the best overall performance but the 1.0 µg dose showing the highest frequency with respect to IgG producers and specific antigen sensitive cells. Again, the salient features of this study are: 1) a significant increase in the overall fusion efficiency; 2) a shift to IgG producers; and 3) an apparent preferential increase in the fusion efficiency of specific antibody-producing cells.

FIG. 52 shows similar data with the exception that a secondary response has been employed. In the case of the PWM induction, the overall PFC performance has decreased somewhat but the fusion efficiency has increased significantly again indicating the possible separation of these phenomenon. In some cases the fusion frequency with respect to specific IgG producing cells is seen to approach quantitative yields. The LPS induction shows similar results but the dose response has not shifted to optimal production at lower LPS concentrations. Thus, overall, with a secondary antigen exposure the degree of optimal induction shifts to lower concentrations. An important difference between the primary and secondary induction is the affinity of the IgG antibody produced. With only preliminary data available, it appears as if there are major increases in affinity as the number of antigen exposures increases.

FIG. 53 shows the effect of antigen dose time, i.e., wherein a primary response is assayed under similar induction conditions as shown in FIG. 51, but with antigen administration 14 days before sacrifice, the PFC production for the PWM, inductions are similar, again indicating that the 2 phenomena are related but separable. The data with the LPS-ALK induction are similar in both cases.

FIG. 54 shows the effect of soluble antigen, human ferritin. In this case both primary and secondary exposures gave similar results. The differences lay in the affinity of the produced antibody, and those experiments are still going on.

In summary, the biomodulator increases antibody production by 100- to 1,000-fold, converts >75% of production to IgG after sine immunization, increases affinity of product, and increases the efficiency of the hybridization process itself. The antigen concentration required is also reduced, 1 to 10 µg as opposed to 1 to 10 mg with the traditional technique. This, coupled with HPBL work in vitro, suggests that monoclonal antibodies can be made much more efficiently and with design control over the major parameters of the product. This data also shows the enhancement of antibody response in vivo which in and of itself is useful for enhanced vaccination response to other antigens.

Example 11

Enhanced Production of Biomolecules Using Biomodulators

A. Enhanced production of monoclonal antibodies

As noted in Examples 2, 3, and 10, biomodulators enhance the production and specificity of immunoobulins produced by immunological-cells, both in vitro and in vivo. The enhancement of production of such biomolecules can be used to produce these biomolecules per se.

B. Biomodulator enhancement of Interleukin 2 (IL-2, a known cellular differentiator and proliferator) production These experiments show the inter-relationship between the primitive biomodulators and an example of the more specific biological response modifiers, in this case IL-2, as well as showing how biomodulators can enhance their production in vitro.

Cultures of HPBL were established and treated with various concentrations of PWM (this particular preparation, although crude, is relatively free of proliferative capacity), and then after 24 hours of culture SRBC specific antigen was added. FIG. 56 shows the results from the IgG anti-SRBC specific response (the PFC assay). In this experiment there was a maximum PFC response after 67 hours of culture. There is a clear time and PWM dose dependency as has been noted above. When supernatants from these cultures were tested for IL-2 production with the Collaborative Research EIA assay kit it was found that the dose kinetics were similar to those seen with the plaque assay in that 1 $\mu$g PWM produced optimal IL-2 expression (approximately 6–9 U). However, the time kinetics indicated that maximum IL-2 expression was at 115 hours of culture, when the functional cell phenotype had already returned to baseline levels. This may suggest; 1) temporal displacement and dissociation of the two phenomena; 2) the differentiation response is inhibited by the high IL-2 production; or 3) there are complex series of effector functions involved in the secretion (IL-2) and membrane regulation of the product (IL-2R) and the simple assay of IL-2 levels is insufficient to establish the full functional picture. Some general comments can be made at this stage. There is a temporal relationship between the biomodulator induced antibody effector function and the IL-2 secretion. Addition of specific antigen to the biomodulator induced non-specific response actually reduces the IL-2 secretion by approximately 30% (data not shown) and shifts the optimal reactivity to longer incubation times at lower biomodulator concentrations. It has also been shown by others that Sw treatment augmented lymphoid IL-2R expression and IL-2 induced proliferation following mitogenic stimulation and further work showed that Sw treatment also augmented the LAK induction at normally sub-optimal stimulation doses (Sw is a potentiator).

C. Enhanced specificity of monoclonal antibody production

Figure 57A:
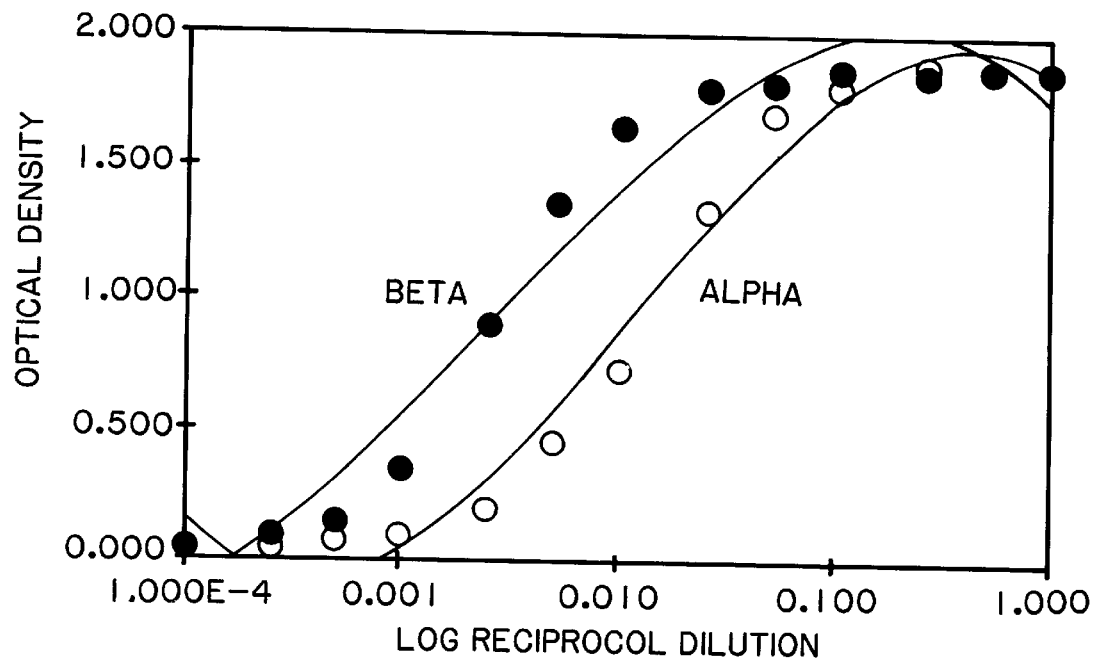
Figure 57B:
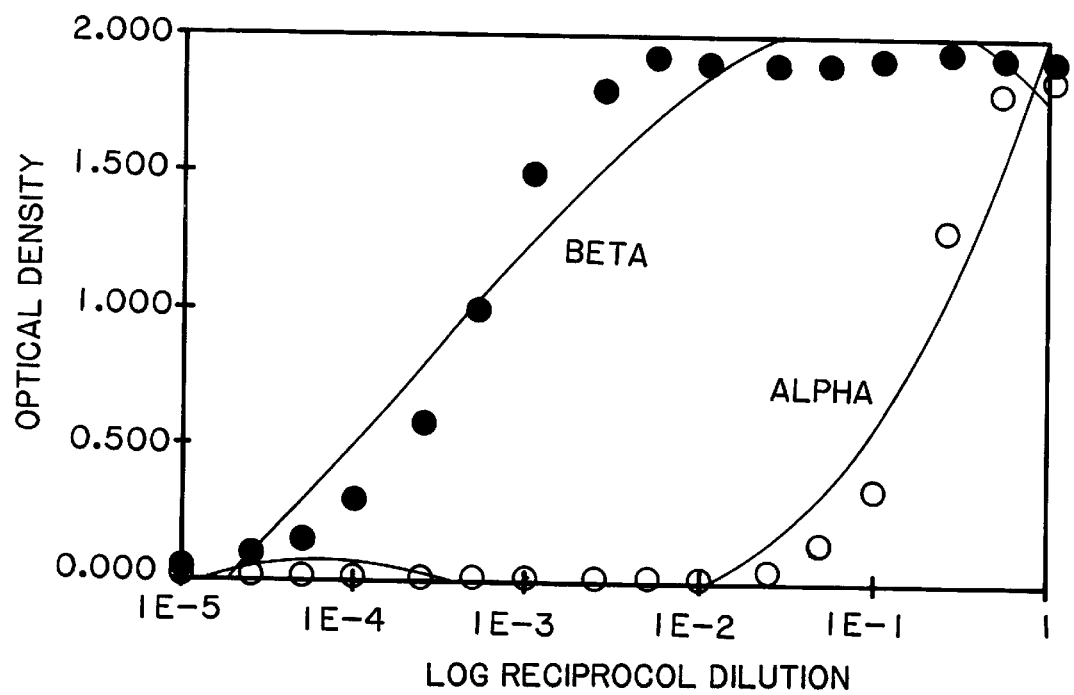

FIG. 57a shows the specificity of traditional monoclonal antibodies produced by the methods of Example 10 (in vivo induction of antibody followed by preparation of a monoclonal culture in vitro). FIG. 57b shows the specificity achieved when the animal is treated with 10 $\mu$g of PWM i.p. 3x/week for three weeks. The PWM stimulated antibody is much more specific for the antigen.

Example 12

Biomodulators Enhance Viability of Organ Transplants

Endothelial cells cultured with biomodulators, e.g., PWM at 1 $\mu$g or CAD at 10 ng/culture, are stable for 2 to 3 months in culture and continue to express their differentiative function. Vascular grafts prepared by growing allogenic endothelial cells on a vascular-graft matrix (e.g., according to Example 8, i.e., on microporous polyurethane) are maintained in culture in a fully prepared form until desired use.

Example 13

Treatment of Autoimmune Disease using Biomodulators

Biomodulators apparently affect the development of autoimmune disease in vivo. Autoimmune disease is the inability of the host to differentiate self from non-self. Therefore it is like the other models a regulation problem. The etiology of this diverse series of symptoms include; development of anti-self antibody (usually expressed as anti-DNA antibodies); thymic atrophy; IgG and IgM hyperproduction; and lymphoid hyperplasia.

BSXB male mice (congenital autoimmune), 4 groups—control, 0.1, 1.0 and 10 $\mu$g PWM i.p. 3x/week for 3, 9 and 14 weeks duration (3 animals per group per concentration per time point). Assays included PFC (protocol given in other examples) to look at immunoglobulin hyperproduction; anti-ANA titrations (see Yoshida et al, J. Clin. Invest. 76, 685–694, (1985)), and T and B cell mitogen responses (for protocol see above) to look at lymphoid hyperplasia.

Figure 58:
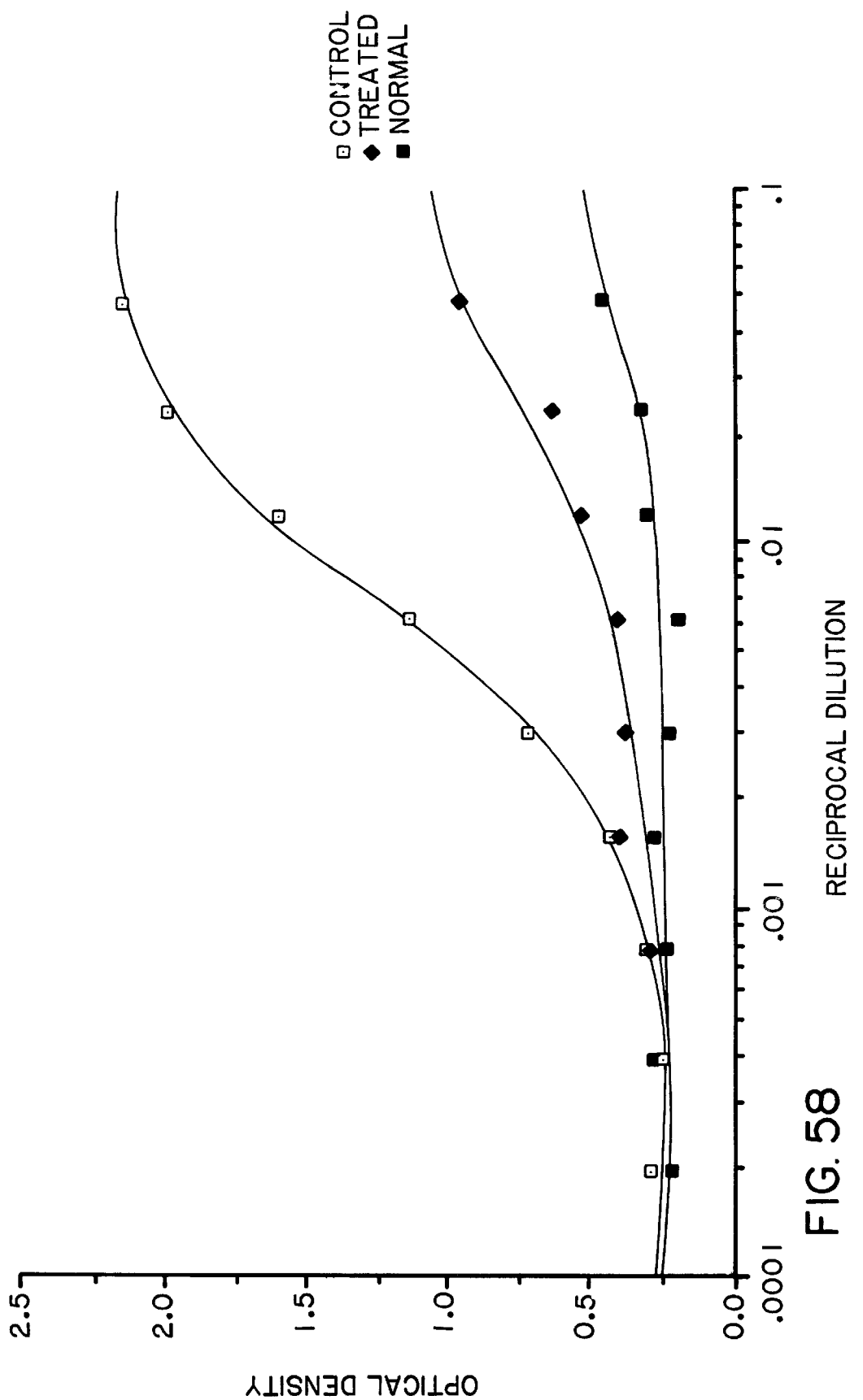

FIG. 58 shows titration curves for an untreated control BSXB mouse, one treated with b 0.1$\mu$g PWM M, W, F for 14 weeks, and a non-autoimmune mouse strain (normal). It is clear that the treatment has significantly decreased the anti-ANA antibody. This is dose-dependent and time-dependent.

Figure 59:
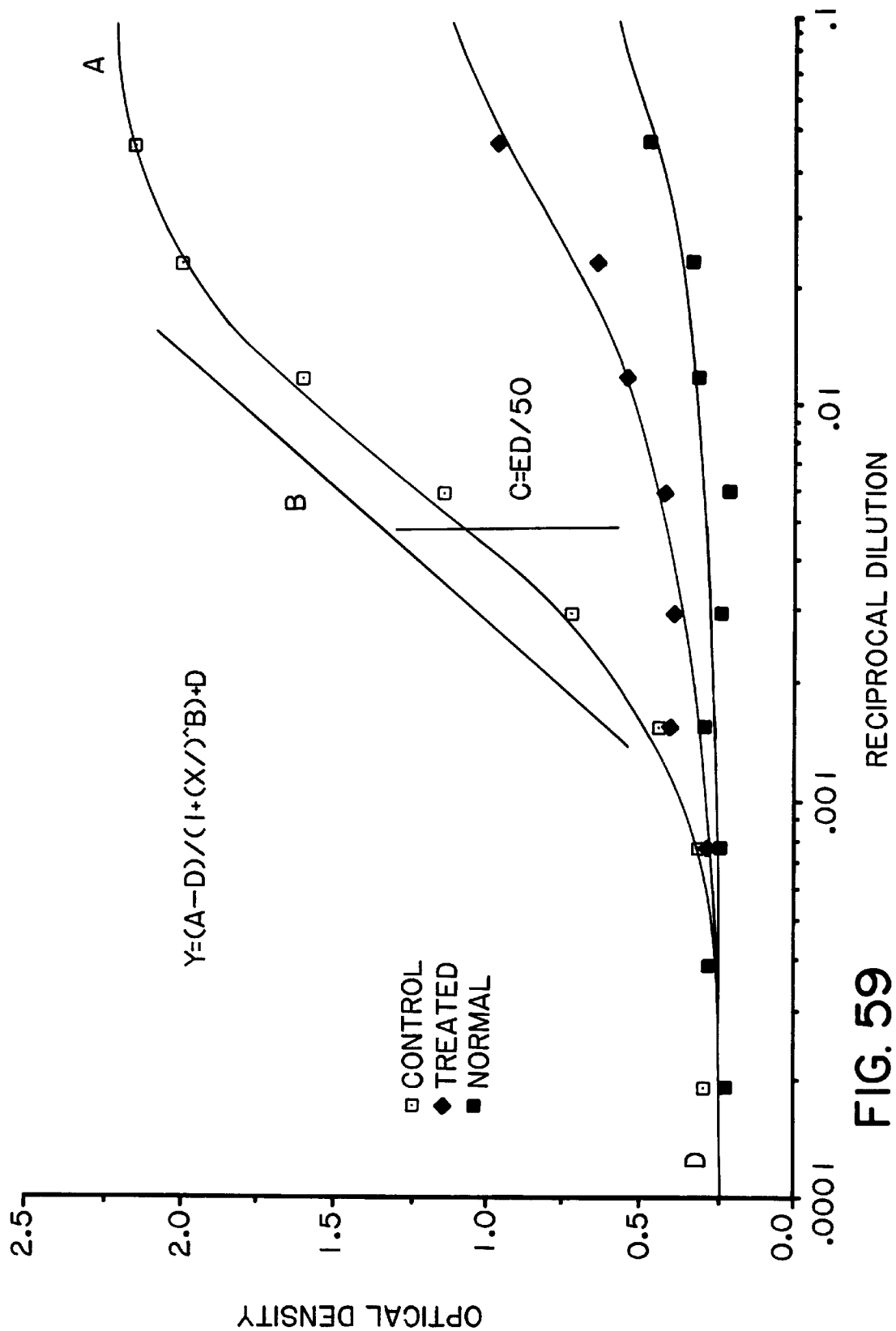

FIG. 59 shows the basis for the analysis of the ANA antibody titer—the four parameter logistic analysis. The B is the slope of the curve and C is the ED/50 (A and D are used for control and statistical comparisons). Using this analysis the BSXB mouse titers were analyzed and the data shown in Table 1. Pay special attention to the B and C parameters and the P values for the comparisons.

Figure 61:
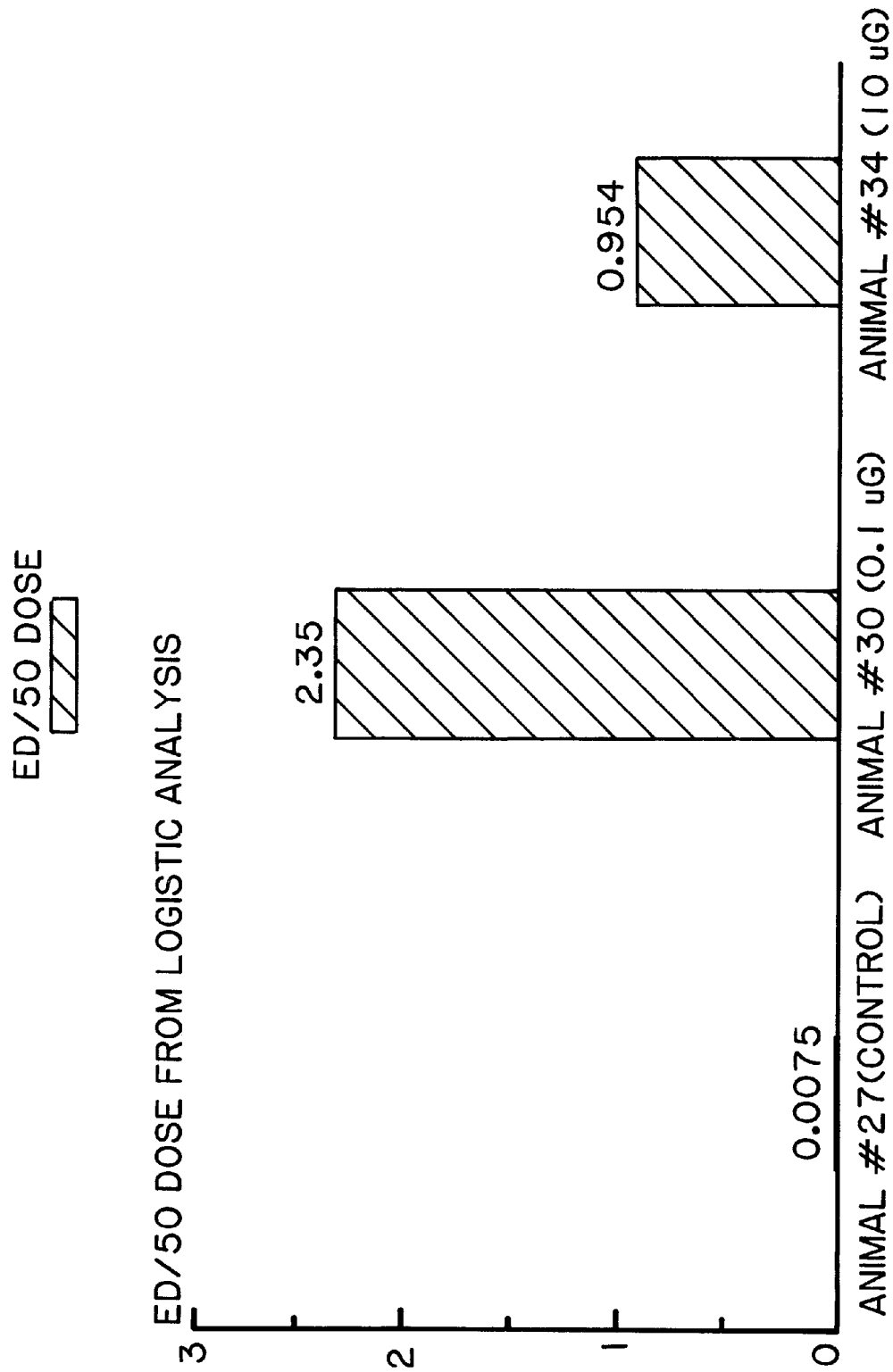

FIG. 60 titer data for Bx3B mice. FIG. 61 shows B (ED/50) data extracted from FIG. 60. The treatment has decreased the ANA titer by almost 3 logs and in fact brings the titration curve close to non-auto-immune levels.

Figure 62:
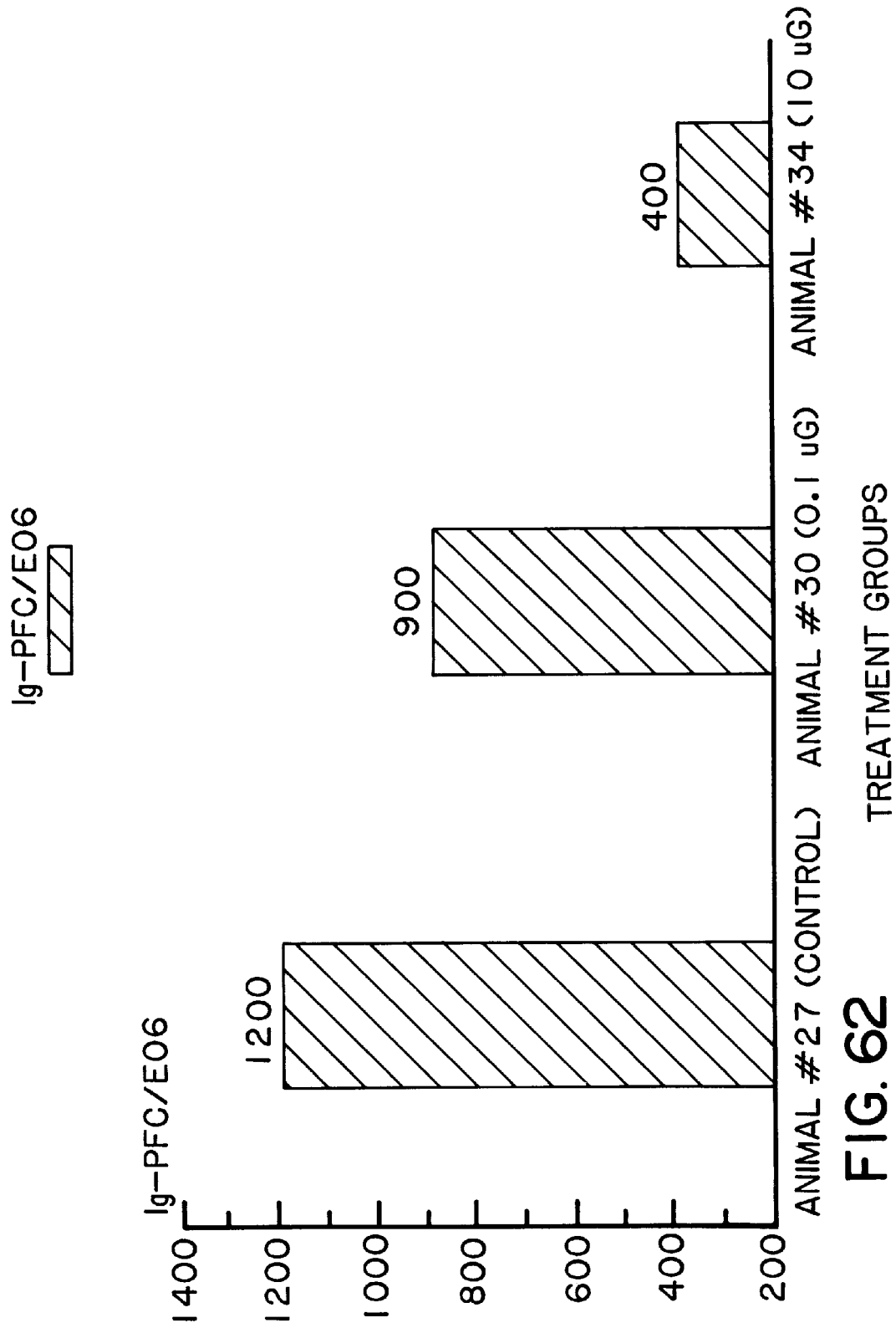

FIG. 62 shows data from the assessment of non-antigen specific immunoobulin. The control animal produces 1200 PFCs per million cells. This is 10 to 20 times normal production (hyper-immunoobulin). Animal #30 (0.1 $\mu$g) produces 900 and the 10 $\mu$g animal group produces only 400. This again represents a dose-dependent reduction (re-assert control) in antibody production.

Figure 63:
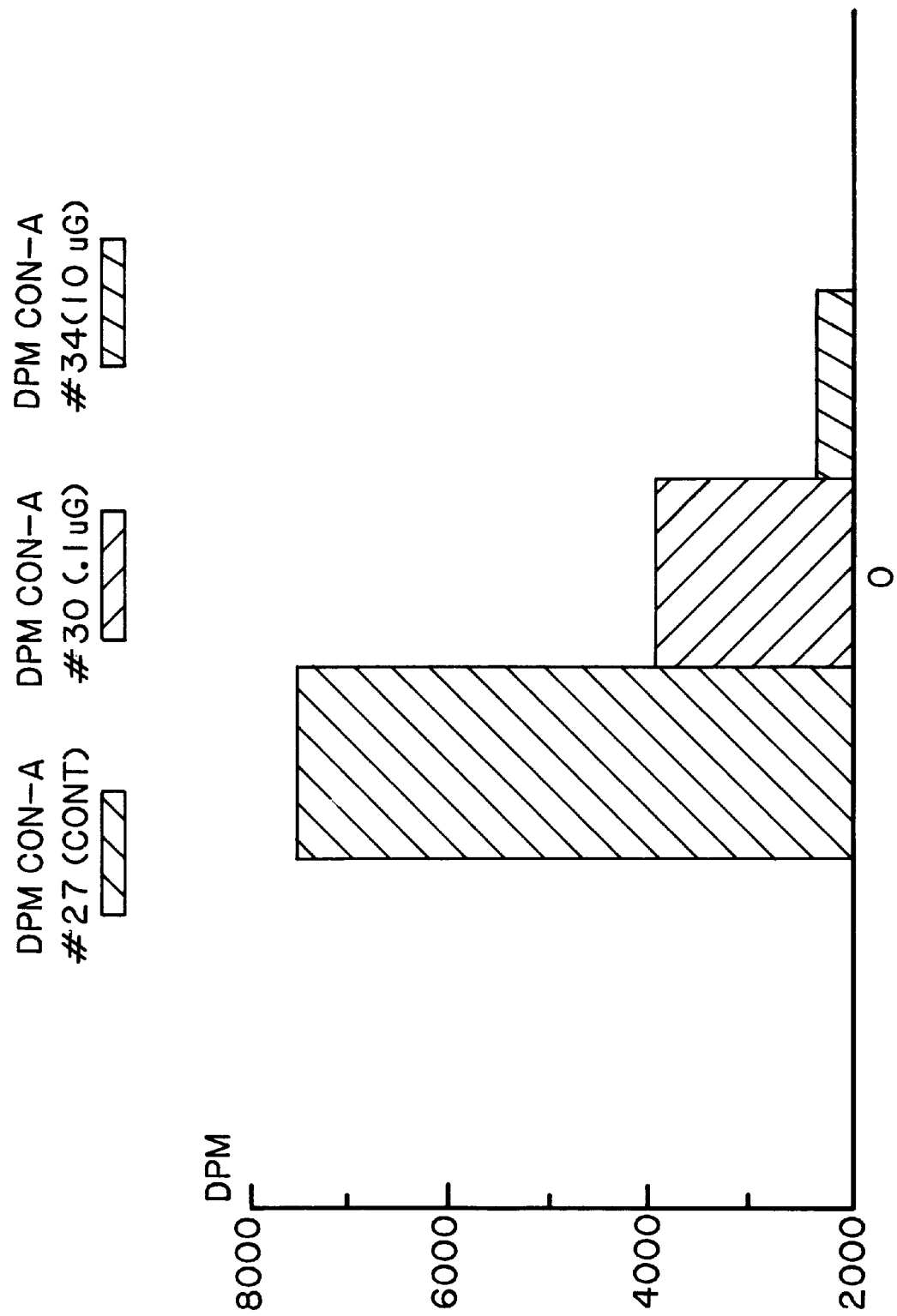

FIG. 63 shows data from the mitogen stimulation experiments. In this case the no mitogen controls show that the untreated animal's spleen background proliferative rate is 4 times greater than the 10 μg treated animal. This addresses the hyper-proliferative symptom of autoimmune disease.

Figure 64:
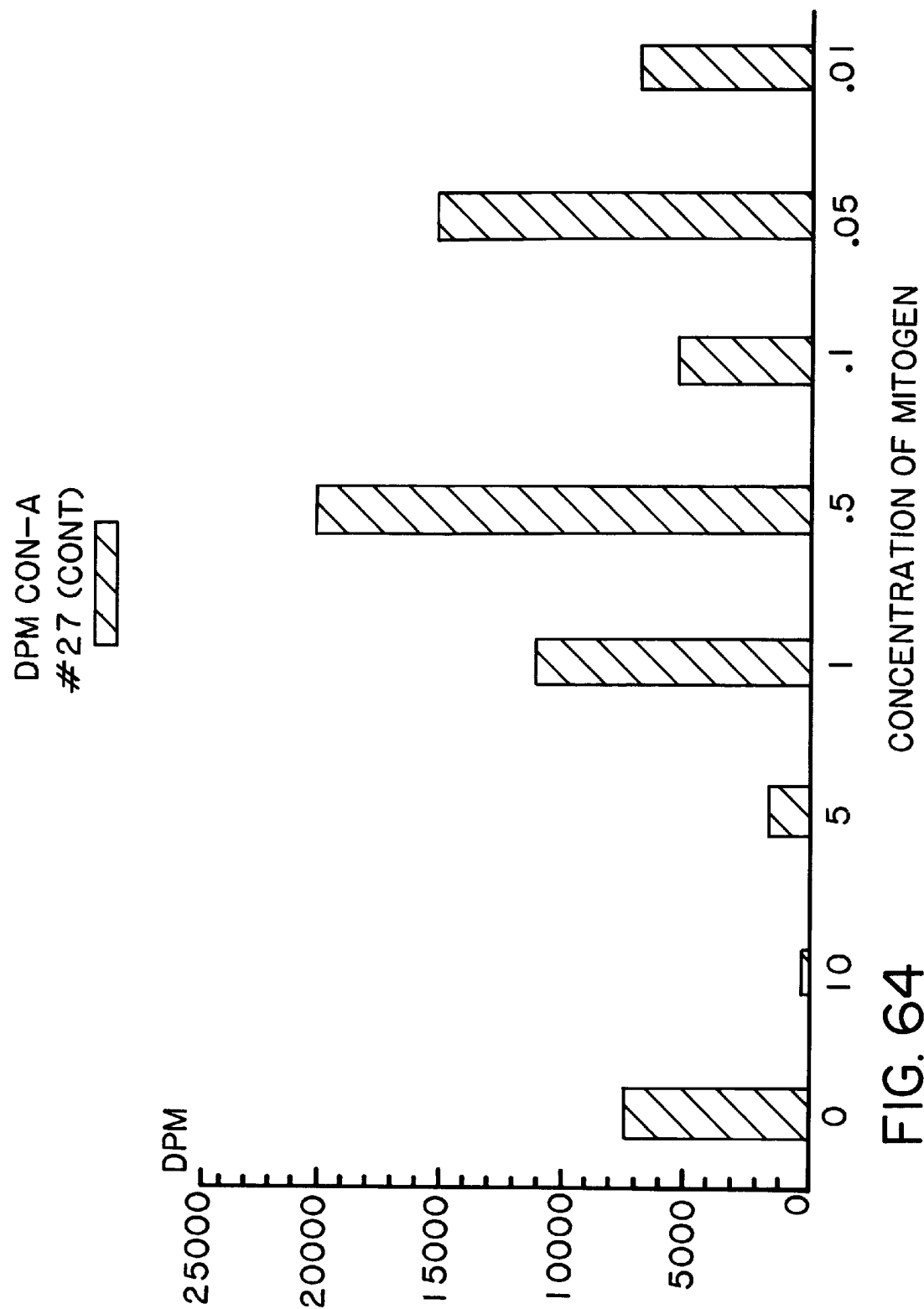
Figure 65:
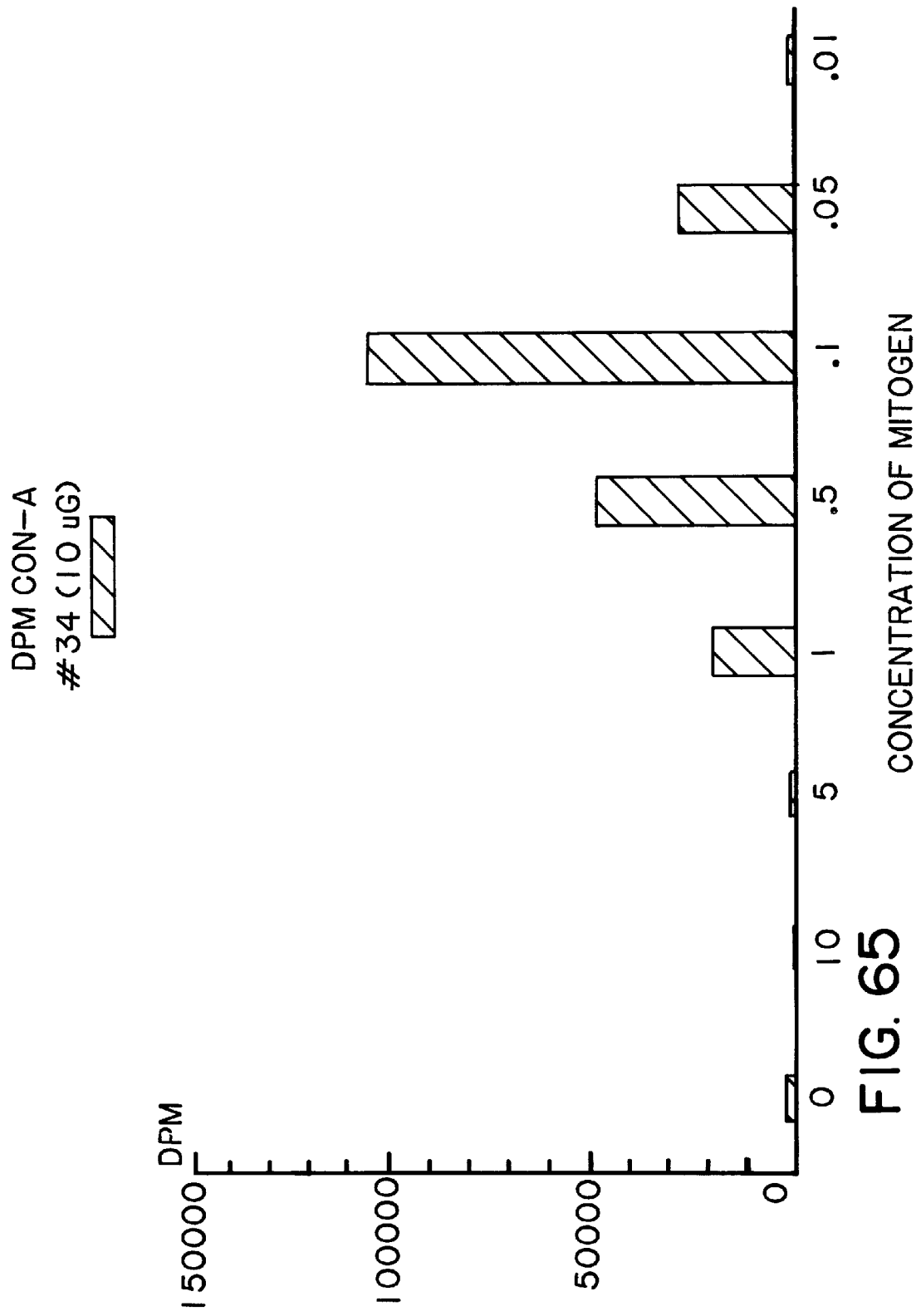

FIG. 64 shows the concentration dose-response curve of untreated control BSXB spleen cells to CON-A, a T-cell mitogen. This curve is typical of an aberrant mix of T-cells. The bell shaped dose-response curve of FIG. 65 (10 μg PWM) is typical in shape of normal T-cell responses. The peak stimulation at 0.1 μg CON-A in FIG. 65 does suggest the predominance of an immature T-cell population in the spleen. This has mechanistic significance for the effect of the biomodulator on the development and severity of autoimmune disease.

METHODS

A. Effect of Pokeweed Mitogen on Mitogen Stimulation

The mitogen assay used four mitogens that stimulate proliferation of different splenocyte populations. These mitogens were PHA (phytohemagutinin—Difco Laboratory), Con-A (concanavalin-A—SIGMA), LPS (lipopolysaccharide—SIGMA) and PWM (pokeweed mitogen prepared by the Reisfeld method). The splenocytes were plated at $1\times10^6$ cells/ml (100 μl/well) into sterile NUNC flat bottom 96 well trays. The concentrations for the mitogens were 10 μg/μl, 5 μg/μl, 1 μg/μl, 0.5 μg/μl, 0.1 μg/μl, 0.05 μg/μl, 0.01 μg/μl/μl and a blank. All the dilutions were done in triplicate. The trays were incubated for 72 hours in a $CO_2$ incubator at 37° C. and 0.5 μCi/10 μl $^3$H-thymidine (ICN, 6.7 Ci/mmole activity) was then added to each well for another 18 hour incubation. After a total of 96 hours the cells were harvested with a 12 channel automatic cell harvester (Richter and Associates) and the activity, as $^3$H-thymidine in newly synthesized DNA, was collected on Whittman cellulose filters. The samples were counted on a LBK/Pharmacia 4110 liquid scintillation counter for one minute, providing a minimal counting statistic of ±5%. The results are presented as a Stimulation Index (S.I.), which is the ratio of the treated mice versus the baseline mice.

B. Effect of Pokeweed Mitogen on Humoral Immunity

The plaque forming cell (PFC) assay was done according to the following method:

The splenocytes were washed in serum-free RPMI-1640 and brought to a final concentration of $1\times10^6$ cell/100 μl. Sheep red blood cells (SRBC), from The Colorado Serum Company, were labelled with protein A from *Staphylococcus aureus* (SIGMA). The sRBC's were washed 3 times with saline (0.85% NaCl), the packed cells were then incubated with 1 ml of protein A (0.5 mg/ml saline) and 10 mls of saline containing 0.1 μl of $CrCl_3$, for 20 minutes. The sRBC's were then washed 3 times with PBS and suspended in PBS to make a 30% solution. The sRBC and splenocytes were combined with SeaPlaque agarose (FMC Corporation) and smeared on a 75 mm×50 mm microscope slide to form a lawn of target red blood cells with uniformly dispersed effector cells. Each sample was done in triplicate. The agarose was allowed to harden and the slides were placed in trays containing serum-free RPMI-1640. The trays were incubated at 37° C. in a $CO_2$ incubator for 90 minutes. After incubation the slides were placed in slide holders containing normal saline for a wash step. The rabbit/anti-mouse antibody (DAKO Corporation) was diluted 1:400 with serum free RPMI-1640 and added to the slide trays. Following another 90 minutes incubation at 37° C. in a $CO_2$ incubator the slides were again washed. Fresh frozen guinea pig compliment (GIBCO) (2%) in serum free RPMI-1640 was added to the slide trays and incubated for another 60 to 90 minutes dependent on the time necessary for plaques formation. The number of plaques were the counted. The results were reported as number of plaque forming cells per $1\times10^6$ splenocytes.

Example 14

Effects of Swainsonine on Tumors, Cellular Immunity and Humoral Immunity

A. Methods

1. Cell Line Culture

The B16 melanoma cells were purchased from American Type Culture Collection (ATCC). They were maintained in complete A-MEM (SIGMA) (with 10% fetal calf serum (FCS) (Sigma), 100 U/ml penicillin (Sigma), 100 μg/ml streptomycin (Sigma) and 2 mM utamine (Sigma)) in Corning 75 cm$^2$ straight necked flasks (T75) and grown with 5.5% $CO_2$ in air with 95% humidity in a New Brunswick Scientific water jacketed incubator. They had a population doubling time of approximately 18 hours and were maintained in log phase growth. They were harvested using 1× Trypsin-EDTA (Sigma), centrifuged at 100×g with a Beckman TJ6 centrifuge, counted using a hemocytometer and stained with trypan blue to determine viability. The cells used for injection into the mice were washed three times in phosphate buffered saline (PBS), counted and resuspended in PBS at a final concentration of $6\times10^6$ cells per ml.

The swainsonine, purchased from Boehringer Mannheim, was initially suspended in PBS at 100 μg/ml. Subsequent dilutions utilized in the following experiments were made in PBS.

2. Effect of Swainsonine on Tumor Growth

Fifteen female C57B1/6 mice (6 weeks old, from Harlan Sprague Dawley Laboratories) were treated 3 times per week on a Monday-Wednesday-Friday (MWF) schedule for three weeks prior to the injection of the $6\times10^5$ B16 melanoma cells. The treatment consisted of 0.1 ml (total volume) intraperitoneal injections of swainsonine in the mornings before 9:00 am. The treatment groups were as follows:

1. Control—tumor with no swainsonine (PBS only)
2. 1.0 μg swainsonine with tumor (40 μg/kg/dose)
3. 0.1 μg swainsonine with tumor (4.0 μg/kg/dose)
4. 0.01 μg swainsonine with tumor (0.4 μg/kg/dose)
5. 0.001 μg swainsonine with tumor (0.04 μg/kg/dose)

The MWF treatment with the swainsonine continued after the tumor cell injection until the termination of the study. Once the tumor was palpable, electronic calipers were used to measure the length (l), width (w) and depth (d) of the tumor. The volume of the tumor was then determined by $V=\pi r^2 \times d$, with the assumption that the tumor is a sphere, then $r=(l+w)/4$.

2. Effect of Swainsonine on Cell Mediated Immunity

The cytotoxicity assay used two targets: YAC-1, for natural killer cell targets and B16 melanoma cells, for cytolytic T-cell targets. The YAC-1 cells were labelled in GKN (ucose/KCl/NaCl) with $^{51}$Cr (NEN-DuPont, 400–1200 Ci/g activity) for 60 min. The B16's were $^{51}$Cr labelled in complete α-MEM media for 60 min. Both targets were washed twice through whole fetal calf serum to remove damaged and dead cells and then suspended in complete RPMI at a final concentration of $1\times10^5$ cells/ml. The spleen cells (effector cells) were plated in round bottom 96 well trays starting at $1\times10^7$ cells/ml (100 μl/well), using a halving dilution that provided splenocyte concentrations of $10^6$, $5\times10^5$, $2.5\times10^5$, $1.25\times10^5$, $6.25\times10^4$ and $3.125\times10^4$, all done in triplicate. The target cells were added at $1\times10^4$ cell/100 μl/well; this gave an effector:target cell ratio ranging from 100:1 to 3:1. Controls included spontaneous $^{51}$Cr release and 100% lysis (10% triton treatment). The trays were centrifuged at 50×g for 5 min. and incubated in a $CO_2$ incubator at 37° C. for 16 hours. The trays were spun again at 50×g for 5 minutes and 100 μl removed from each well for counting. A Packard gamma counter (United Technologies) was used for counting. Each sample was counted for 1 min. giving a 5% counting efficiency. The following equation was used to determine percent lysis.

(cpm sample—cpm spon. release)
(cpm 100% lysis—cpm spon.release)×100

The effector:target ratios were then plotted against percent lysis and a simple line equation was determined for each treatment group. The slope of this line was then used to determine the total effector kill efficiency.

3. Effect of Swainsonine on Humoral Immunity

The plaque forming cell (PFC) assay was done according to the method developed by Jerne and Nordin (1963). The splenocytes were washed in serum-free RPMI-1640 and brought to a final concentration of 1×10⁶ cell/100 μl. Sheep red blood cells (sRBC), from The Colorado Serum Company, were labelled with protein A from *Staphylococcus aureus* (Sigma). The sRBC's were washed 3 times with saline (0.85% NaCl), the packed cells were then incubated with 1 ml of protein A (0.5 mg/ml saline) and 10 ml of saline containing 0.1 μl of $CrCl_3$ (35% solution) (Aldrich), for 20 minutes. The sRBC's were then washed 3 times with PBS and suspended in PBS to make a 30% solution. The sRBC's (50 μl) and splenocytes (100 μl) were combined with Sea-Plaque agarose (FMC Corporation) and smeared on a 75 mm×50 mm microscope slide to form a lawn of target red blood cells with uniformly dispersed effector cells. Each sample was done in triplicate. The agarose was allowed to harden and the slides were placed in trays containing serum-free RPMI-1640. The trays were incubated at 37° C. in a $CO_2$ incubator for 90 min. After incubation the slides were placed in slide holders containing normal saline for a wash step. The rabbit/anti-mouse antibody (DAKO Corporation) was diluted 1:400 with serum free RPMI-1640 and added to the slide trays. Following another 90 min. incubation at 37° C. in a $CO_2$ incubator, the slides were again washed. Fresh frozen guinea pig complement (GIBCO) (2%) in serum-free RPMI-1640 was added to the slide trays and incubated for another 60 to 90 min. depending on the time necessary for plaque formation. The number of plaques were counted and the results reported as number of plaque forming cells per 1×10⁶ splenocytes.

B. Results

1. Effect of swainsonine on solid tumor growth

Figure 66:
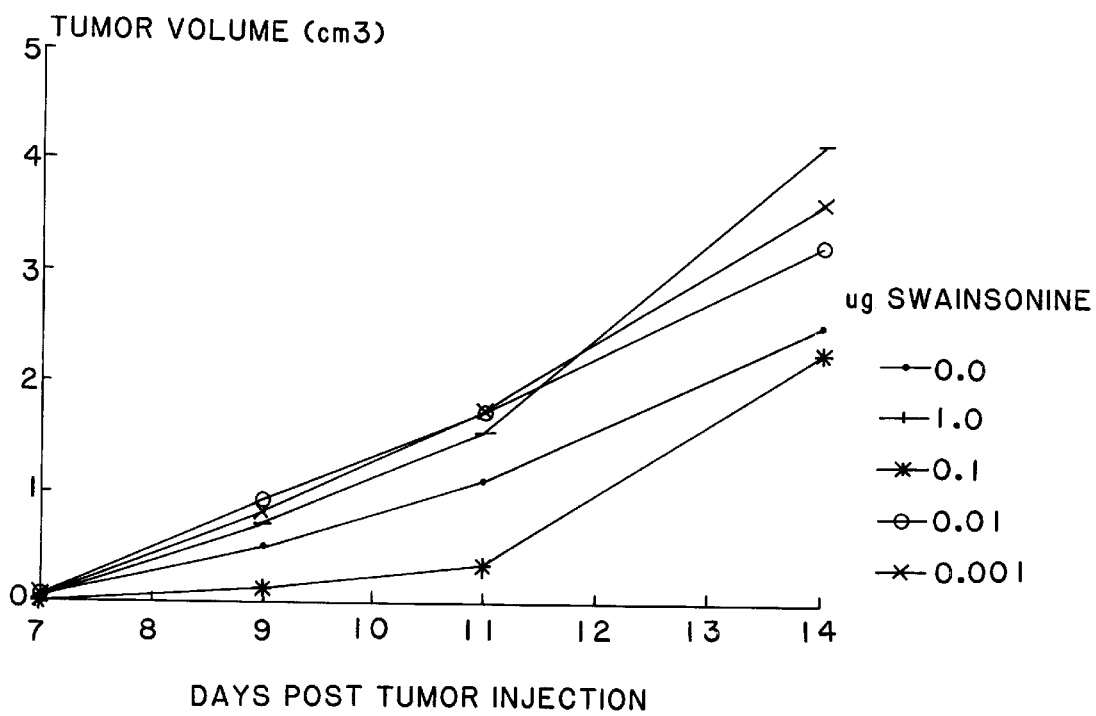

The effect of swainsonine on the growth of B16 melanoma solid tumors in vivo was investigated by pretreating the mice for 3 weeks and then injecting melanoma cells into the right shoulder area. Palpable tumors in the control group (0.0 μg Sw) were present on day 5 post tumor cell injection. These tumors were the size of a grain of rice and could not be accurately measured. FIG. 66 graphically presents tumor growth rate versus time. Tumors whose size could be reliably measured were present on day 7 in the controls (Table I). Swainsonine showed a dose-dependent effect on tumor growth. The mice that were treated with 0.1 μg Sw did not have palpable tumors until day 7 and measurable tumors until day 9. This was a delay of two day in both instances. The 0.1 μg Sw slowed growth of the melanoma tumor. The tumors in the 0.1 μg Sw group were 74% (p=0.03) smaller in size on day 9 compared to the controls and 68% (p=0.003) smaller on day 11. The highest dose (1.0 μg Sw) and the lower doses (0.01 and 0.001 μg Sw) were less effective at inhibiting the B16 growth (p<0.5).

2. Effect of swainsonine on cytotoxic T-lymphocytes

Figure 67:
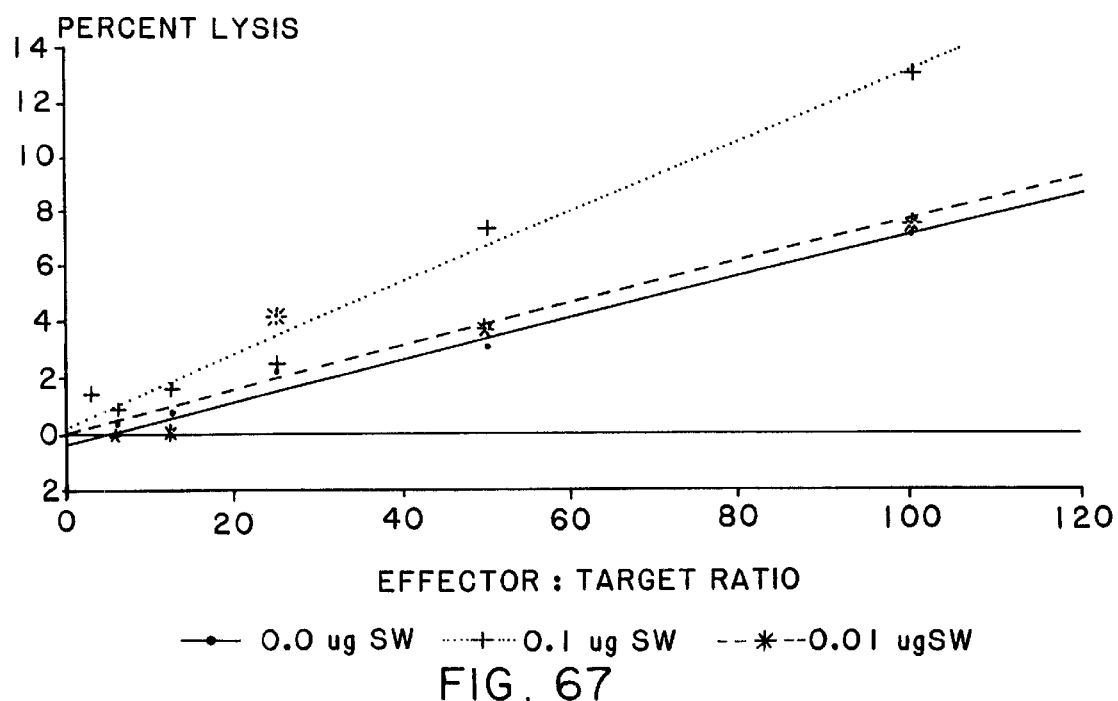
Figure 68:
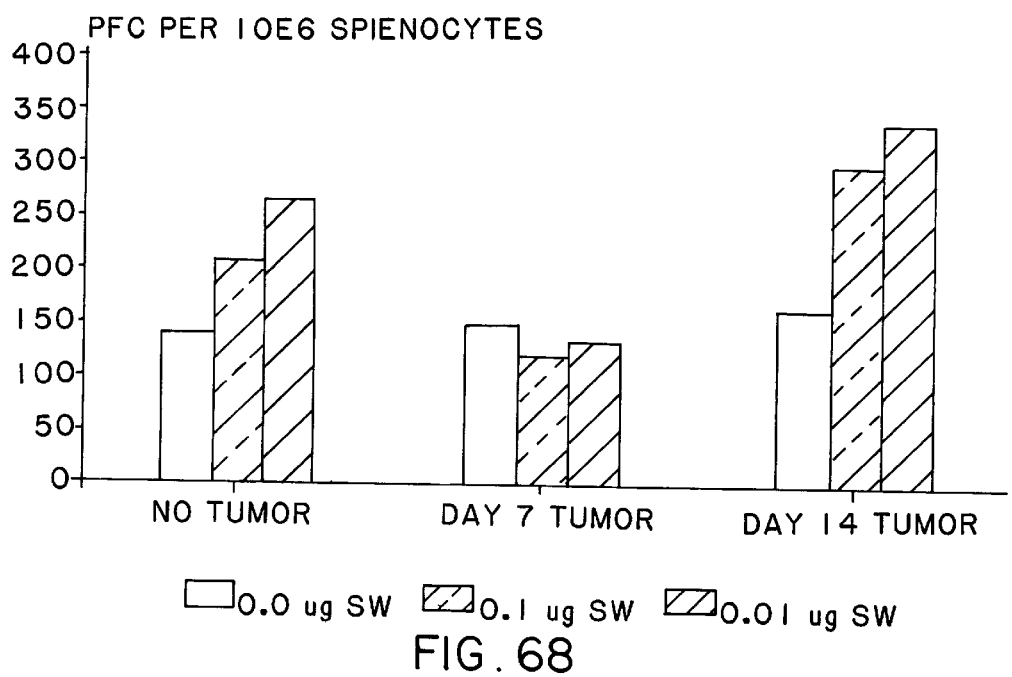
Figure 69:
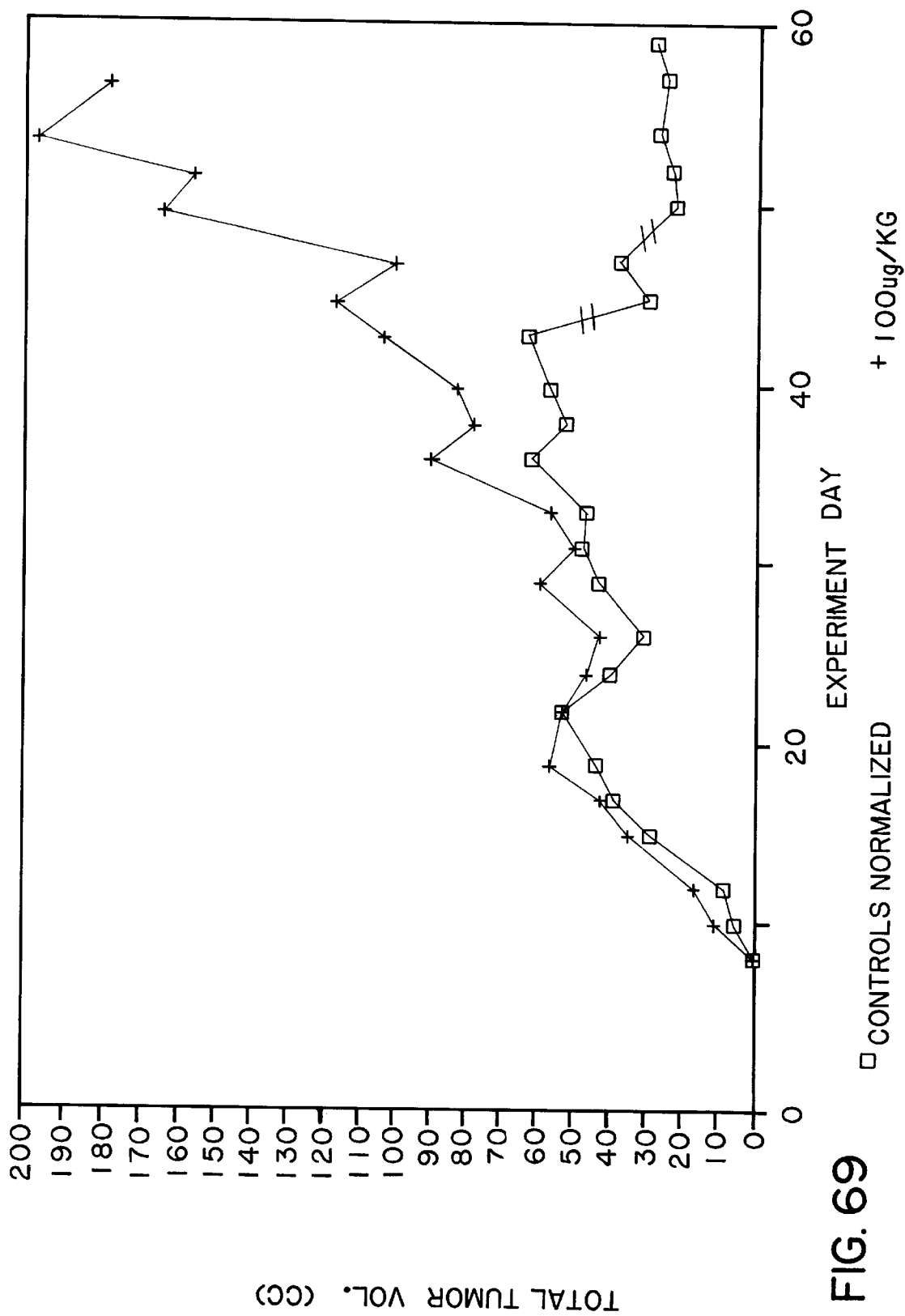
Figure 70:
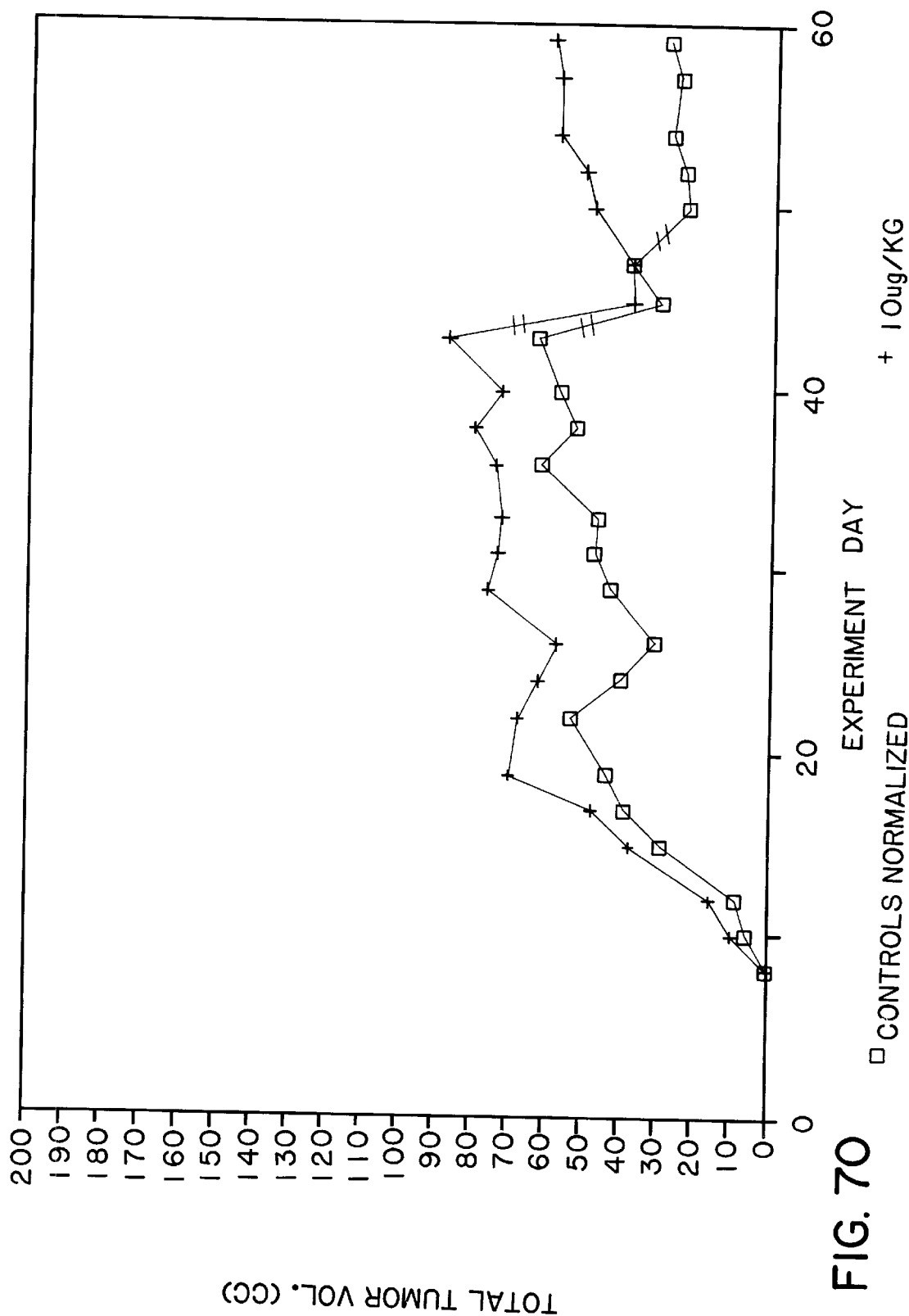
Figure 71:
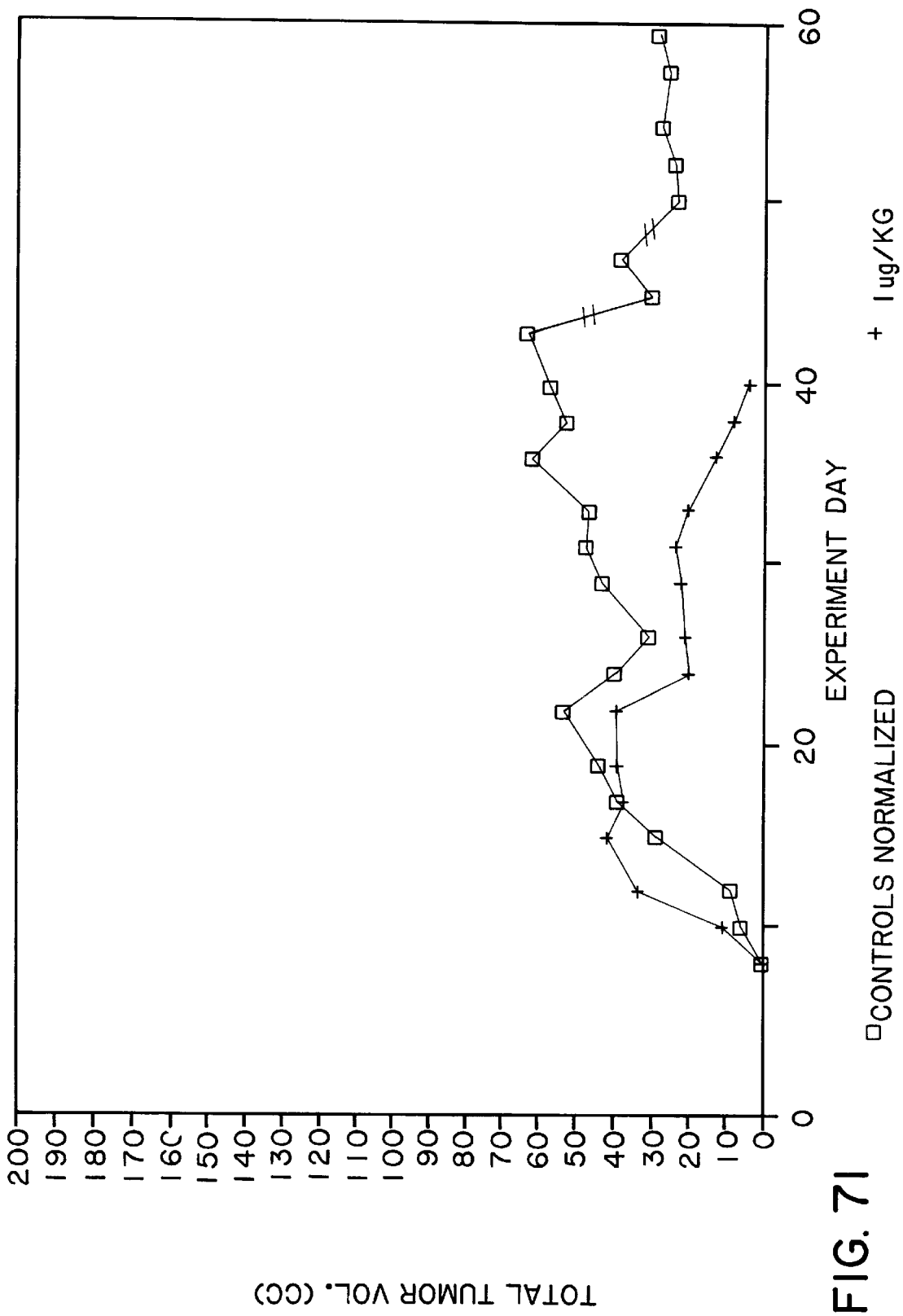

The ⁵¹Cr cytotoxicity assay was also run with the B16 melanoma cells as the target and the splenocytes from the same mice as above as the effector cells. See FIG. 67. The baseline mice (no tumor/no Sw) and the control mice (tumor/no SW) had very similar line shapes and slopes. There were significant differences (p=0.03) between the presence and absence of tumor (see Table in FIG. 68). The slope of the 0.1 μg Sw treated mice was greater than that of the control and of the 0.01 μg treated mice. Swainsonine had a positive effect on the CTL response. Mice that received 0.1 μg Sw alone had a 104% increase in the line slope indicating an increase in kill efficiency. The addition of tumor (7 day) caused a 228% increase above baseline and a 127% increase over the control mice with day 7 tumor.

Swainsonine shifted the cytotoxicity from non-specific natural killer activity to specific CTL activity. There was a 17.5% convertability from NK to CTL in the tumor control mice. There was 39% convertability from NK to CTL with the 0.1 μg Sw treated mice with tumors present. These data indicate a Sw dependent effect on both host immunity and the tumor itself.

3. Effect of swainsonine on humoral immunity

Figure 1C:
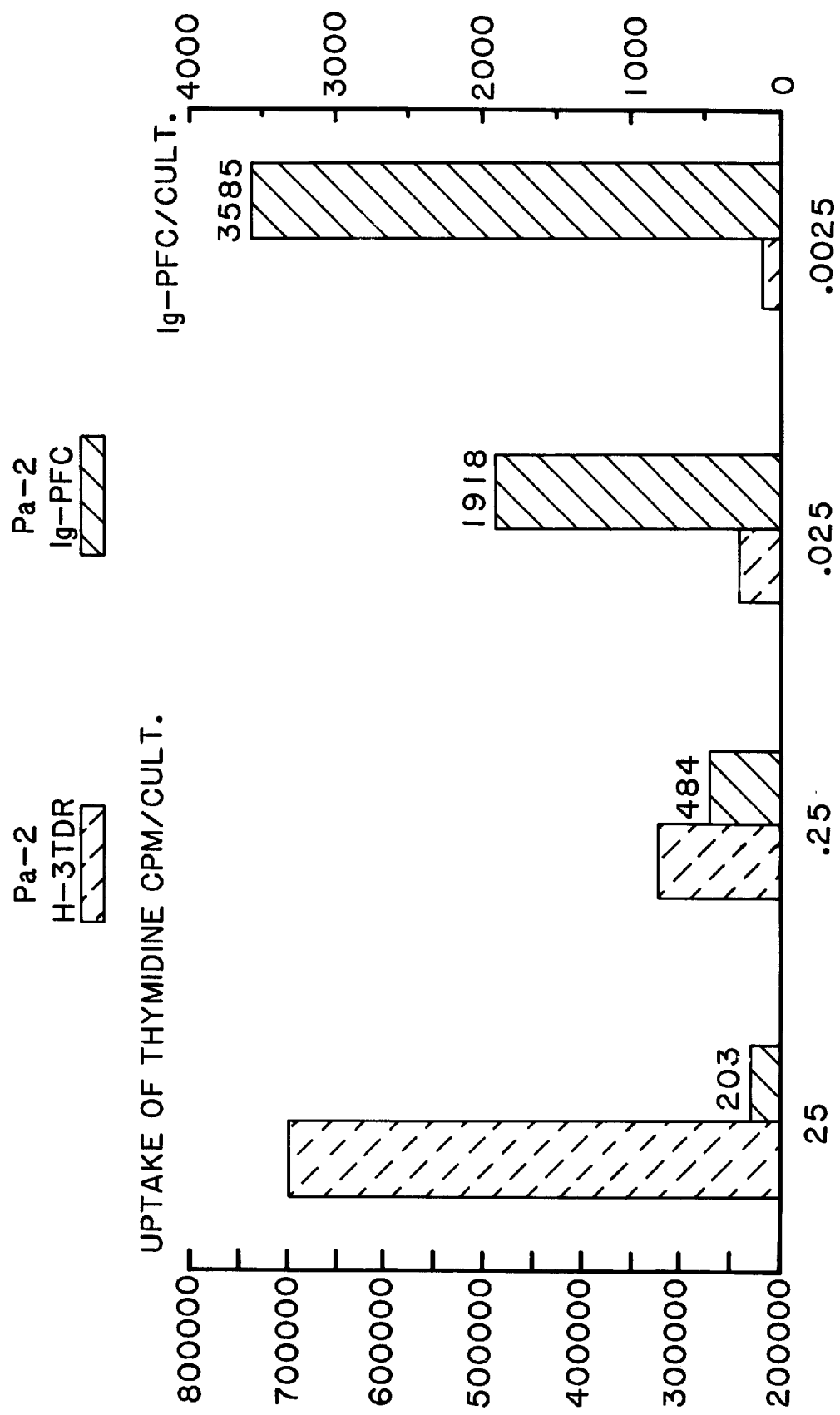
Figure 1D:
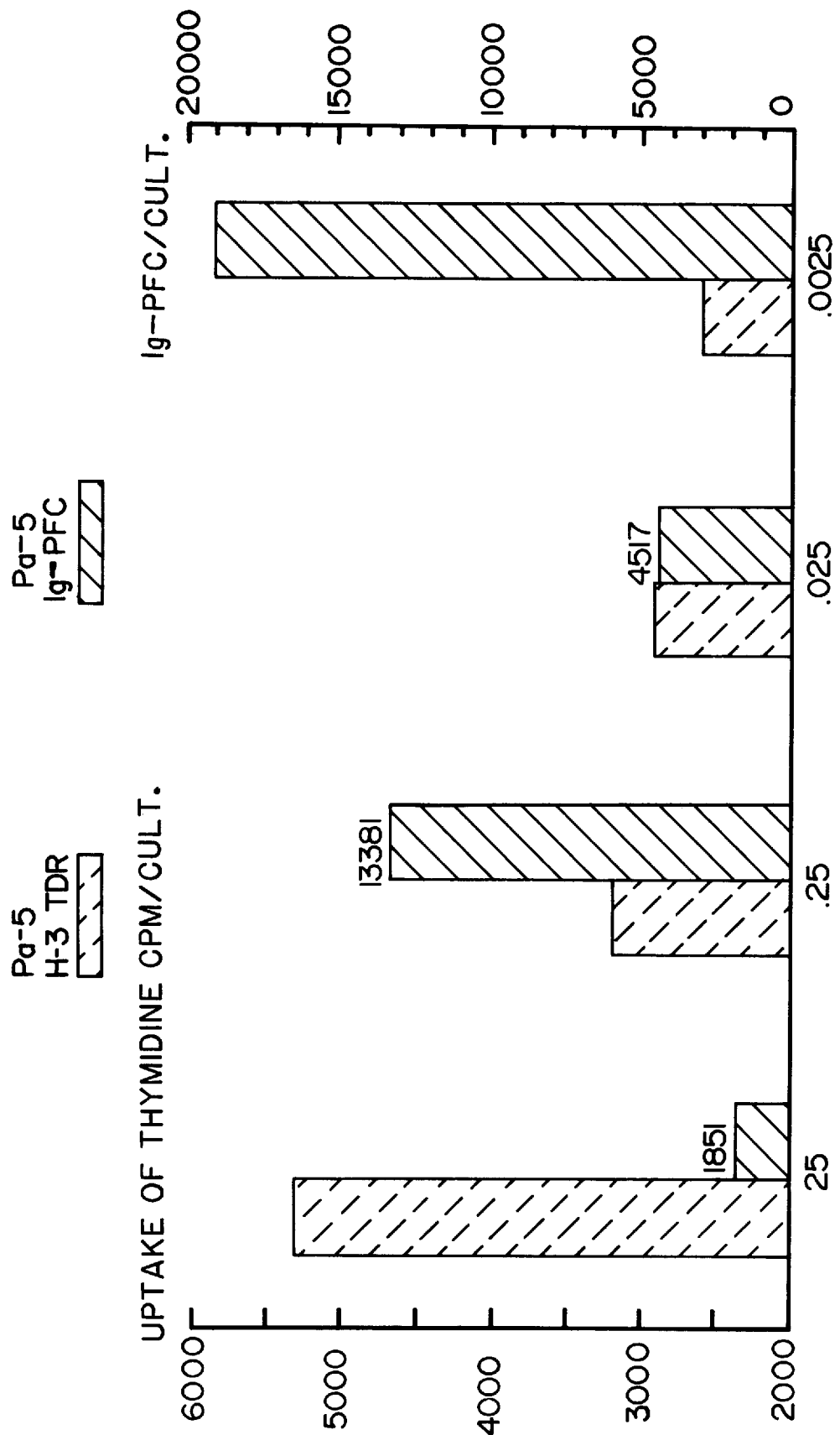
Figure 2:
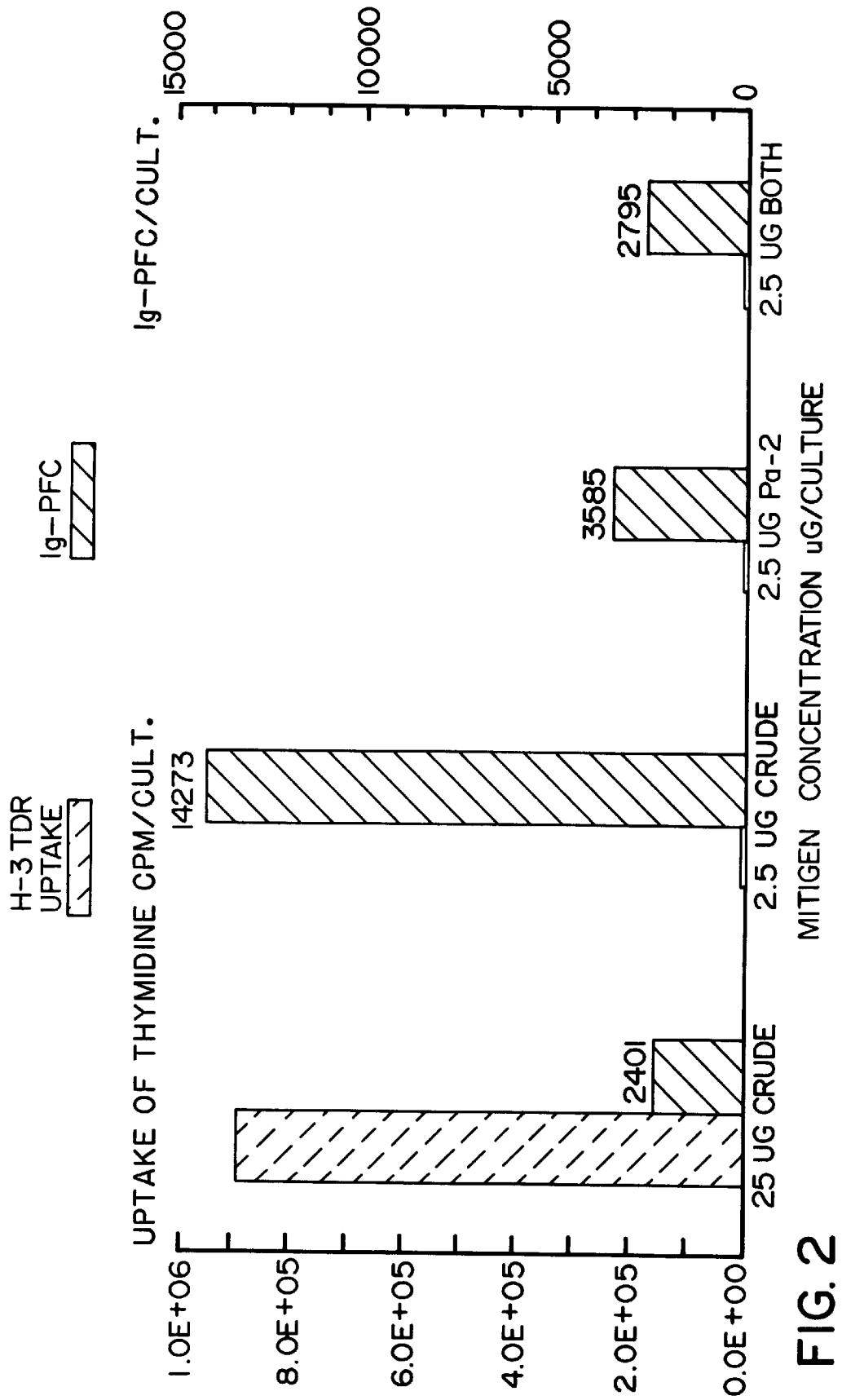
Figure 3:
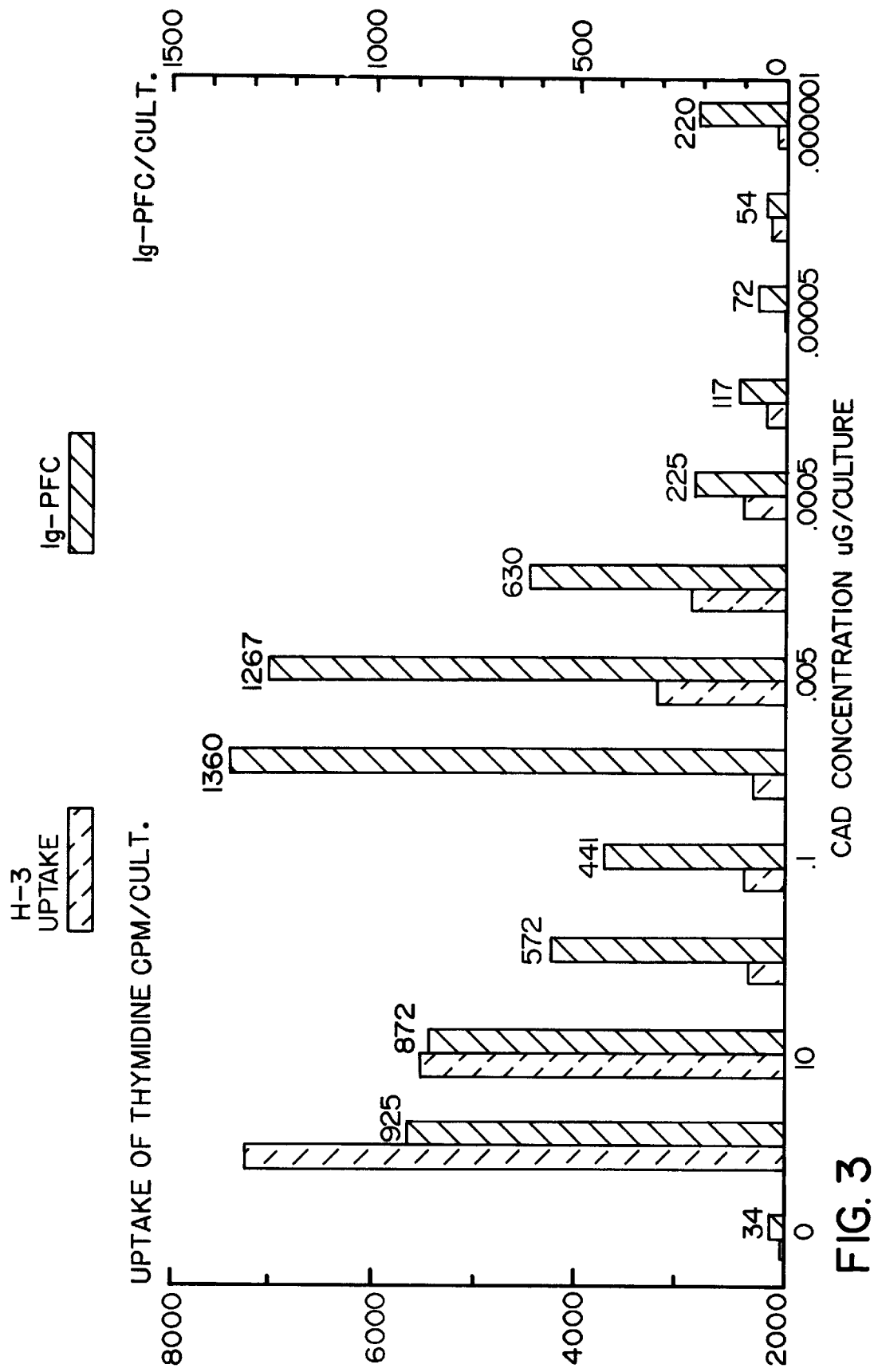
Figure 4A:
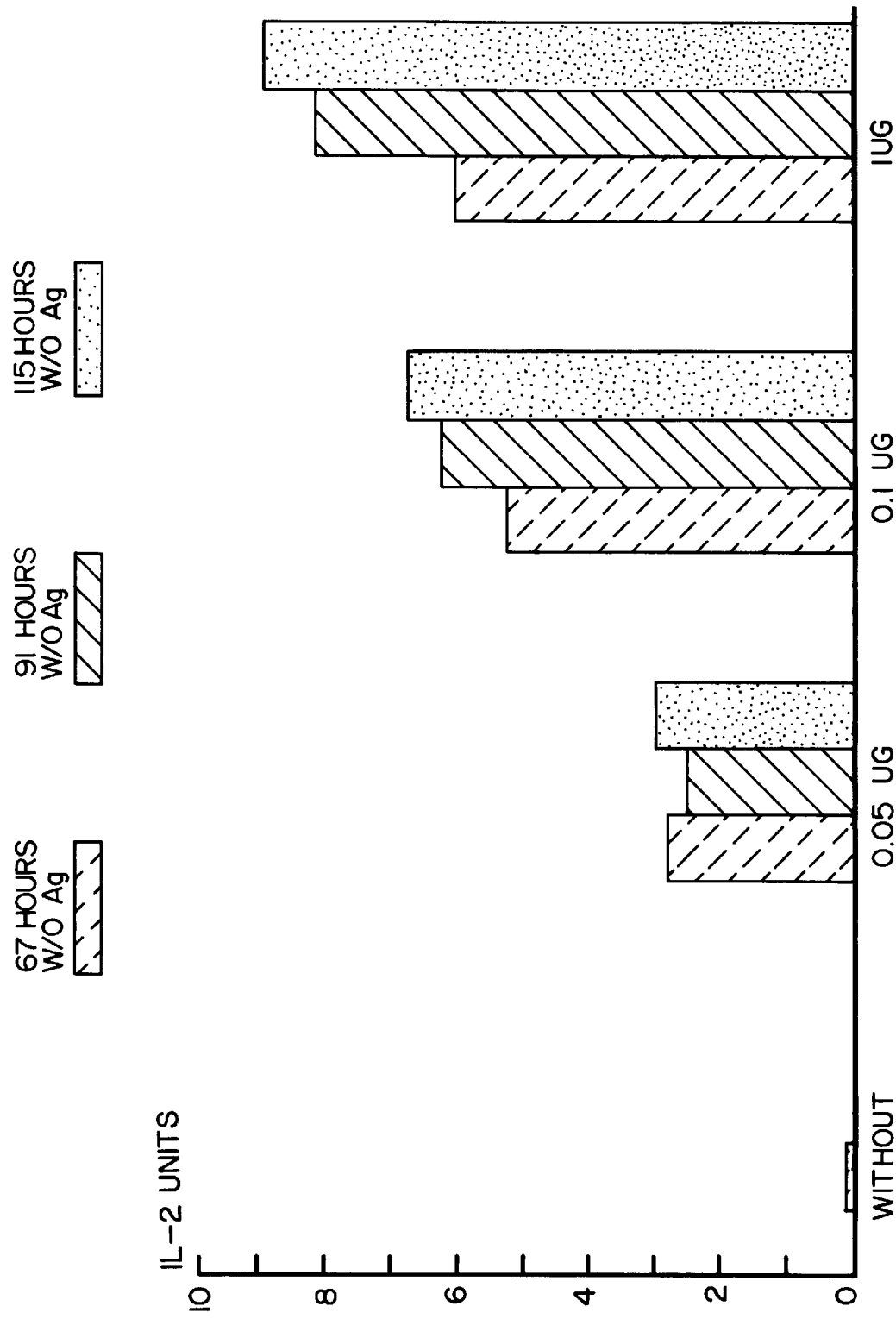
Figure 5A:
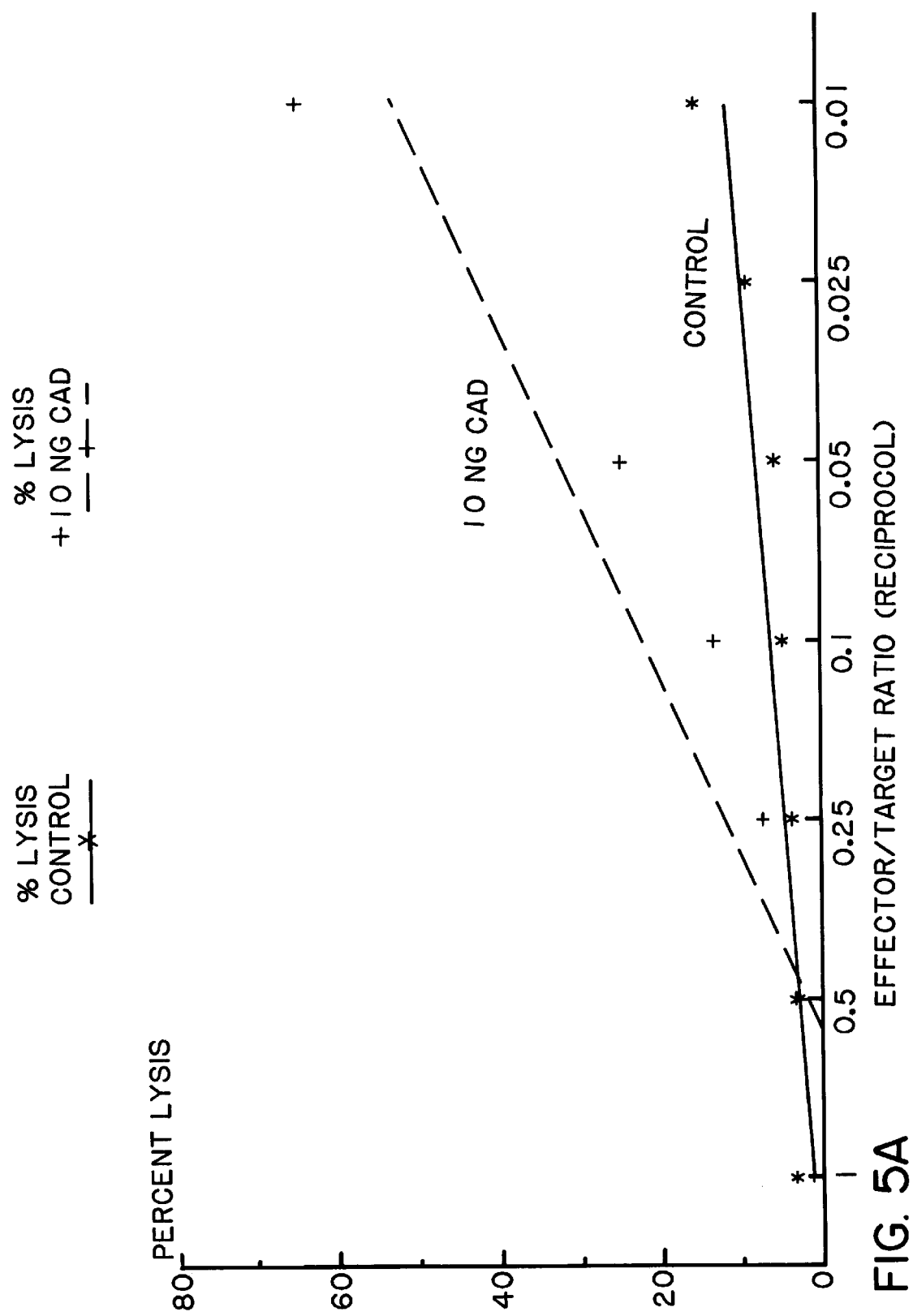
Figure 6:
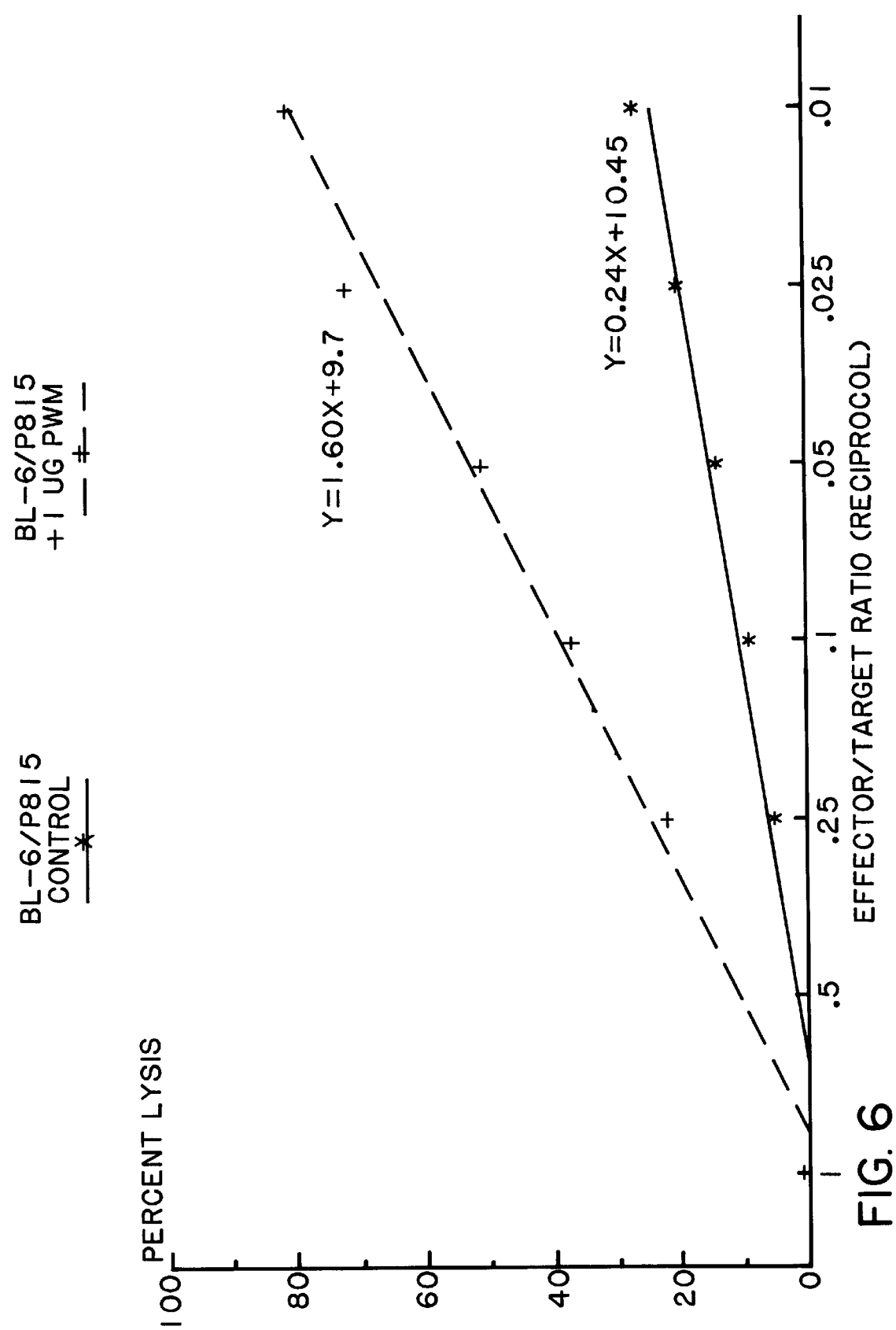

Mice were pretreated for 3 weeks with Sw (0.1 μg and 0.01 μg), and then received B16 cells. At 3 time points post tumor cell injection (day 0, 7 and 14), the mice were sacrificed and the spleens were removed. The cells were then used to determine the effect of Sw on humoral immunity. The mice pretreated with 0.01 μg Sw had a 89% increase in plaque forming cells (PFC) over the mice not receiving Sw (p=0.001) (see Table IV and FIG. 6). The 0.1 μg Sw group without tumor was not as significantly different from the control group (p=0.04) as the 0.01 μg Sw treatment grout. The presence of a day 7 tumor caused a return to baseline for all the groups. A significant difference (p=0.001) was seen on day 14 post tumor injection with the mice treated with 0.01 μg Sw. The PFC's of these mice increased 108% above those of the mice without Sw treatment with day 14 tumors and a 144% increase over those of the mice without tumors or treatment. The mice treated with 0.1 μg Sw showed a similar trend but there was not a significant difference between the controls and these treated mice (p=0.13).

C. Discussion

The tumors that arise from the implantation of B16 cells are rapid growing. They overwhelm an animal in less than 20 days. Swainsonine has a dose-dependent effect on the growth of solid B16 melanoma tumors. A dosage of 0.1 μg effectively delays the onset of growth for two days. Higher (1.0 μg) and lower dosages (0.01 μg and 0.001 μg) have no effect on delaying growth. Swainsonine has been shown to delay growth in several other solid tumor models (Dennis 1986; Dennis et al. 1989; Dennis et al. 1990). The tumors used in these earlier studies were slower growing and in some instances were combined with biological response modifiers (interferon (INF) or polyinosinic:polycytidylic acid (polyI:C) which stimulates INF production). Dennis. hypothesizes the effect on tumor growth is the Sw inhibitory action on α-mannosidase II and the alteration of the oligosaccharides on the tumor cell surface. However, the concentration of the SW administered in vivo (0.5 mg/kg/day) is too low to effectively inhibit the enzyme to the extent required to effect the processing of the oligosaccharides. If this were the case, then the higher doses of Sw should have had a greater inhibitory effect on tumor growth; instead 1.0 μg Sw causes enhanced growth. The action of Sw in vivo must involve interaction between Sw, host and tumor. The immune system is the important interaction point in tumor formation.

Another important part of cell mediated immunity is the stimulation of CTL. The activation of CTL is dependent on the presentation of antigen. There is no stimulation of CTL in mice that received Sw in drinking water (3 µg/ml) for 24 hours prior to CTL evaluation with the B16F10 cells in a $^{51}$Cr cytotoxicity assay (Humphries et al., 1988). In this study, the treatment of mice with 0.1 µg Sw for 3 weeks resulted in a significant increase in the CTL activity even before the mice had been exposed to a specific target (B16 cells). This is a Sw effect on the host component. The presence of tumor (specific antigen) increases the CTL response as would be expected. The decline of activity as the tumor grows to large proportions is also expected since CTL also responds to suppressor agents.

Host humoral immunity (antibody production) can affect tumor growth. There can be two types of antibodies present, spontaneous (non-specific) and antigen specific (tumor specific) (Klein 1982). Antibodies can alter tumor growth in several ways. They can cause tumor death by blocking proliferation, by causing cell lysis when combined with complement, and initiating antibody-dependent cellular cytotoxicity. Antibodies can also enhance tumor growth by covering the cell and masking it from the immune response, increase malignancy, and cause the production of suppressor products (Den Otter 1987). Swainsonine has been reported to effect humoral immunity. Kino et al. (1985) reported Sw could return antibody formation capability to mice that had been treated with an immunosuppressive factor obtained from tumor bearing mice. The mice were given Sw (3.7–100 mg/kg) through i.p. injections for 5 consecutive days and the immunosuppressive factor showed a return to normal levels of antibody production compared to mice receiving no Sw or factor, tested by PFC assay. Kino et al. (1985) observed no changes in PFC numbers in the mice receiving SW alone. In this study, the 3 week treatment of 0.01 µg Sw caused significant changes in the formation of plaques prior to tumor exposure. Although more detailed studies are required, these data suggest that it is a Sw dose-dependent differentiation effect on splenocytes. There was a suppression of antibody production after 7 days of tumor exposure, perhaps related to the tumor dependent splenocyte proliferation. This is a feasible hypothesis since the antibody production returns to the levels prior to tumor exposure and the mice receiving 0.01 fg Sw had even higher levels.

E. References for Example 14

Bolhuis, R. L. H., van De Griend, R. J., and Mukherji, B. (1987) Lymphoid effector cells against tumor cells. In: Den Otter, W. and Ruitenberg, E. J. (eds) Tumor Immunology-Mechanisms, Diagnosis, Therapy. Elsevier Science Publishers B. V. 61–88.

Bowlin, T. L., McKown, B. J., Kang, M. S., and Sunkara, P. S. (1989) Potentiation of human lymphokine-activated killer cell activity by swainsonine, an inhibitor of glycoprotein processing. Cancer Res. 49:4109–4113.

Broquist, H. P., Mason, P. S., Hagler, W. M., and Croom, Jr., W. J. (1985) Transmission of swainsonine into milk. Fed. Proc. 44:1860.

Calabresi, P., and Parks, R. E. (1985) Chemotherapy of neoplastic diseases—introduction. In: Gilman, A. G., Goodman, L. S., Rall, T. D., and Murad, F. (eds) Goodman and Gilman's The Pharmacological Basis of Therapeutics (7th Edition). MacMillan Publishing Company. 1240–1246.

Cenci Di Bello, I., Fleet, G., Namgoong, S. K., Tadano, K. -I., and Winchester, B. (1989) Structure-activity relationship of swainsonine. Biochem. J. 259, 855–861.

Den Otter, W. (1987) Evaluation of knowledge of in vivo tumoricidal effector mechanisms. In: Den Otter, W. and Ruitenberg, E. J. (eds) Tumor Immunology—Mechanisms, Diagnosis, Therapy. Elsevier Science Publishers B. V. 109–123.

Dennis, J. W. (1986) Effects of swainsonine and polyinosinic:polycytidylic acid on murine tumor cells growth and metastasis. Cancer Res. 46, 5131–5136.

Dennis, J. W., Koch, K., Beckner, D. (1989) Inhibition of human ht29 colon carcinoma growth in vitro and in vivo by swainsonine and human interferon-α2. J. Natl. Cancer Inst. 81, 1028–1033.

Dennis, J. W., Koch, K., Yousefi, S., and VanderElst, I. (1990) Growth inhibition of human melanoma tumor—xenografts in athymic nude mice by swainsonine. Cancer Res. 50, 1867–1872.

Elbein, A. D. (1984) Inhibitors of the biosynthesis and processing of n-linked oligosaccharides. CRC Crit. Rev. Biochem. 16, 21–49.

Elbein, A. D., Solf, R., Dorling, P. R., and Vosbeck, K. (1981) Swainsonine: an inhibitor of glycoprotein processing. Proc. Natl. Acad. Sci. USA 78(12), 7393–7397.

Fidler, I. J. (1973) Selection of successive tumour lines for metastasis. Nature 242, 148–149.

Fidler, I. J., Nicolson, G. L. (1976) Organ selectivity for implantation survival and growth of B16 melanoma variant tumor lines. J. Natl. Cancer Inst. 57, 1199–1202.

Hart, I. R. (1979) The selection and characterization of an invasive variant of the B16 melanoma. Am. J. of Path. 97(3), 587–600.

Hino, M., Nakayama, O., Tsurumi, Y., Adachi, K., Shibata, T., Terano, H., Kohsaka, M., Aoki, H. and Imanaka, H. (1985) Studies of an immunomodulator, swainsonine I. Enhancement of immune response by swainsonine in vitro. J. Antibiotics 38(7), 926–935.

Humphries, M. J., Matsumoto, K., White S. L., and Olden, K. (1986) Oligosaccharide modification by swainsonine treatment inhibits pulmonary colonization by B16-F10 murine melanoma cells. Proc. Natl. Acad. Sci. USA 83, 1752–1756.

Humphries, M. J., Matsumoto, K., White, S. L., Molyneux, R. J., and Olden, K. (1988) Augmentation of murine natural killer cell activity by swainsonine, a new antimetastatic immunomodulator. Cancer Res. 48, 1410–1415.

Humphries, M. J., Matsumoto, K., White, S. L., Molyneux, R. J., and Olden, K. (1990) An assessment of the effects of swainsonine on survival of mice injected with B16-F10 melanoma cells. Clin. Expl. Metastasis 8(1), 89–102.

Itoh, K., Tilden, A. B., and Balch, C. M. (1986) Lysis of human solid tumor cells by lymphokine-activated natural killer cells. J. of Immunol. 136(10), 3910–3915.

Jerne, N. K., Nordin A. A. (1963) Plaque formation in agar by sine antibody producing cells. Science 140, 405–407.

Klein, J. (1982) IMMUNOLOGY The Science of Self-Nonself Discrimination. John Wiley & Sons, New York. 623–648.

Kino, T., Inamura, N., Nakahara, K., Kiyoto, S., Goto, T., Terano, H., Kohsaka, M., Aoki, H., and Imanaka, H. (1985) Studies of an immunomodulator, swainsonine II. Effect of swainsonine on mouse immunodeficient system and experimental murine tumor. J. of Antibiotics 38(7), 936–940.

Lau Laursen, M. (1989) Chemotherapy of malignant tumors—A self defeating form of immunotherapy? Med. Hypothesis 29, 9–15.

Mann, P. L., (1988) Membrane oligosaccharides: Structure and function during differentiation. Inter. Rev. Cyto. 112, 67–95.

Mann, P. L., Lopez-Colberg, I., and Kelley, R. O. (1987a) Cell surface oligosaccharide modulation during differentiation. I. Modulation of lectin binding. Mech. Ageing Devel. 38, 207–217.

Mann, P. L., Swartz, C. M., and Kelley, R. O. (1987b) Cell surface oligosaccharide modulation during differentiation. II. Membrane mobility of oligosaccharide lectin conjugates. Mech. Ageing Devel. 38, 219–230.

Mann, P. L., Swartz, C. M., and Holmes, D. T. (1988a) Cell surface oligosaccharide modulation during differentiation: III. Lectin affinity class distributions. Mech. Ageing Devel. 44, 1–16.

Mann, P. L., Swartz, C. M., and Holmes, D. T. (1988b) Cell surface oligosaccharide modulation during differentiation: IV. Normal and transformed cell growth control. Mech. Ageing Devel. 44, 17–33.

Mann, P. L., Eshima, D., Bitner, D. M., Griffey, R. H., Wenk, R., Born, J. L. and Matwiyoff, N. A. (1991) Biomodulation: an integrated approach to access and manipulate biological information. Biosymposium: Lectins and Cancer. Stuttgard, Germany; Springer Verlog. In press.

Mayer, D. K. (1990) Biotherapy: Recent advances and nursing implications. Adv. in Oncology Nursing 291–308.

Mohla, S., Humphries, M. J., White, S. L., Matsumoto, K., Newton, S. A., Sampson, C. C., Bowen, D., and Olden. K. (1988) Swainsonine: a new antineoplastic immunomodulator. J. Natl. Med. Assoc. 81(10), 1049–1055.

Newton, S. A., White, S. L., Humphries, M. J., and Olden, K. (1989) Swainsonine inhibition of spontaneous metastasis J. Natl. Cancer Inst. 81, 1024–1028.

Olden, K., Mohla, S., Newton, S. A., White, S. L., and Humphries, M. J. (1989) Use of antiadhesive peptide and swainsonine to inhibit metastasis. Ann. NY Acad. Sci. 551, 421–442.

Oldham, R. (1987). In: Oldham R. (ed) Principles of Cancer Biotherapy. New York, Raven Press. 1–20.

Poste, G., Doll, J., Brown, A. E., Tzeng, J., and Zeidman, I. (1982) Comparison of the metastatic properties of B16 melanoma clones isolated from cultured cell lines, subcutaneous tumors, and individual lung metastases. Cancer Res. 42, 2770–2778.

Price, J. E., (1990) The biology of cancer metastasis. In Effects of Therapy on Biology and Kinetics of the Residual Tumor, Part A: Pre-Clinical Aspects, Wiley Liss Inc. 237–255.

Tulsiani, D. R. P. and Touster, O. (1983) Swainsonine, a potent mannosidase inhibitor, elevates rat liver and brain lysosomal α-D-mannosidase, decreases golgi α-D-mannosidase II, and increases the plasma levels of several of several acid hydrolases. Arch. Biochem. Biophys. 224(2), 594–600.

Tulsiani, D. R. P., Harris, T. M., and Touster, O. (1982) Swainsonine inhibits the biosynthesis of complex glycoproteins by inhibition of golgi mannosidase II. J. of Biol. Chem. 257(14), 7936–7939.

Tulsiani, D. R. P., Harris, H. P., James, L. F. and Touster, O. (1984) The similar effects of swainsonine and locoweed on tissue ycosidases and oligosaccharides of the pig indicate that the alkaloid is the principle toxin responsible for the induction of locoism. Arch. Biochem. Biophys. 232(1), 76–85.

Wall, K. A., Pierce, J. D., and Elbein, A. D. (1988) Inhibitors of glycoprotein processing alter T-cell proliferative responses to antigen and to interleukin 2. Proc. Natl. Acad. Sci. USA 85, 5644–5648.

White, S. L., Schweitzer, K., Humphries, M. J., and Olden, K. (1988) Stimulation of DNA synthesis in murine-lymphocytes by the drug swainsonine: immunomodulatory properties. Biochem. Biophys. Res. Comm. 150, 615–625.

Yagita, M., and Saksela, E. (1990) Swainsonine, an inhibitor of glycoprotein processing, enhances cytotoxicity of large granular lymphocytes. Scand. J. Immunol. 31, 275–282.

Example I

In the following Examples, the compounds employed are compounds of the formulas IIa–IIc,

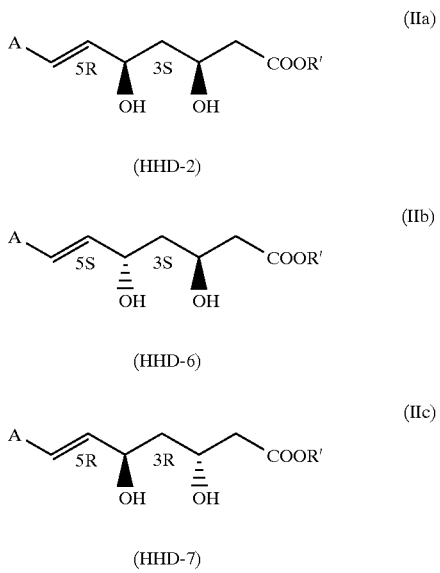

wherein A is

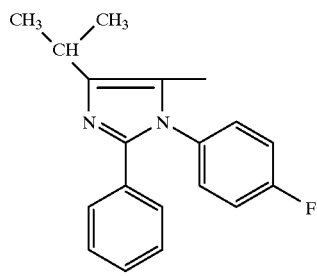

and R' is isopropyl herein designated as IIa', IIb', and IIc'. Comparison compound IId' is

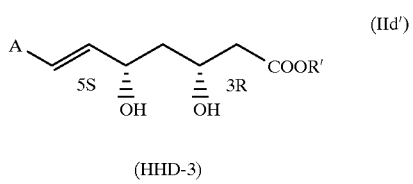

(HHD-3)

wherein A and R' are the same as in compounds IIa'-IIc'. "Compound" IIe' is a racemic mixture of compounds IIb' and IIc'.

Compound is:

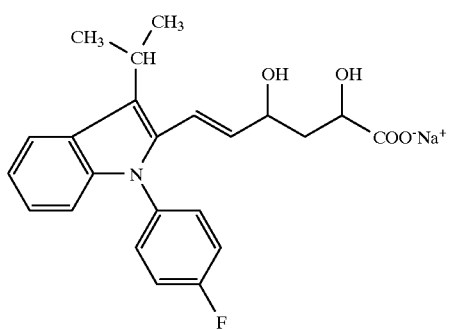

Compound TF-002 is:

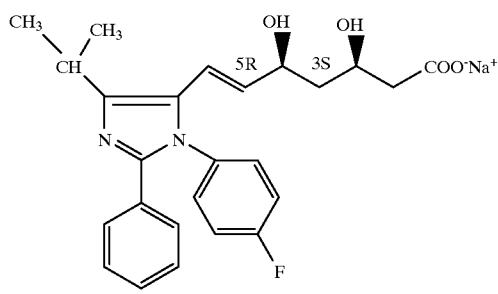

Example II

Immunological Activity In Vitro

A. Immune Response of Human Peripheral Blood Leukocytes (HPBL)

Human peripheral blood leukocytes were cultured in a standard tissue culture medium. Aliquots of these cultured cells (1,000,000 cells/ml medium) were cultured for 6 hours, and the specified amount of Formula II compound was added; the cells were then cultured for an additional 90 hours. Sheep red blood cells (SRBC) conditioned with class-specific (IpG) goat anti-human antiserum (1:400) for 2 hours; then guinea pig complement (2%) for 2 hours were conjugated to Protein A as described in detail in *Radioimmunoimaging and Radioimmunotherapy*, Eds. S. W. Burchiel and B. A. Rhodes, Elsevier Science Publishing; New York, 1983, pp. 125–127, incorporated herein by reference.

Results of this study for compounds of the Formulae IIa'–IIe' are given in Table I below:

TABLE I

| Compound | Inhibitory Concentration[1] | Stimulation of IgG Production Concentration/Percent | $IC_{50}$[2] | Proliferation[3] |
|---|---|---|---|---|
| IIa' | none found | 200 pm/1700 | 3.150 | 0.98 |
| IIb' | none found | 200 pM/1700 | 1.350 | 1.0 |
| IIc' | none found | 100 pM/6200 | 0.022 | 1.2 |
| IId' (comparison) | 1.2 μM | 100 nM/320 | 0.002 | 0.66 |
| IIe' | 1.2 μM | 1&100 nM/1990 | 0.003 | 0.85 |

[1]Concentration inhibiting nonspecific IgG production below normal production.
[2]Concentration (μM) for 50% inhibition of rat liver HMG-CoA reductase activity; data obtained according to Example IA.
[3]Measured by ($^3$H) thymidine incorporation into DNA.

As is apparent from the above results, each of the cytostatic compounds of the invention (IIa', IIb', IIc', IIe') stimulated IgG production. Compound IIe' suppressed IgG production at a concentration of 1.2 μM, and exhibited substantially no significant enhancement (less than 350%) at lower concentrations (100 nM). In contrast, compounds IIa' and IIb' each stimulated IgG production 1700% at 200 pM concentration, and compound IIc' stimulated IgG production 6200% at 100 pM. There was no apparent correlation between induction of immunological activity and Inhibition of HMG-CoA reductase activity ($IC_{50}$).

It is contemplated that therapeutic dosages of compounds which inhibit IgG production at relatively high concentrations in vitro according to the present Example (e.g., IIe') should be carefully controlled in vivo to avoid this effect.

Example III

Immune Response In Vivo

1. Humoral Immunity

Tumor-Specific Antibody Production

Titer of CG-specific antibody was compared to control [no administration of compound IIc' and no implantation of CG (canine glioma cells]. As is apparent in the results described below in Table II, after administration of compound IIc' in the absence of antigen, titers of antibody increased over the control antibody titer significantly. Following implantation of the CG tumor cells, CG-specific antibody (IgG) production increased significantly (Table II). This increase in titer continued with time until tumor regression was noted by independent measurement (NMR evaluation, below). At this point, the CG-specific antibody rapidly (within a few days) reverted to baseline control levels (Table II).

Figure 7:
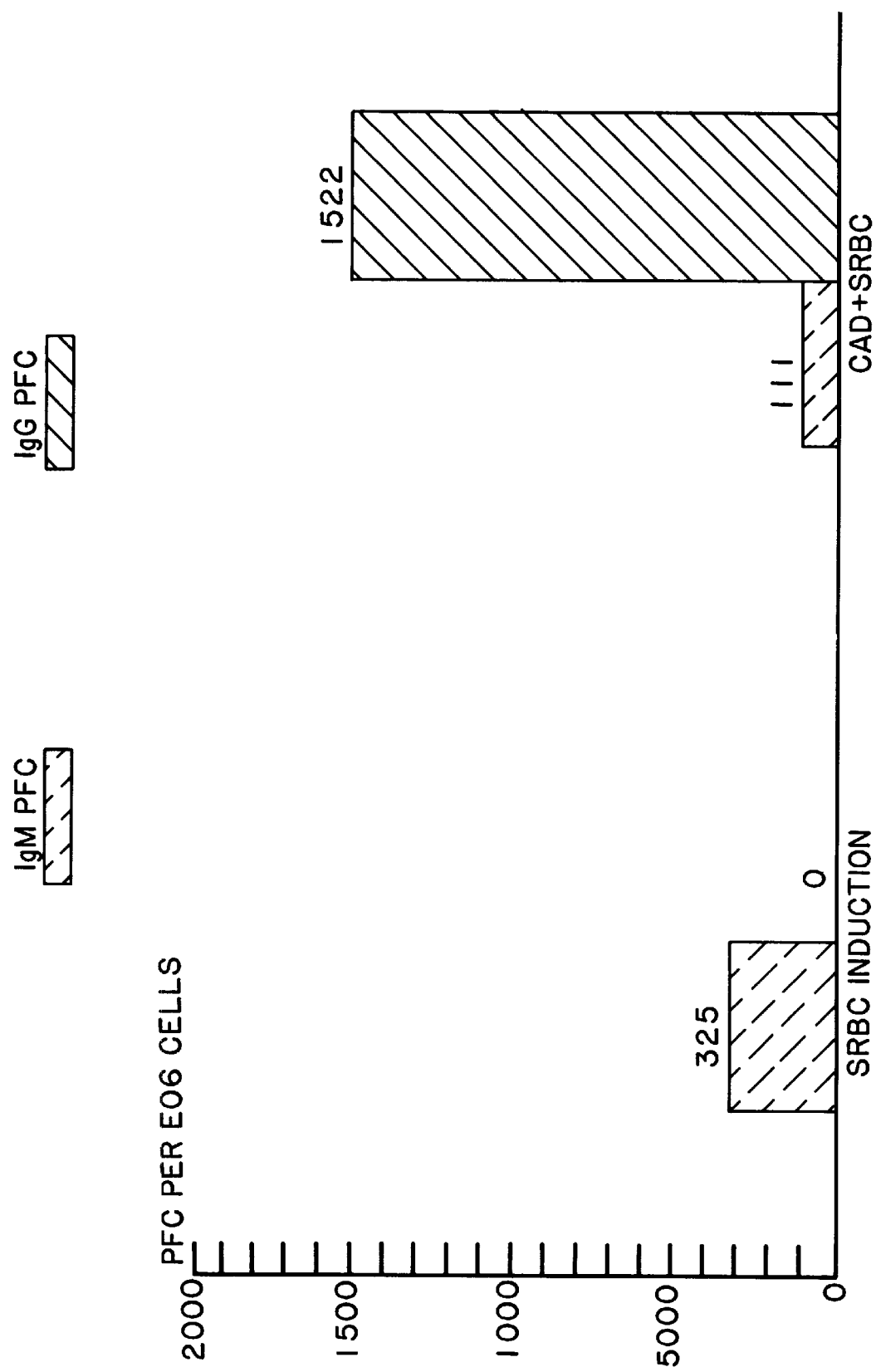
Figure 8:
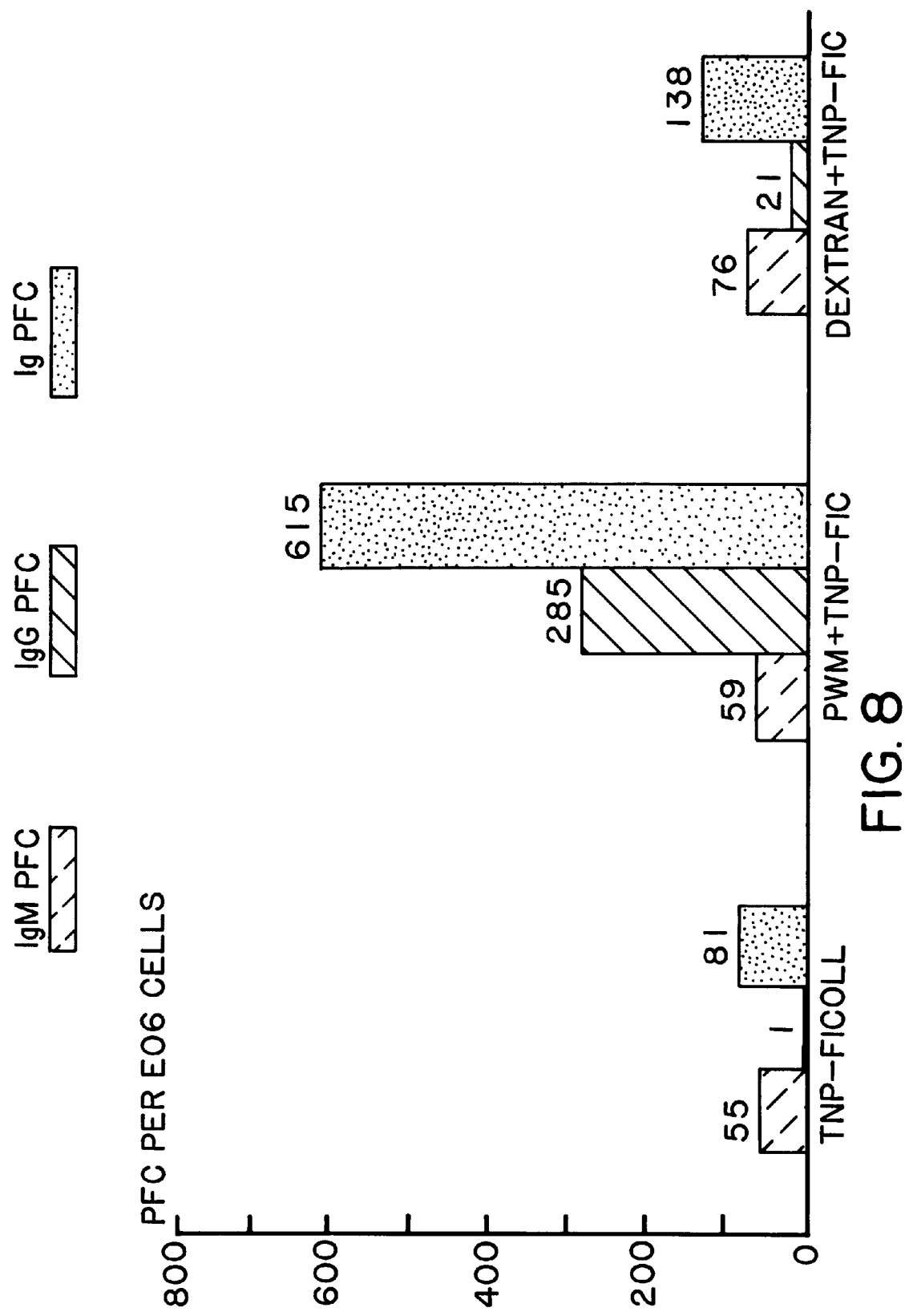
Figure 9:
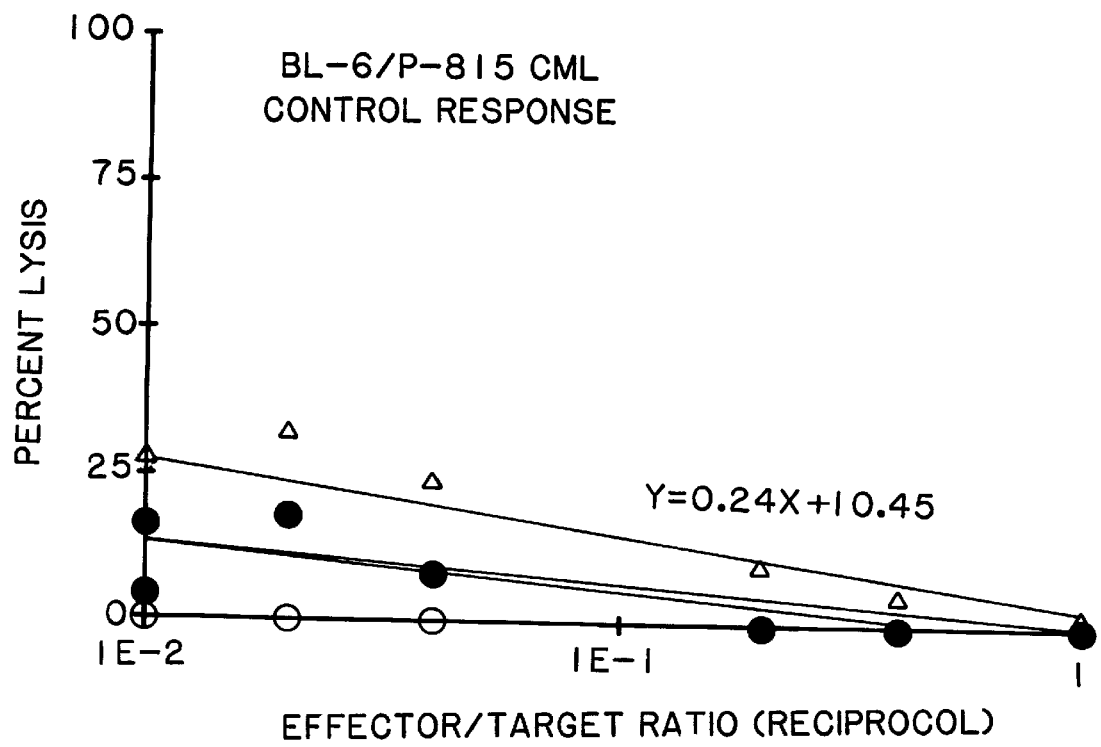
Figure 10:
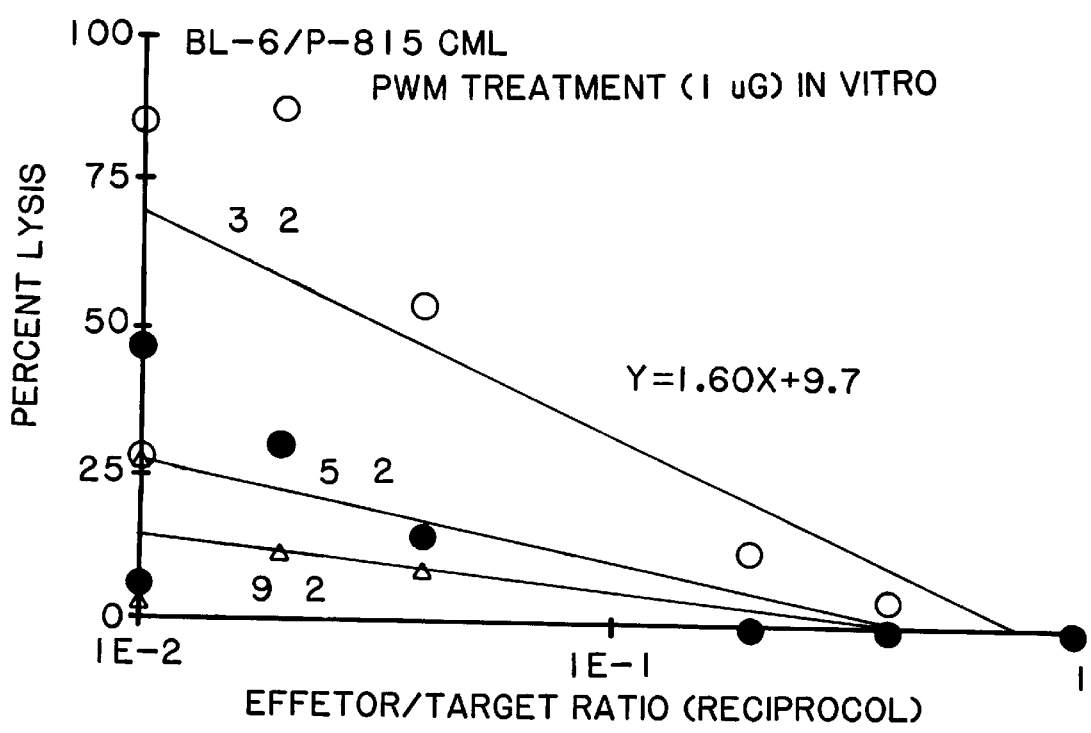
Figure 11A:
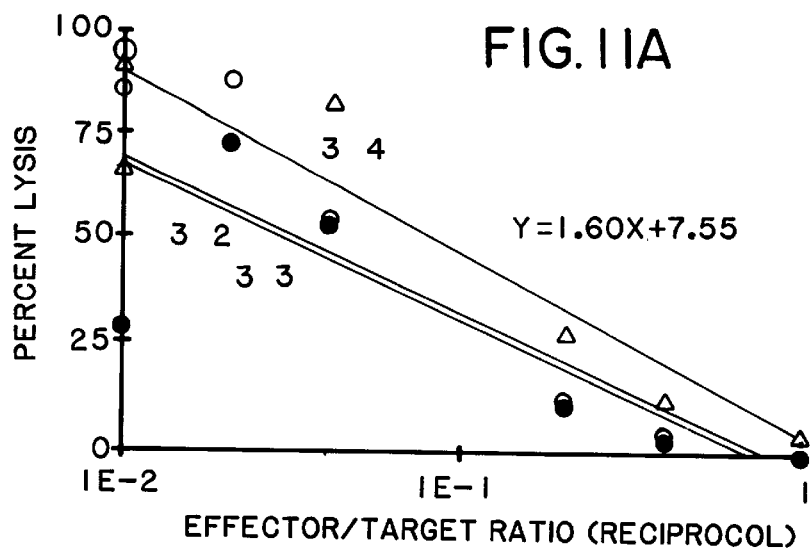
Figure 11B:
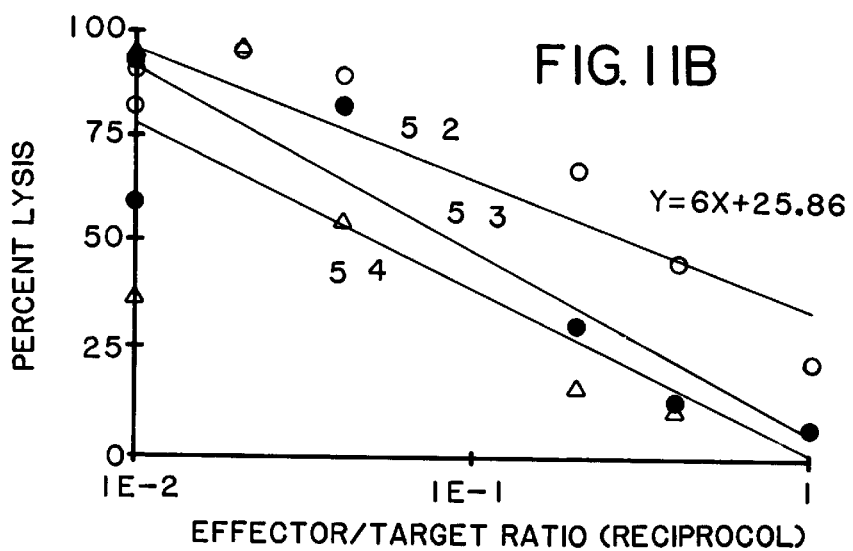
Figure 11C:
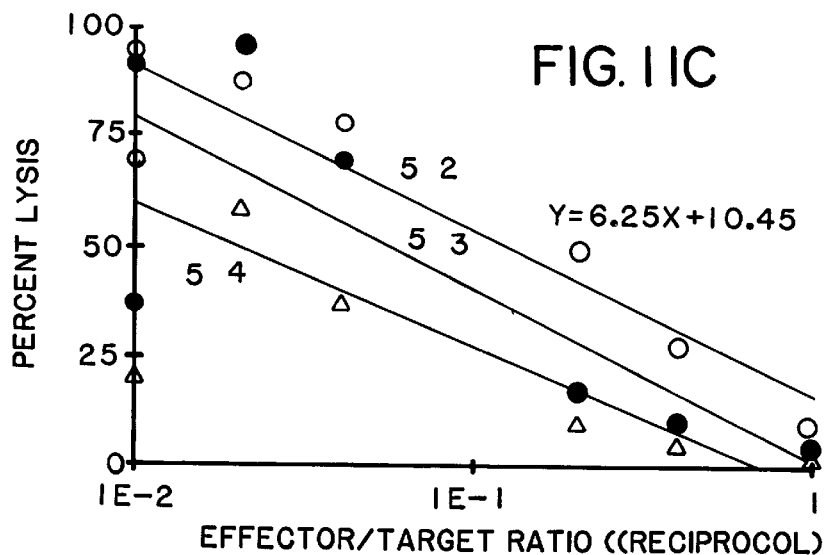
Figure 13A:
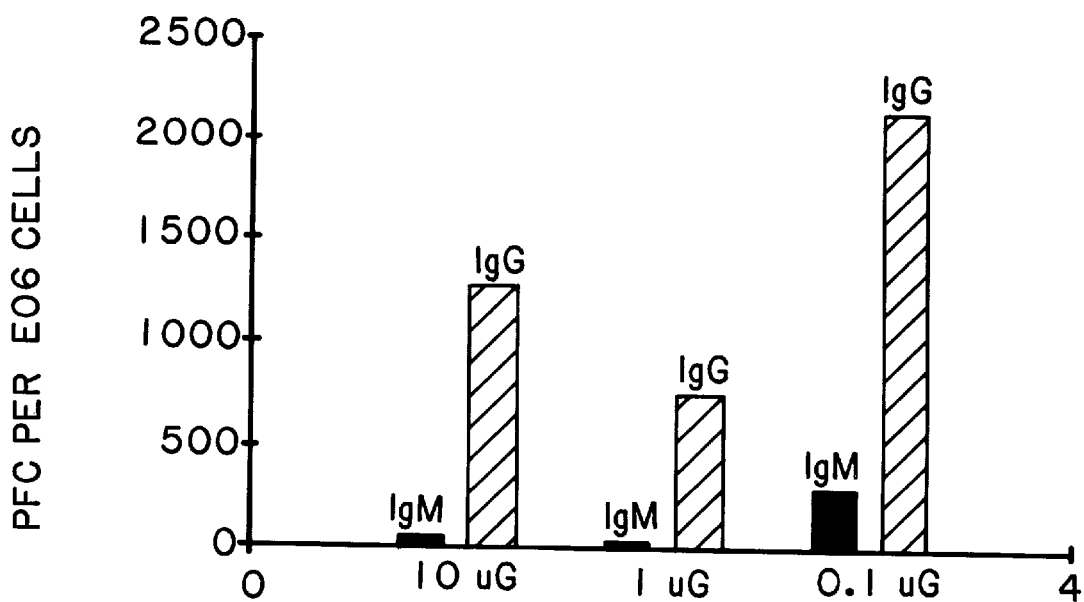
Figure 13B:
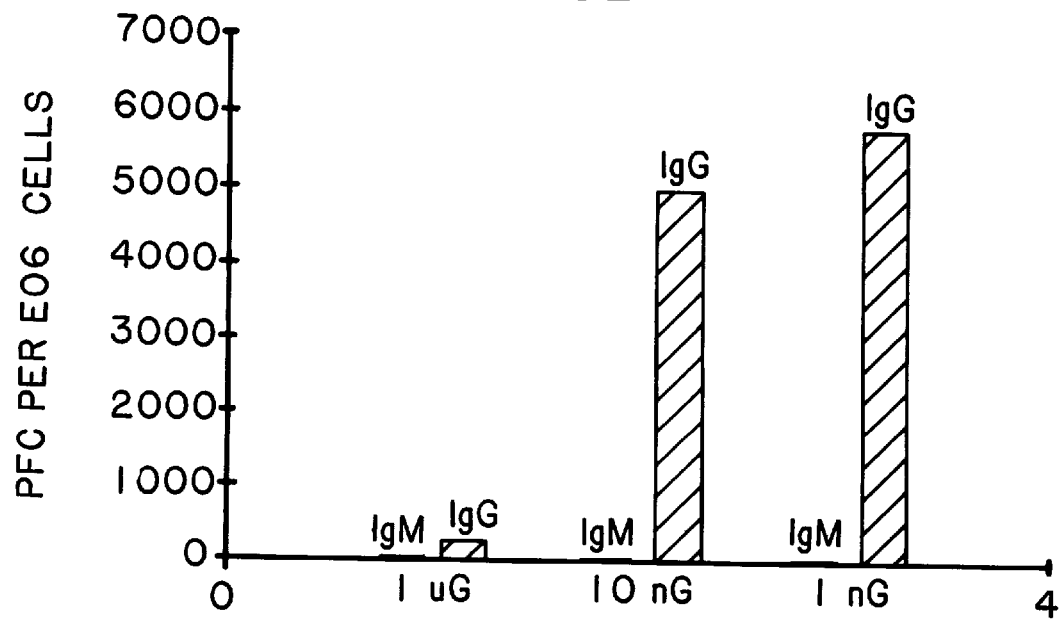
Figure 14:
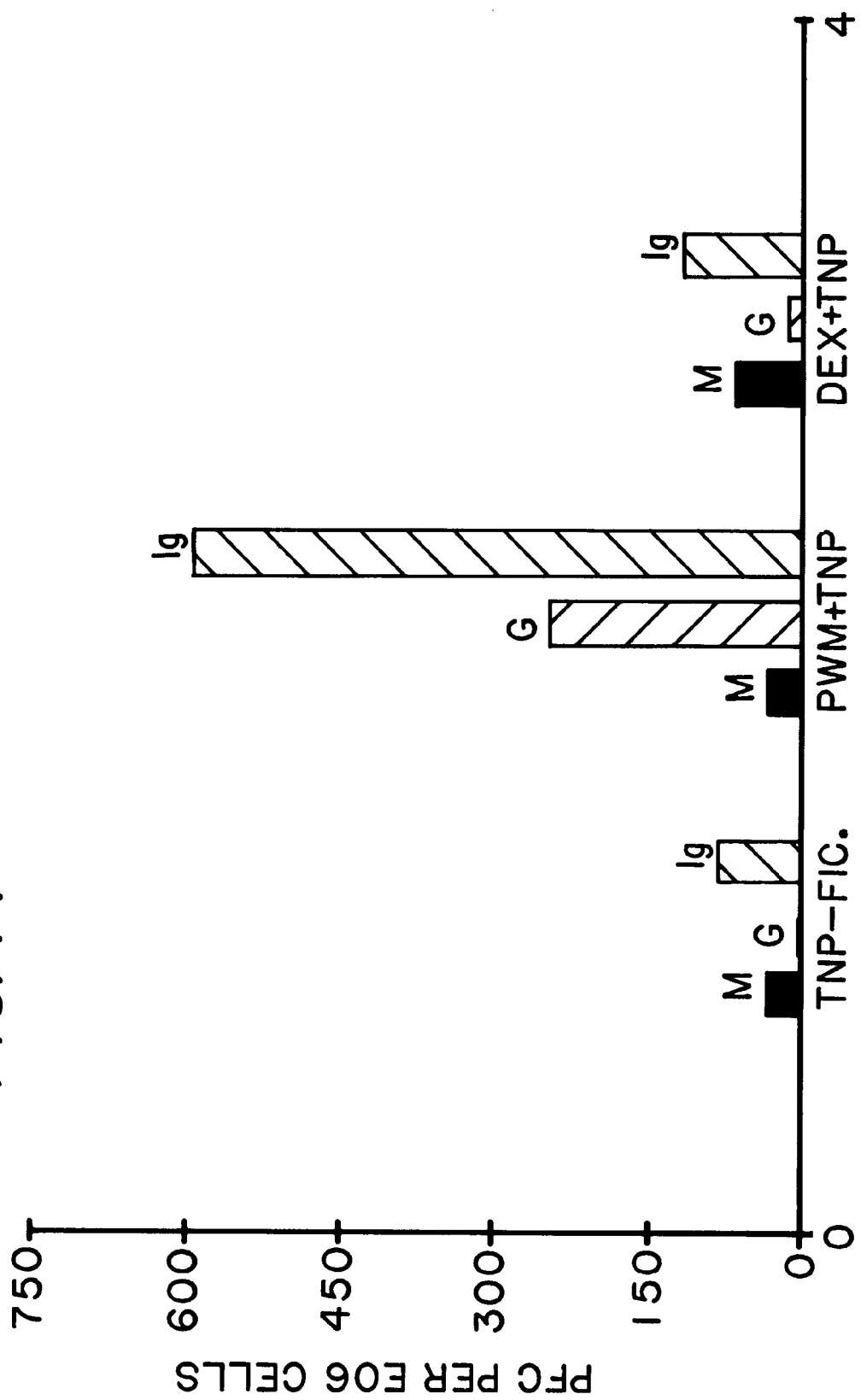
Figure 15:
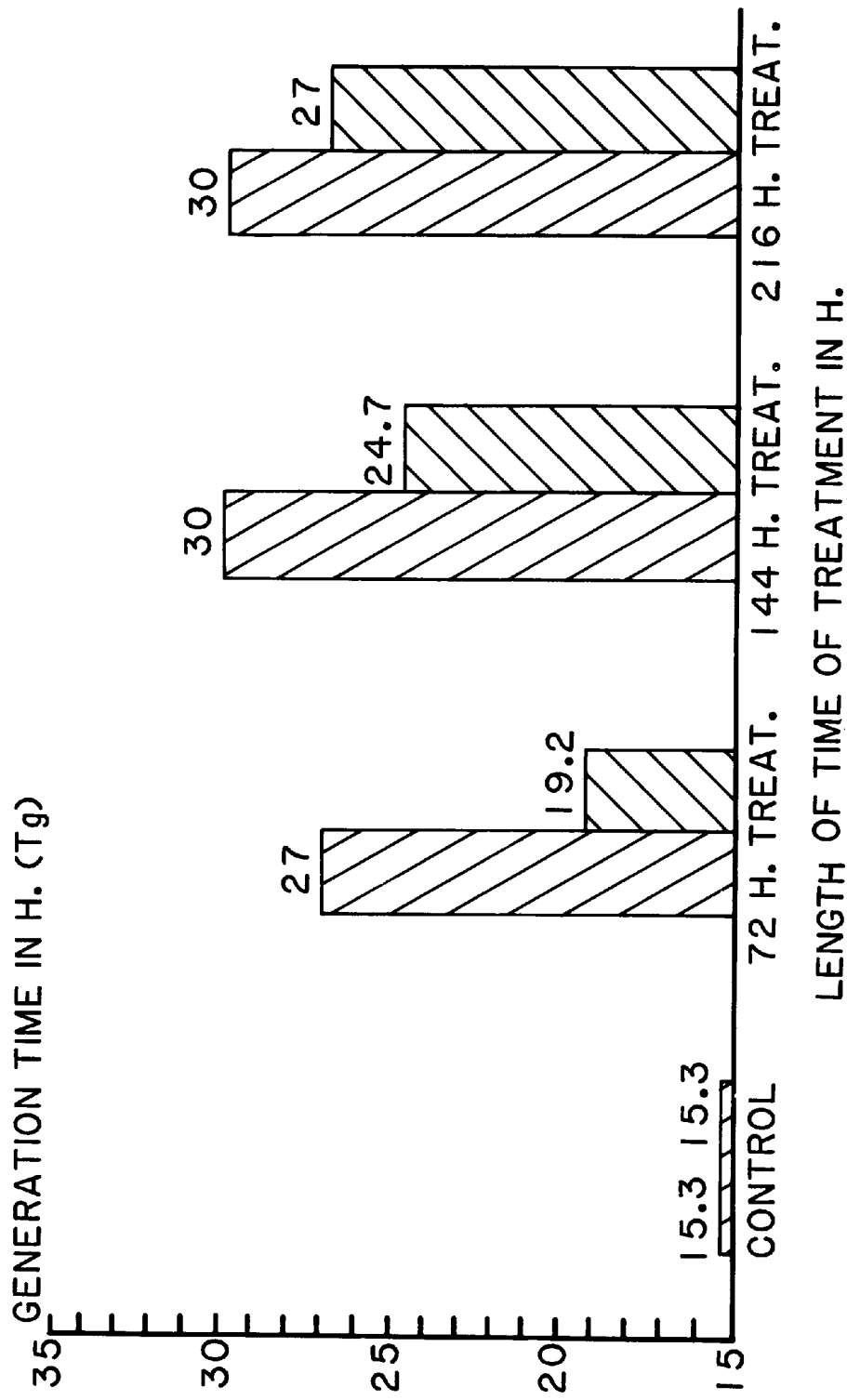
Figure 17A:
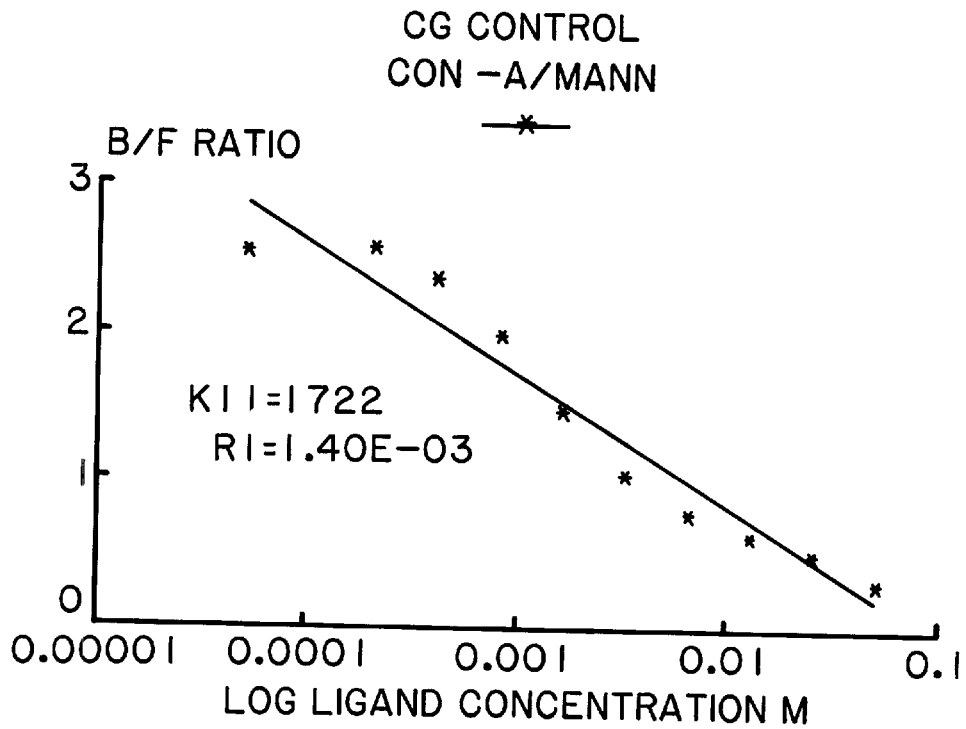
Figure 17B:
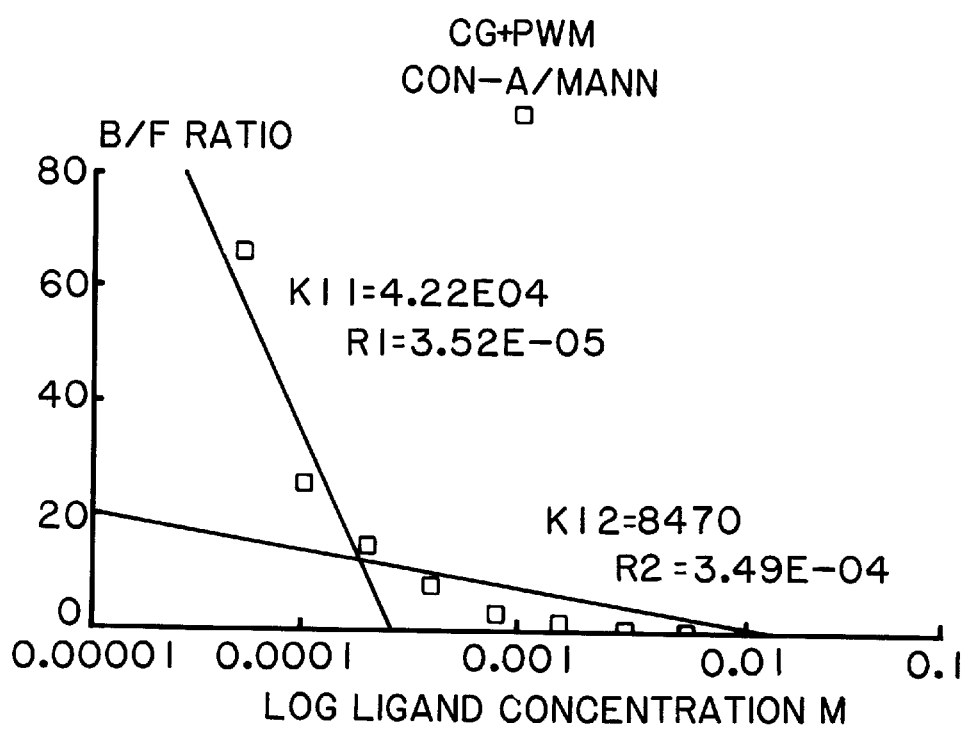
Figure 18A:
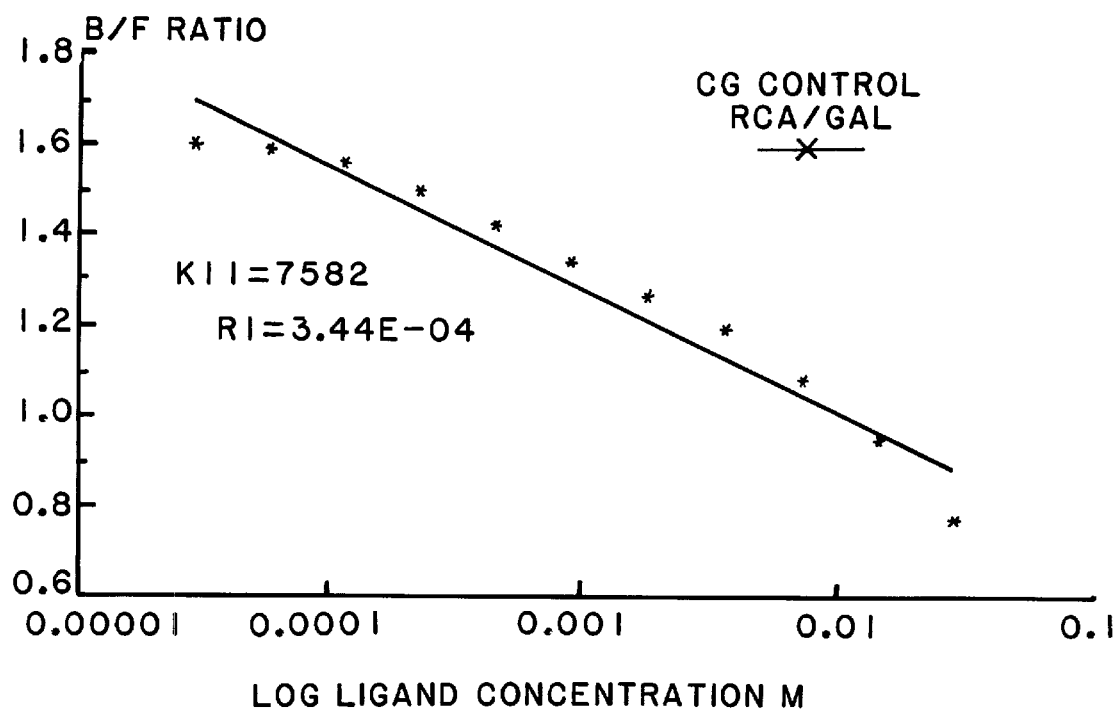
Figure 18B:
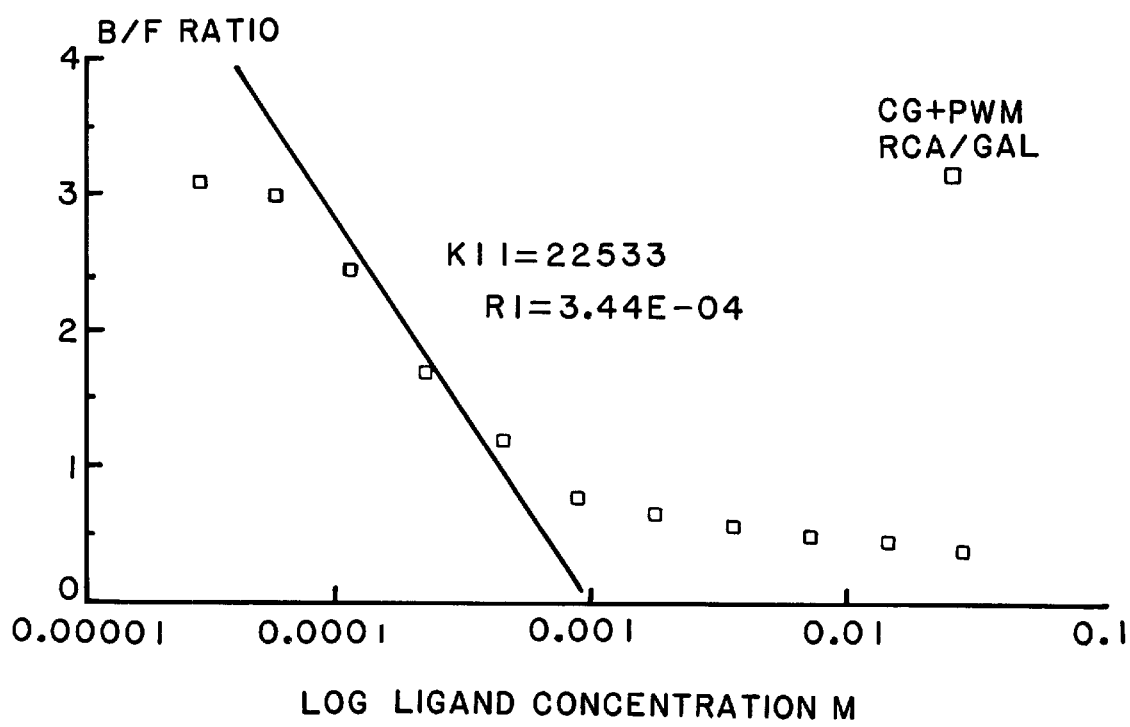
Figure 21A:
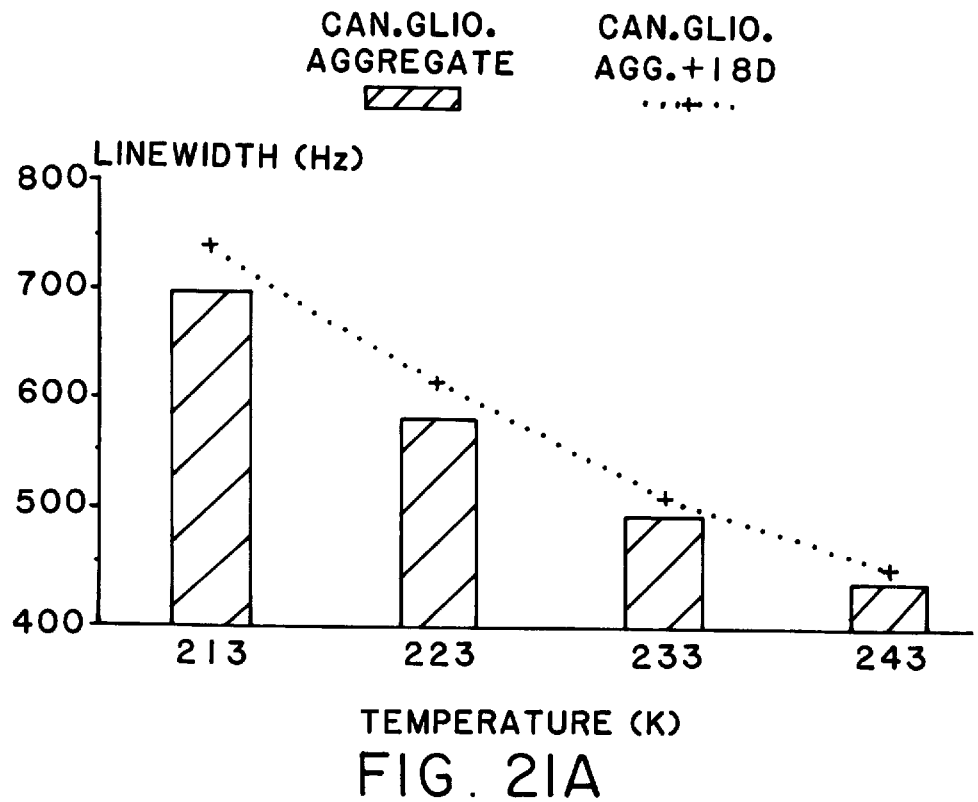
Figure 21B:
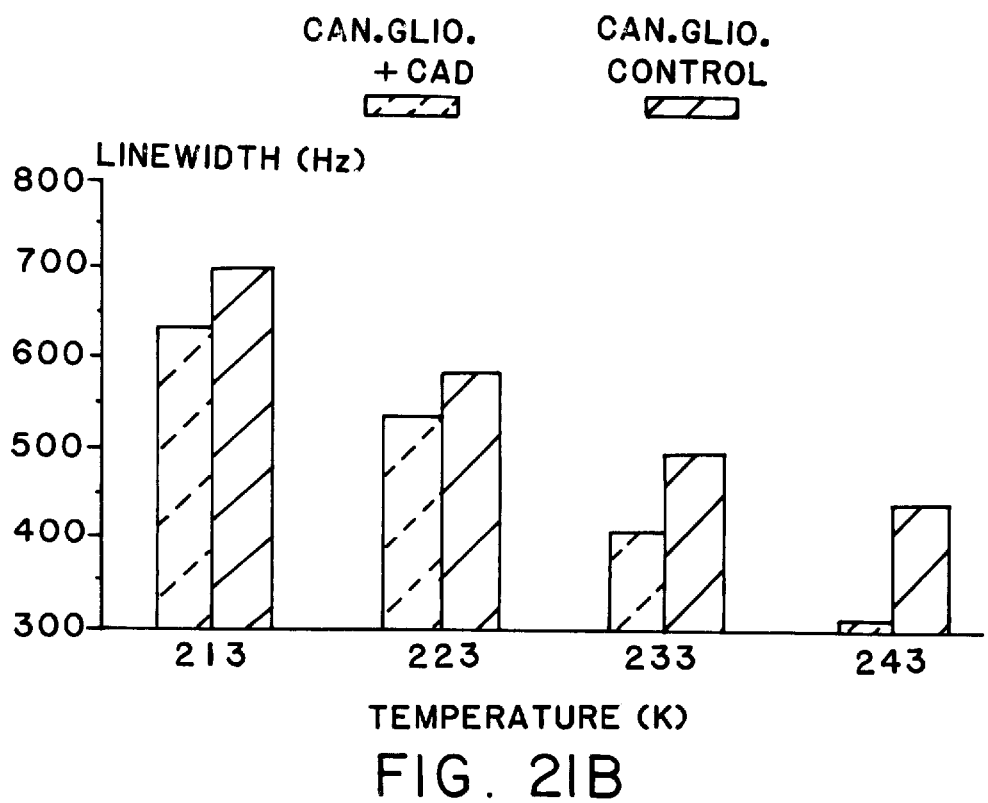
Figure 21C:
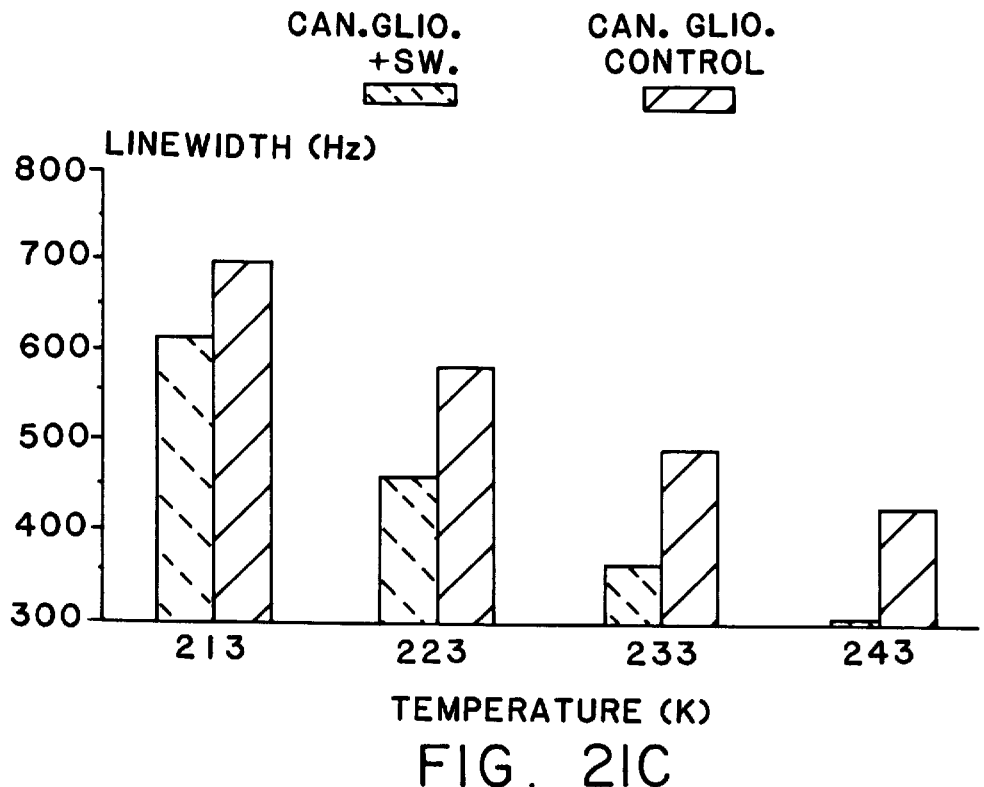
Figure 21D:
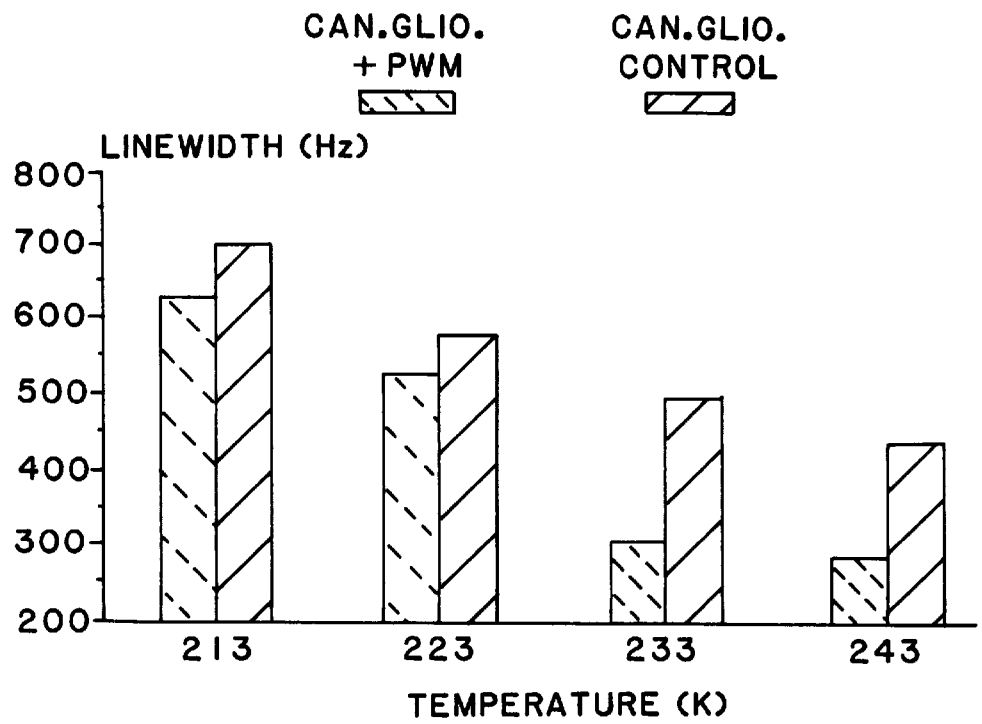
Figure 22:
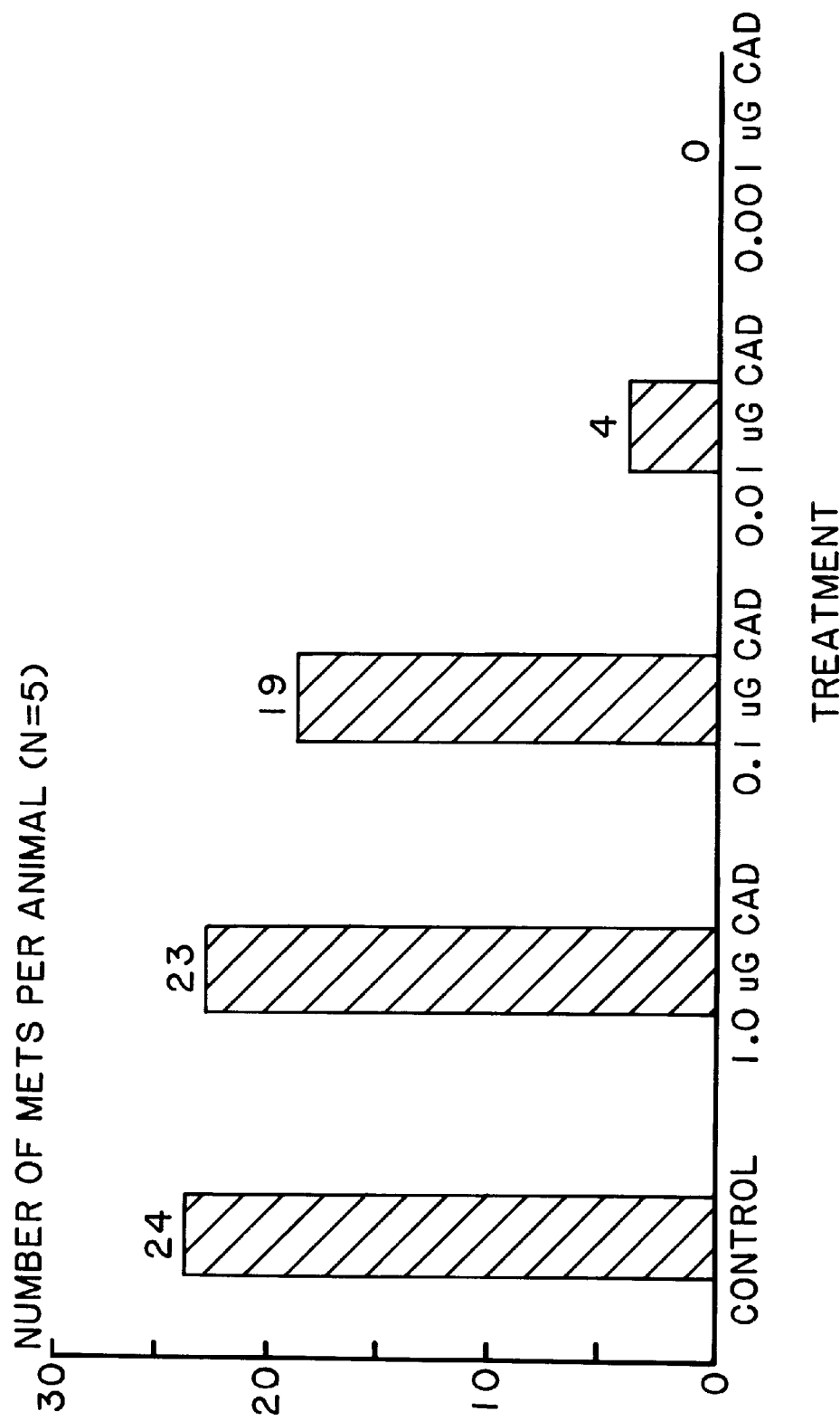
Figure 23:
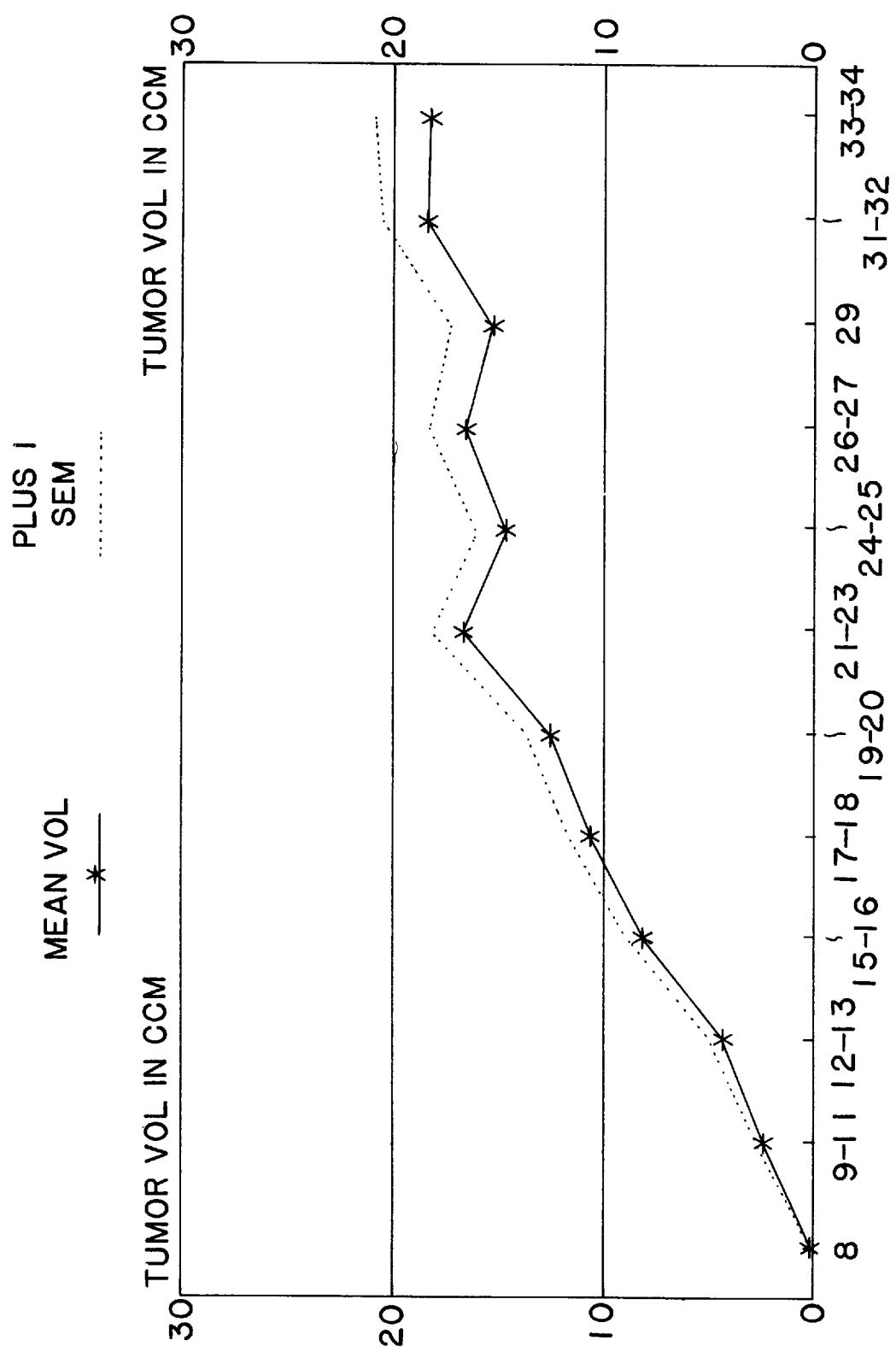
Figure 24:
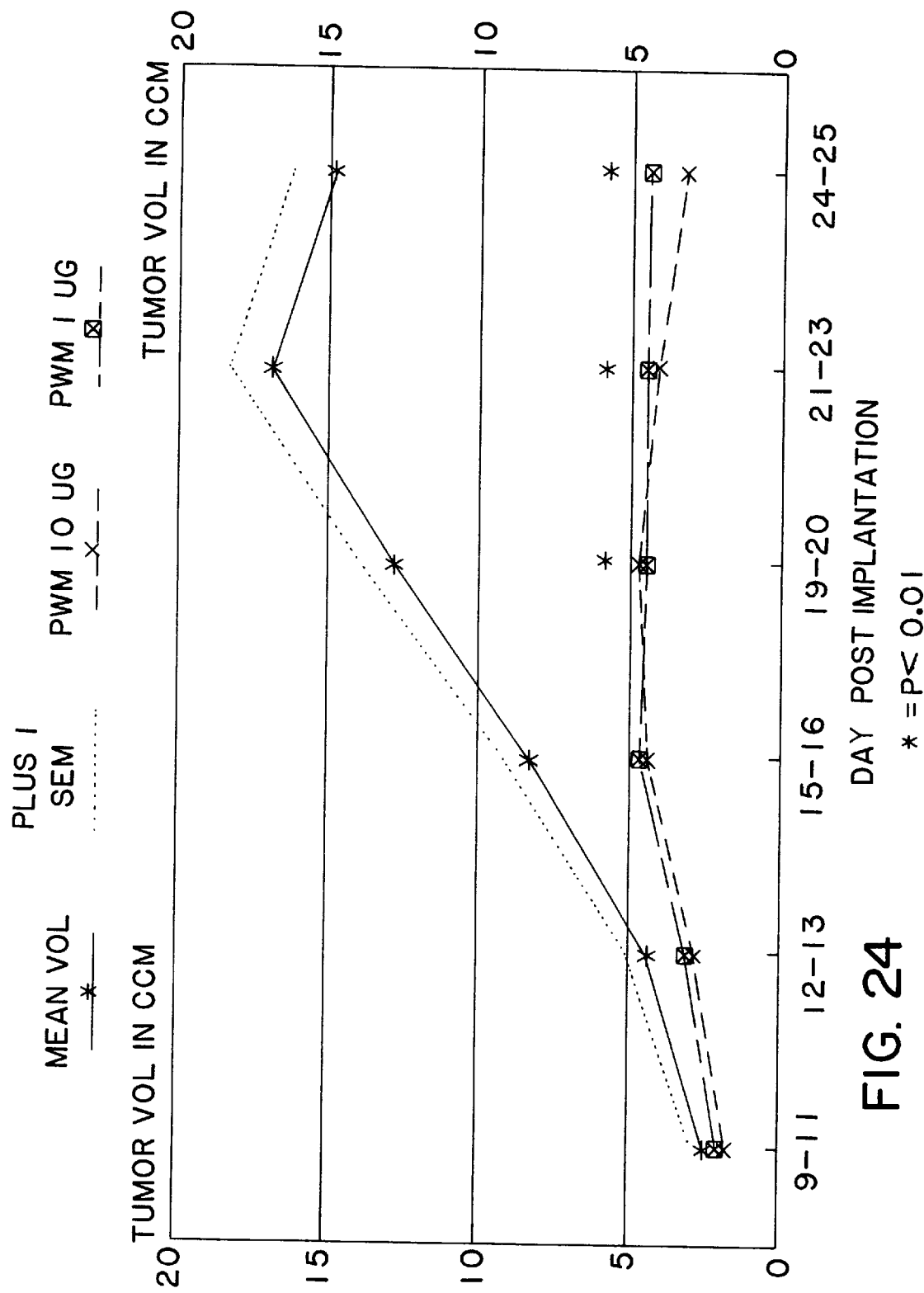
Figure 25:
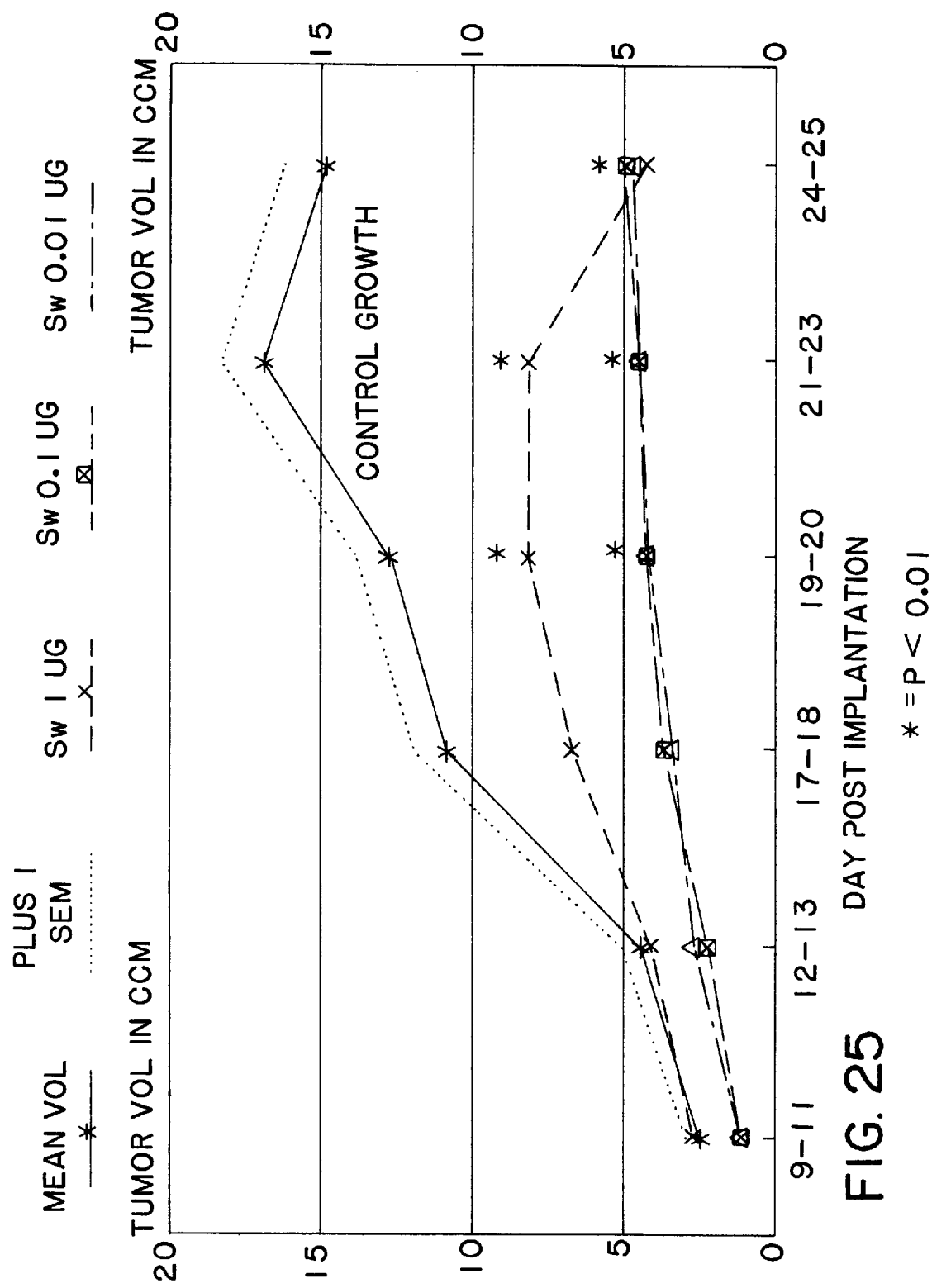
Figure 26:
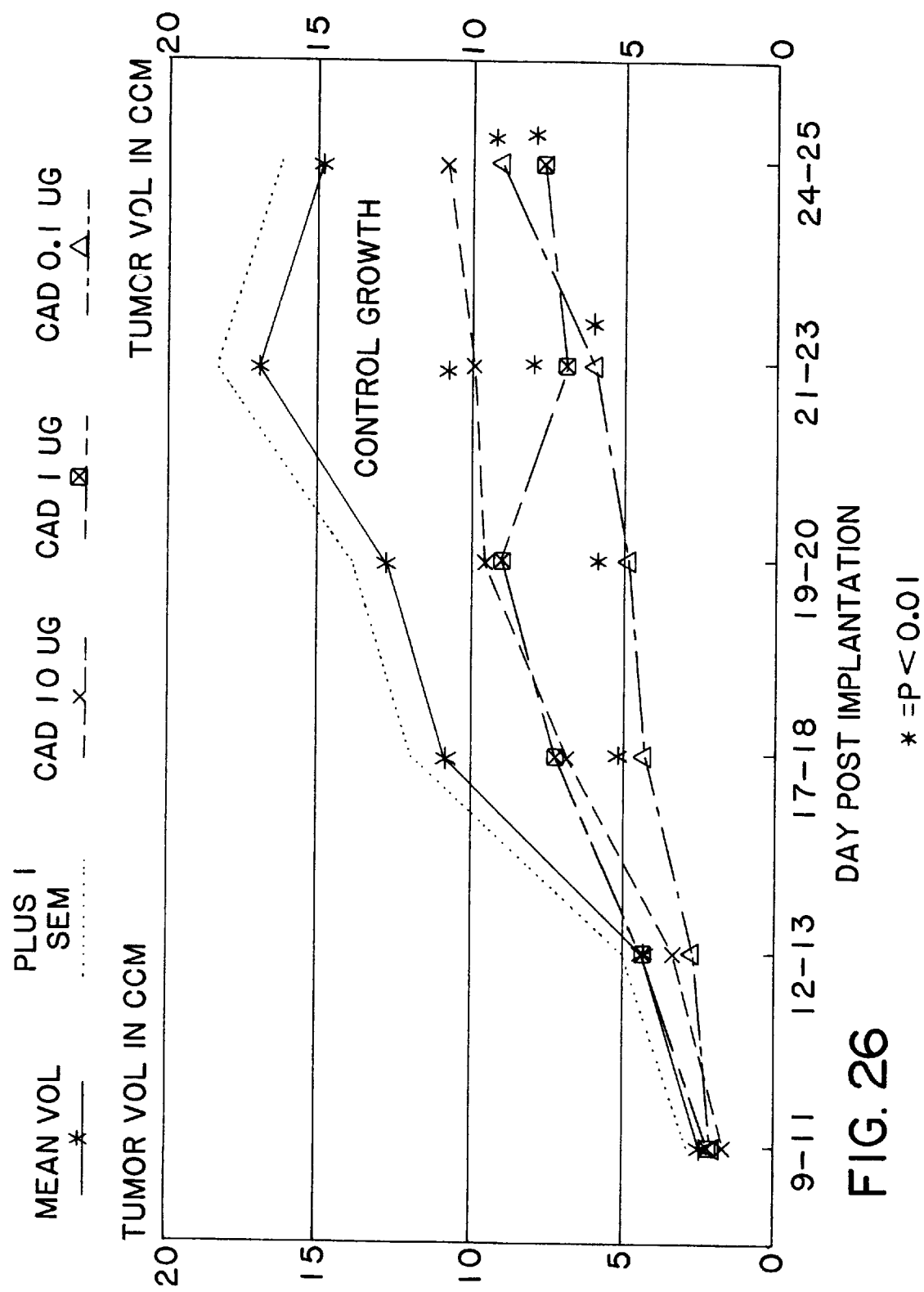
Figure 27:
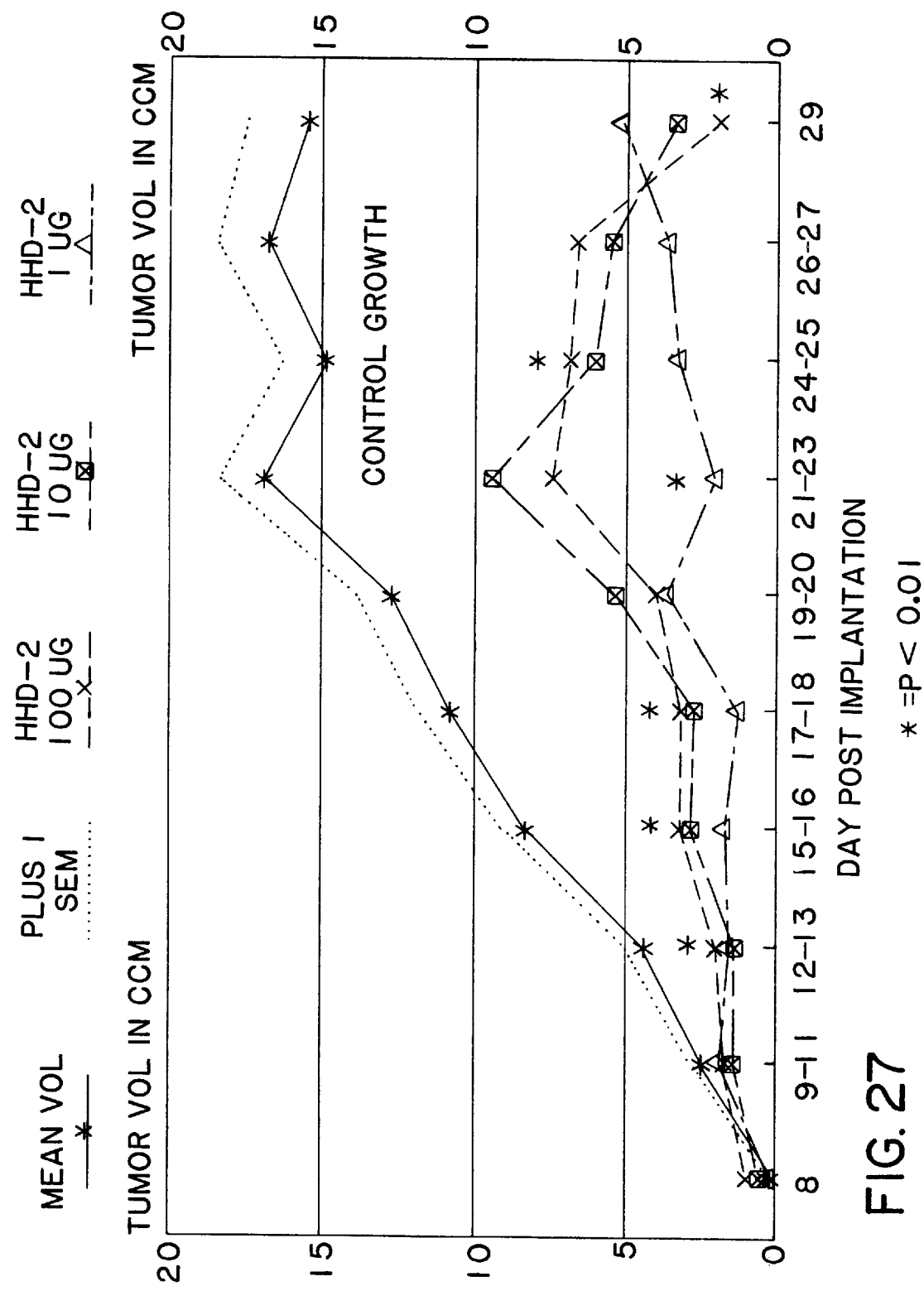
Figure 28:
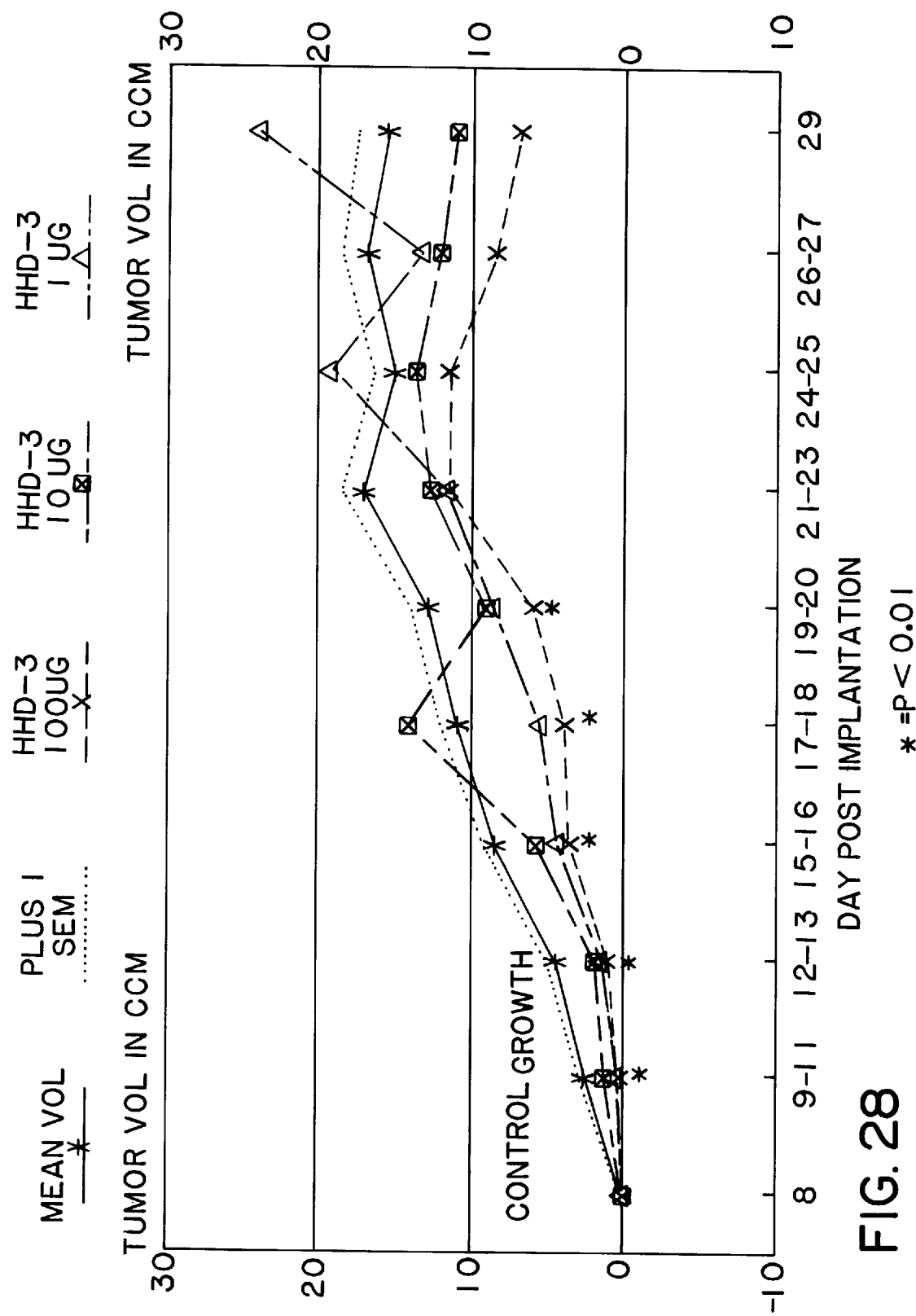
Figure 29:
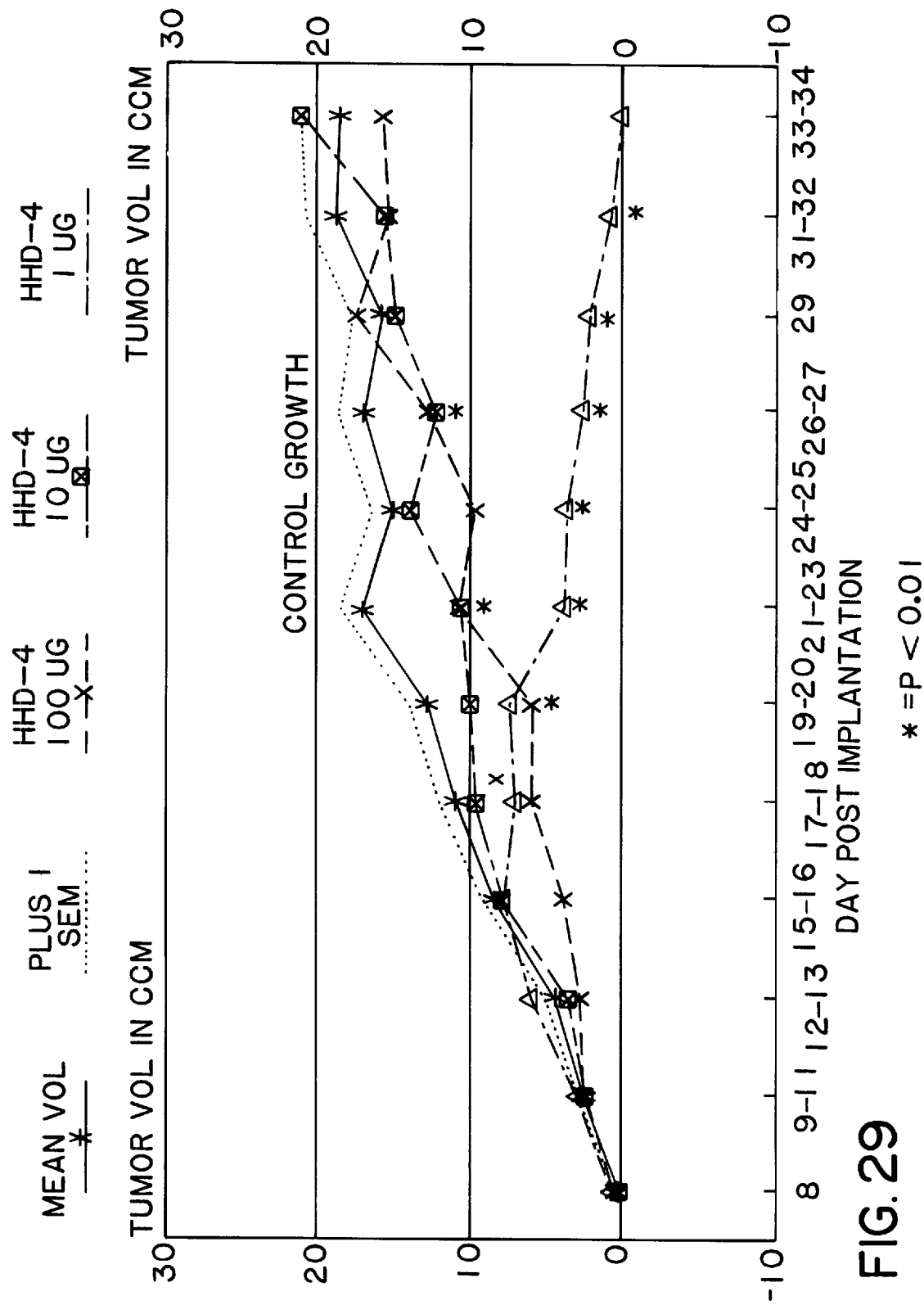
Figure 30:
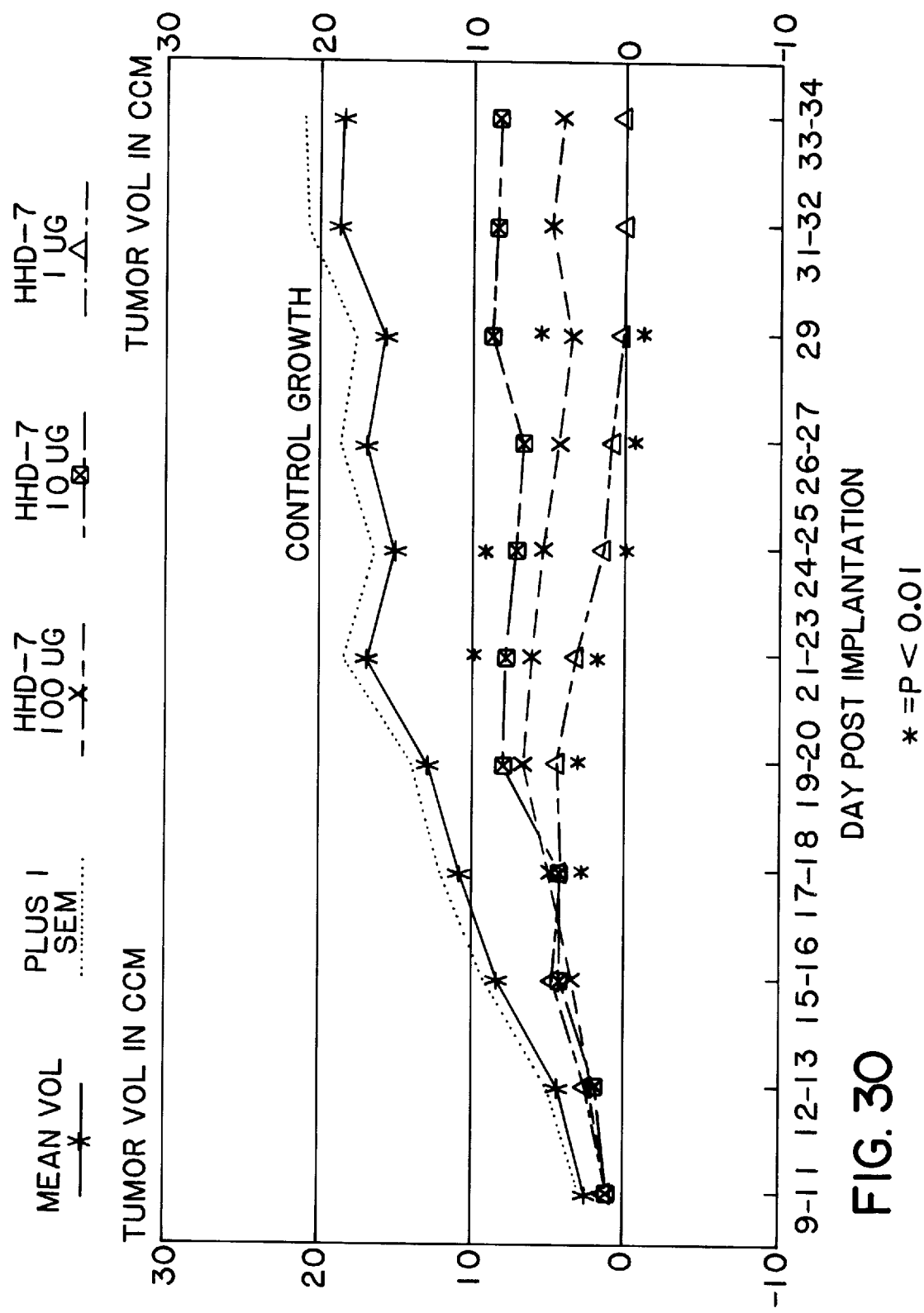
Figure 32A:
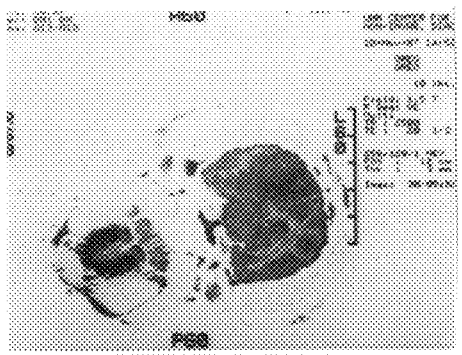
Figure 32C:
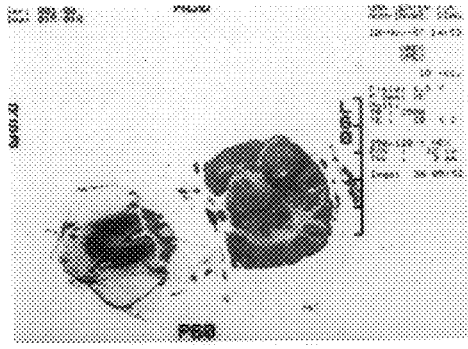
Figure 32B:
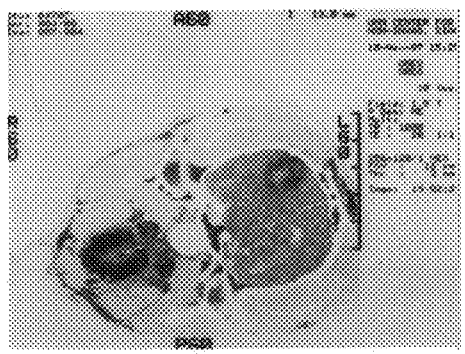
Figure 32D:
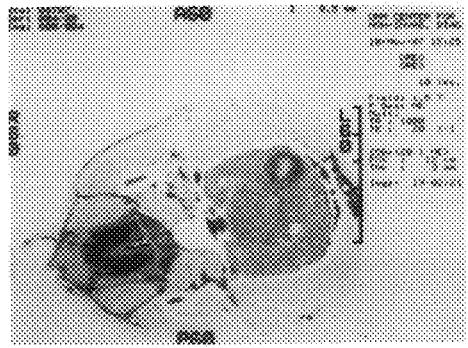
Figure 33A:
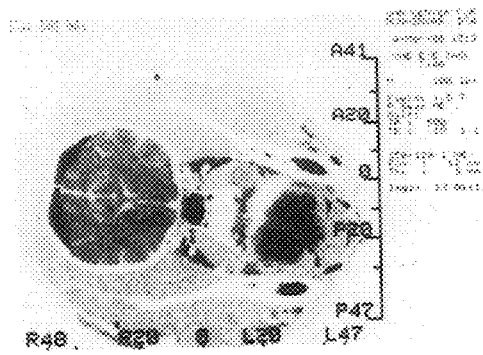
Figure 33C:
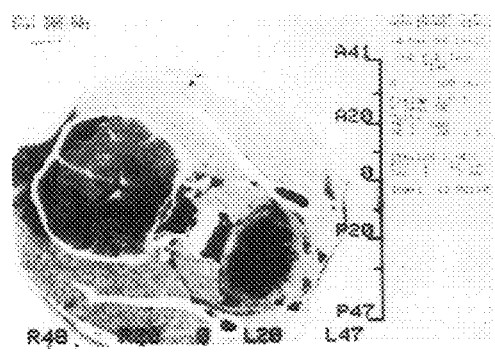
Figure 33B:
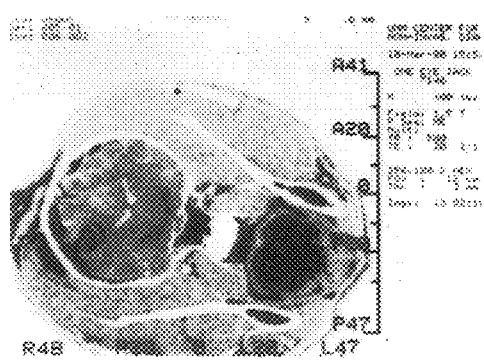
Figure 33D:
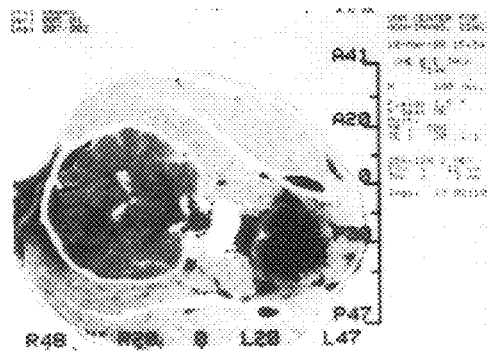
Figure 34A:
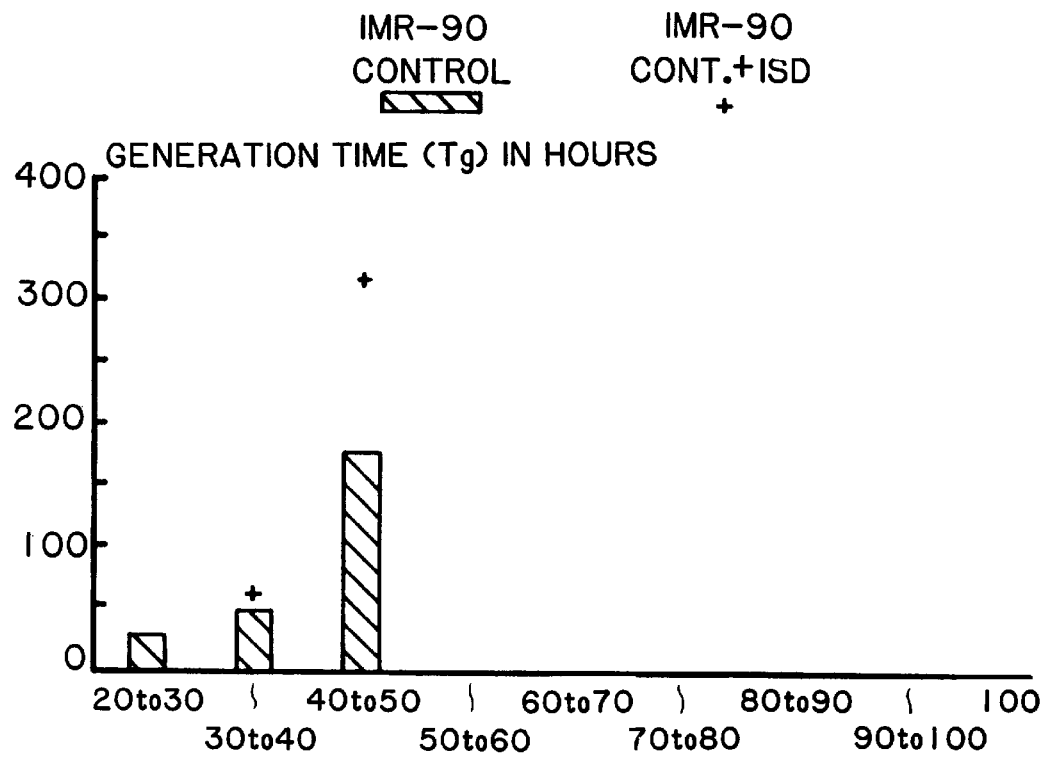
Figure 34B:
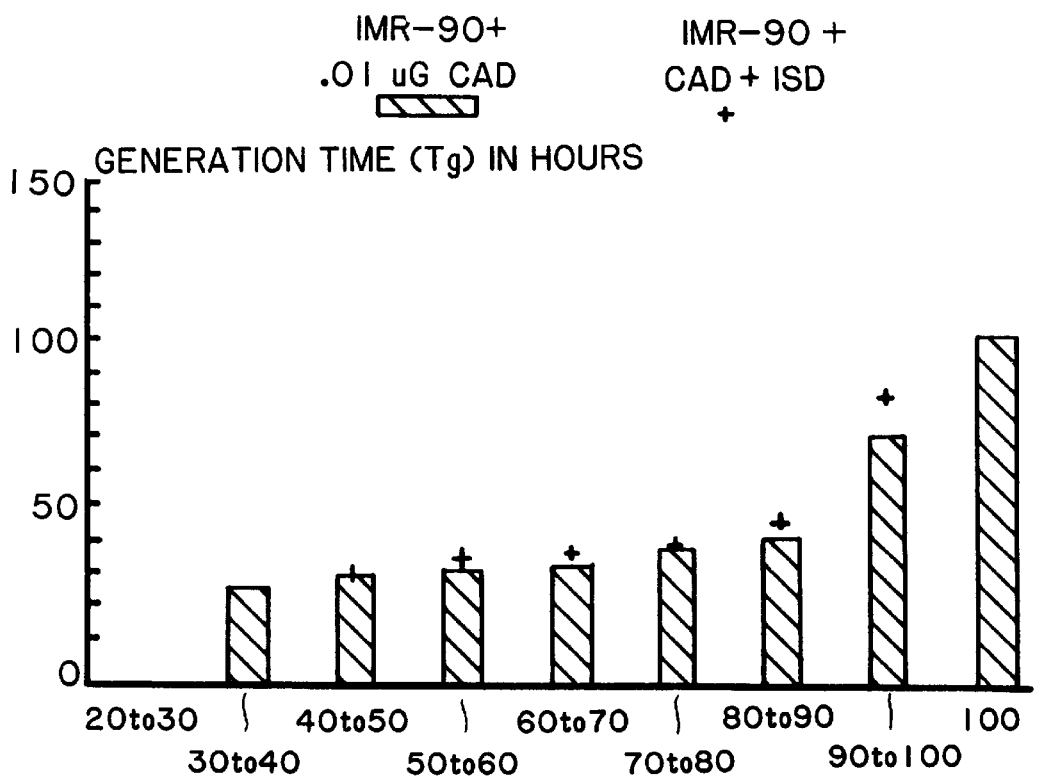
Figure 35A:
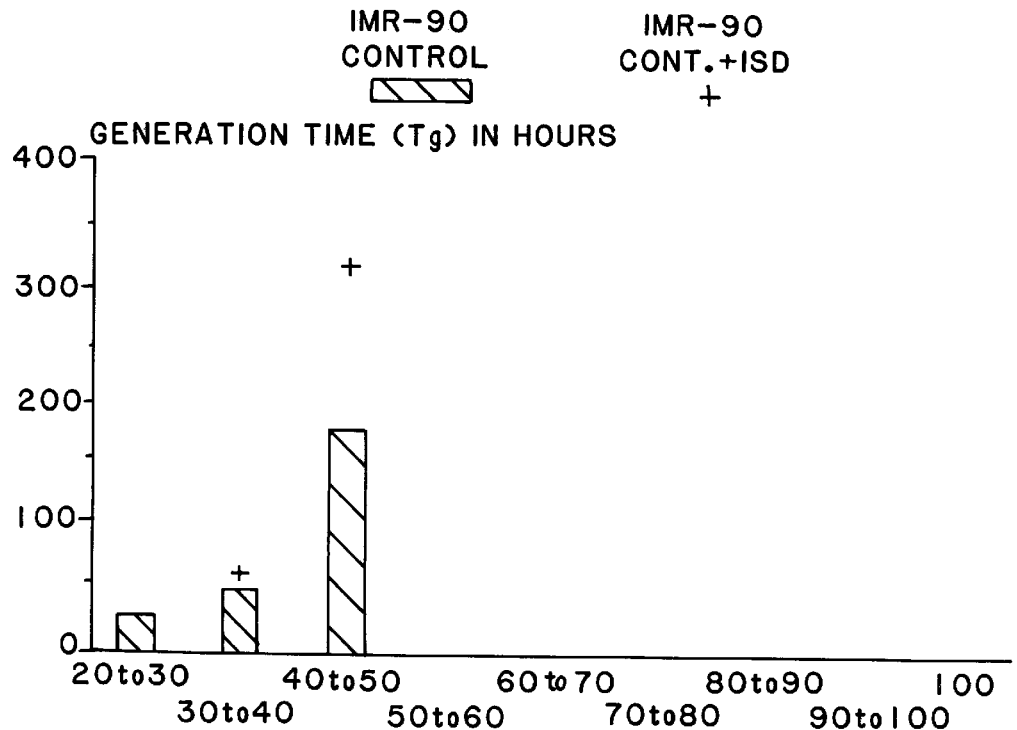
Figure 35B:
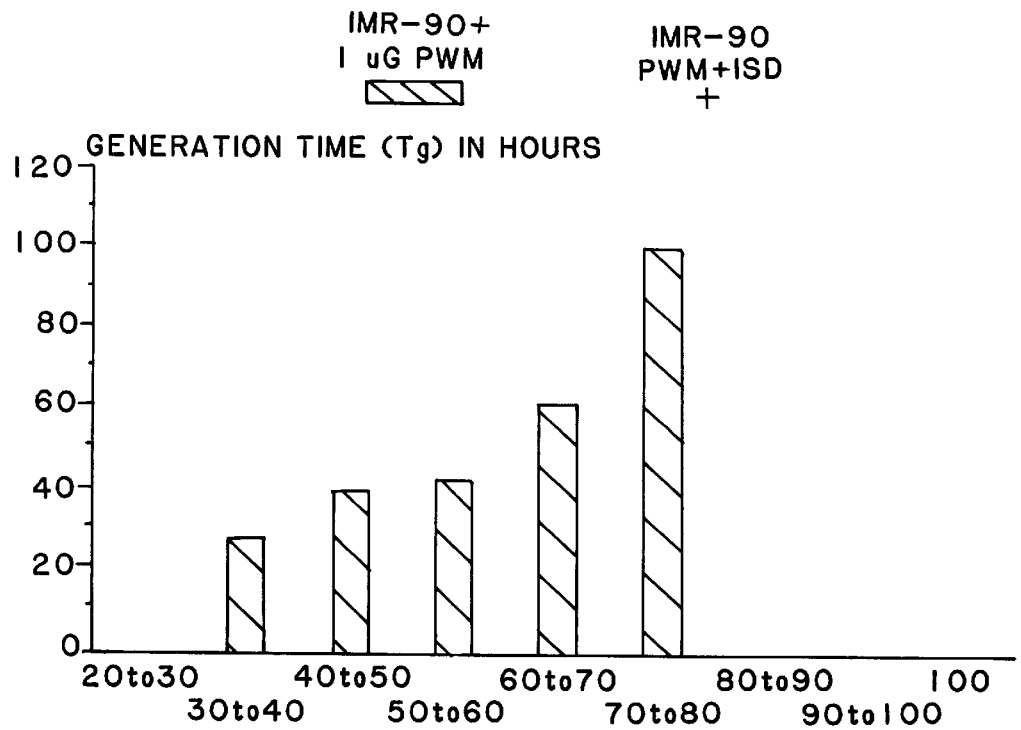
Figure 36A:
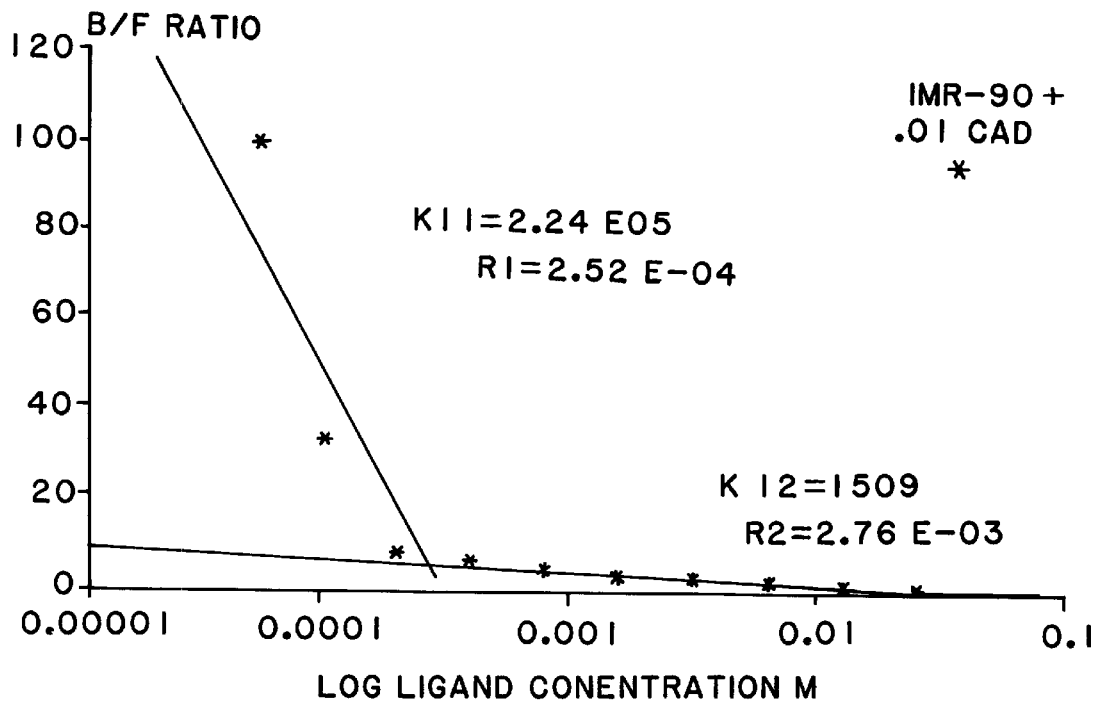
Figure 36B:
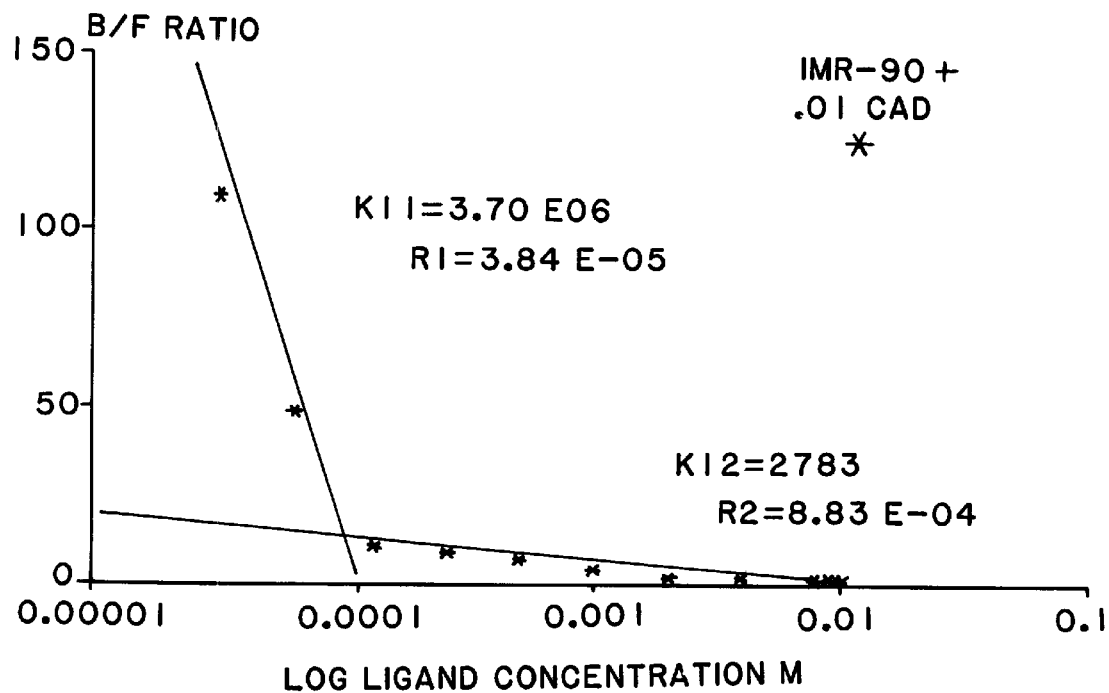
Figure 37:
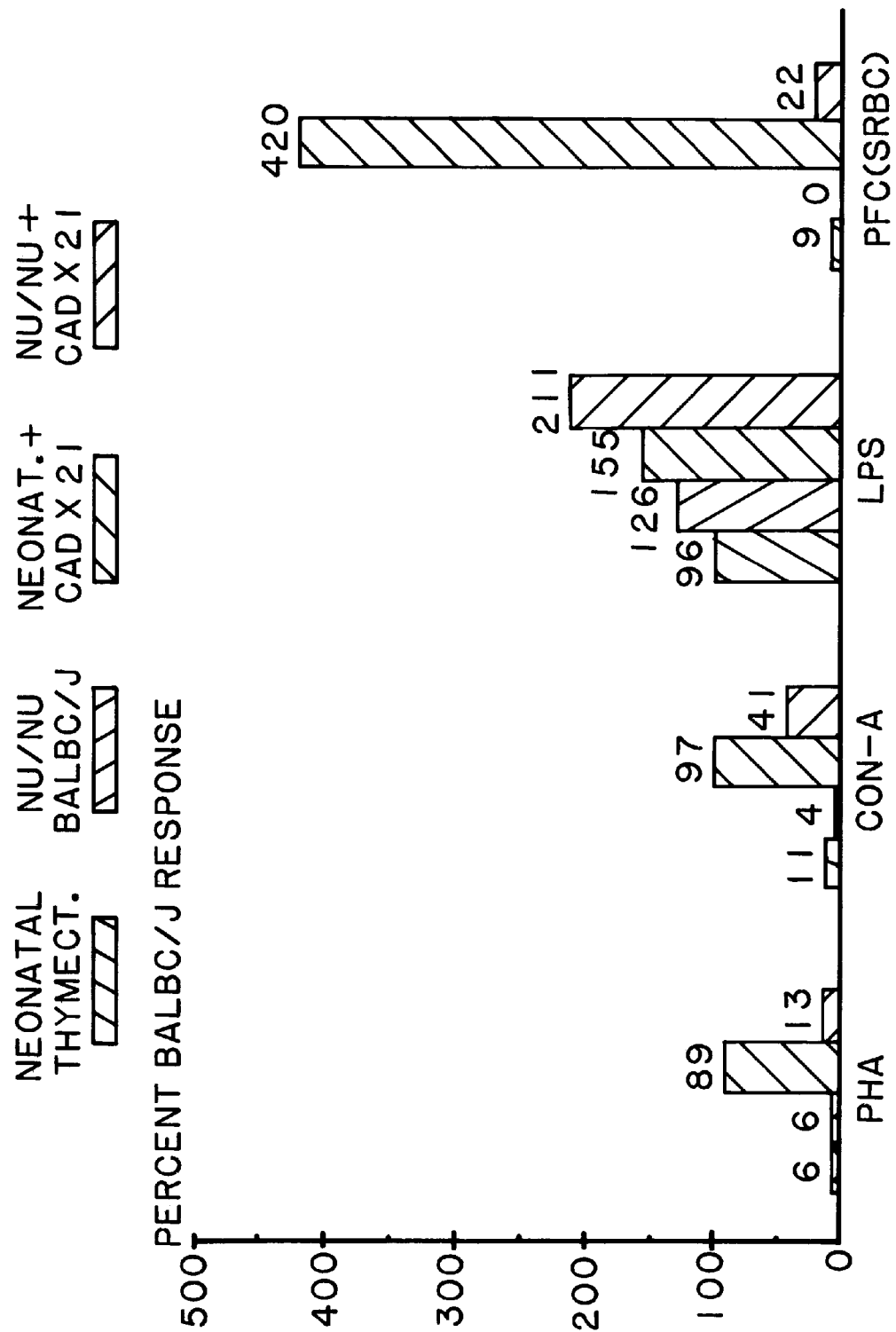
Figure 38:
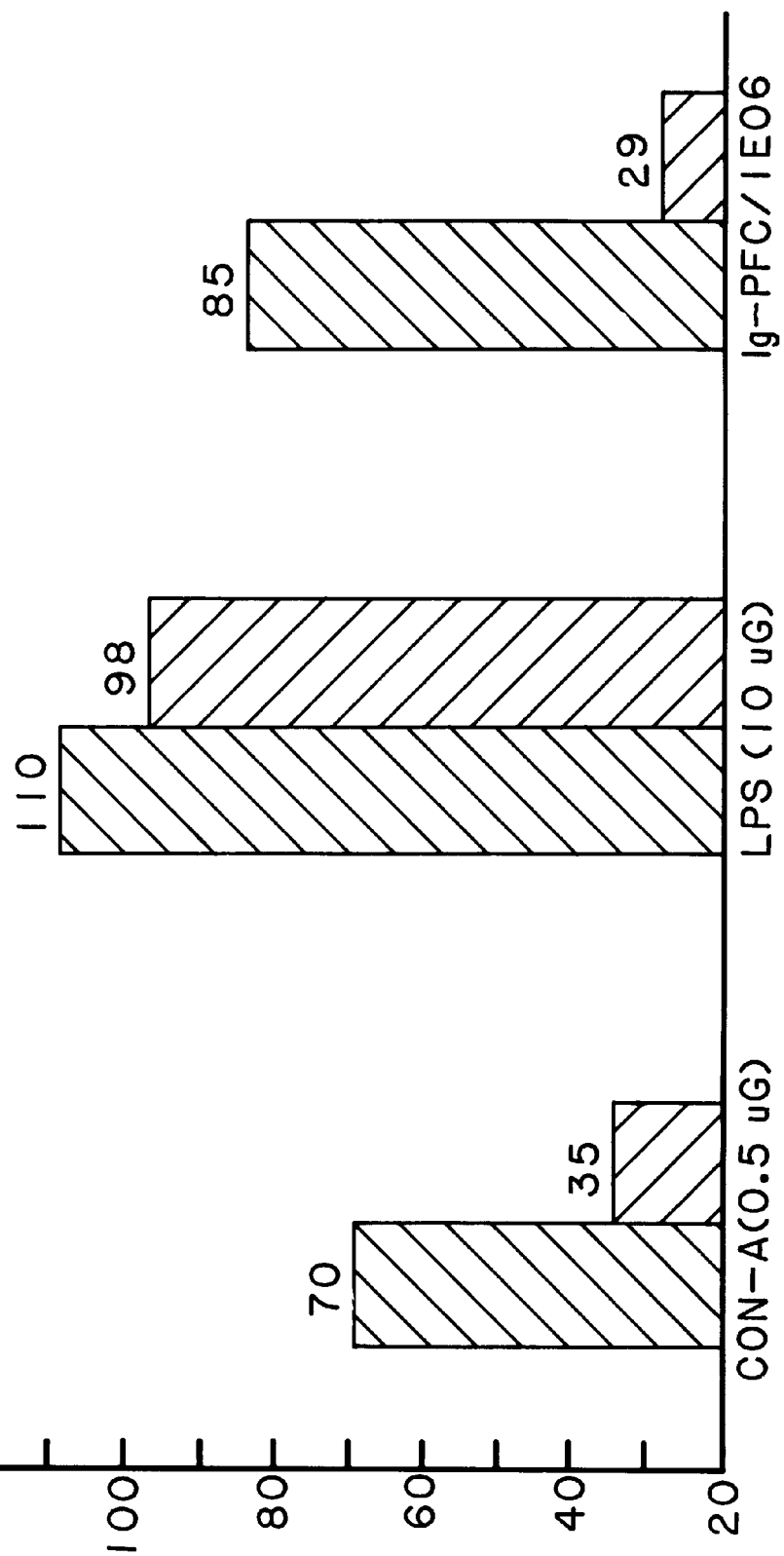
Figure 39:
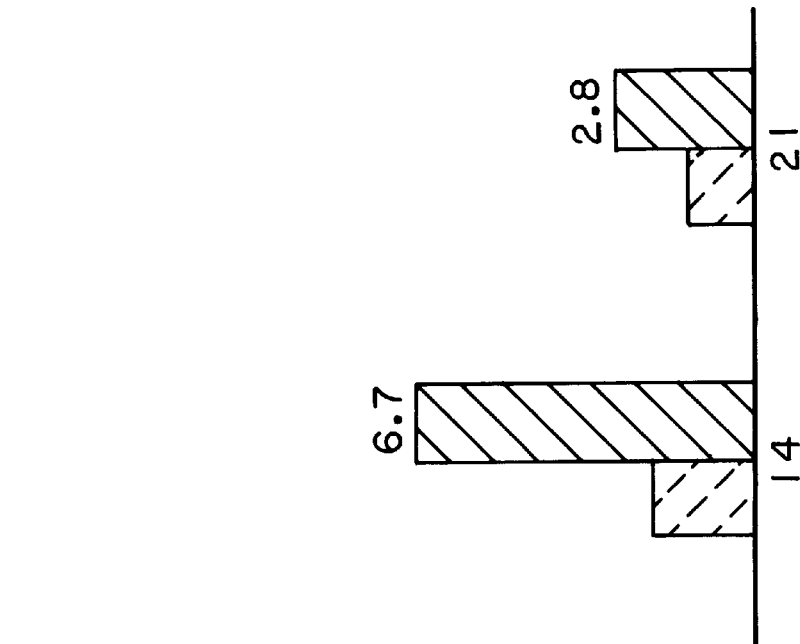
Figure 41A:
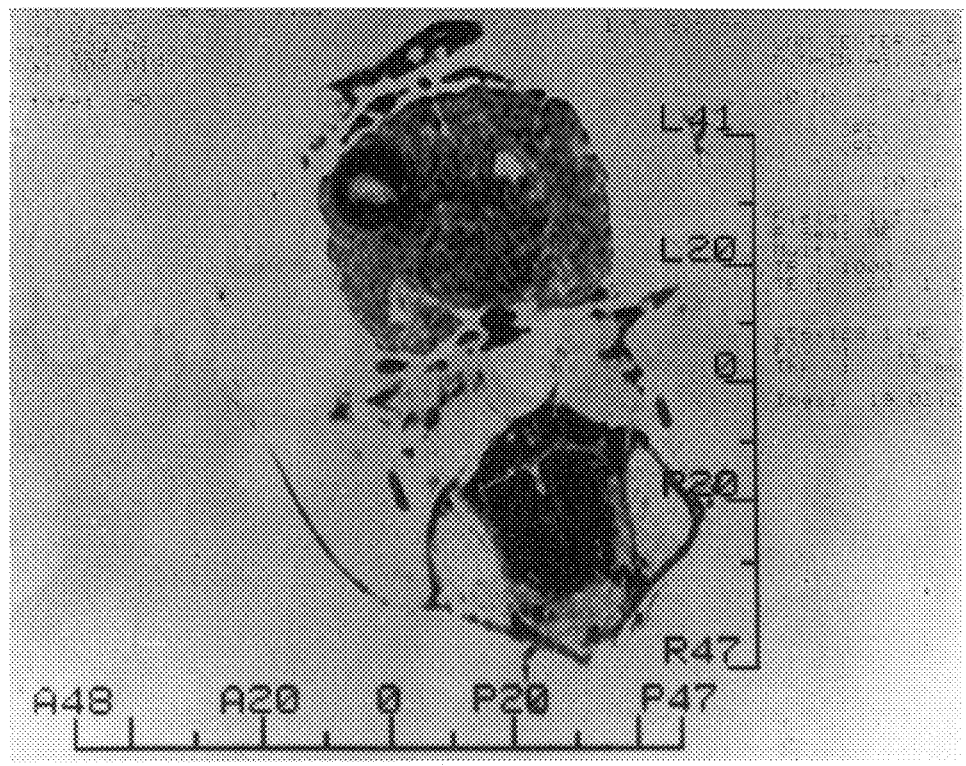
Figure 41B:
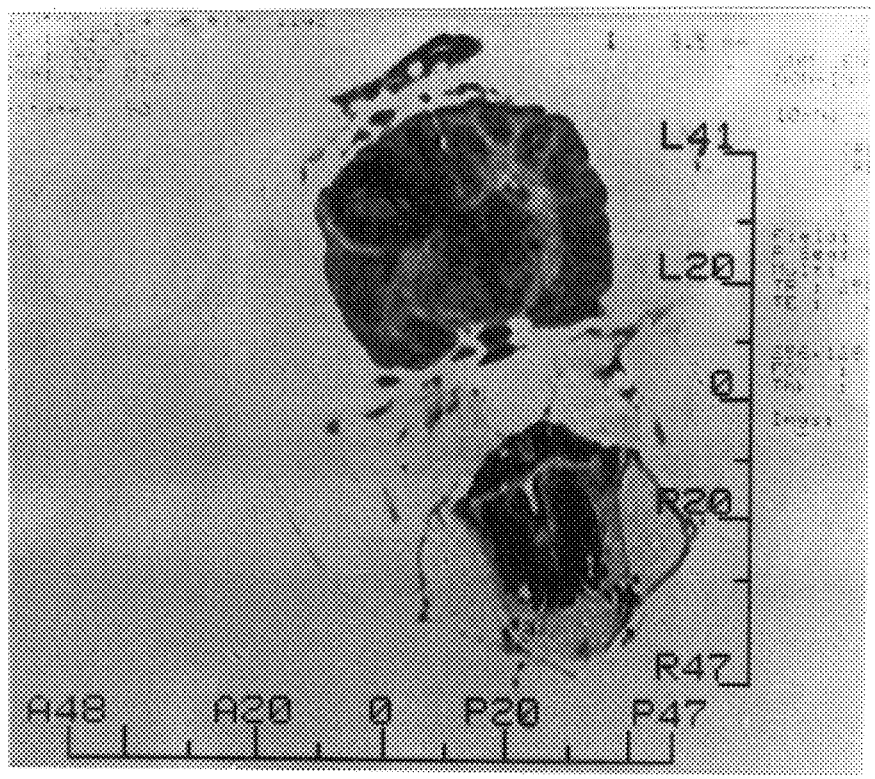
Figure 42A:
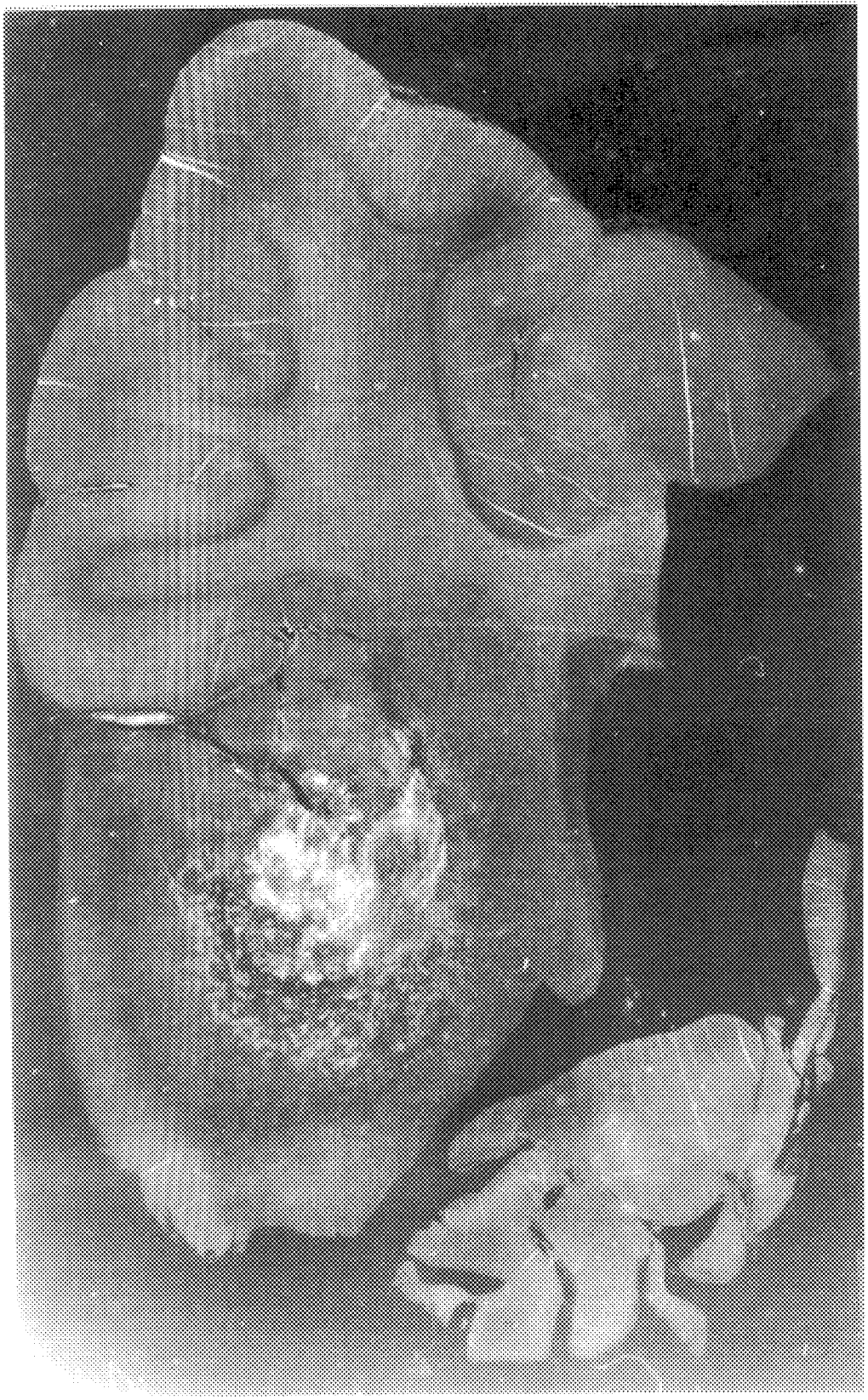
Figure 42B:
Figure 43A:
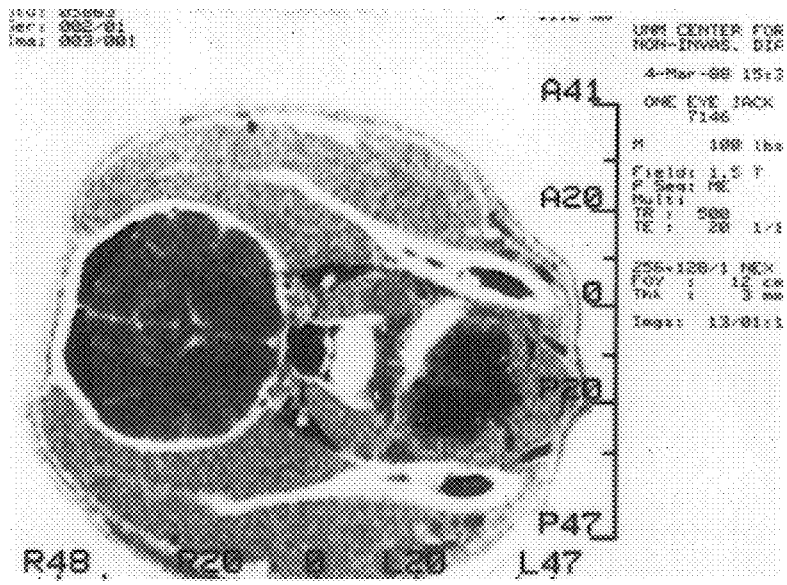
Figure 43B:
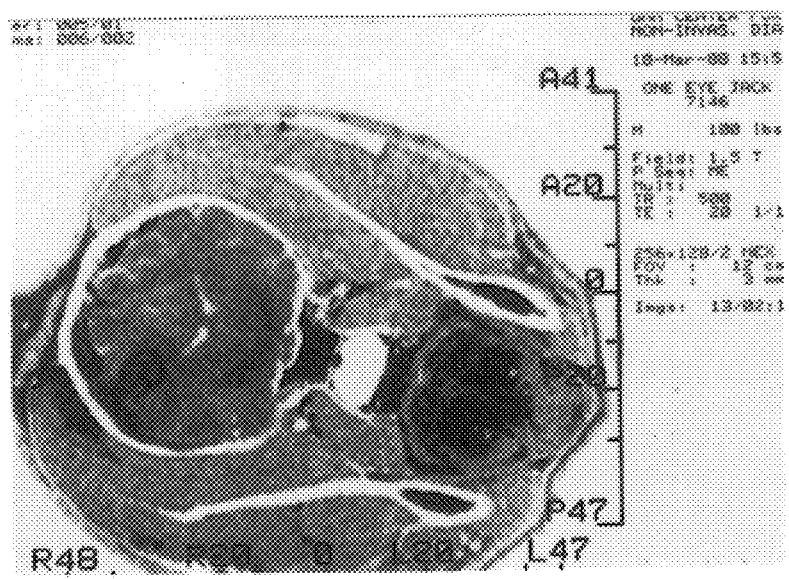
Figure 43C:
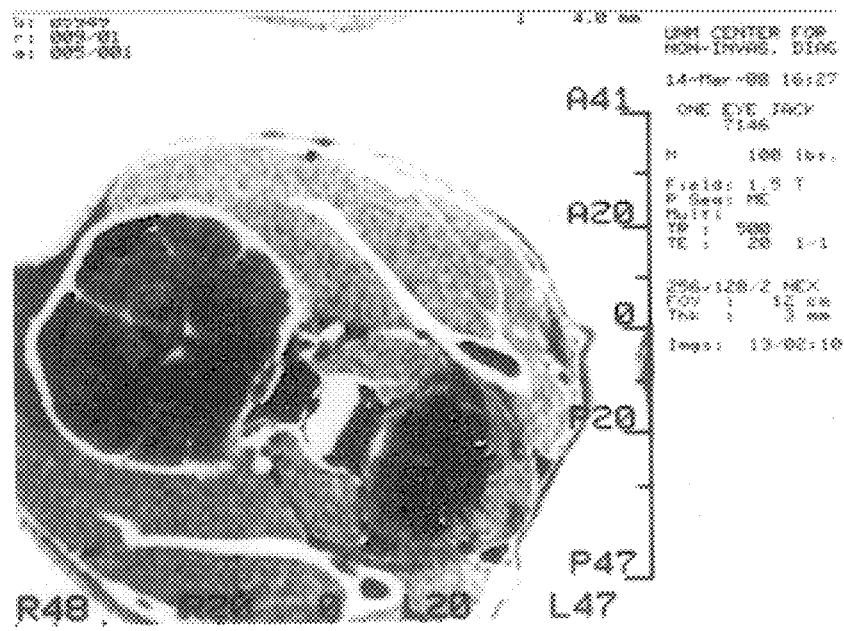
Figure 43D:
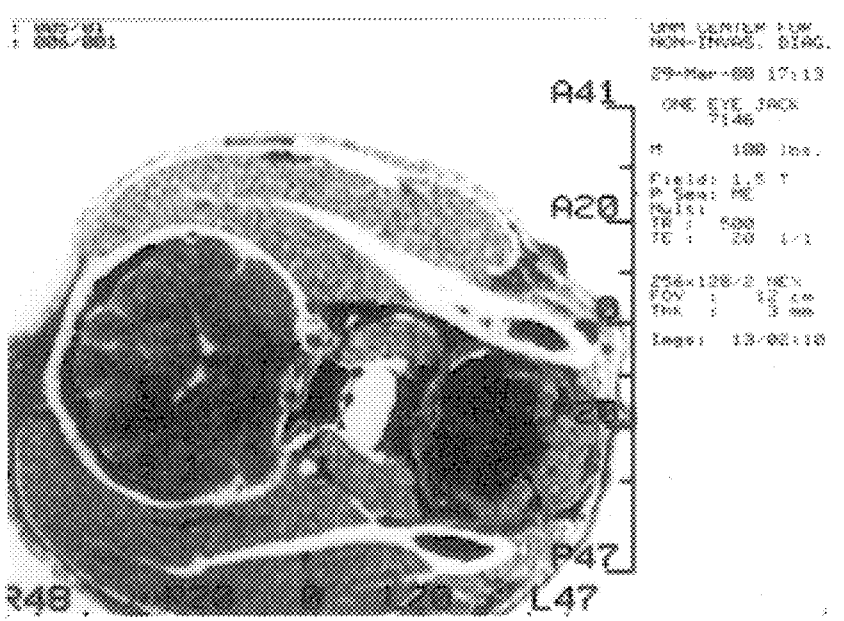
Figure 44A:
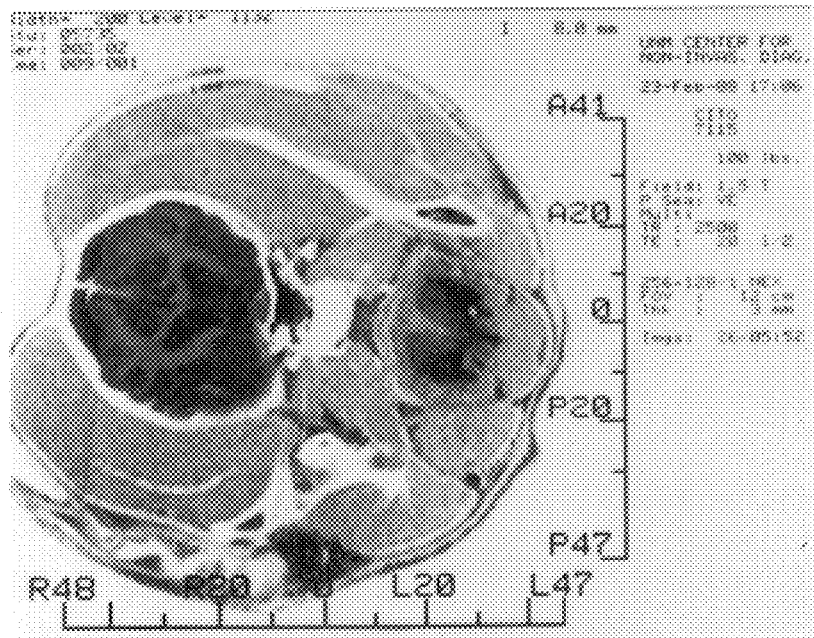
Figure 44B:
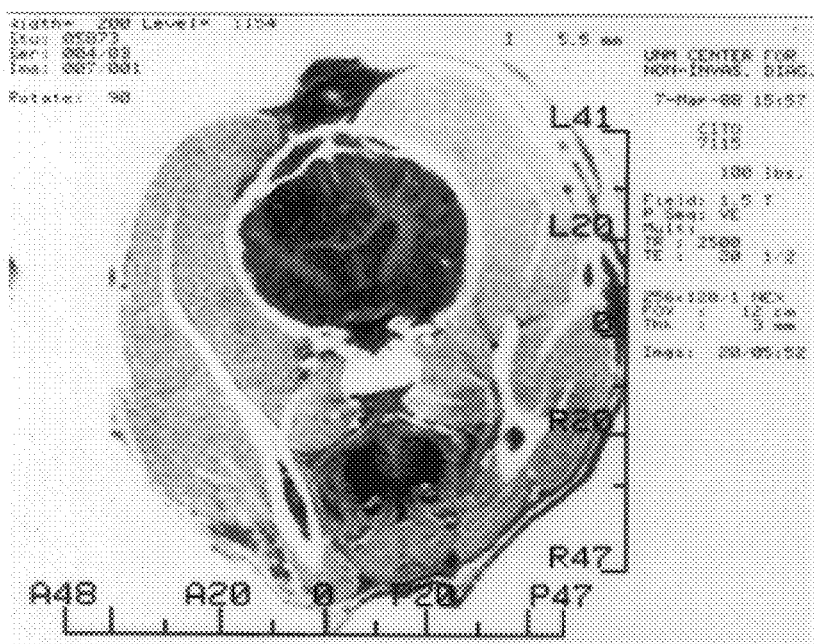
Figure 44C:
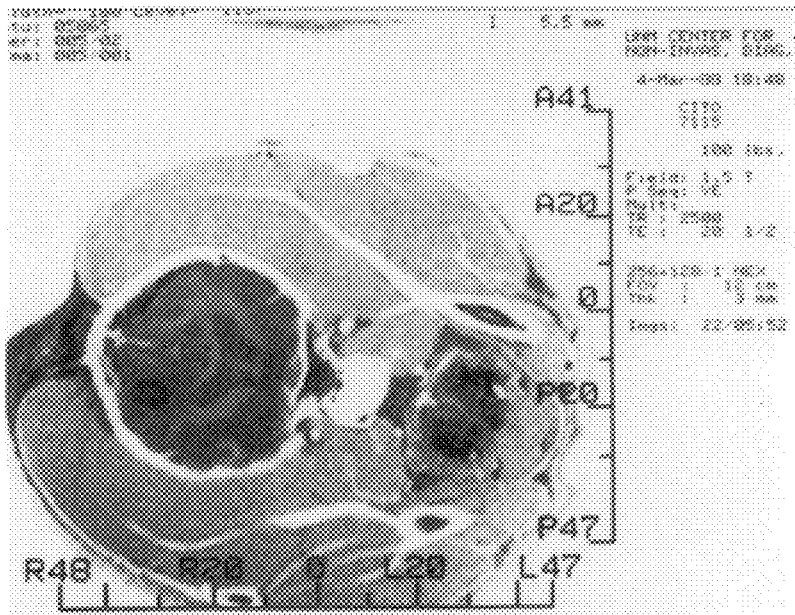
Figure 44D:
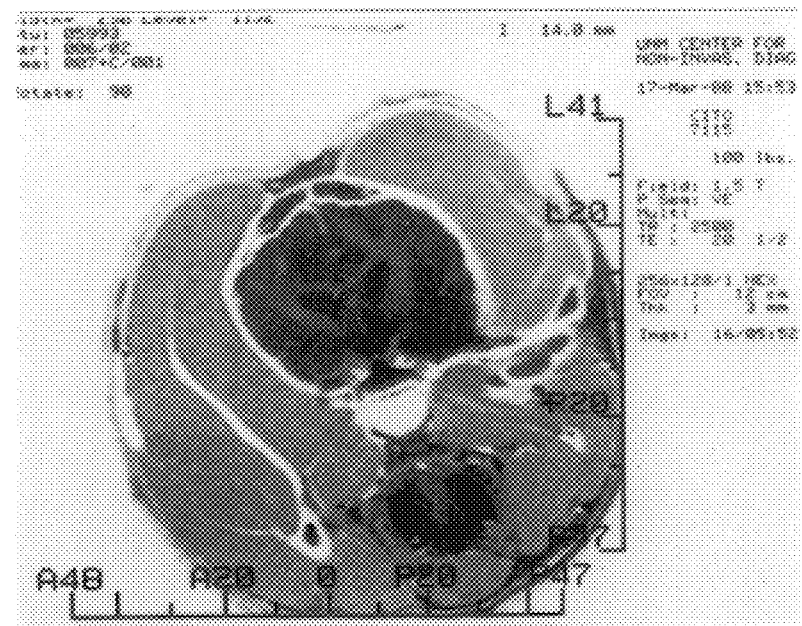
Figure 45:
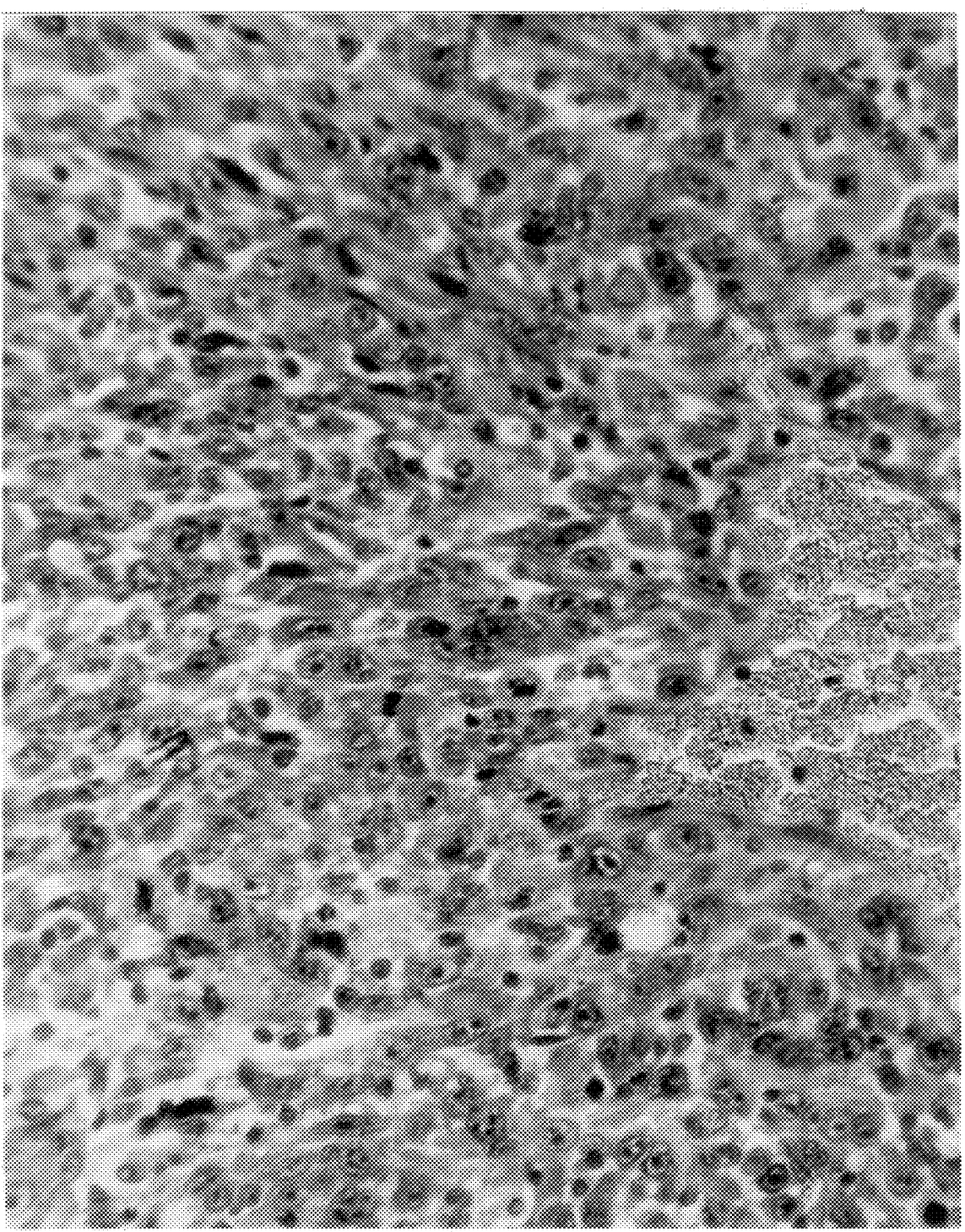
Figure 46A:
Figure 46B:
Figure 46C:
Figure 46D:
Figure 47A:
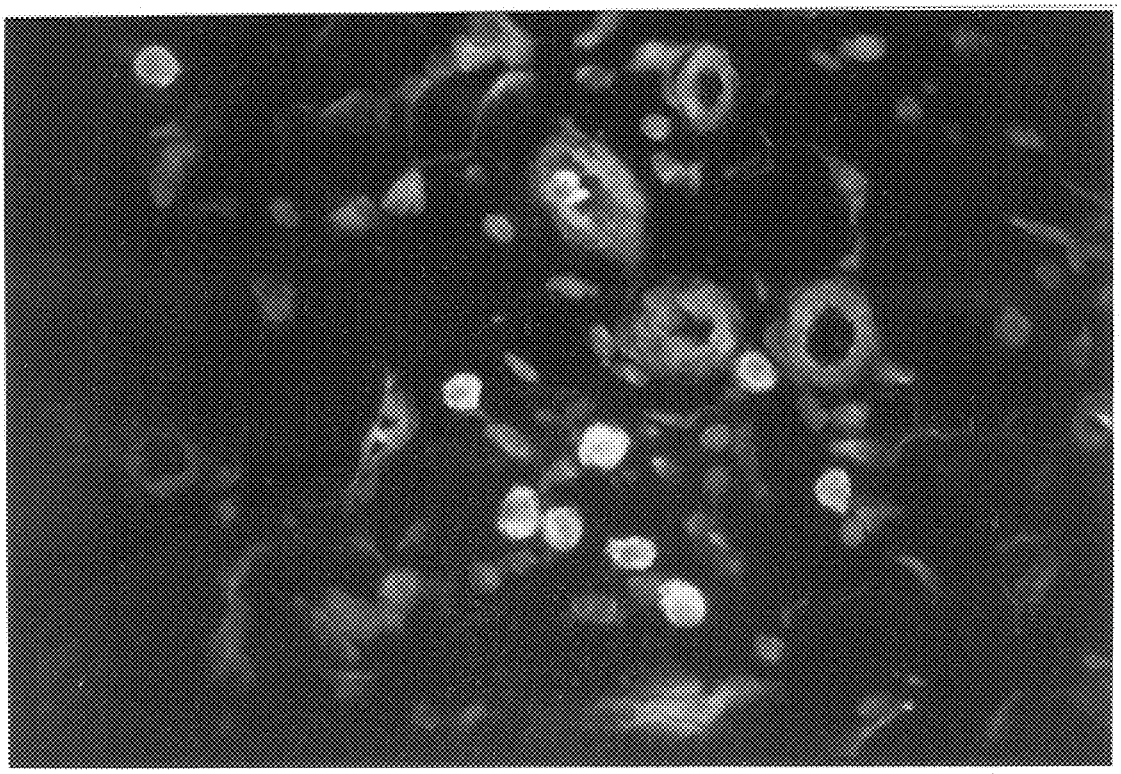
Figure 47B:
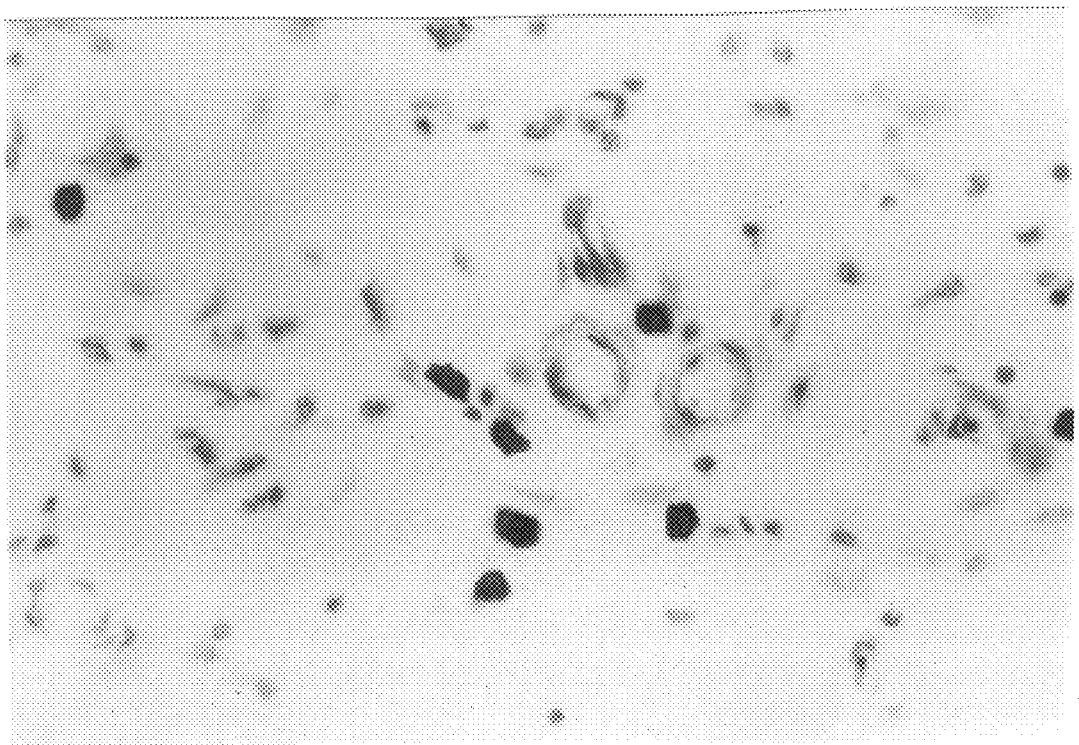
Figure 55A:
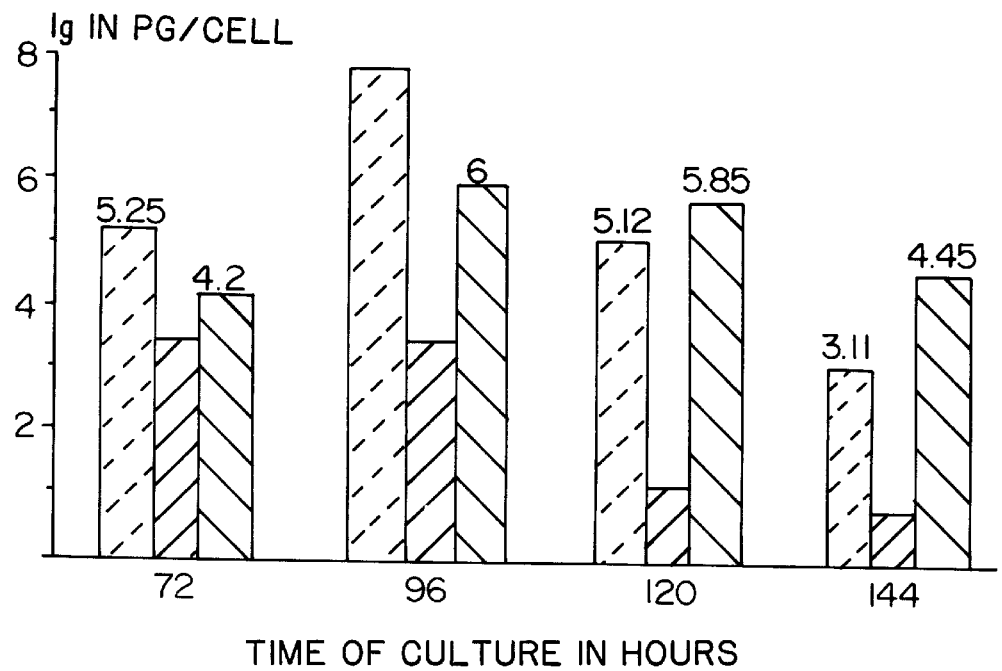
FIG. 55a shows the control values obtained for the production of various antibodies by monoclonal antibody producing cells in static culture under standard culturing conditions. It can be seen that production increases at first but drops off over time.
Figure 55B:
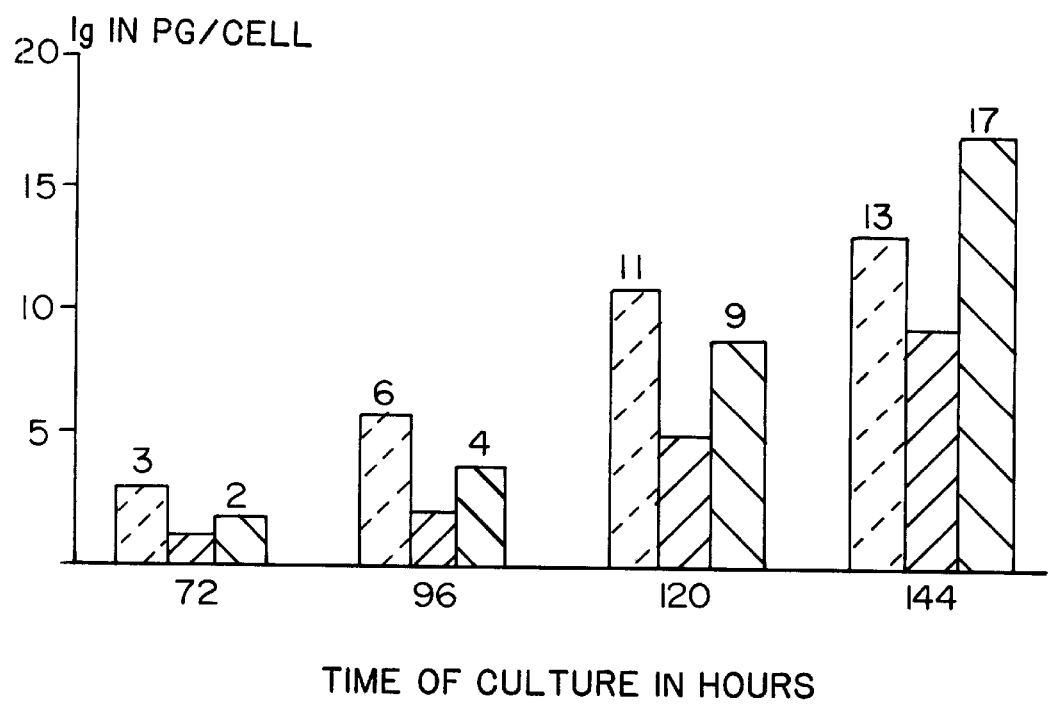
FIG. 55b shows the same cell lines in static culture but cultivated in the presence of PWM. It can be seen that the production of antibody has been increased and stays high long after the untreated static culture production declines.
Figure 55C:
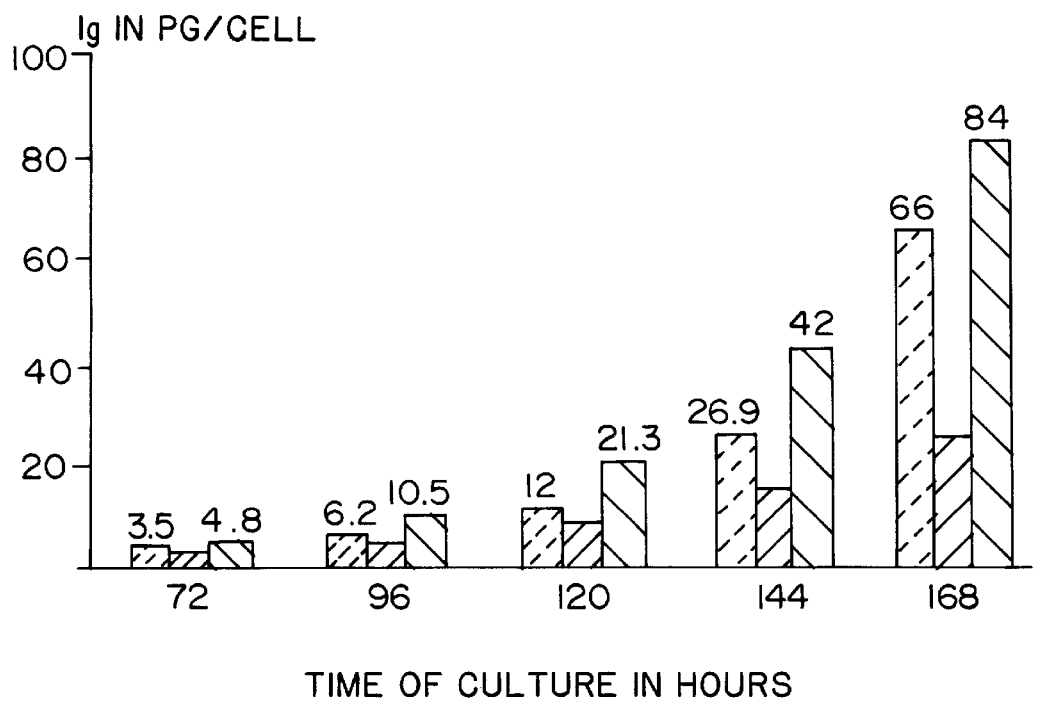
FIG. 55c shows the same cell lines cultured in Spinner flasks on a Cultispher-G ) gelatin matrix. Production is delayed as compared with the static culture.
Figure 55D:
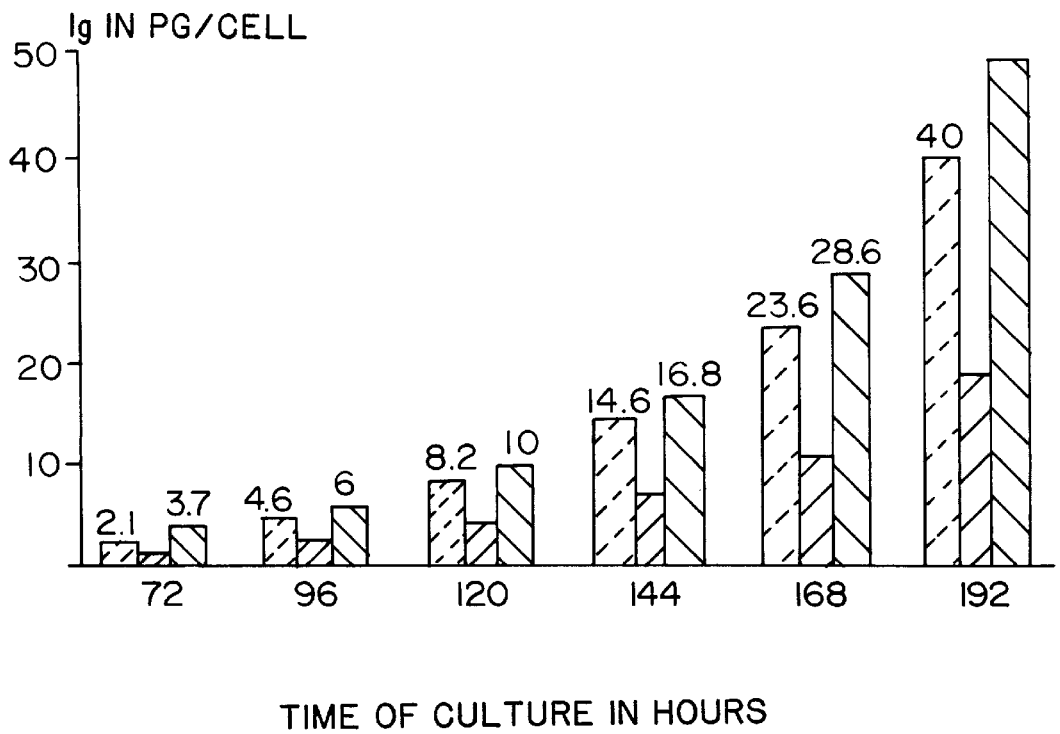
FIG. 55d shows the same cell lines cultured in Spinner flasks on a Cultispher-G gelatin matrix plus PWM. There is a synergistic effect of both the biomodulator and the matrix on the production of antibodies by the cells under these conditions, as well as an extension of the production kinetics over time.

The results demonstrate an in vivo temporal and quantitative correlation between enunciation and degree of tumor-specific immunoobulin response and the progression and ultimate regression of the tumor. The results are particularly striking as the experimental tumor (brain glioma) is generally considered to enjoy a privileged position beyond the blood/brain barrier, substantially beyond the reach of the humoral immune system. Experimental protocols are described in detail below (FIGS. 7–9, Example VII).

TABLE II

Production of Specific Anti-CG IgG
Antibodies in a Dog Treated with Compound IIc'

| Treatment | CG Implantation | IC-50% Titer (Anti-CG) |
|---|---|---|
| No | No | Baseline Values |
| Yes (2 months) | No | 0.0156 |
| Yes (2 months) | Yes (10–15 days) | 0.001 |
| Yes (2+ months) | Tumor Regressed | Baseline Values |

2. Cellular Immunity

Cellular immune response reflected the results reported in III, 1 above. As set forth in Table III, below, chromium-release cell-mediated lympholysis (CML) of the canines employed in Example III, 1 above, demonstrate a comparable cellular immunity to the humoral immunity therein set forth. After 14 days of administration (I.P. injection in physiological saline, M, W, F) of compound IIIc', only baseline levels of CG-specific CML were present. After an additional 2 months of administration of compound IIc', there was a significant increase in CML. This also is in the absence of CG antigen exposure. Then, after only a few days of exposure to the CG tumor implant, there was a large increase in the CML reactivity (see Table III). Then, after 5 weeks, at which time the tumor had totally regressed by independent measurement, the CML reactivity again returned to baseline. Thus, both cellular and humoral immunity appear to be modulatable in the absence of antigen by the compounds of the instant invention.

TABLE III

Cellular Cytotoxicity vs. CG Tumor in a Dog
Treated with Compound IIc'

| Date of Assay | Y = "M"X + B (Linear Regression of Toxicity) |
|---|---|
| December 14, 1987 | Y = 0.05 X + B |
| February 9, 1988 | Y = 0.35 X + B |
| February 17, 1988 | Y = 0.75 X + B |
| March 31, 1988 | Y = 0.05 X + B |

Example IV

Inhibition of Tumor Cells In Vitro

Canine glioma cells were cultured as below with varying concentrations of compound IIe' and compactin (U.S. Pat. No. 3,983,140) for different times of exposure. Cytotoxicity was determined as a function of simple survival ($T_{50\%}$), adherence ($ADH_{50\%}$) and thymidine incorporation ($I_{50\%}$) of the cells. Results are summarized in Tables IV and V, below:

TABLE IV

Canine Glioma Cells
The 50% Toxicity and Inhibition of Adherence Levels

| Drug | Time of Exposure (h) | T 50% (nM) | $ADH_{50\%}$ (nM) |
|---|---|---|---|
| IIe' | 24 | 750 | 75 |
|  | 72 | 800 | 70 |
|  | 96 | 900 | 75 |
| Compactin | 24 | 500 | 50 |
|  | 72 | 200 | 75 |
|  | 96 | 350 | 75 |

Estimates of the 50% inhibitory concentrations of the various drugs tested on simple survival ($T_{50\%}$) and adherence ($ADH_{50\%}$) for canine glioma cells.

TABLE V

Canine Glioma Cells
The 50% Inhibition of Thymidine Incorporation

| Drug | Time of Exposure (h) | $I_{50\%}$ (nM) |
|---|---|---|
| IIe' | 24 | 50 |
|  | 48 | 75 |
|  | 72 | 80 |
|  | 96 | 50 |
|  | 24 | 100 |
|  | 48 | 75 |
|  | 72 | 30 |
|  | 96 | 50 |

Estimates of the $I_{50\%}$ of the various drugs tested on thymidine incorporation of canine glioma cells in culture.

As is apparent from Table IV, compound IIe' was cytotoxic to tumor cells in the range of 700 to 900 nM.

In the same concentration range, compound IIe' significantly inhibited thymidine incorporation into DNA ($I_{50\%}$ 50–80 nM, Table V).

Compound IIe' is a potent inhibitor of HMG-CoA reductase, having an $IC_{50}$ of 3 nM and $ED_{50}$ of 25 µg/kg (Example I).

Example V

Effect on Tumor Cell Generation Time

A. Canine Glioma Cells

Canine glioma cells were cultured as described in Example IV and exposed to either a 10 nM concentration of compound IIe' and DMSO (dimethylsulfoxide), or DMSO alone as control. The cells were harvested every 72 hours after the controls had reached 85% confluency. Generation time (Tg) was determined as the number of hours required for the cell population to double. Results are summarized in Table VI.

TABLE VI

The Effect of Compound IIe' on
Canine Glioma Generation Times

| | Conditions | Exposure Time (h) | Tg (h) | % Change |
|---|---|---|---|---|
| 10 | Nm (Experimental) | 72 | 25.3 | 136 |
| 0 | (Control) | 72 | 18.6 + 4.2 | |
| 10 | nM | 72x2 | 24.0 | 129 |
| 10 | nM | 72x3 | 33.4 | 180 |
| 10 | nM | 72x4 | 28.9 | 155 |

Mean of triplicate determinations. Canine glioma cells were grown under conditions to promote exponential growth characteristics; $2 \times 10^5$ cells in a T-25 flask. The cells were harvested every 72 hours after the controls had reached approximately 85% confluency. The drug was added at the initiation of culture in DMSO, the control cultures had just DMSO. The drug concentration was adjusted with DMS0 so that the final concentration of DMS0 was always 0.5%.

As is seen from the table, after three passages, there was an increase in the generation time from 18.6 h (control tumor cells) to 33.4 h (experimental) for three passages. This represents a 1.8-fold slowing of the growth rate. In addition, tumor cells treated with compound IIe' showed evidence of contact inhibition as the cells approached confluency, a phenomenon seen with nontransformed cells but not seen in transformed cell lines. (Control canine glioma cells continue to grow rapidly when reaching confluency and do not exhibit appropriate contact inhibition.)

B. Human Colon Carcinoma Cells

The procedure of Example VA, above, was repeated except a human colon carcinoma cell line (LS-174) was used instead of the canine glioma cell line. Results are summarized in Table VII below.

TABLE VII

The Effect of Compound IIe' on LS-174 Generation Times

| | Conditions | Exposure Time (h) | Tg (h) | % Change |
|---|---|---|---|---|
| 10 | Nm (Experimental) | 72 | 84.9 | 320 |
| 0 | (Control) | 72 | 26.5 | |
| 10 | nM | 72 × 2 | 106.2 | 400 |
| 10 | nM | 72 × 3 | 110.3 | 416 |
| 10 | nM | 12 × 4 | 109.6 | 414 |

Mean of triplicate determinations. LS-174 cells (human colon carcinoma) were grown under conditions to promote exponential growth characteristics; $2 \times 10^5$ cells in a T-25 flask. The cells were harvested every 72 hours after the controls had reached approximately 85% confluency. The drug was added at the initiation of culture in DMSO, the control cultures had just DMS0. The drug concentration was adjusted with DMSO so that the final concentration of DMS0 was always 0.5%.

The results in slowing of the generation time were similar to those set forth in Table VI, but were more striking. Untreated control tumor cells had a generation time of 26.5 h. After three passages in the presence of Compound IIe', the generation time was prolonged by 4.16-fold to 110.3 h. When the drug was withdrawn (two passages), the generation time returned to control levels (data not shown).

Example VI

In Vivo Tumor Inhibition: Murine Model Canine Glioma

Fifty four nude rats (Harlan) were injected in the right flank with $5 \times 10^6$ canine glioma cells. Animals at the time of injection were between 52 and 63 days old and weighed approximately 200 g. The rats were divided into 7 groups, each group having a total number of 7 rats except for the control group, which totalled 12 animals. Compound IIc' was administered to the experimental animals at one of the following doses for each experimental group: 100 μg/kg, 10 μg/kg, 1 μg/kg, 0.1 μg/kg, 0.01 μg/kg and 0.001 μg/kg (phosphate buffer saline, M, W, F, I.P.). The control animals were injected with PBS (phosphate buffered saline) only. The volume of each injection was 100 μl. The injections of drug were simultaneously begun with injection of tumor cells. The animals were injected with the appropriate dosage of drug (1 ng/kg to 100 ng/kg) by I. P. injection and tumor length, width and depth were measured using caliphers each Monday, Wednesday and Friday (M, W, F) morning for approximately 9 weeks. Each point on the graphs represents the total of all rats for each group. Where the points where a break (") is shown did not regress to the baseline in the experimental dosages, the rats were sacrificed. The data were normalized for the greater number of control animals by multiplying the total tumor volume for the control animals by $7/12$.

Results are summarized in FIGS. 69–74.

Figure 72:
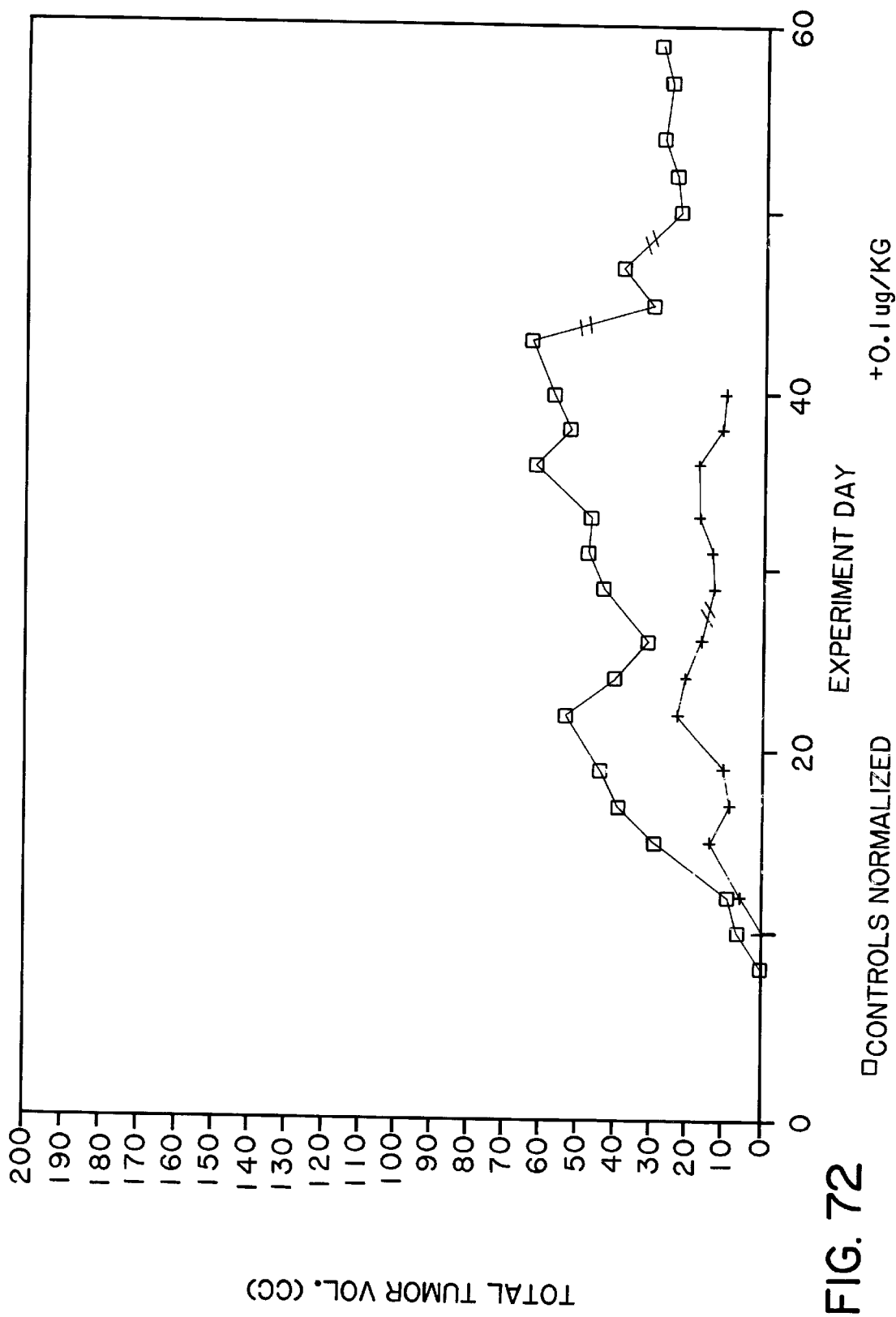
Figure 73:
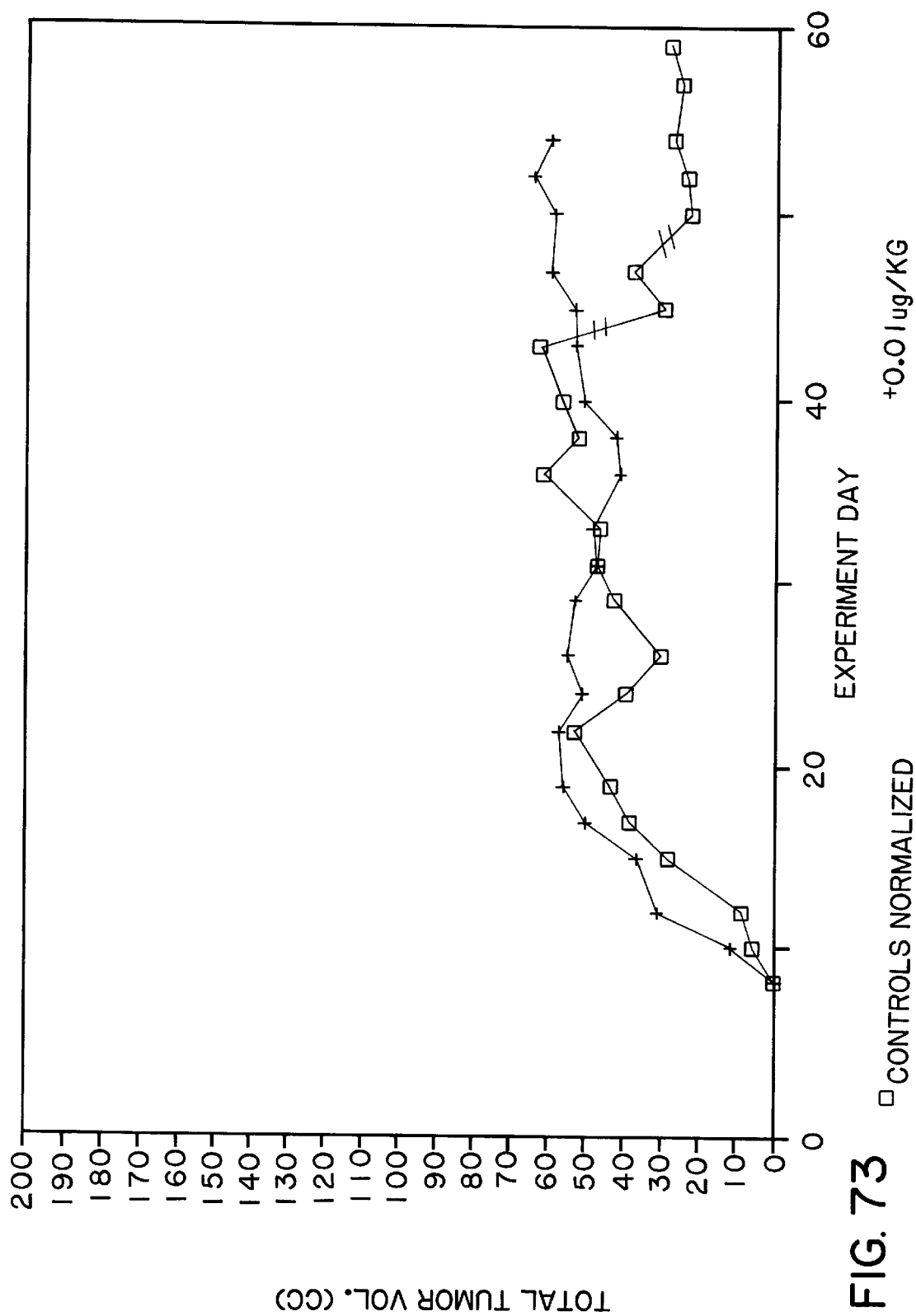
Figure 74:
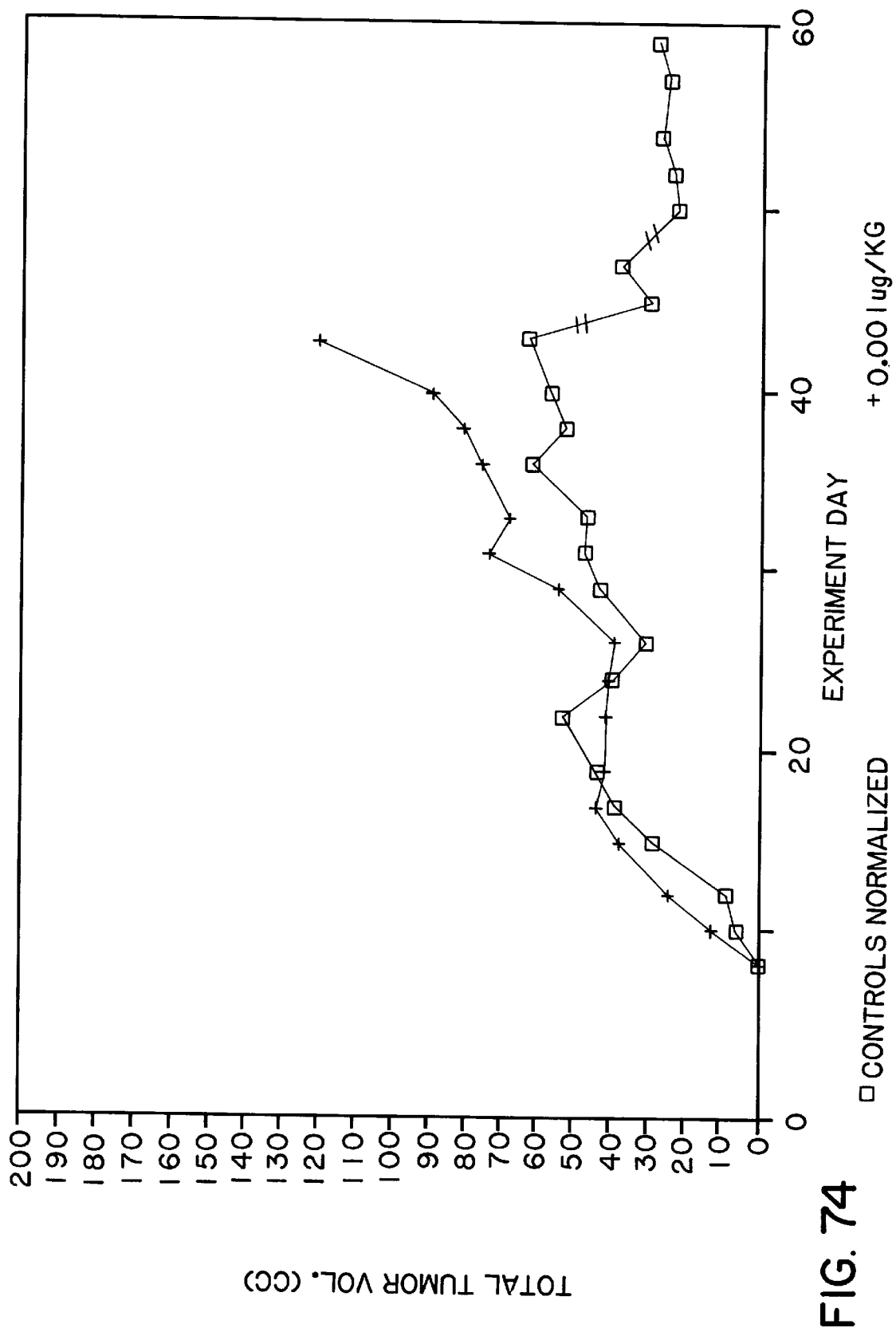

The Harlan nude rat model employed has partially compromised immunological competency. The experimental compound IIc' is a potent immune stimulant (see Examples, above). The most effective dosage for inhibition of canine glioma cells in this model was 100 ng/kg (FIG. 72). Little or no cytostatic activity was exhibited at the higher doses employed (10 and 100 μg/kg) or at the lowest dose of 1 ng/kg. The optimal dosage for cytostatic activity in vivo closely correlates with the optimal dosage for immune stimulation in vitro (Example IIA, HPBL assay). The optimal dose in vivo (100 ng/kg, equivalent to 250 pM with uniform distribution) compares to the optimal dose in vitro, 100 pM.

Similar anti-tumor activity has been observed with Compounds IIa', IIe' and TF004.

Example VII

In Vivo Tumor Inhibition: Canine Model

Canine glioma was implanted surgically into the brains of four outbred dogs ($2 \times 10^6$ cells). This procedure normally causes death by tumor growth in 14–28 days.

Simultaneous with implantation, the dogs were each placed on a regimen of compounds according to the invention, Compounds IIa', IIe' and TF004 in various dosages were administered on alternate days (M, W, F) by I.P. injection in phosphate buffered saline.

Tumor progress was assessed at weekly intervals by NMR, employing GdDTPA as imaging agent. This method illuminates vascularization at the surface of the tumor, and provides images which correlate well with neuropathological observations. The compounds were found to have a direct, early effect on the tumor, evidenced in this NMR procedure as a substantial edema in the vicinity of the tumor.

Figure 75:
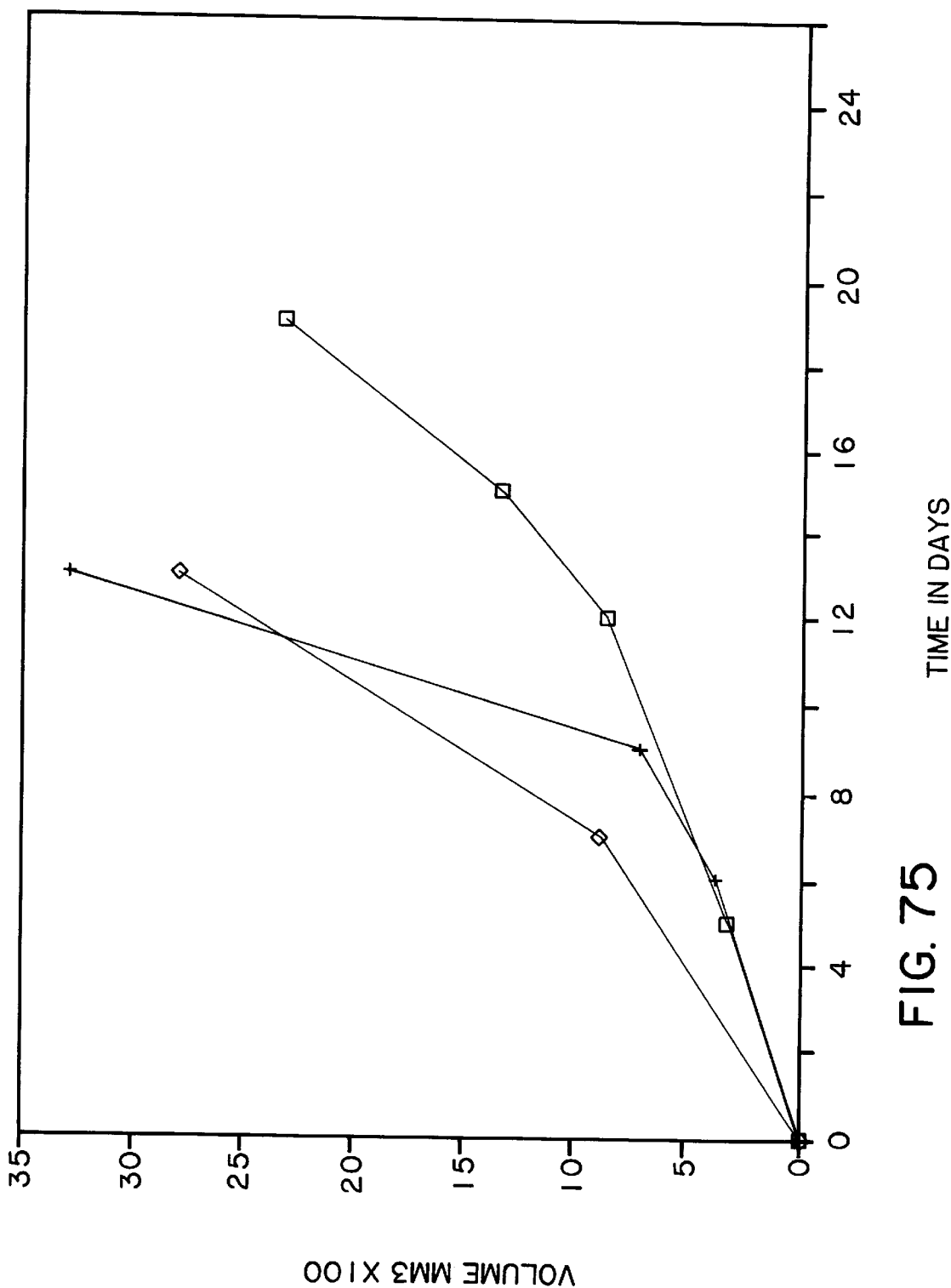

The experiments and results are summarized as follows:

FIG. 75 shows the rapid and progressive growth of the canine glioma tumor after implantation in the left frontal lobe of three dogs. These animals were sacrificed at 12 to 19 days because they were showing significant neurological deficit. This tumor would certainly kill the dogs by 14 to 28 days.

Figure 76:
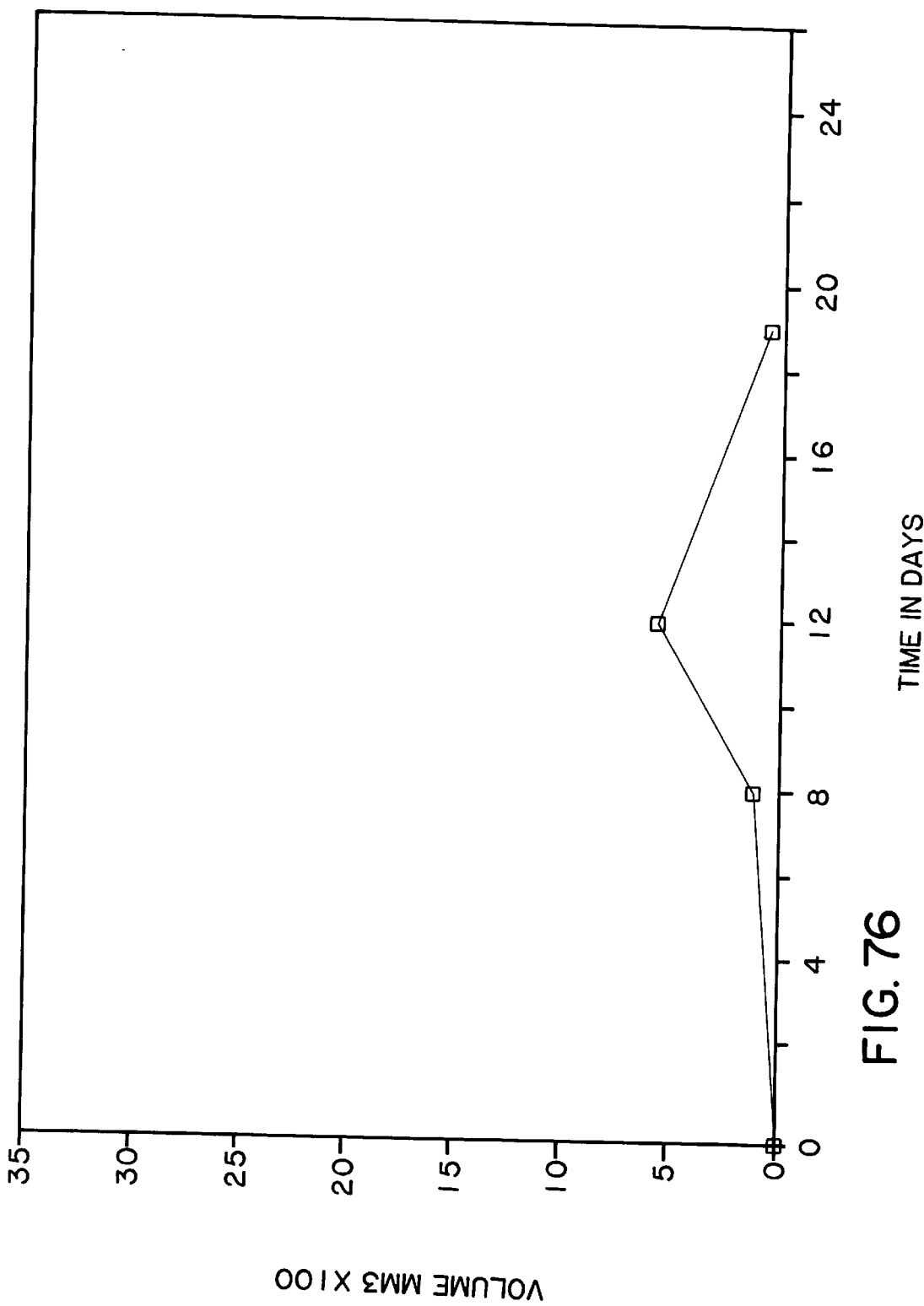

FIG. 76 shows a dog with an implanted canine glioma in the left frontal lobe of the brain. This animal was pre-treated with TF-002. After implantation treatment with TF-002 [10 ng/kg, I.P., on alternate days (M, W, F)] was continued. A small tumor appeared on Day 12. It regressed by Day 19. Later studies (date not shown) showed this animal to be free of tumor.

Figure 77:
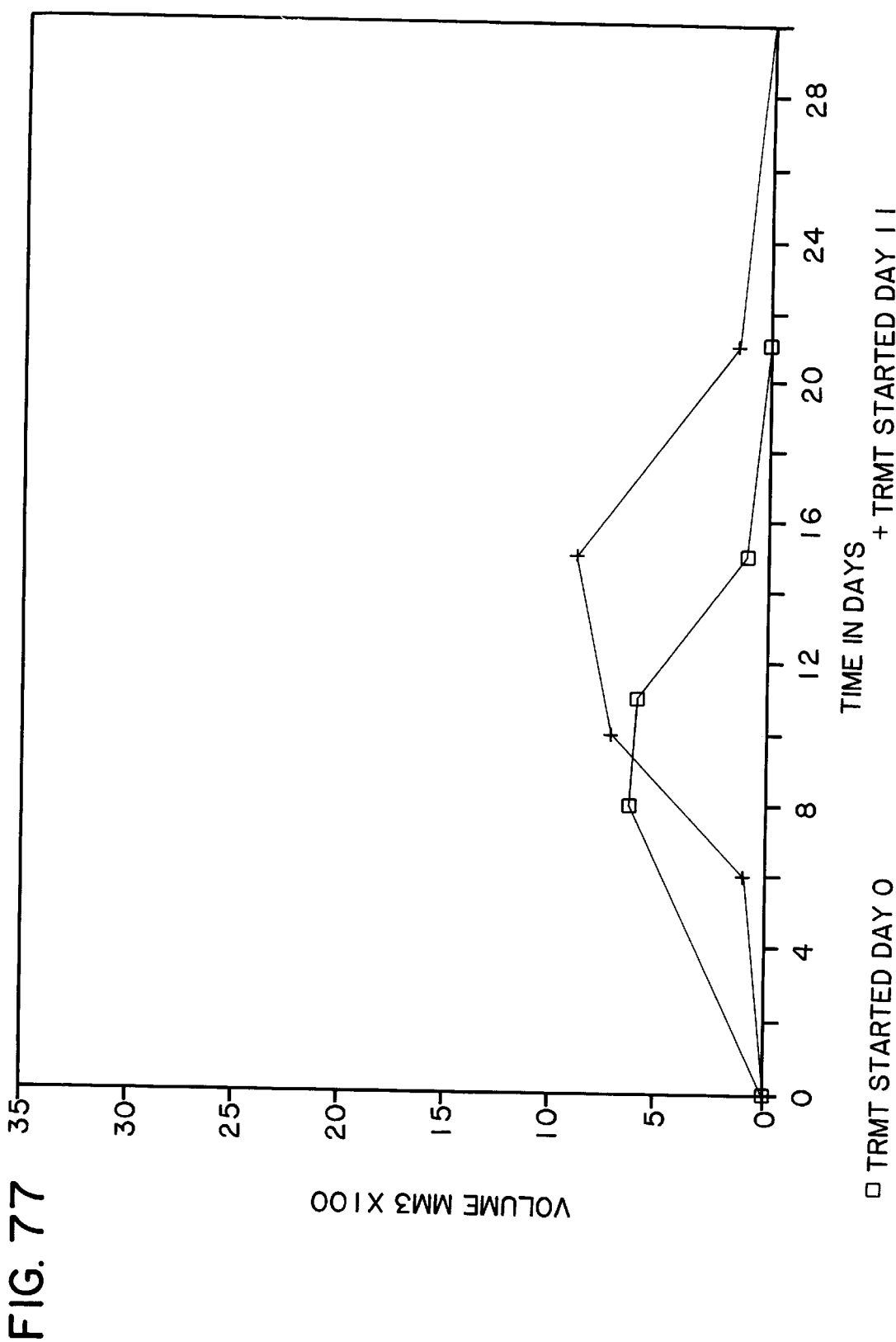

FIG. 77 shows two dogs treated with TF-004. The line shown by squares (□—□) represents tumor size in the dog where treatment was begun ont eh same day (1 ng/kg I.P. on alternate days, i.e., M, W, F) as tumor implantation. A tumor was visible on Days 8 and 12. Substantial regression had occurred by Day 15 and complete regression occurred by Day 21. Another dog (x—x) received a canine glioma in the left frontal lobe by surgical implantation. A tumor was visible at Day 10. Treatment with TF-004 was begun on Day 11. Substantial regression was observed by Day 21 and complete regression was observed by Day 30.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating or preventing melanoma, ovarian tumors, cervical tumors, breast tumors, stomach tumors, hepatocellular tumors, pancreatic tumors, midgut tumors, bladder tumors, prostate tumors, brain tumors, myeloma, larynx tumors, leukemia, lymphoma, lung tumors, and colon tumors, comprising administering to a host in need thereof, or contacting a culture, tissue or organ with, an effective amount of a compound of formula (I)

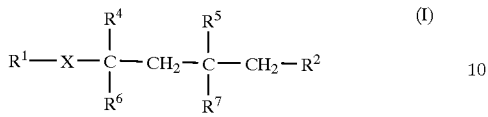

wherein

R$^1$ is an optionally substituted aromatic, cycloaliphatic or heterocyclic ring system, R$^2$ is —CH$_2$OH, —CHO, —COOR$^3$, —COSR$^3$, —CONR$^8$R$^9$ or the corresponding lactone

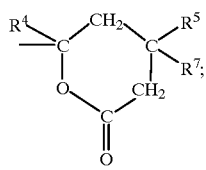

wherein

R$^3$ is H or C$_{1-10}$-alkyl,

R$^4$ and R$^5$ are each independently H or C$_{1-6}$-alkyl,

R$^6$ and R$^7$ are each independently OR, NHR or SR wherein R is H or C$_{1-4}$-alkanoyl, R$^8$ and R$^9$ are each independently H or C$_{1-10}$-alkyl, and X is C$_{2-3}$-alkylene, C$_{2-3}$-alkenylene, C$_{2-3}$-alkynylene, a cyclopropylene group, —OCH$_2$— or —SCH$_2$—.

2. The method of claim 1 wherein said brain tumor is a glioma.

3. The method of claim 1 wherein the compound has a stereoconfiguration of 3R,5R, 3S,5S or, where X is saturated, 3R,5S or, when X is unsaturated, 3S,5R.

4. The method of claim 1 wherein the compound is

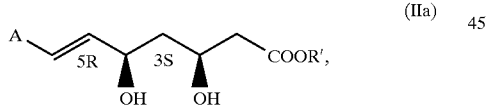

(HHD-2)

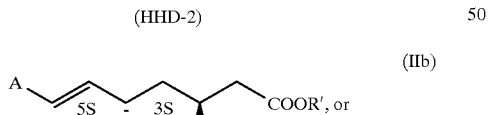

(HHD-6)

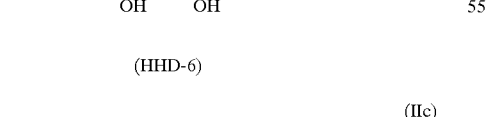

(HHD-7)

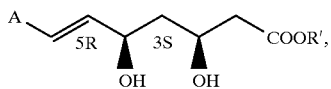

(HHD-2)

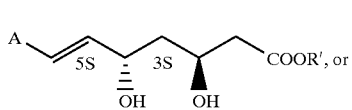

(HHD-6)

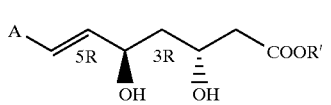

(HHD-7)

wherein A is

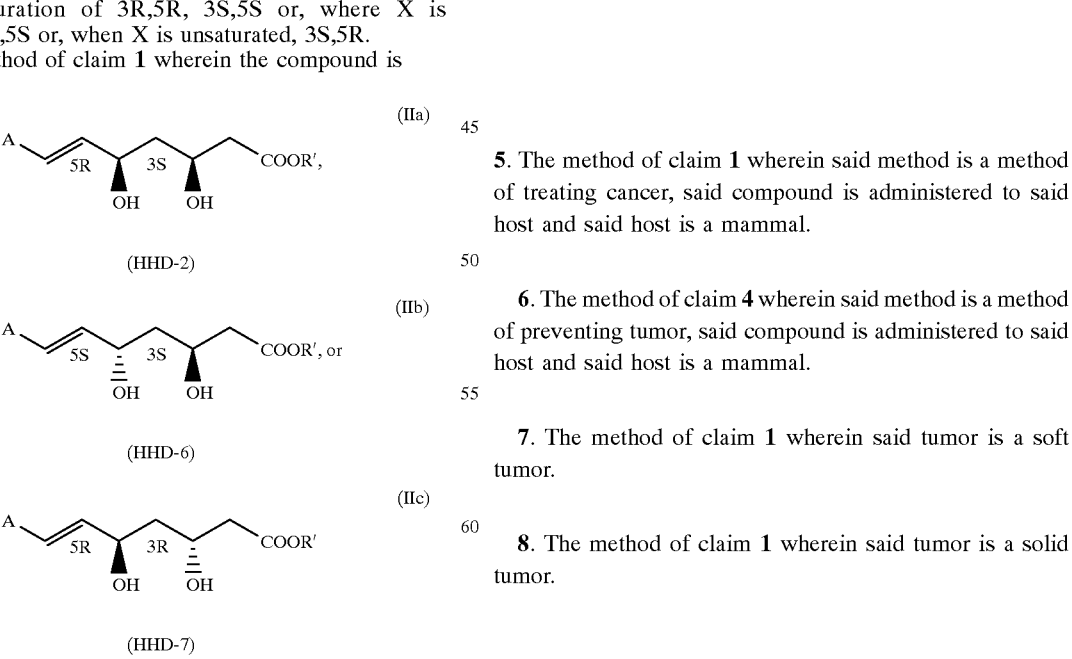

5. The method of claim 1 wherein said method is a method of treating cancer, said compound is administered to said host and said host is a mammal.

6. The method of claim 4 wherein said method is a method of preventing tumor, said compound is administered to said host and said host is a mammal.

7. The method of claim 1 wherein said tumor is a soft tumor.

8. The method of claim 1 wherein said tumor is a solid tumor.

* * * * *